(12) United States Patent
Chari et al.

(10) Patent No.: US 10,046,063 B2
(45) Date of Patent: Aug. 14, 2018

(54) BENZODIAZEPINES AND CONJUGATES THEREOF

(71) Applicant: ImmunoGen, Inc., Waltham, MA (US)

(72) Inventors: Ravi V. J. Chari, Newton, MA (US); Michael Louis Miller, Framingham, MA (US)

(73) Assignee: IMMUNOGEN, INC., Waltham, MA (US)

( * ) Notice: Subject to any disclaimer, the term of this patent is extended or adjusted under 35 U.S.C. 154(b) by 0 days.

(21) Appl. No.: 15/416,797

(22) Filed: Jan. 26, 2017

(65) Prior Publication Data

US 2017/0274091 A1    Sep. 28, 2017

Related U.S. Application Data

(63) Continuation of application No. 14/548,533, filed on Nov. 20, 2014, now Pat. No. 9,555,125, which is a continuation of application No. PCT/US2013/042566, filed on May 24, 2013.

(60) Provisional application No. 61/651,948, filed on May 25, 2012.

(51) Int. Cl.
*C07D 487/04* (2006.01)
*A61K 47/68* (2017.01)
*C07D 519/00* (2006.01)
*C07K 16/30* (2006.01)
*C07K 19/00* (2006.01)

(52) U.S. Cl.
CPC ........ *A61K 47/6803* (2017.08); *C07D 487/04* (2013.01); *C07D 519/00* (2013.01); *C07K 16/30* (2013.01); *C07K 19/00* (2013.01)

(58) Field of Classification Search
CPC .................................................. C07D 487/04
See application file for complete search history.

(56) References Cited

U.S. PATENT DOCUMENTS

2011/0256157 A1   10/2011   Howard et al.

OTHER PUBLICATIONS

Kamal et al, "Pyrrolo[2,1-c][1,4]benzodiazepine-β-glucoronide prodrugs with a potential for selective therapy of solid tumors by PMT and ADEPT strategies," *Bioorg. Med. Chem. Lett.*, 18:3769-3773 (2008).

*Primary Examiner* — Bruck Kifle
(74) *Attorney, Agent, or Firm* — McCarter & English, LLP; Yu Lu; Xin Zhang

(57) ABSTRACT

Conjugates and compounds for making conjugates which are PBD molecules linked via the N10 position are disclosed, along with the use of the conjugates for treating proliferative diseases, including cancer.

21 Claims, 18 Drawing Sheets

BENZODIAZEPINES AND CONJUGATES THEREOF

RELATED APPLICATIONS

This application is a Continuation of U.S. patent application Ser. No. 14/548,533, filed on Nov. 20, 2014, which is a Continuation of International Application No. PCT/US2013/042566, filed on May 24, 2013 and published as WO 2013/177481; which claims the benefit of the filing date of U.S. Provisional Application No. 61/651,948, filed on May 25, 2012, the entire contents of which are incorporated herein by reference.

FIELD OF THE INVENTION

The present invention relates to certain pyrrolobenzodiazepines (PBDs) and indolinobenzodiazepines (IBDs), in particular pyrrolobenzodiazepines and indolinobenzodiazepines having a labile N10 protecting group, in the form of a linker to a cell binding agent (CBA).

BACKGROUND OF THE INVENTION

Pyrrolobenzodiazepines and Indolinobenzodiazepines

Some pyrrolobenzodiazepines (PBDs) have the ability to recognize and bond to specific sequences of DNA; the preferred sequence is PuGPu. The first PBD antitumor antibiotic, anthramycin, was discovered in 1965 (Leimgruber et al., *J. Am. Chem. Soc.*, 87:5793-5795 (1965); Leimgruber et al., *J. Am. Chem. Soc.*, 87:5791-5793 (1965)). Since then, a number of naturally occurring PBDs have been reported, and over 10 synthetic routes have been developed to a variety of analogues (Thurston et al., *Chem. Rev.* 1994:433-465 (1994)). Family members include abbeymycin (Hochlowski et al., *J. Antibiotics*, 40:145-148 (1987)), chicamycin (Konishi et al., *J. Antibiotics*, 37:200-206 (1984)), DC-81 (Japanese Patent 58-180 487; Thurston et al., *Chem. Brit.*, 26:767-772 (1990); Bose et al., *Tetrahedron*, 48:751-758 (1992)), mazethramycin (Kuminoto et al., *J. Antibiotics*, 33:665-667 (1980)), neothramycins A and B (Takeuchi et al., *J. Antibiotics*, 29:93-96 (1976)), porothramycin (Tsunakawa et al., *J. Antibiotics*, 41:1366-1373 (1988)), prothracarcin (Shimizu et al., *J. Antibiotics*, 29:2492-2503 (1982); Langley and Thurston, *J. Org. Chem.*, 52:91-97 (1987)), sibanomicin (DC-102) (Hara et al., *J. Antibiotics*, 41:702-704 (1988); Itoh et al., *J. Antibiotics*, 41:1281-1284 (1988)), sibiromycin (Leber et al., *J. Am. Chem. Soc.*, 110:2992-2993 (1988)) and tomamycin (Arima et al., *J. Antibiotics*, 25:437-444 (1972)). PBDs are of the general structure:

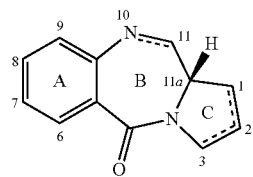

They differ in the number, type and position of substituents, in both their aromatic A rings and pyrrolo C rings, and in the degree of saturation of the C ring. In the B-ring there is either an imine (N=C), a carbinolamine (NH—CH(OH)), or a carbinolamine methyl ether (NH—CH(OMe)) at the N10-C11 position which is the electrophilic center responsible for alkylating DNA. All of the known natural products have an (S)-configuration at the chiral C11a position which provides them with a right-handed twist when viewed from the C ring towards the A ring. This gives them the appropriate three-dimensional shape for isohelicity with the minor groove of B-form DNA, leading to a snug fit at the binding site (Kohn, In Antibiotics III. Springer-Verlag, New York, pp. 3-11 (1975); Hurley and Needham-VanDevanter, *Acc. Chem. Res.*, 19:230-237 (1986)). Their ability to form an adduct in the minor groove, enables them to interfere with DNA processing, hence their use as antitumor agents.

Indolinobenzodiazepines (IBDs) differ from PBDs, in that the PBD C ring is replaced by an indolino ring. For the sake of convenience, certain A ring and B ring positions in the IBDs adopt the same nomenclature as those in the PBDs, such as the C6-C9, N10, and C11 positions.

Antibody-Drug Conjugates

Antibody therapy has been established for the targeted treatment of patients with cancer, immunological and angiogenic disorders (Carter, P. (2006) *Nature Reviews Immunology* 6:343-357). The use of antibody-drug conjugates (ADC), i.e., immunoconjugates, for the local delivery of cytotoxic or cytostatic agents, i.e., drugs to kill or inhibit tumor cells in the treatment of cancer, targets delivery of the drug moiety to tumors, and intracellular accumulation therein, whereas systemic administration of these unconjugated drug agents may result in unacceptable levels of toxicity to normal cells as well as the tumor cells sought to be eliminated (Xie et al. (2006) *Expert. Opin. Biol. Ther.* 6(3):281-291; Kovtun et al. (2006) *Cancer Res.* 66(6):3214-3121; Law et al. (2006) *Cancer Res.* 66(4):2328-2337; Wu et al. (2005) *Nature Biotech.* 23(9):1137-1145; Lambert J. (2005) *Current Opin. in Pharmacol.* 5:543-549; Hamann P. (2005) *Expert Opin. Ther. Patents* 15(9):1087-1103; Payne, G. (2003) *Cancer Cell* 3:207-212; Trail et al. (2003) *Cancer Immunol. Immunother.* 52:328-337; Syrigos and Epenetos (1999) *Anticancer Research* 19:605-614).

Maximal efficacy with minimal toxicity is sought thereby. Efforts to design and refine ADC have focused on the selectivity of monoclonal antibodies (mAbs) as well as drug mechanism of action, drug-linking, drug/antibody ratio (loading), and drug-releasing properties (Chari, R V J (2008) *Acc. Chem. Res.*, 41:98-107, Junutula et al., 2008b *Nature Biotech.*, 26(8):925-932; Dornan et al. (2009) *Blood* 114 (13):2721-2729; U.S. Pat. No. 7,521,541; U.S. Pat. No. 7,723,485; WO 2009/052249; McDonagh (2006) *Protein Eng. Design & Sel.* 19(7):299-307; Doronina et al. (2006) *Bioconj. Chem.* 17:114-124; Erickson et al. (2006) *Cancer Res.* 66(8):1-8; Sanderson et al. (2005) *Clin. Cancer Res.* 11:843-852; Jeffrey et al. (2005) *J. Med. Chem.* 48:1344-1358; Hamblett et al. (2004) *Clin. Cancer Res.* 10:7063-7070). Drug moieties may impart their cytotoxic and cytostatic effects by mechanisms including tubulin binding, DNA binding, or topoisomerase inhibition. Some cytotoxic drugs tend to be inactive or less active when conjugated to large antibodies or protein receptor ligands.

The present inventors have developed a novel approach to forming PBD conjugates and IBD conjugates with cell binding agents, and in particular PBD or IBD antibody conjugates.

SUMMARY OF THE INVENTION

Cytotoxic benzodiazepine dimers disclosed in the art possess two imine functionalities in their free form or reversibly protected form, such as a hydrate, alkoxylate or sulfonate. The presence of these two imine functionalities results in crosslinking of DNA (S. G. Gregson et al., (2001) *J. Med. Chem.*, 44:737-748). The present invention is partly based on the unexpected finding that cell binding agent conjugates of new cytotoxic benzodiazepine derivatives, such as PBD and IBD dimers that are devoid of two imine functionalities (e.g., possess one imine functionality and one amine functionality, or two amine functionalities), and thus incapable of crosslinking DNA, display a much higher therapeutic index (ratio of maximum tolerated dose to minimum effective dose) in vivo compared to benzodiazepine derivatives that can crosslink DNA that are previously disclosed in the art.

Thus in a general aspect the present invention provides a conjugate comprising a PBD dimer compound or an IBD dimer compound, in which one monomer unit is connected through the N10 position via a linker to a cell binding agent. Preferably, only one monomer unit is connected through the N10 position via the linker to the cell binding agent, and the other monomer unit is not linked to cell binding agent. The linker is a labile linker, and may be an enzyme labile linker, such that an imine bond is formed at the N10-C11 position after the cell binding agent linked to the N10 position is released from the monomer, while an amine bond is maintained at the N10-C11 position of the other monomer of the dimer compound. The cell binding agent is preferably an antibody.

In one embodiment, the conjugate comprises a cell binding agent connected to a spacer, the spacer connected to a trigger, the trigger connected to a self-immolative linker, and the self-immolative linker connected to the N10 position of a monomer unit in the PBD or IBD dimer compound.

Thus in a first aspect, the present invention provides novel conjugate comprising a cell-binding agent (CBA) covalently linked to a dimer compound, or a salt or solvate of the dimer compound, wherein the dimer compound comprises:

i) a monomer unit of formula (I):

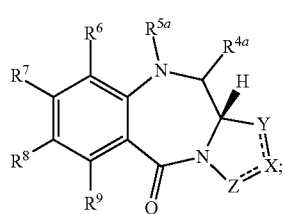

(I)

ii) a monomer unit of formula (II):

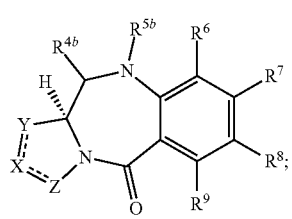

(II)

wherein:
the dotted lines indicate the optional presence of a double bond;
when X is attached to Z and Y via single bonds, X is selected from O, $(CH_2)_n$, $CR^2R^2$, $NR^{4'}$ and S, or when X is attached to Z or Y via a double bond, X is $CR^{2'}$ or N;

when Y is attached to X via a single bond, Y is selected from $CR^3R^3$, $NR^3$, O and S; or when Y is attached to X via a double bond Y is selected from $CR^3$ or N;

when Z is attached to X via a single bond, Z is selected from $CR^1R^1$, $NR^1$, O, S, C(=O), BH, SO and $SO_2$; or when Z is attached to X via a double bond Z is selected from $CR^1$ or N; provided that the bond between X and Y or X and Z is not an epoxide, S—S, O—O, or O—S;

$R^1$ and $R^3$ are each, independently, hydrogen, halogen, hydroxyl or alkyl;

each $R^2$ is independently selected from —H, —OH, —CN, —$R^{1'}$, —$OR^{1'}$, —O—$SO_2$—$R^{1'}$, —$CO_2R^{1'}$, —$COR^{1'}$, or halo, or both $R^2$ taken together, are =O, =$CH_2$, =CH—$R^a$, or =$C(R^a)_2$;

each $R^{2'}$ is independently selected from —H, —OH, —CN, —$R^{1'}$, —$OR^{1'}$, —O—$SO_2$—$R^{1'}$, —$CO_2R^{1'}$, —$COR^{1'}$ or halo;

optionally, $R^1$ and $R^2$, or $R^2$ and $R^3$, together with the atoms to which they are bound form an optionally substituted 6-membered aryl ring;

$R^{4a}$ is selected from —H, an oxo group, an optionally substituted linear, branched or cyclic alkyl, alkenyl or alkynyl having from 1 to 10 carbon atoms, an optionally substituted 6- to 18-membered aryl, an optionally substituted 5- to 18-membered heteroaryl ring containing one or more heteroatoms independently selected from nitrogen, oxygen, or sulfur, and an optionally substituted 3- to 18-membered heterocyclic ring having 1 to 6 heteroatoms;

$R^{4b}$ is —H or a leaving group selected from —$OR^{6'}$, —$OCOR^{4'}$, —$OCOOR^{4'}$, —$OCONR^{4'}R^{5'}$, —$NR^{4'}R^{5'}$, —$NR^{4'}COR^{5'}$, —$NR^{4'}NR^{4'}R^{5'}$, an optionally substituted 5- or 6-membered nitrogen-containing heterocycle (e.g., piperidine, tetrahydropyrrole, pyrazole, morpholine), a guanidinum represented by —$NR^{4'}$(C=NH)$NR^{4'}R^{5'}$, an amino acid, or a peptide represented by —$NR^{6'}COP'$, wherein P' is an amino acid or a polypeptide containing between 2 to 20 amino acid units, —$SR^{6'}$, —$SOR^{4'}$, —$SO_2M$, —$SO_3M$, —$OSO_3M$, halogen, cyano and an azido;

$R^{5a}$ is —H, a protecting group, a peptide, an optionally substituted linear, branched or cyclic alkyl, alkenyl or alkynyl having from 1 to 10 carbon atoms, a polyethylene glycol unit —$(CH_2CH_2O)_n$—$R^c$, an optionally substituted aryl having 6 to 18 carbon atoms, an optionally substituted 5- to 18-membered heteroaryl ring containing one or more heteroatoms independently selected from nitrogen, oxygen, and sulfur, and an optionally substituted 3- to 18-membered heterocyclic ring containing 1 to 6 heteroatoms independently selected from O, S, N and P, $R^{5b}$ is a linker connected to the cell binding agent;

$R^6$, $R^7$, $R^8$, and $R^9$ are independently selected from —H, —$R^{1'}$, —OH, —$OR^{1'}$, —SH, —$SR^{1'}$, —$NH_2$, —$NHR^{1'}$, —$NR^{1'}R^{3'}$, —$NO_2$, $Me_3Sn$ and halo; or, $R^7$ or $R^8$ of formula (I) are bonded to $R^7$ or $R^8$ of formula (II) forming a dimer; and, $R^{1'}$ and $R^{3'}$ are each independently selected from optionally substituted $C_{1-12}$ alkyl, $C_{3-20}$ heterocyclyl or $C_{5-20}$ aryl groups, and optionally in relation to the group —$NR^{1'}R^{3'}$, $R^{1'}$ and $R^{3'}$ together with the nitrogen atom to which they are attached form an optionally substituted 4-, 5-, 6- or 7-membered heterocyclic ring; or any pair of adjacent groups from $R^6$ to $R^9$ together form a group —O—$(CH_2)$—O—, where p is 1 or 2;

$R^{4'}$ and $R^{5'}$ are each independently selected from —H, —OH, —$OR^{6'}$, —$NHR^{6'}$—$NR^{6'}_2$, —$COR^{6'}$, an optionally substituted linear, branched or cyclic alkyl, alkenyl or alkynyl having from 1 to 10 carbon atoms, a polyethylene glycol unit —(CH$_2$CH$_2$O)$_n$—R$^b$, or an optionally substituted 3-18-membered heterocyclic ring having 1 to 6 heteroatoms independently selected from O, S, N or P;

R$^{6'}$, for each occurrence, is independently selected from the group consisting of —H, an optionally substituted linear, branched or cyclic alkyl, alkenyl or alkynyl having from 1 to 10 carbon atoms, a polyethylene glycol unit —(CH$_2$CH$_2$O)$_n$—R$^b$, an optionally substituted aryl having 6 to 18 carbon atoms, an optionally substituted 5- to 18-membered heteroaryl ring containing one or more heteroatoms independently selected from nitrogen, oxygen, or sulfur, and an optionally substituted 3- to 18-membered heterocyclic ring containing 1 to 6 heteroatoms independently selected from O, S, N or P;

R$^a$ is independently selected from —R$^{1'}$, —CO$_2$R$^{1'}$, —COR$^{1'}$, —CHO, —CO$_2$H, or halo;

R$^b$ is —H or a substituted or unsubstituted linear or branched alkyl having 1 to 4 carbon atoms;

M is H or a pharmaceutically acceptable cation; and n is an integer from 1 to 24.

Preferably, the linker in R$^{5b}$ is a labile linker that permits the removal of the linked CBA, and the subsequent formation of an imine bond in the monomer at the N10-C11 position upon the removal of the leaving group R$^{4b}$. Preferably, both R$^{4a}$ and R$^{5a}$ are H.

In one embodiment, i) the monomer unit of formula (I) is represented by formula (IIIa):

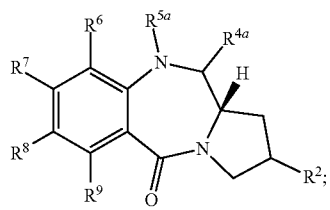

(IIIa)

and, ii) the monomer unit of formula (II) is represented by formula (IVa):

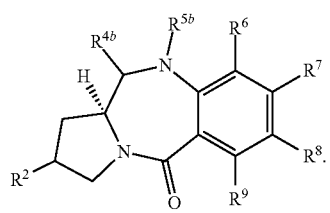

(IVa)

Preferably, both R$^{4a}$ and R$^{5a}$ are H.

In another embodiment, i) the monomer unit of formula (I) is represented by formula (IIIb):

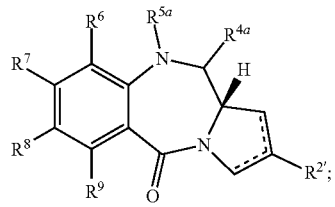

(IIIb)

ii) the monomer unit of formula (II) is represented by formula (IVb):

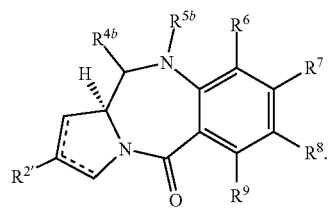

(IVb)

Preferably, both R$^{4a}$ and R$^{5a}$ are H.

In one embodiment, i) the monomer unit of formula (I) is represented by formula (V):

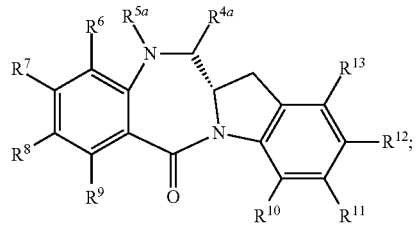

(V)

and ii) the monomer unit of formula (II) is represented by formula (VI):

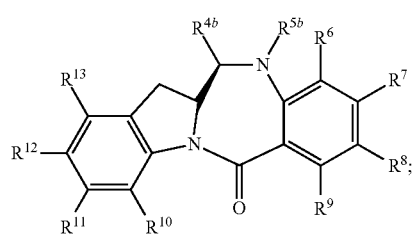

(VI)

wherein:

R$^{10}$, R$^{11}$, R$^{12}$ and R$^{13}$ are each independently selected from the group consisting of —H, an optionally substituted linear, branched or cyclic alkyl, alkenyl or alkynyl having from 1 to 10 carbon atoms, a polyethylene glycol unit —(OCH$_2$CH$_2$)$_n$—R$^b$, halogen, guanidinium [—NH(C=NH)NH$_2$], —OR$^{6'}$, —NR$^{4'}$R, R$^{5'}$, —NO$_2$, —NCO, —NR$^{4'}$COR$^{5'}$, —SR$^{6'}$, a sulfoxide represented by —SOR$^{4'}$, a sulfone represented by —SO$_2$R$^{4'}$, a sulfonate —SO$_3^-$M$^+$, a sulfate —OSO$_3^-$M$^+$, a sulfonamide represented by —SO$_2$NR$^{4'}$R$^{5'}$, cyano, an azido, —COR$^{4'}$, —OCOR$^{4'}$, —OCONR$^{4'}$R$^{5'}$.

In one embodiment, i) the monomer unit of formula (I) is represented by formula (VII):

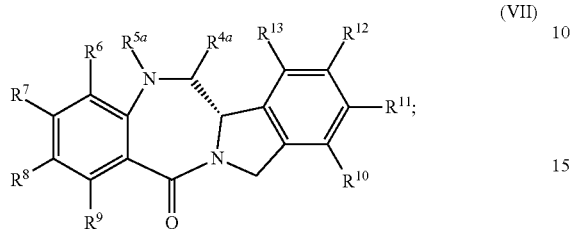

(VII)

and ii) the monomer unit of formula (II) is represented by formula (VIII):

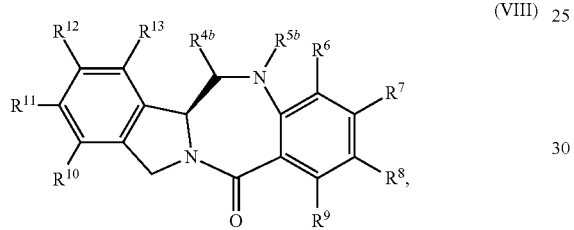

(VIII)

wherein:

R$^{10}$, R$^{11}$, R$^{12}$ and R$^{13}$ are each independently selected from the group consisting of —H, an optionally substituted linear, branched or cyclic alkyl, alkenyl or alkynyl having from 1 to 10 carbon atoms, a polyethylene glycol unit —(OCH$_2$CH$_2$)$_n$—R$^b$, halogen, guanidinium [—NH(C═NH)NH$_2$], —OR$^{6'}$, —NR$^{4'}$R$^{5'}$, —NO$_2$, —NCO, —NR$^{4'}$COR$^{5'}$, —SR$^{6'}$, a sulfoxide represented by —SOR$^{4'}$, a sulfone represented by —SO$_2$R$^{4'}$, a sulfonate —SO$_3^-$M$^+$, a sulfate —OSO$_3^-$M$^+$, a sulfonamide represented by —SO$_2$NR$^{4'}$R$^{5'}$, cyano, an azido, —COR$^{4'}$, —OCOR$^{4'}$, —OCONR$^{4'}$R$^5$.

In one embodiment, R$^{5b}$ is removable from the N10 position to form an imine.

In one embodiment, the dimer formed by linking R$^7$ or R$^8$ of formula (I) and R$^7$ or R$^8$ of formula (II) is linked by a dimer bridge having the formula —X'—R$^{3''}$—X'—; wherein R$^{3''}$ is a C$_{3-12}$ alkylene group, which chain may be interrupted by one or more heteroatoms, e.g., —O—, —S—, —N(H)—, —NMe and/or aromatic rings, e.g., benzene or pyridine, which rings are optionally substituted by —NH$_2$; and each X', for each occurrence, is independently —O—, —S— or —N(H)—.

In one embodiment, the conjugate is represented by a structural formula selected from:

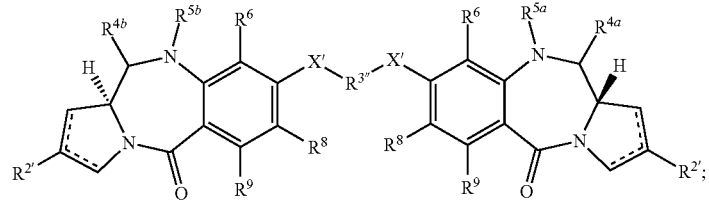

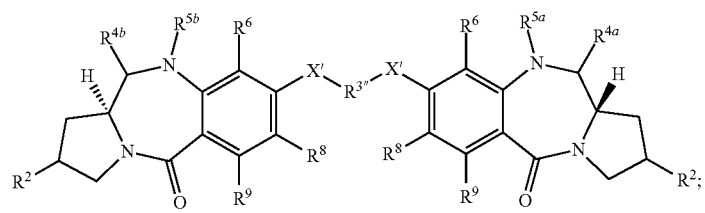

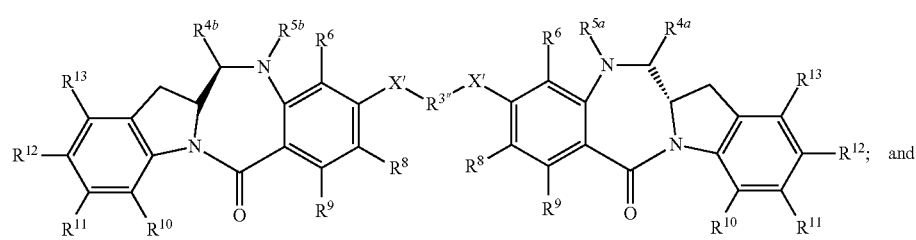

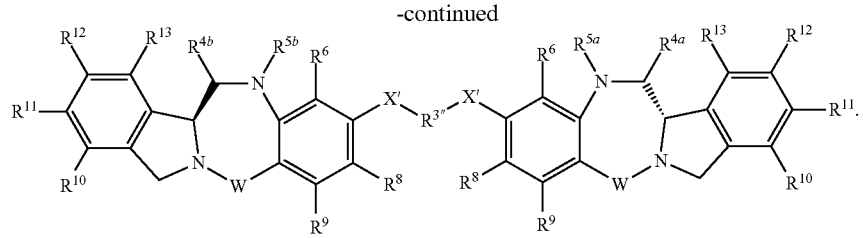
In one embodiment, the conjugate has a formula selected from:
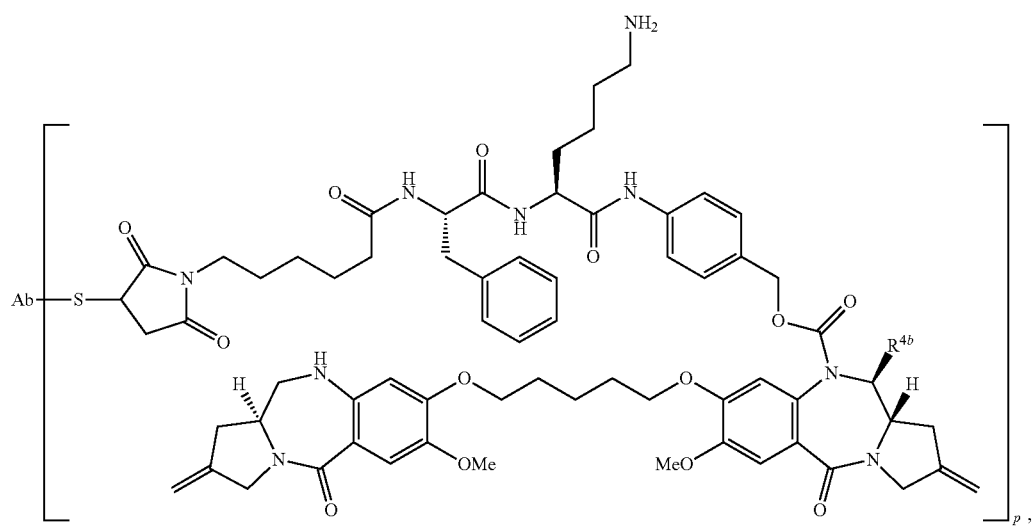
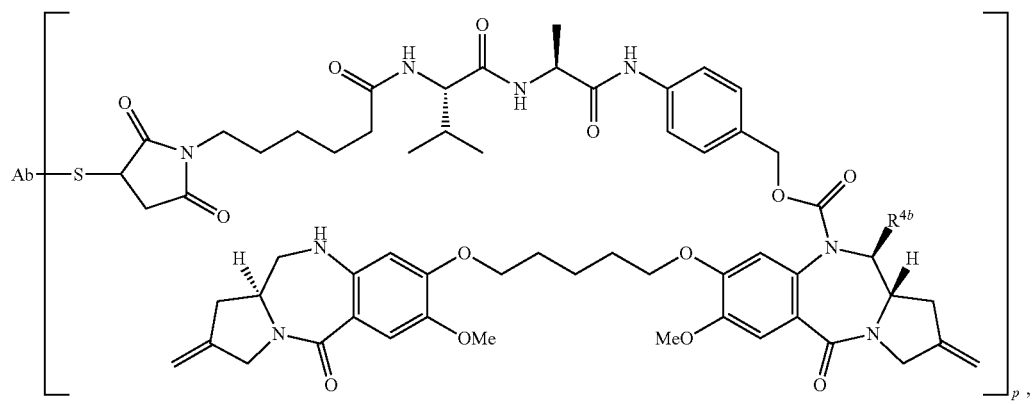

-continued
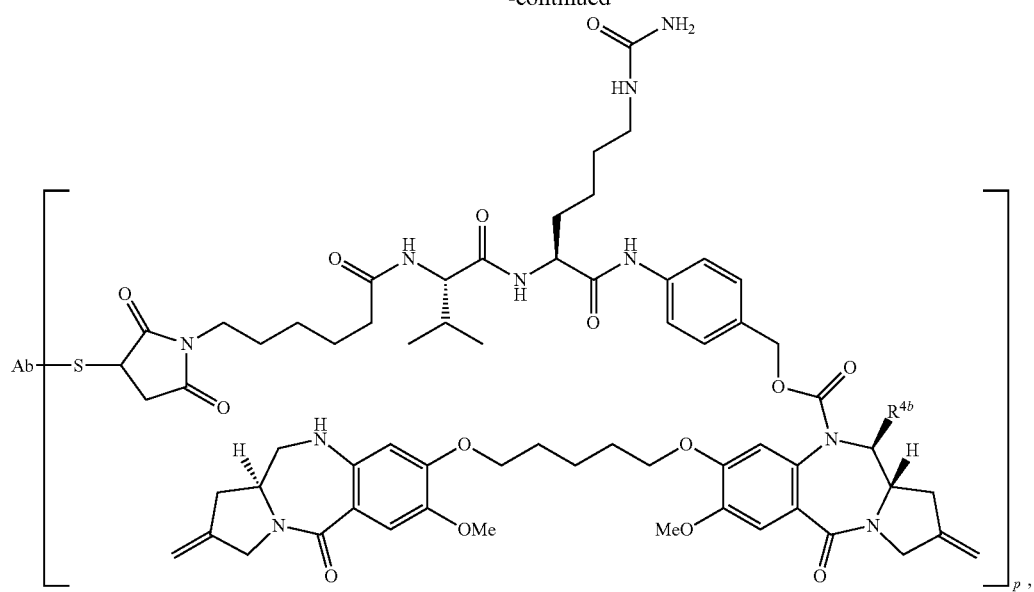
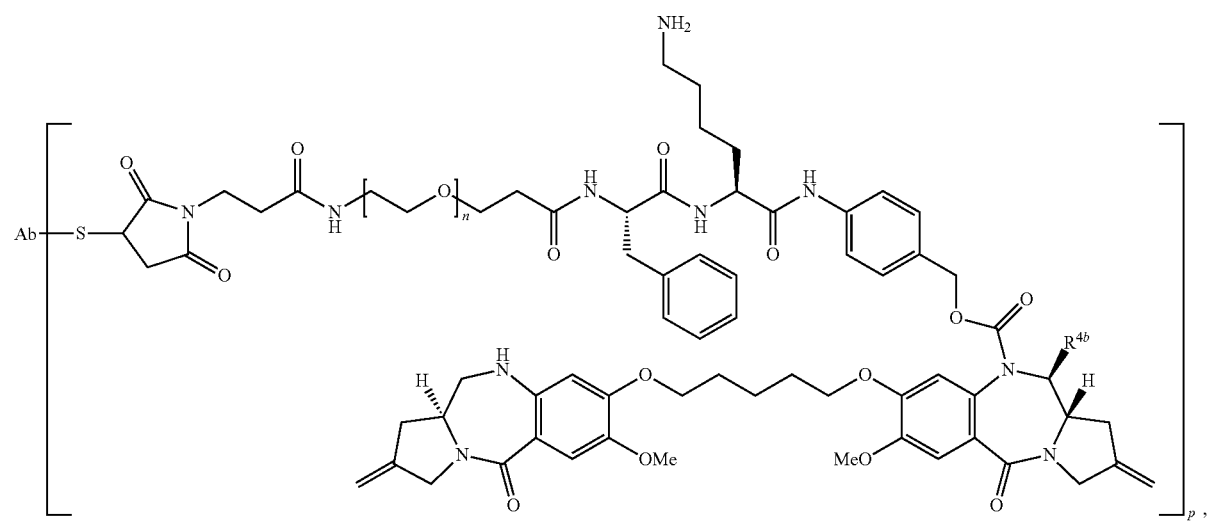
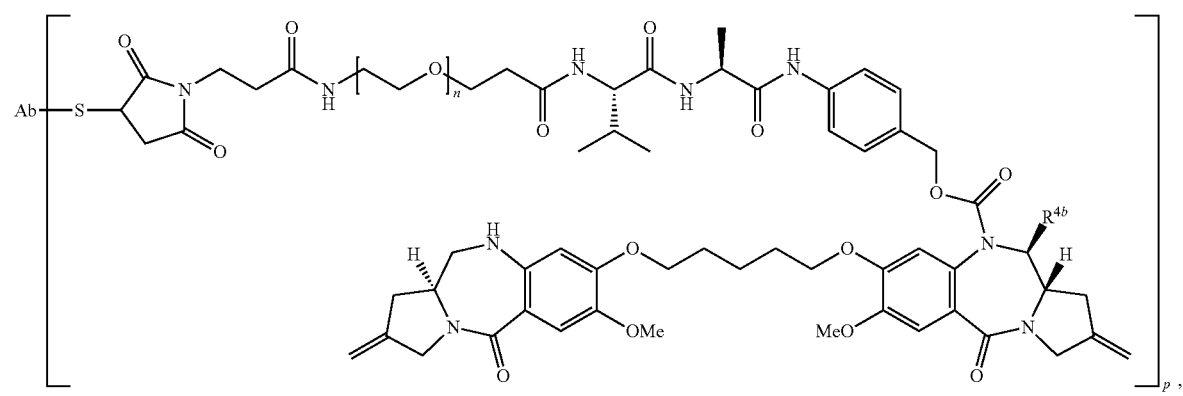

-continued
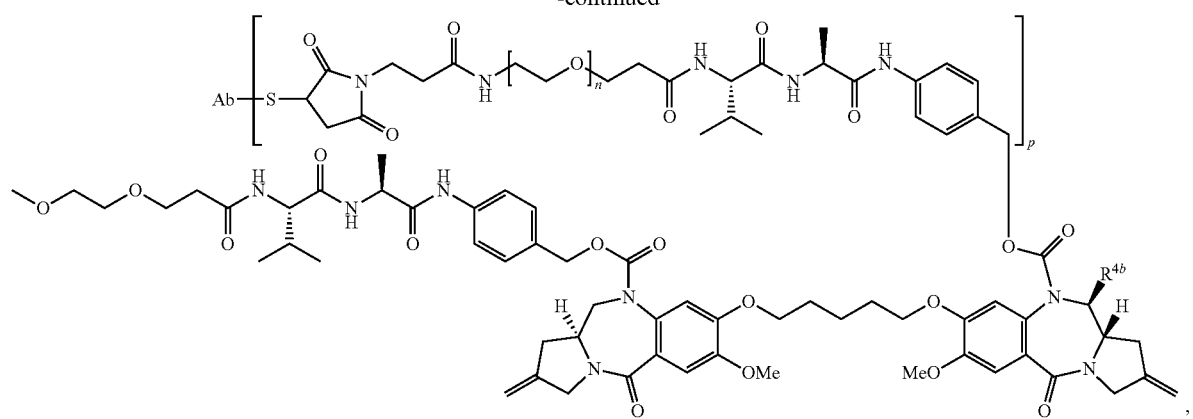
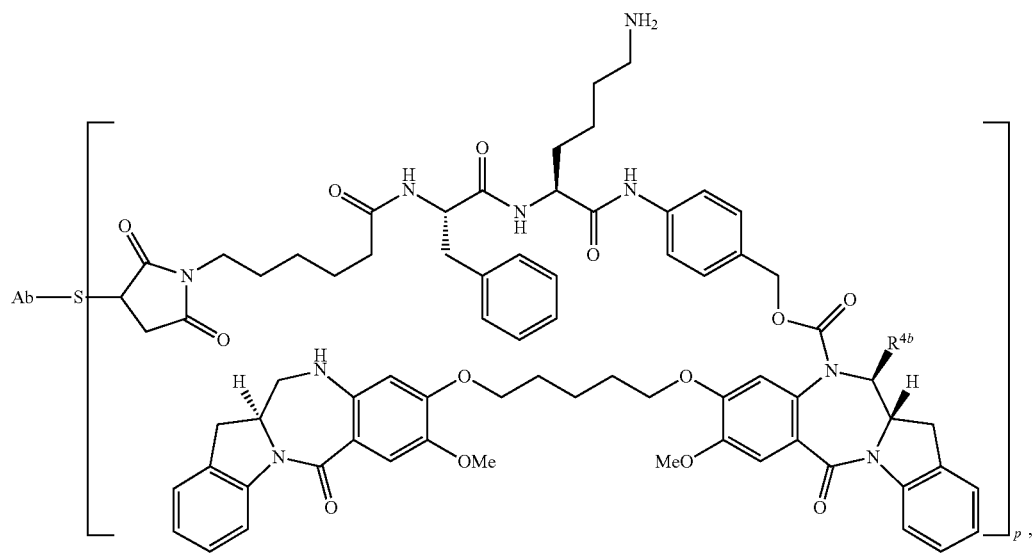
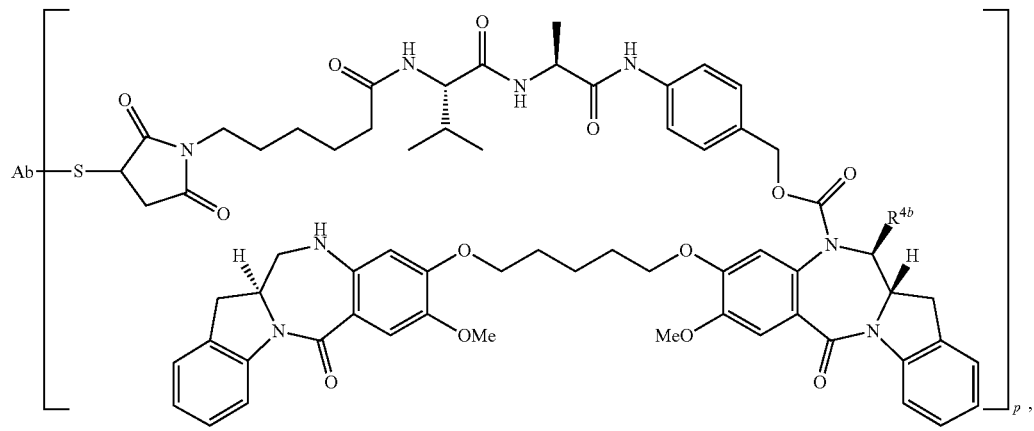

-continued
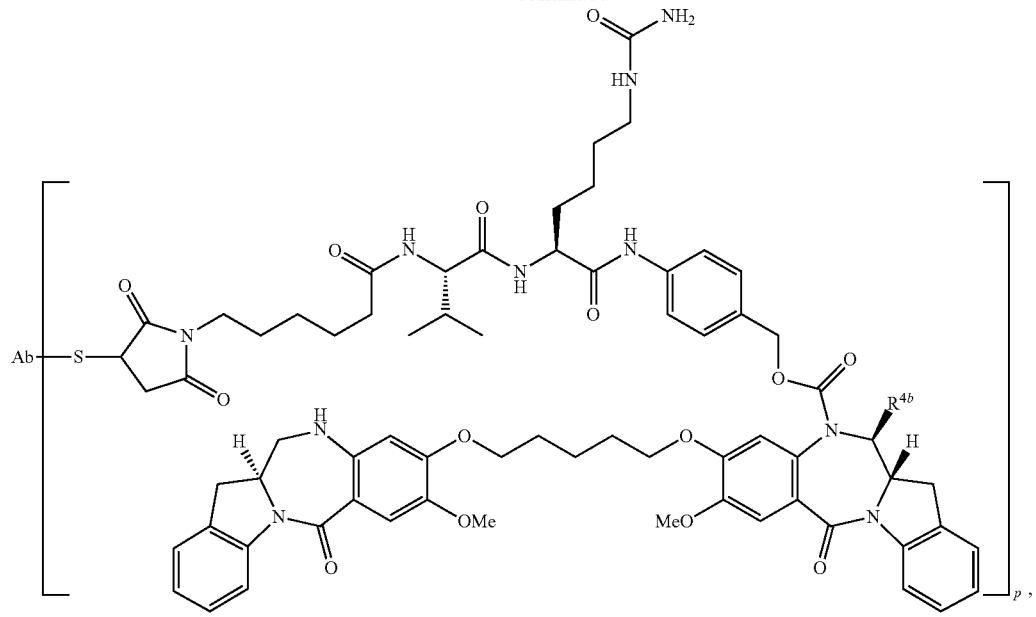
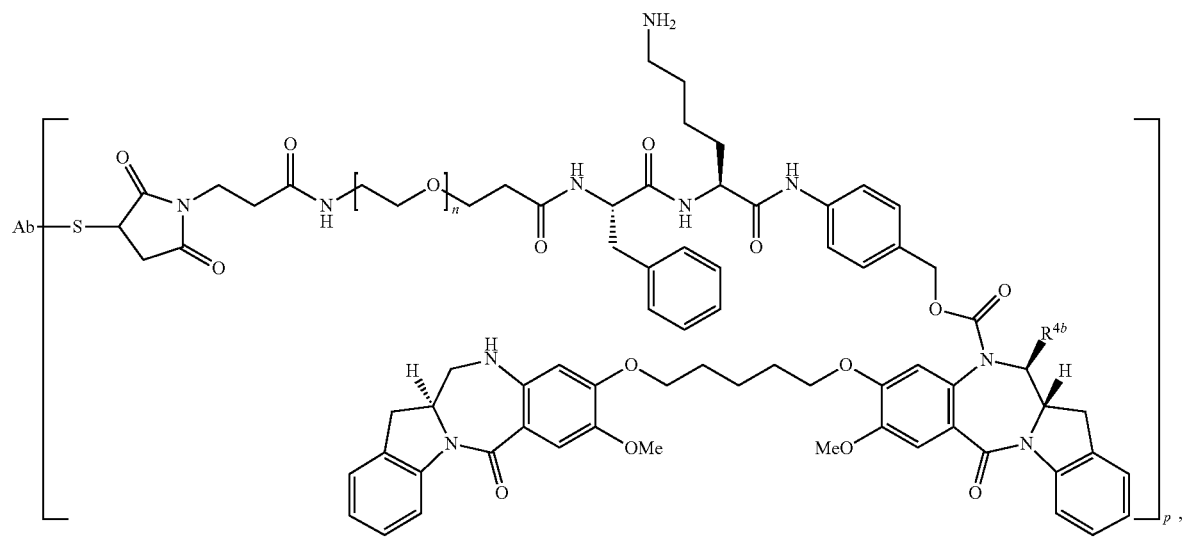
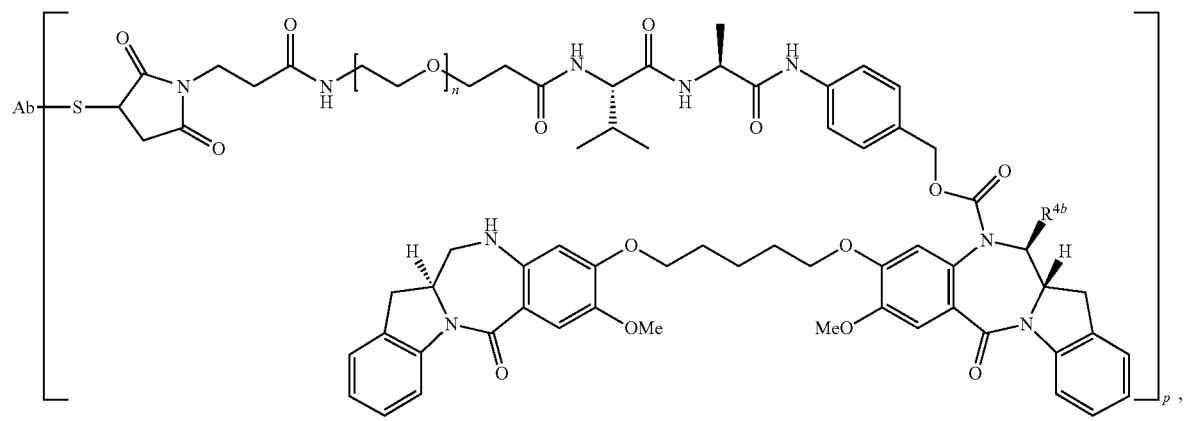

-continued
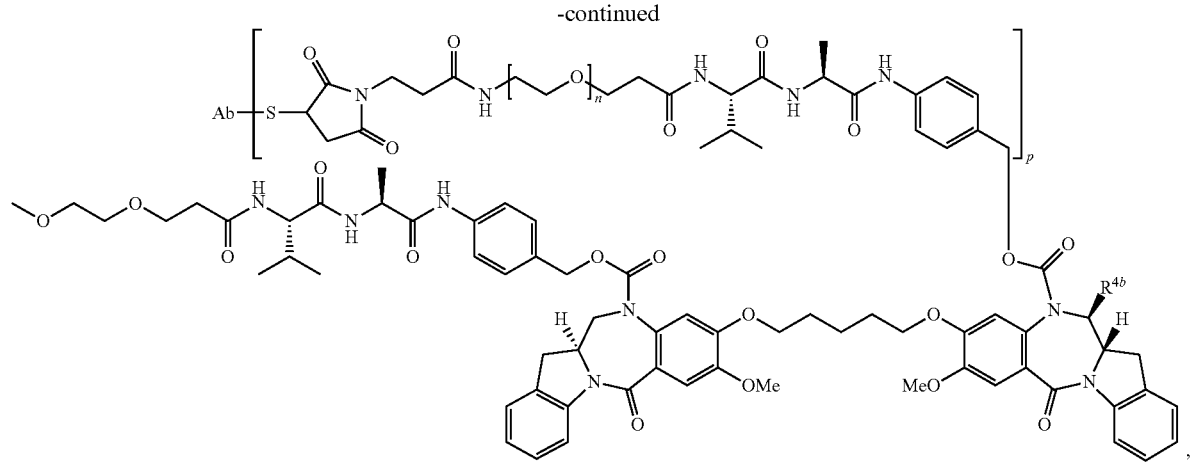
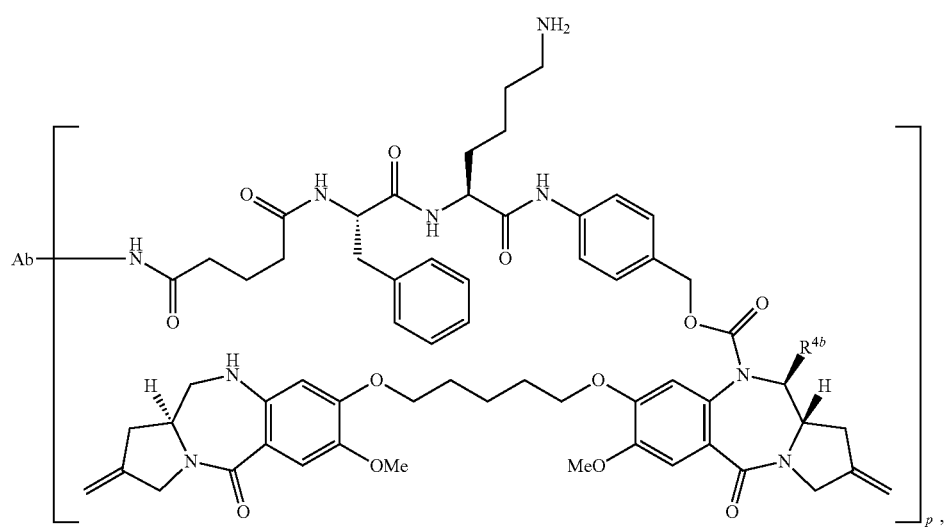
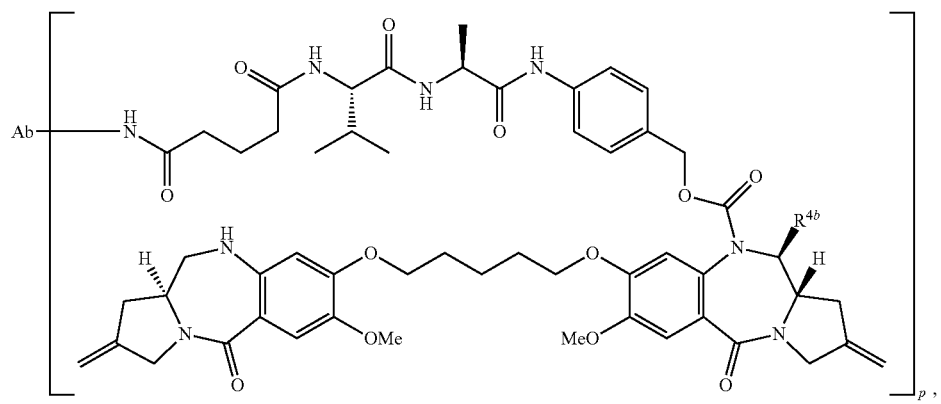

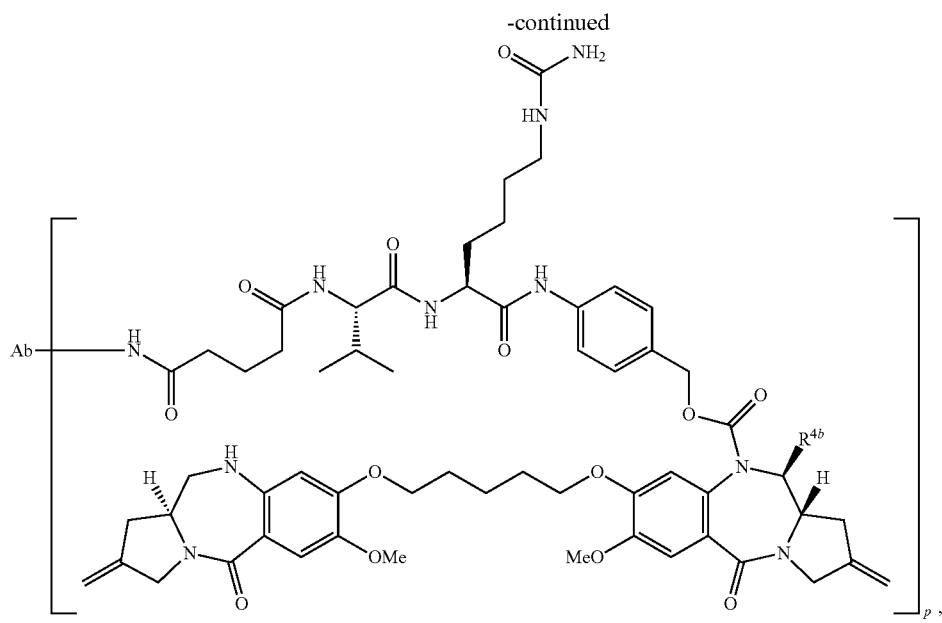
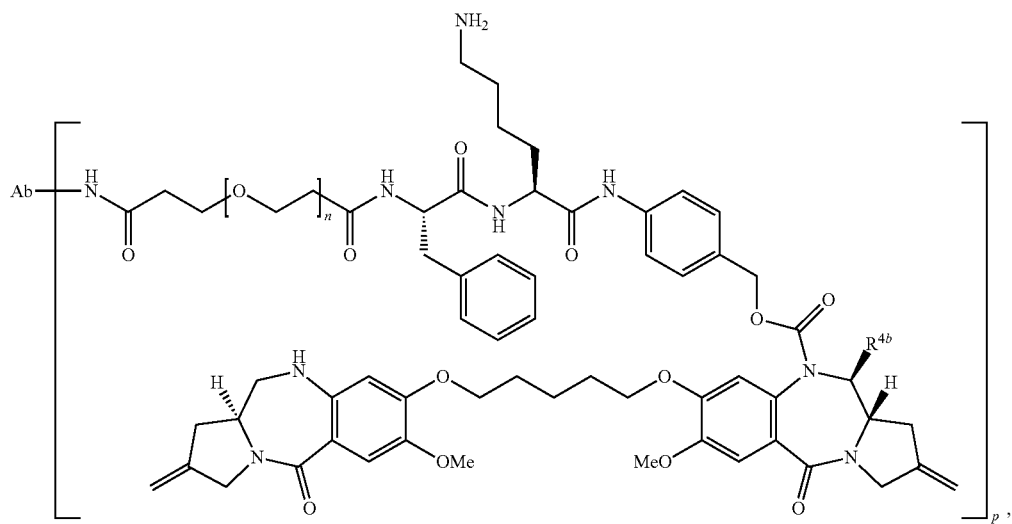
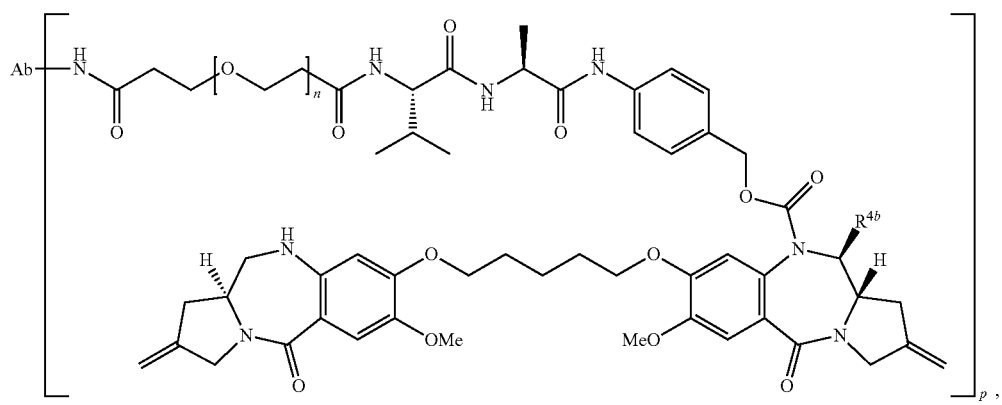

-continued
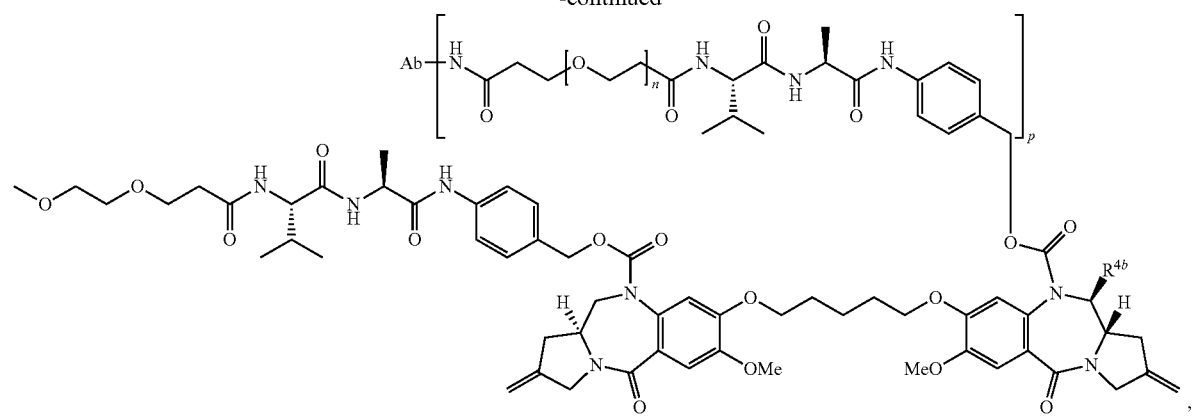
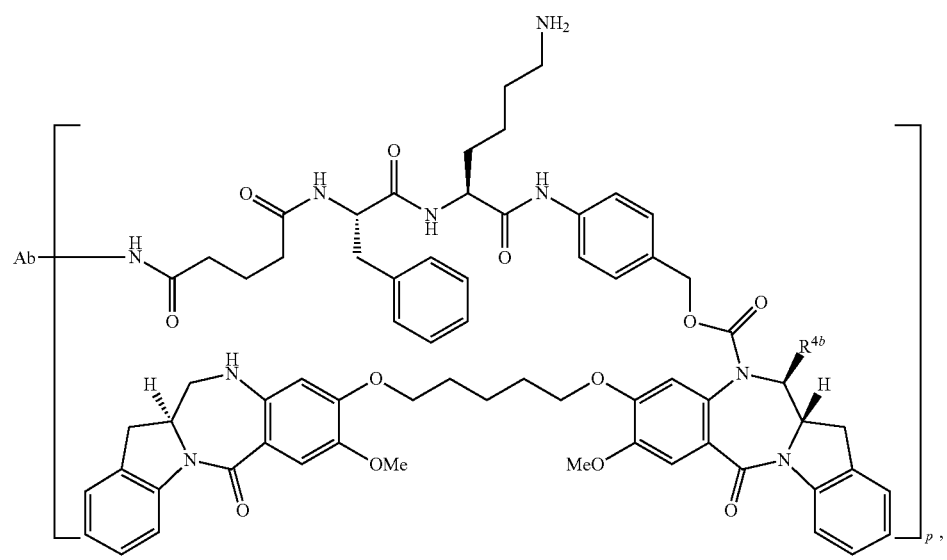
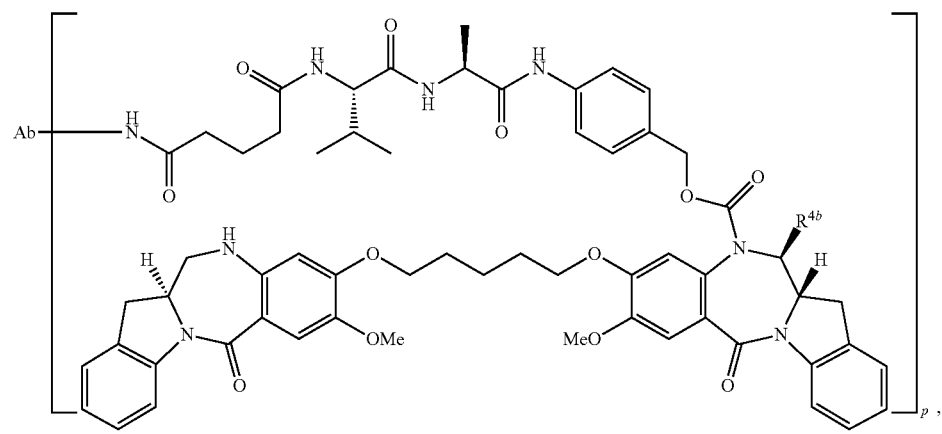

-continued
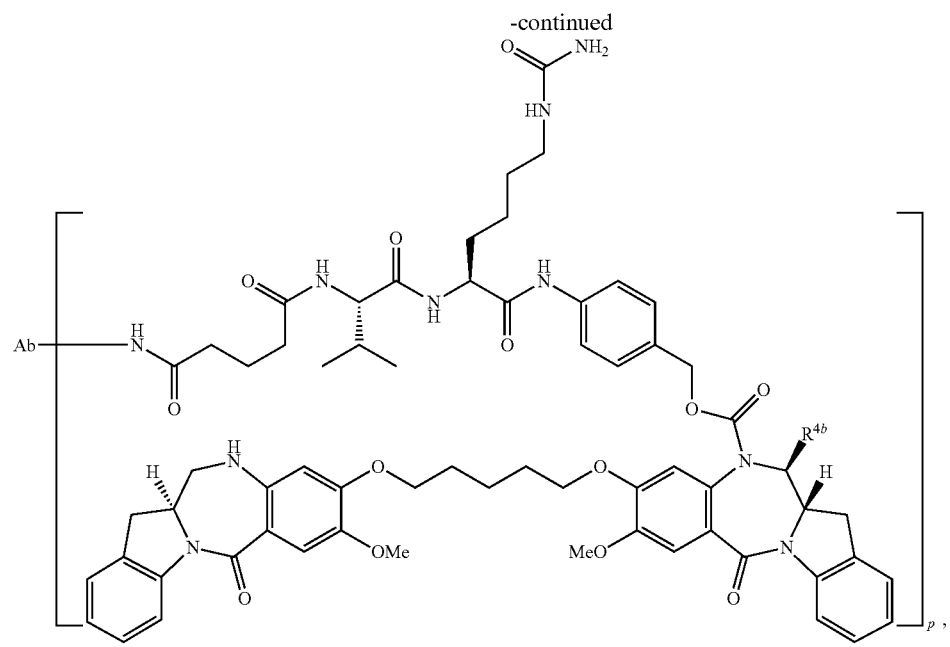
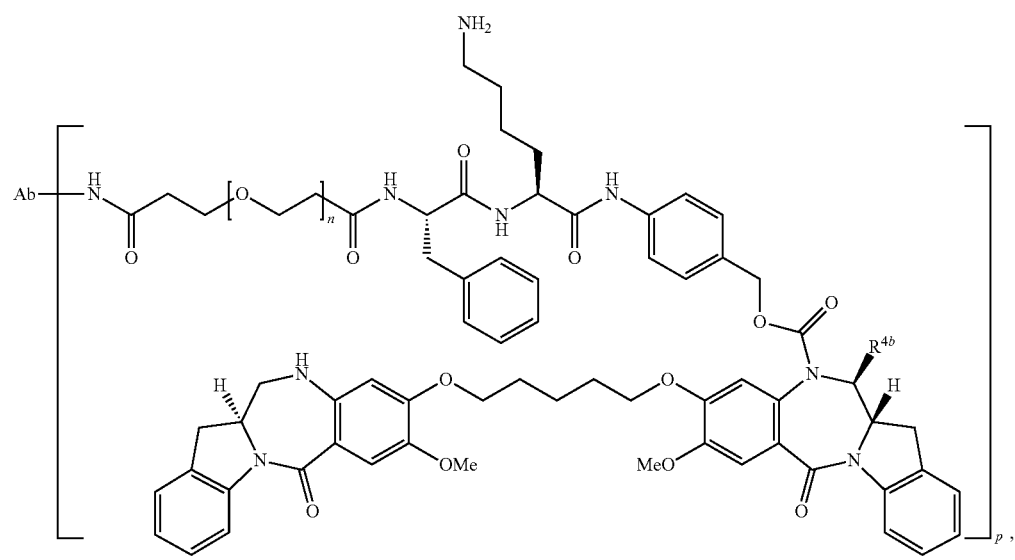
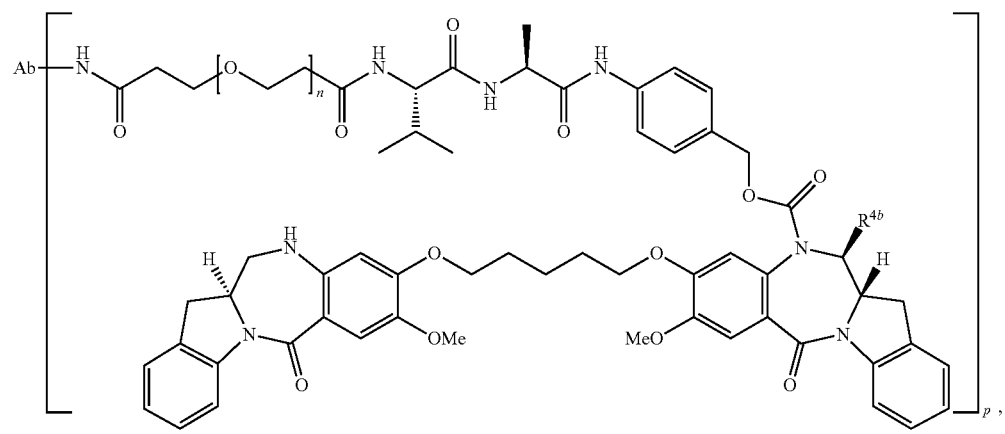

-continued

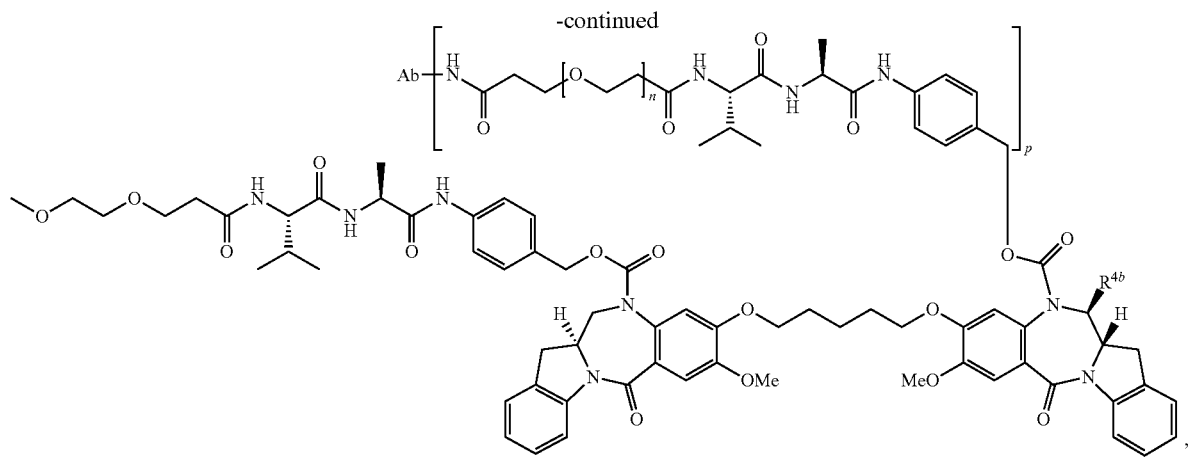

where n is an integer from 1 to 24 (e.g., 1-12, or 4-8), and $R^{4b}$ is as described above. In a specific embodiment, $R^{4b}$ is —H, —OR$^{6'}$, —SO$_3$M, or —OSO$_3$M, wherein $R^{6'}$ and M are as described above. In another specific embodiment, $R^{4b}$ is —H. Alternatively, $R^{4b}$ is —OH.

In one embodiment, the conjugate is for use in therapy.

In one embodiment, the conjugate is for use in the treatment of a proliferative disease (such as cancer) in a subject.

A second aspect of the invention provides a pharmaceutical composition comprising the conjugate of the invention described herein, and a pharmaceutically acceptable diluent, carrier or excipient.

In one embodiment, the pharmaceutical composition further comprises a therapeutically effective amount of a chemotherapeutic agent.

A third aspect of the invention provides a use of a conjugate of the invention described herein, in the preparation of a medicament for use in the treatment of a proliferative disease in a subject.

A fourth aspect of the invention provides a method of treating cancer, comprising administering to a patient the pharmaceutical composition of the invention described herein.

In one embodiment, the patient is administered a chemotherapeutic agent, in combination with the conjugate.

A fifth aspect of the invention provides a use of a conjugate of the invention as described herein, or salts and solvates thereof, to provide a compound at a target location, wherein the compound is a dimer, or a salt or solvate thereof, comprising: i) a monomer derived from formula (I), wherein $R^{5a}$ in formula (I) remains, and the N10-C11 bond is an amine bond; and, ii) a monomer derived from formula (II), wherein $R^{4b}$ is eliminated as a leaving group, and the N10-C11 bond is an imine bond.

In one embodiment, the target location is a proliferative cell population.

A sixth aspect of the invention provides a dimer compound, or a salt or solvate of the dimer, comprising:

i) a monomer unit of formula (I):

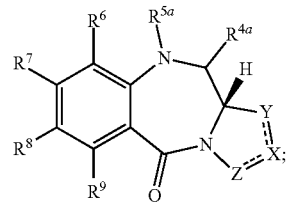

and, ii) a monomer unit of formula (II'):

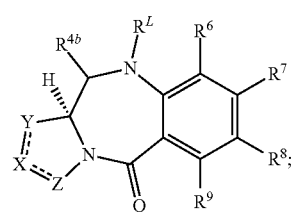

wherein:

the dotted lines indicate the optional presence of a double bond;

X, Y, Z, $R^1$, $R^2$, $R^{2'}$, $R^3$, $R^{4a}$, $R^{4b}$, $R^{5a}$, $R^6$, $R^7$, $R^8$, $R^9$, $R^{1'}$, $R^{3'}$, $R^{4'}R^{5'}R^{6'}R^a$, $R^b$, M, and n are as defined above for the conjugates of the first aspect of the invention.

Preferably, the linker in $R^L$ is a labile linker that, upon linking with the CBA, permits the removal of the linked CBA, and the subsequent formation of an imine bond in the monomer at the N10-C11 position upon the removal of the leaving group $R^{4b}$.

Preferably, both $R^{4a}$ and $R^{5a}$ are H.

In one embodiment, i) the monomer unit of formula (I) is represented by formula (IIIa):

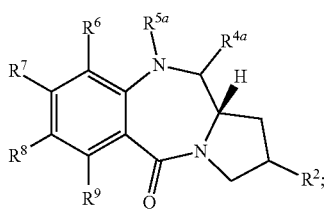

(IIIa)

and ii) the monomer unit of formula (II) is represented by formula (IVa'):

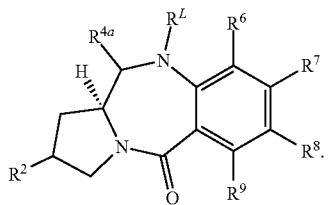

(IVa')

In one embodiment, i) the monomer unit of formula (I) is represented by formula (IIIb):

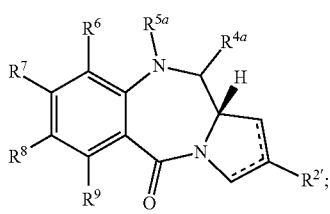

(IIIb)

and ii) the monomer unit of formula (II) is represented by formula (IVb'):

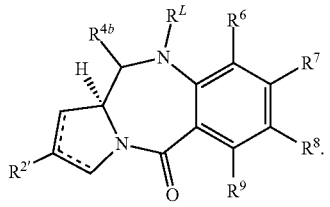

(IVb')

In one embodiment, i) the monomer unit of formula (I) is represented by formula (V):

(V)

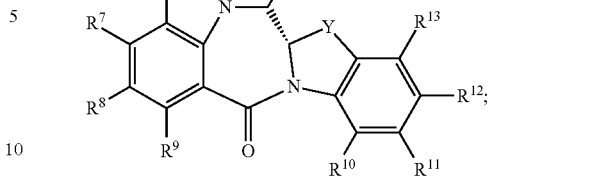

and ii) the monomer unit of formula (II) is represented by formula (VI'):

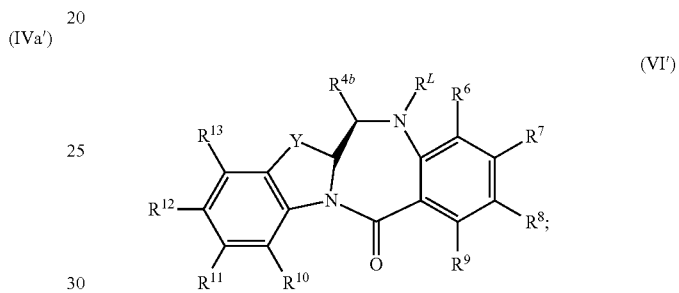

(VI')

wherein:

$R^{10}$, $R^{11}$, $R^{12}$ and $R^{13}$ are each independently selected from the group consisting of —H, an optionally substituted linear, branched or cyclic alkyl, alkenyl or alkynyl having from 1 to 10 carbon atoms, a polyethylene glycol unit —(OCH$_2$CH$_2$)$_n$—R$^b$, halogen, guanidinium [—NH(C=NH)NH$_2$], —OR$^{6'}$, —NR$^{4'}$R$^{5'}$, —NO$_2$, —NCO, —NR$^{4'}$COR$^5$, —SR$^{6'}$, a sulfoxide represented by —SOR$^{4'}$, a sulfone represented by —SO$_2$R$^{4'}$, a sulfonate —SO$_3^-$M$^+$, a sulfate —OSO$_3^-$M$^+$, a sulfonamide represented by —SO$_2$NR$^{4'}$R$^{5'}$, cyano, an azido, —COR$^{4'}$, —OCOR$^{4'}$, —OCONR$^{4'}$R$^{5'}$.

In one embodiment, i) the monomer unit of formula (I) is represented by formula (VII):

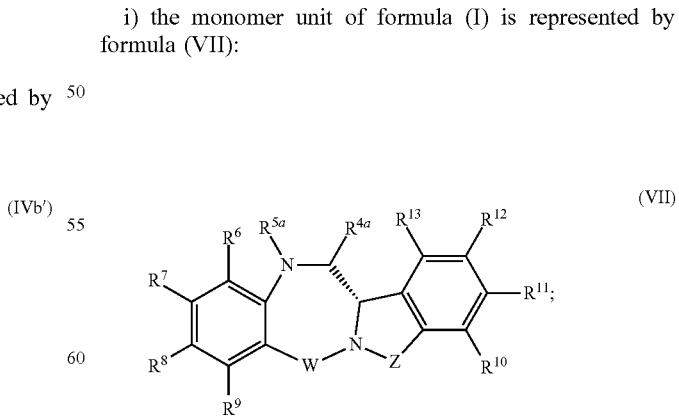

(VII)

and ii) the monomer unit of formula (II) is represented by formula (VII'):

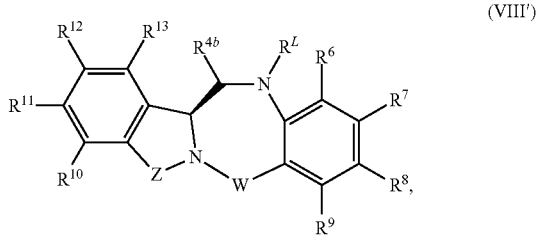

(VIII')

wherein:

$R^{10}$, $R^{11}$, $R^{12}$ and $R^{13}$ are each independently selected from the group consisting of —H, an optionally substituted linear, branched or cyclic alkyl, alkenyl or alkynyl having from 1 to 10 carbon atoms, a polyethylene glycol unit —(OCH$_2$CH$_2$)$_n$—R$^b$, halogen, guanidinium [—NH(C=NH)NH$_2$], —OR$^{6'}$, —NR$^{4'}$R$^{5'}$, —NO$_2$, —NCO, —NR$^{4'}$COR$^5$, —SR$^{6'}$, a sulfoxide represented by —SOR$^{4'}$, a sulfone represented by —SO$_2$R$^{4'}$, a sulfonate —SO$_3$⁻M⁺, a sulfate —OSO$_3$⁻M⁺, a sulfonamide represented by —SO$_2$NR$^{4'}$R$^5$, cyano, an azido, —COR$^{4'}$, —OCOR$^{4'}$, —OCONR$^{4'}$R$^5$.

In one embodiment, $R^L$ is removable from the N10 position.

In one embodiment, the dimer formed by linking $R^7$ or $R^8$ of formula (I) and $R^7$ or $R^8$ of formula (II) is linked by a dimer bridge having the formula —X'—R$^{3''}$—X'—; wherein $R^{3''}$ is a C$_{3-12}$ alkylene group, which chain may be interrupted by one or more heteroatoms, e.g., —O—, —S—, —N(H)—, —NMe and/or aromatic rings, e.g., benzene or pyridine, which rings are optionally substituted by —NH$_2$; and each X', for each occurrence, is independently —O—, —S— or —N(H)—.

In one embodiment, the compound is represented by a structural formula selected from:

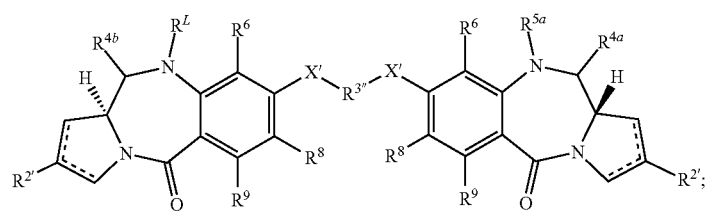

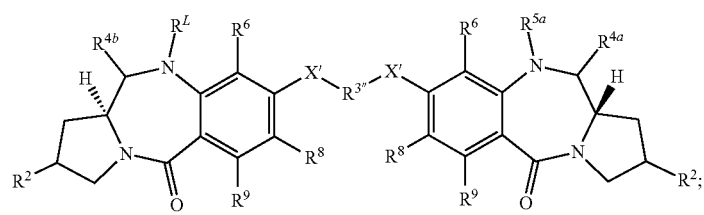

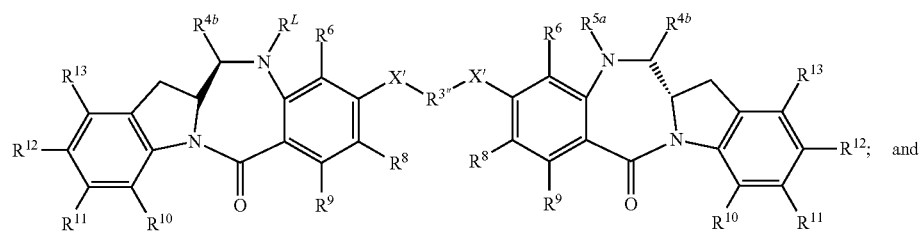

and

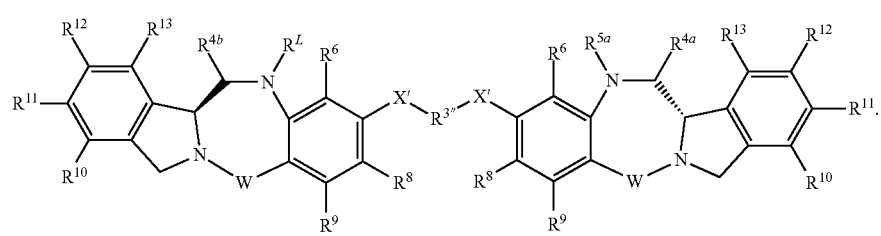

In one embodiment, the compound has a formula selected from:
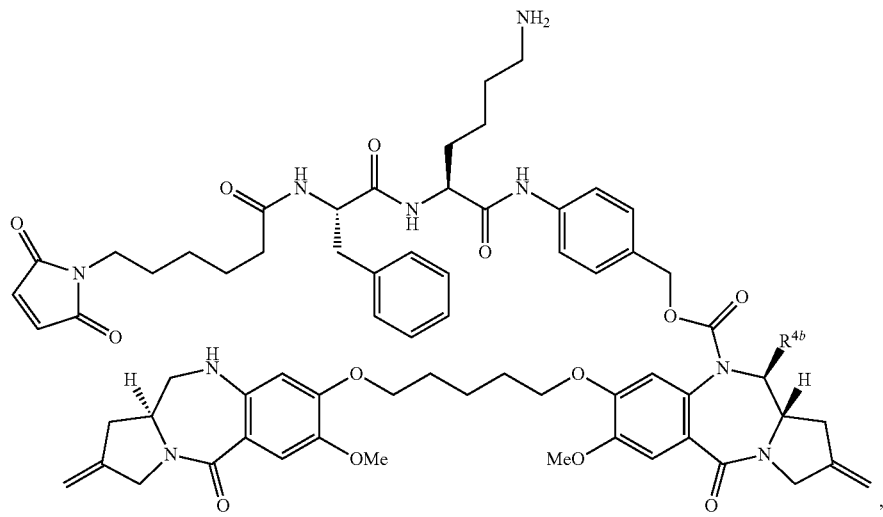
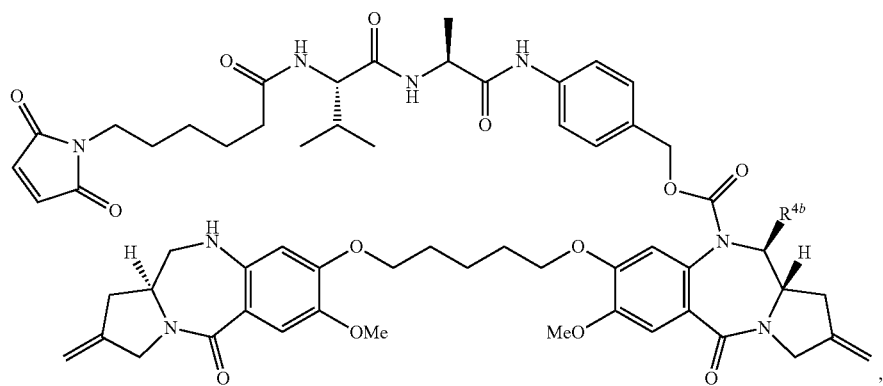
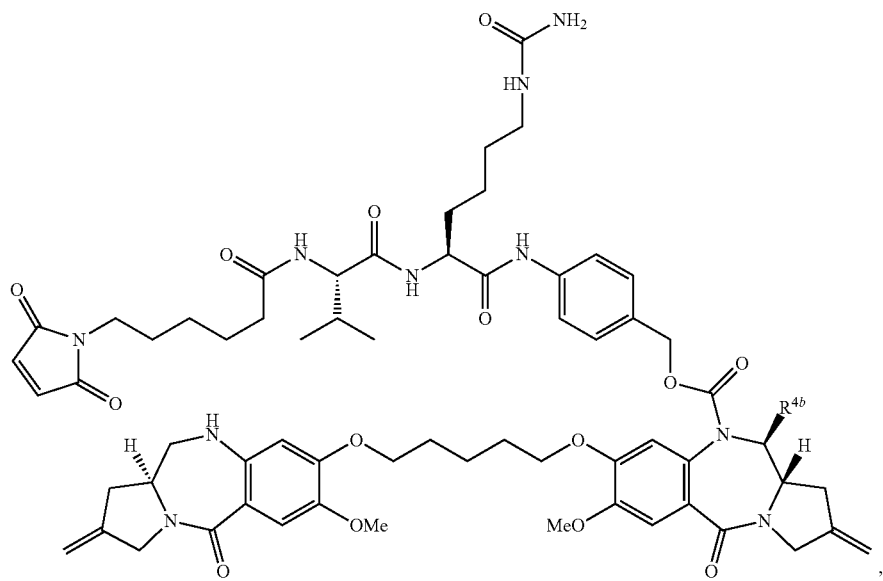

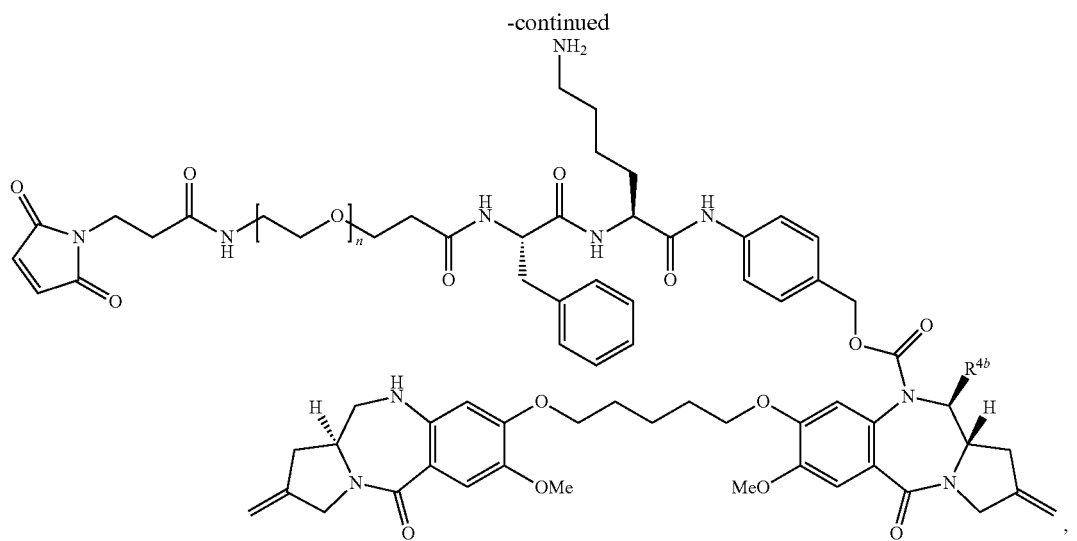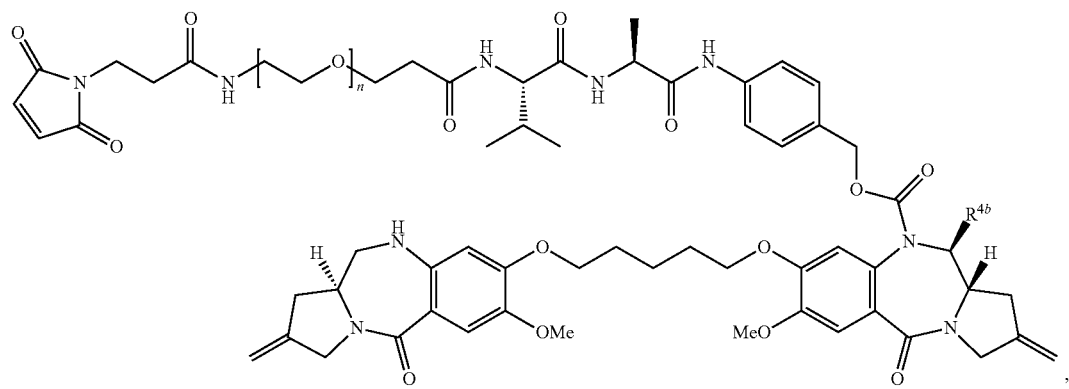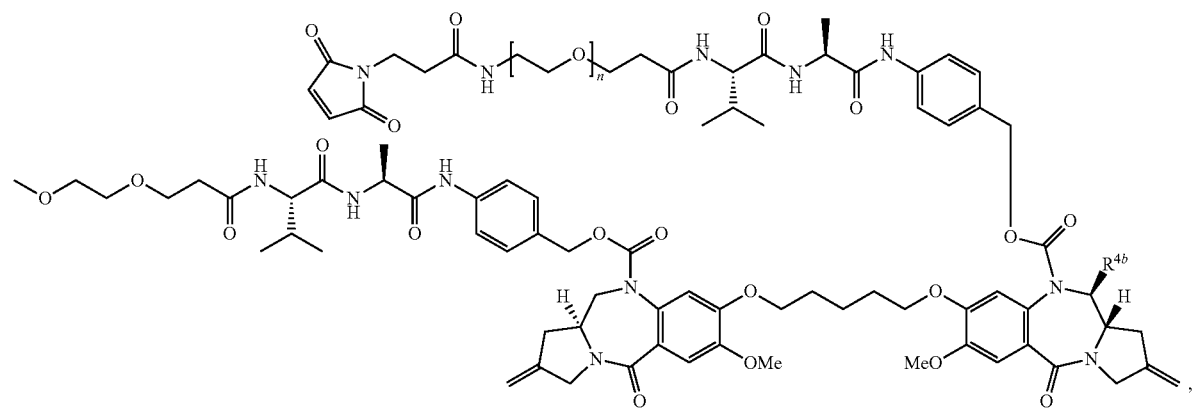

-continued
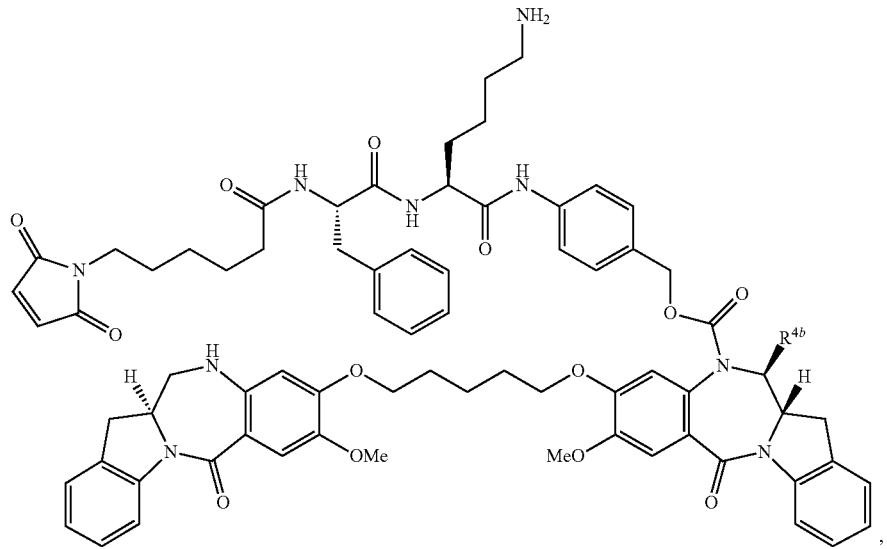
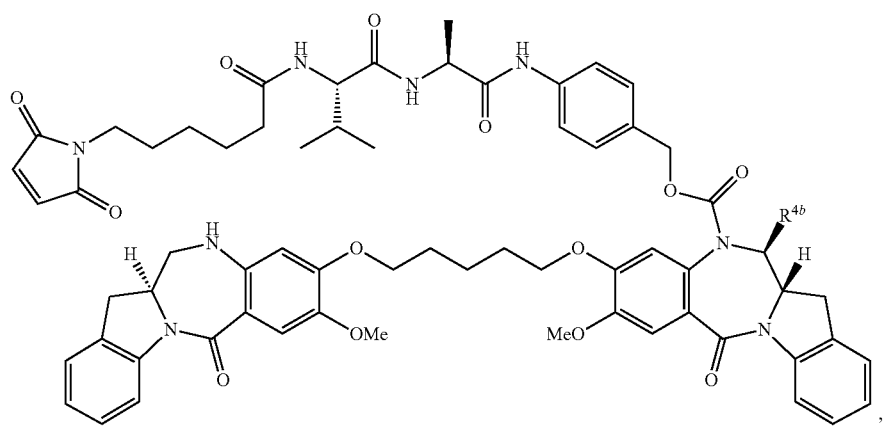
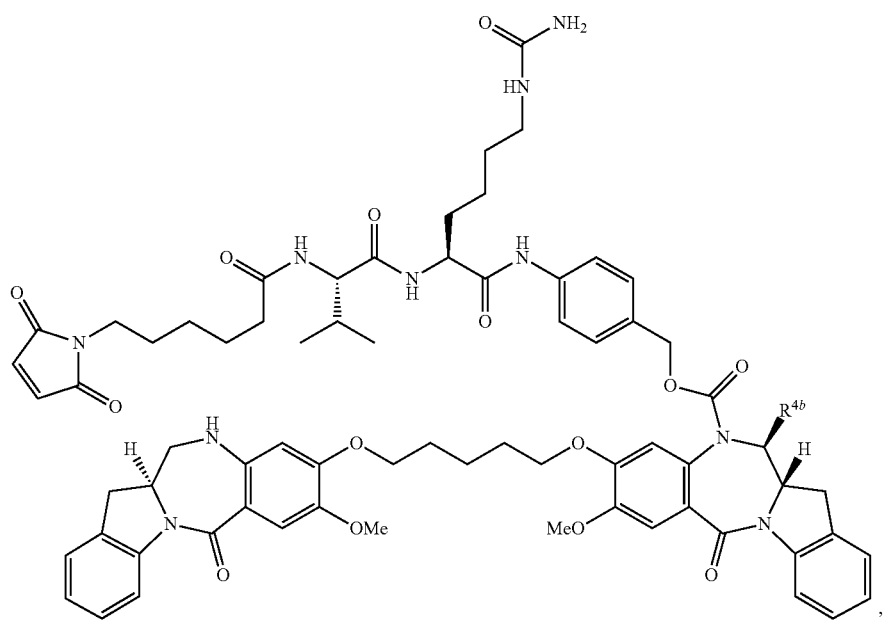

-continued
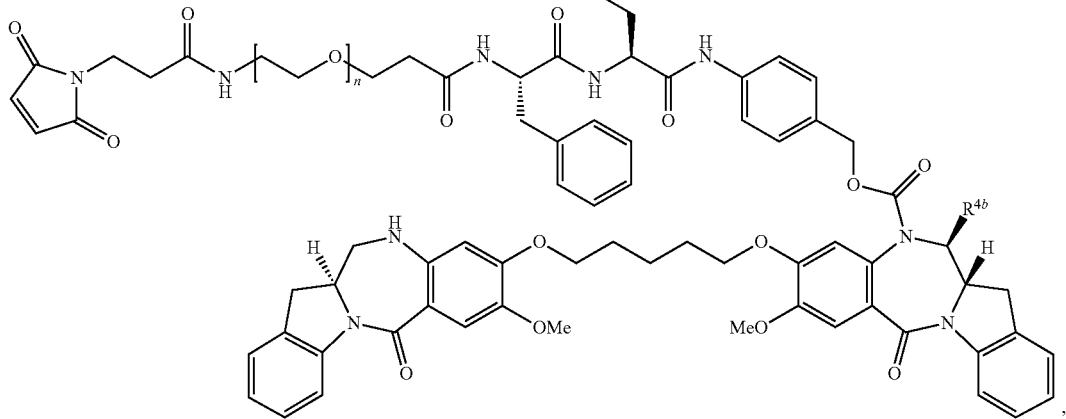
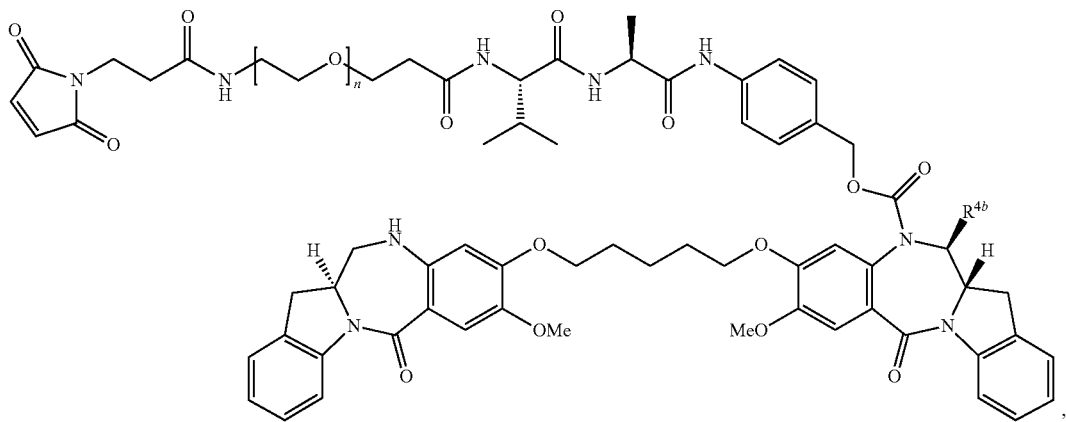
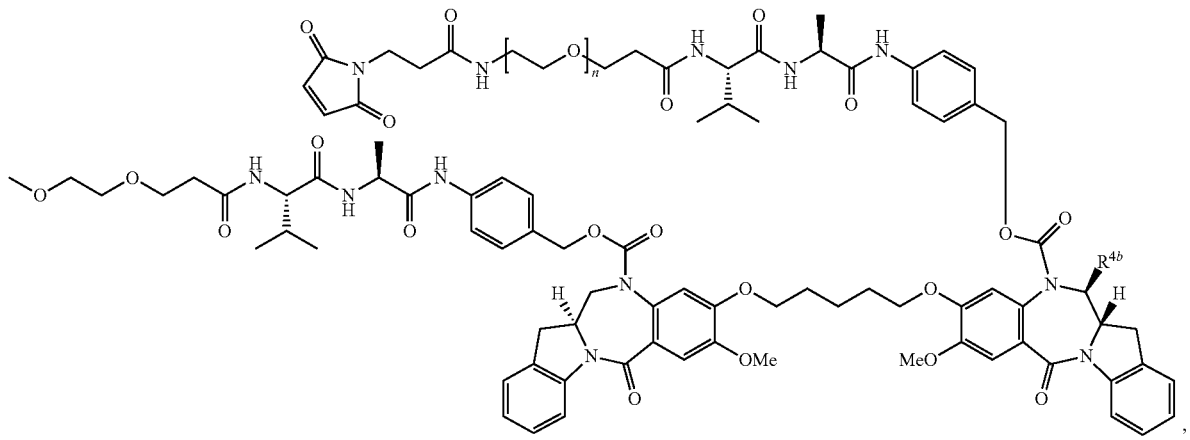

-continued
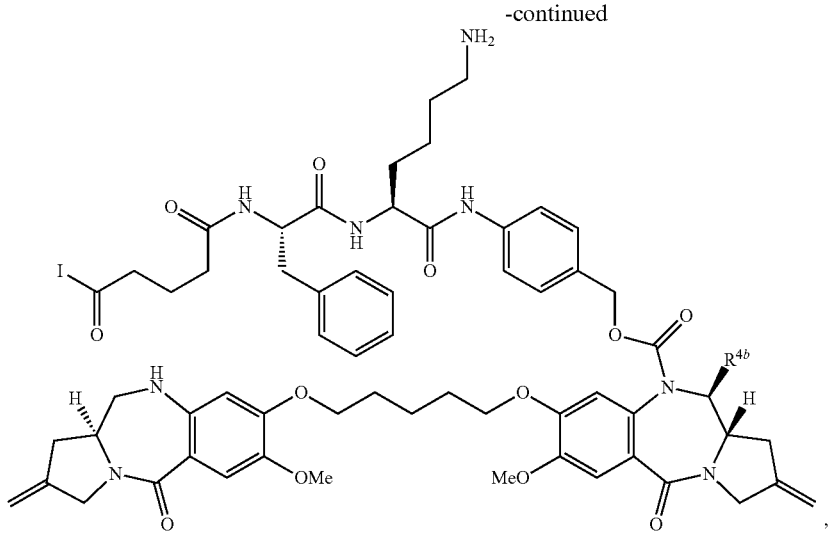
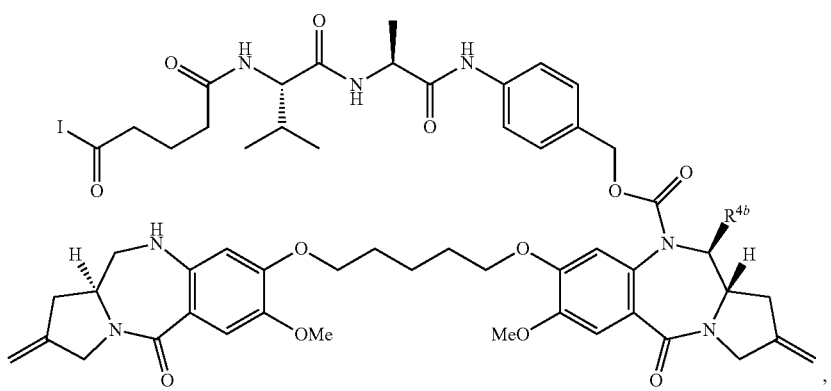
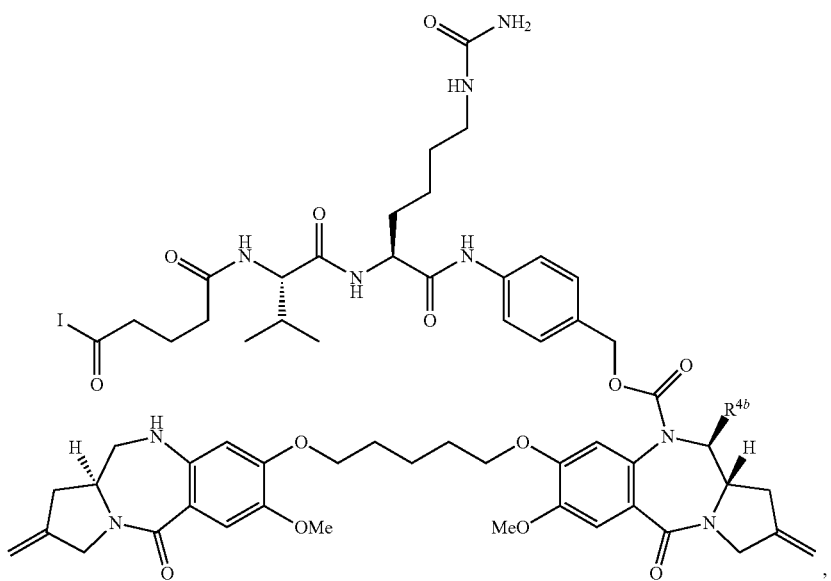

-continued
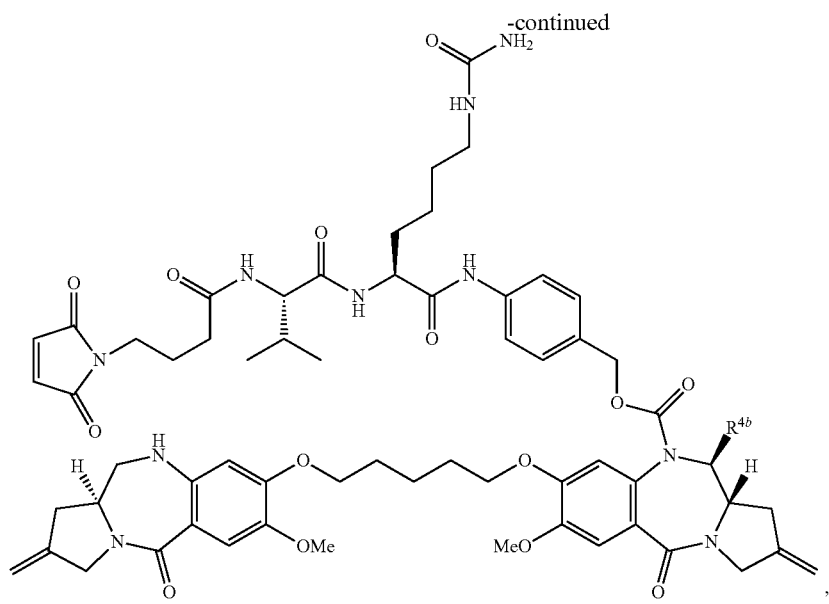
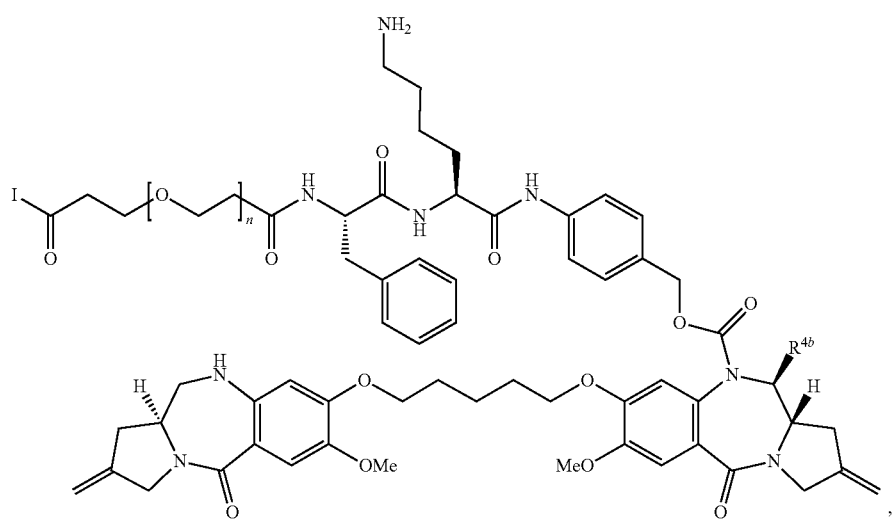
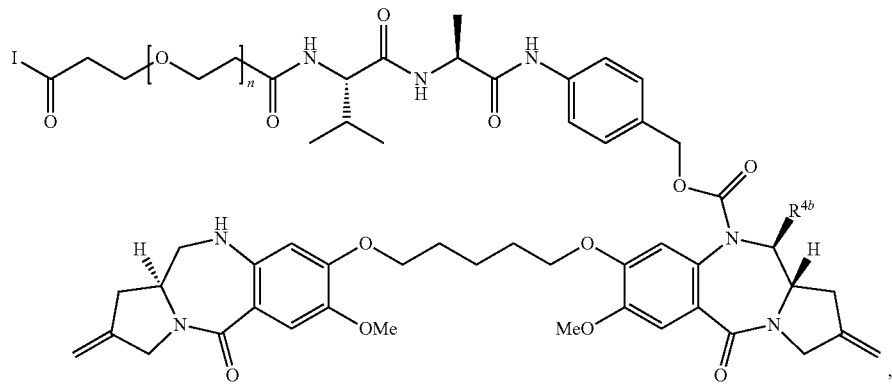

-continued
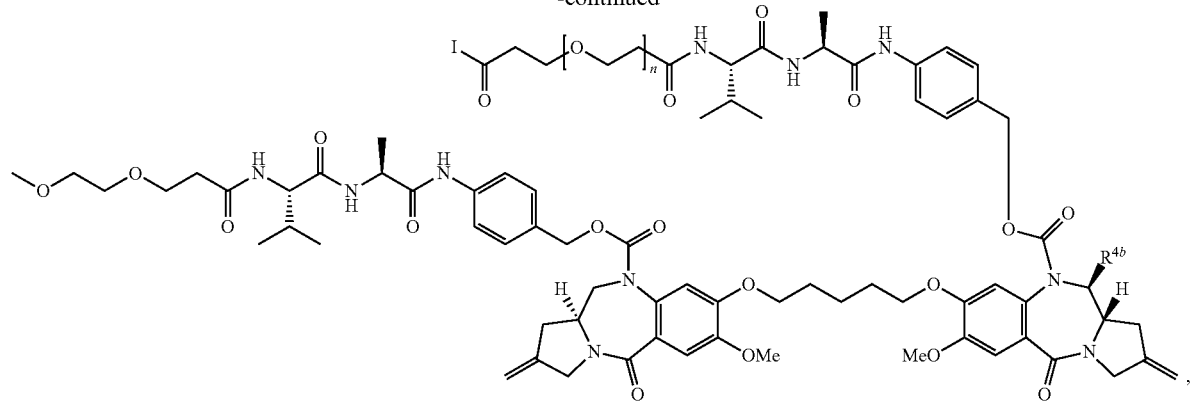
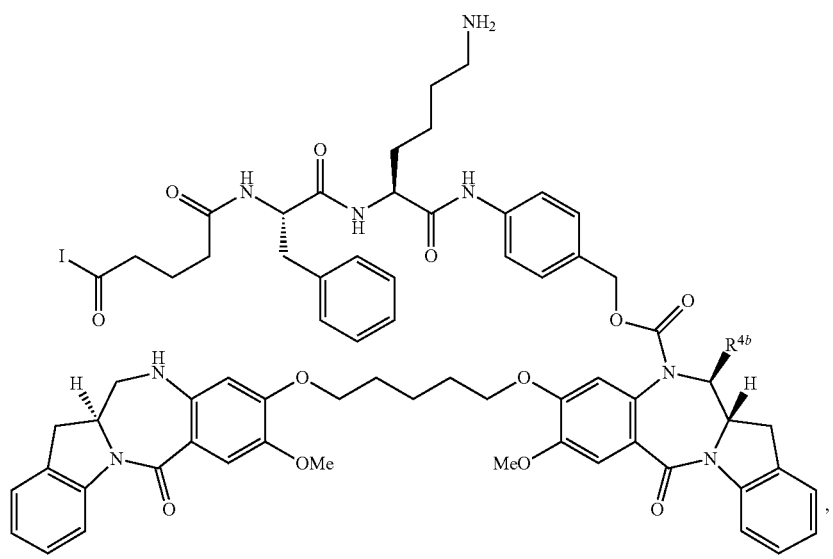
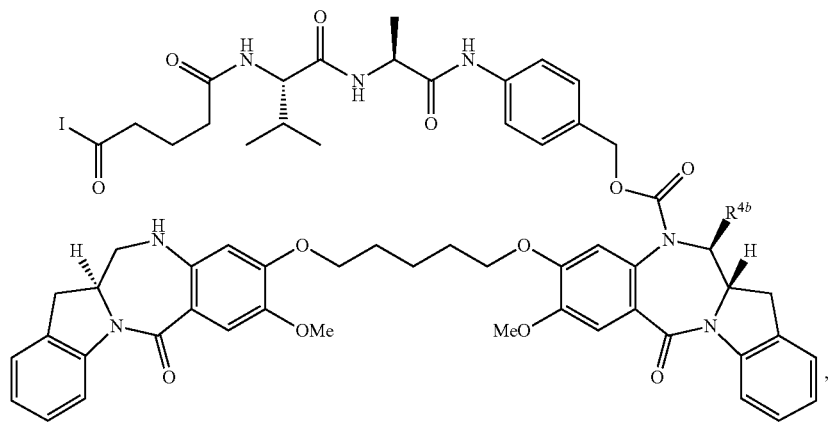

-continued
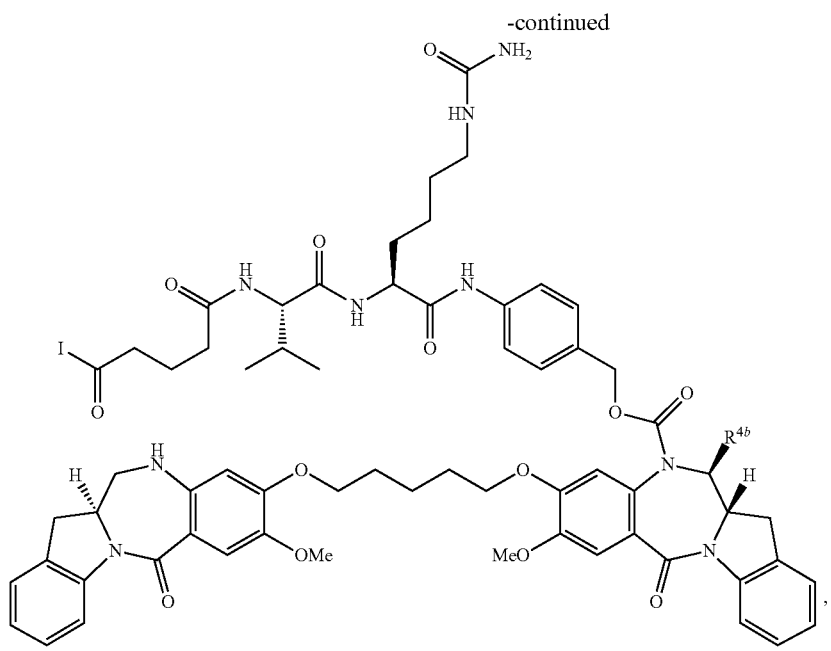
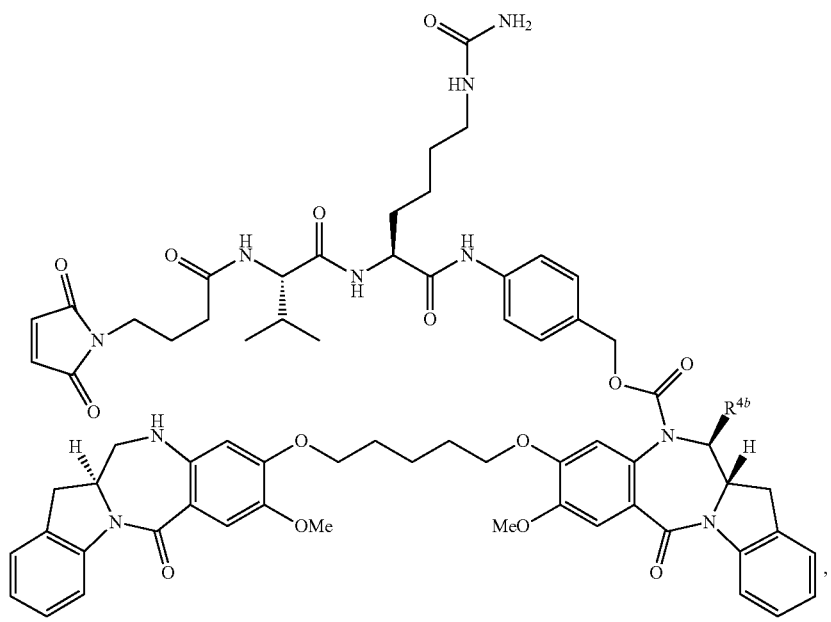

-continued

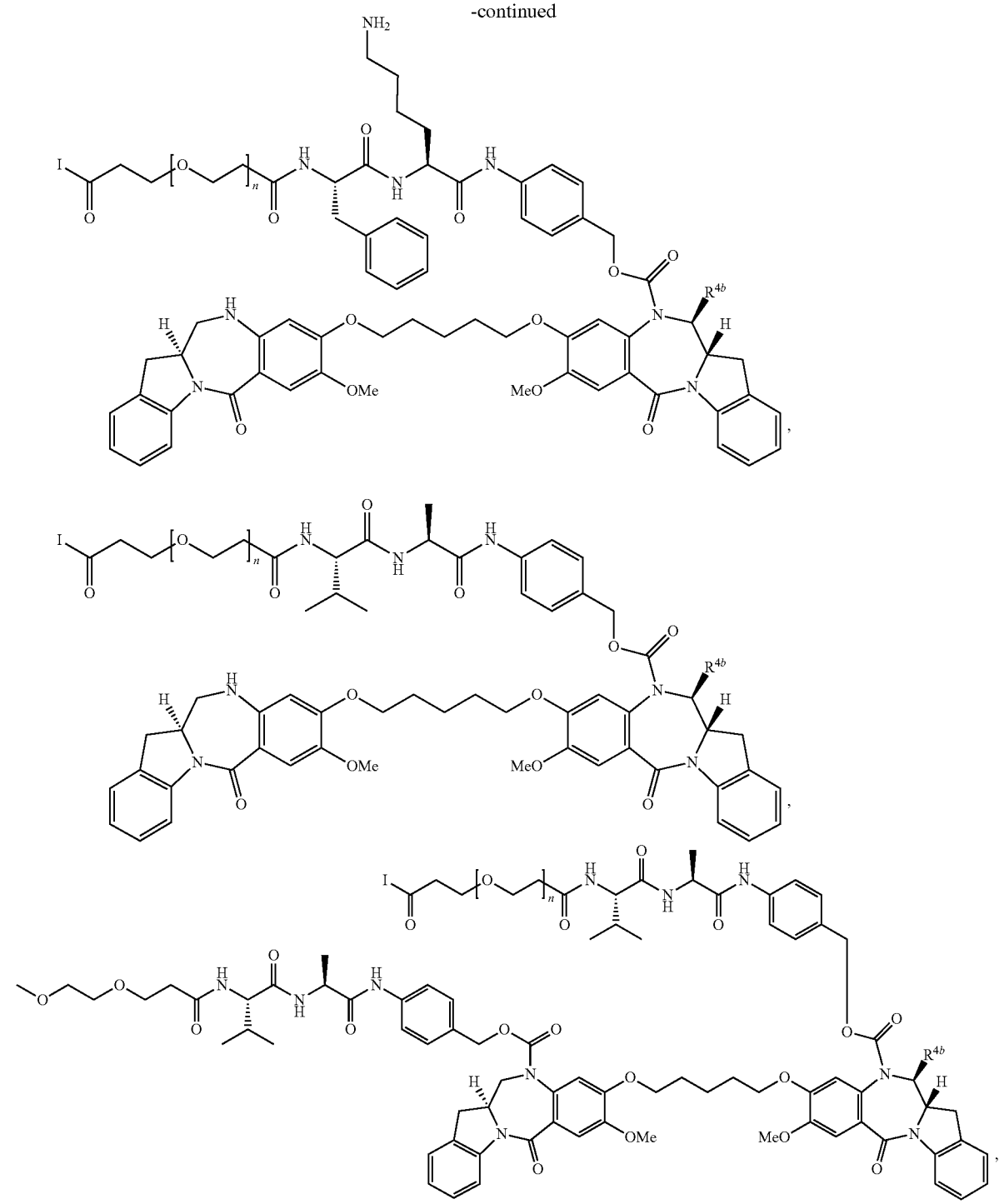

where n is an integer from 1 to 24 (e.g., from 1-12, or 4-8), and $R^{4b}$ is as described above. In a specific embodiment, $R^{4b}$ is —H, —$OR^{6'}$, —$SO_3M$, or —$OSO_3M$, wherein $R^{6'}$ and M are as described above. In another specific embodiment, $R^{4b}$ is —H. Alternatively, $R^{4b}$ is —OH.

A seventh aspect of the invention provides a method of preparing a conjugate of the invention described herein, or salts and solvates thereof, the method comprising the step of reacting a cell binding agent with a compound of the invention described herein.

An eighth aspect of the invention provides an article of manufacture comprising a pharmaceutical composition of the invention described herein; a container; and a package insert or label indicating that the pharmaceutical composition can be used to treat cancer.

It should be understood that any and all embodiments described herein, including those described under different aspects of the invention, can be combined with any other embodiment(s) where applicable. In addition, specific teach-

DETAILED DESCRIPTION OF THE INVENTION

Figure 8:
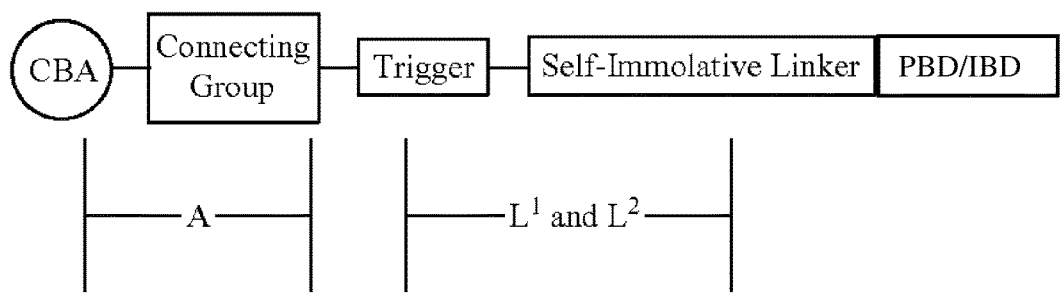
FIG. 8 shows an exemplary embodiment of a conjugate comprising a cell binding agent connected to a spacer connecting group, the spacer connected to a trigger, the trigger connected to a self-immolative linker, and the self-immolative linker connected to the N10 position of the PBD/IBD compound, where "CBA" is a cell binding agent, "PBD" is a pyrrolobenzodiazepine compound and "IBD" is an indolinobenzodiazepine compound.

The present invention provides a conjugate comprising a PBD or IBD compound connected through the N10 position via a linker to a cell binding agent. One embodiment of the instantly disclosed conjugates is shown in FIG. 8. FIG. 8 is $R^{5b}$, which includes the CBA, A, $L^1$ and $L^2$, in certain embodiments of the invention.

The present invention is suitable for use in providing a PBD/IBD compound to a preferred site in a subject. In the preferred embodiments, the conjugate allows the release of an active PBD/IBD compound that does not retain any part of the linker. There is no stub present that could affect the reactivity of the PBD/IBD compound. The released PBD/IBD dimer compound contains one imine bond at the N10-C11 position of one monomer (which is previously linked to the CBA), and one amine bond at the N10-C11 position of the other monomer. In some embodiments, the released PBD/IBD dimer compound contains an amine bond at the N10-C11 position of one monomer (which is previously linked to the CBA), and one amine bond at the N10-C11 position of the other monomer.

In certain embodiments, the invention provides conjugates comprising a PBD/IBD dimer group having a linker connected to a cell binding agent. The present inventors describe herein methods of synthesis that enable such dimer conjugates to be prepared by the use of novel desymmetrization techniques.

Preferences

The following preferences may apply to all aspects of the invention as described above, or may relate to a single aspect. The preferences may be combined together in any combination.

Double Bond

In one embodiment, there is no double bond present between X, Y, and Z in formulas (I) and (II).

In one embodiment, the dotted lines indicate the optional presence of a double bond between C2 and C3 of the C ring, as shown below:

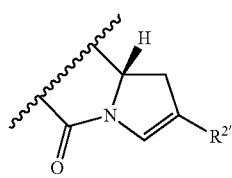

In one embodiment, a double bond is present between C2 and C3 (e.g., when X in formula I or formula II is $CR^{2'}$), wherein $R^{2'}$ may be $C_{5-20}$ aryl or $C_{1-12}$ alkyl.

In one embodiment, the dotted lines indicate the optional presence of a double bond between C1 and C2, as shown below:

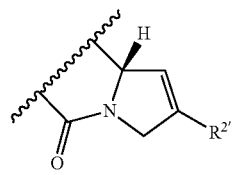

In one embodiment, a double bond is present between C1 and C2 (e.g., when X in formula I or formula II is $CR^2$), wherein $R^{2'}$ may be $C_{5-20}$ aryl or $C_{1-12}$ alkyl.

In one embodiment, when X is attached to Z and Y via single bonds, X is selected from O, $(CH_2)_n$, $CR^2R^2$, $NR^{4'}$ and S, or when X is attached to Z or Y via a double bond, X is $CR^{2'}$ or N;

when Y is attached to X via a single bond, Y is selected from $CR^3R^3$, $NR^3$, O and S; or when Y is attached to X via a double bond Y is selected from $CR^3$ or N; and, when Z is attached to X via a single bond, Z is selected from $CR^1R^1$, $NR^1$, O, S, C(=O), BH, SO and $SO_2$; or when Z is attached to X via a double bond Z is selected from $CR^1$ or N;

provided that the bond between X and Y or X and Z is not an epoxide, S—S, O—O, or O—S.

$R^1$ and $R^3$ $R^1$ and $R^3$ are each, independently, hydrogen, halogen, hydroxyl or alkyl.

In one embodiment, $R^1$ and $R^3$ are both H.

$R^2$

In one embodiment, each $R^2$ is independently selected from H, OH, CN, $R^{1'}$, $OR^{1'}$, O—$SO_2$—$R^{1'}$, $CO_2R^{1'}$ or $COR^{1'}$, optionally further selected from halo or dihalo, or both $R^2$ taken together, are =O, =$CH_2$, =CH—$R^a$, or =C($R^a$)$_2$.

In one embodiment, $R^2$ is independently selected from H, or $R^{1'}$, or both $R^2$ taken together, are =O, =$CH_2$, =CH—$R^a$, or =C($R^a$)$_2$.

In one embodiment, $R^2$ is independently H.

In one embodiment, both $R^2$ taken together are =O.

In one embodiment, both $R^2$ taken together are =$CH_2$.

In one embodiment, both $R^2$ taken together are =CH—$R^a$. Within the PBD compound, the group =CH—$R^a$ may have either configuration shown below:

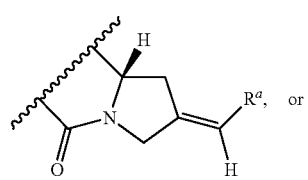

(I)

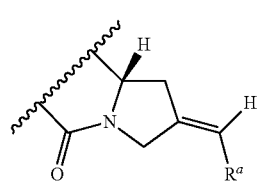

(II)

In one embodiment, the configuration is configuration (I).

In one embodiment, both $R^2$ taken together are $=C(R^{1'})_2$.

In one embodiment, both $R^2$ taken together are $=CF_2$.

In one embodiment, $R^2$ is halo or dihalo. In one embodiment, $R^2$ is —F or —$F_2$, which substituents are illustrated below as (III) and (IV) respectively:

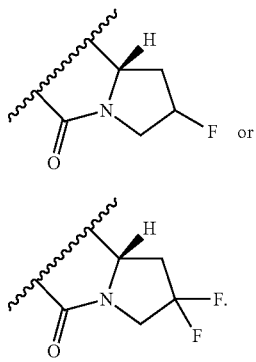

$R^{2'}$

In one embodiment, $R^{2'}$ is independently selected from H, OH, CN, $R^{1'}$, $OR^{1'}$, O—$SO_2$—$R^{1'}$, $CO_2R^{1'}$ and $COR^{1'}$, and optionally halo. In one embodiment, $R^{2'}$ is independently selected from H, OH, CN, $R^{1'}$, $OR^{1'}$, O—$SO_2$—$R^{1'}$, $CO_2R^{1'}$ and $COR^{1'}$.

In one embodiment, $R^{2'}$ is independently selected from H or $R^{1'}$.

In one embodiment, $R^{2'}$ is independently H.

In one embodiment, $R^{2'}$ is independently $R^{1'}$.

In one embodiment, $R^{2'}$ is independently optionally substituted $C_{5-20}$ aryl.

In one embodiment, $R^{2'}$ is independently optionally substituted $C_{1-12}$ alkyl.

In one embodiment, $R^{2'}$ is independently optionally substituted $C_{5-7}$ aryl.

In one embodiment, $R^{2'}$ is independently optionally substituted $C_{8-10}$ aryl.

In one embodiment, $R^{2'}$ is independently optionally substituted phenyl.

In one embodiment, $R^{2'}$ is independently optionally substituted napthyl.

In one embodiment, $R^{2'}$ is independently optionally substituted pyridyl.

In one embodiment, $R^{2'}$ is independently optionally substituted quinolinyl or isoquinolinyl.

In one embodiment, $R^{2'}$ bears one to three substituent groups, with 1 and 2 being more preferred, and singly substituted groups being most preferred. The substituents may be any position.

Where $R^{2'}$ is a $C_{5-7}$ aryl group, a single substituent is preferably on a ring atom that is not adjacent the bond to the remainder of the compound, i.e., it is preferably β or γ to the bond to the remainder of the compound. Therefore, where the $C_{5-7}$ aryl group is phenyl, the substituent is preferably in the meta- or para-positions, and more preferably is in the para-position.

In one embodiment, $R^{2'}$ is selected from:

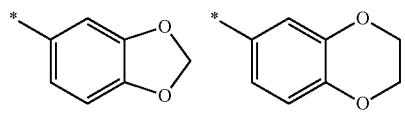

where the asterisk indicates the point of attachment.

Where $R^{2'}$ is a $C_{8-10}$ aryl group, for example quinolinyl or isoquinolinyl, it may bear any number of substituents at any position of the quinoline or isoquinoline rings. In some embodiments, it bears one, two or three substituents, and these may be on either the proximal and distal rings or both (if more than one substituent).

In one embodiment, where $R^{2'}$ is optionally substituted, the substituents are selected from those substituents given in the substituent section below.

Where $R^{1'}$ is optionally substituted, the substituents are preferably selected from: Halo, Hydroxyl, Ether, Formyl, Acyl, Carboxy, Ester, Acyloxy, Amino, Amido, Acylamido, Aminocarbonyloxy, Ureido, Nitro, Cyano and Thioether.

In one embodiment, where $R^{1'}$ or $R^{2'}$ is optionally substituted, the substituents are selected from the group consisting of $R^{1'}$, $OR^{1'}$, $SR^{1'}$, $NR^{1'}R^{3'}$, $NO_2$, halo, $CO_2R^{1'}$, $COR^{1'}$, $CONH_2$, $CONHR^{1'}$, and $CONR^{1'}R^{3'}$.

Where $R^{2'}$ is $C_{1-12}$ alkyl, the optional substituent may additionally include $C_{3-20}$ heterocyclyl and $C_{5-20}$ aryl groups.

Where $R^{2'}$ is $C_{3-20}$ heterocyclyl, the optional substituent may additionally include $C_{1-12}$ alkyl and $C_{5-20}$ aryl groups.

Where $R^{2'}$ is $C_{5-20}$ aryl groups, the optional substituent may additionally include $C_{3-20}$ heterocyclyl and $C_{1-12}$ alkyl groups.

If a substituent on $R^{2'}$ is halo, it is preferably F or Cl, more preferably Cl.

If a substituent on $R^{2'}$ is ether, it may in some embodiments be an alkoxy group, for example, a $C_{1-7}$ alkoxy group (e.g., methoxy, ethoxy) or it may in some embodiments be a $C_{5-7}$ aryloxy group (e.g., phenoxy, pyridyloxy, furanyloxy).

If a substituent on $R^{2'}$ is $C_{1-7}$ alkyl, it may preferably be a $C_{1-4}$ alkyl group (e.g., methyl, ethyl, propyl, butyl).

If a substituent on $R^{2'}$ is $C_{3-7}$ heterocyclyl, it may in some embodiments be C6 nitrogen containing heterocyclyl group, e.g., morpholino, thiomorpholino, piperidinyl, piperazinyl. These groups may be bound to the rest of the PBD moiety via the nitrogen atom. These groups may be further substituted, for example, by $C_{1-4}$ alkyl groups.

If a substituent on $R^{2'}$ is bis-oxy-$C_{1-3}$ alkylene, this is preferably bis-oxy-methylene or bis-oxy-ethylene.

Particularly preferred substituents for $R^{2'}$ include methoxy, ethoxy, fluoro, chloro, cyano, bis-oxy-methylene, methyl-piperazinyl, morpholino and methyl-thienyl.

Particularly preferred substituted $R^{2'}$ groups include, but are not limited to, 4-methoxy-phenyl, 3-methoxyphenyl, 4-ethoxy-phenyl, 3-ethoxy-phenyl, 4-fluoro-phenyl, 4-chloro-phenyl, 3,4-bisoxymethylene-phenyl, 4-methylthienyl, 4-cyanophenyl, 4-phenoxyphenyl, quinolin-3-yl and quinolin-6-yl, isoquinolin-3-yl and isoquinolin-6-yl, 2-thienyl, 2-furanyl, methoxynaphthyl, and naphthyl.

In one embodiment, $R^{2'}$ is halo. In one embodiment, $R^{2'}$ is —F.

Optionally, $R^1$ and $R^2$, or $R^2$ and $R^3$, together with the atoms to which they are bound form an optionally substituted 6-membered aryl ring.

$R^a$

In one embodiment, $R^a$ is independently selected from $R^{1'}$, $CO_2R^{1'}$, $COR^{1'}$, CHO, $CO_2H$, and halo.

In one embodiment, $R^a$ is independently $R^{1'}$.

In one embodiment, $R^a$ is independently halo.

$R^9$

In one embodiment, $R^9$ is independently selected from H, $R^{1'}$, OH, $OR^{1'}$, SH, $SR^{1'}$, $NH_2$, $NHR^{1'}$, $NR^{1'}R^{3'}$, $NO_2$, Me3Sn— and Halo.

In one embodiment, $R^9$ is independently selected from H, OH, $OR^{1'}$, SH, $NH_2$, $NO_2$ and Halo.

In one embodiment, $R^9$ is independently selected from H and Halo.

In one embodiment, $R^9$ is independently H.

In one embodiment, $R^9$ and $R^8$ together form a group —O—$(CH_2)_n$—O—, where p is 1 or 2.

$R^8$ $R^8$ is independently selected from H, $R^{1'}$, OH, $OR^{1'}$, SH, $SR^{1'}$, $NH_2$, $NHR^{1'}$, $NR^{1'}R^{3'}$, $NO_2$, Me3Sn and halo.

In one embodiment, $R^8$ is independently $OR^{1'}$.

In one embodiment, $R^8$ is independently $OR^{8A}$, where $R^{8A}$ is independently optionally substituted $C_{1-6}$ alkyl.

In one embodiment, $R^{8A}$ is independently optionally substituted saturated $C_{1-6}$ alkyl, such as optionally substituted saturated $C_{1-4}$ alkyl.

In one embodiment, $R^{8A}$ is independently optionally substituted $C_{2-4}$ alkenyl.

In one embodiment, $R^{8A}$ is independently Me.

In one embodiment, $R^{8A}$ is independently $CH_2Ph$.

In one embodiment, $R^{8A}$ is independently allyl.

In one embodiment, the compound is a dimer where the $R^8$ groups of each monomer form together a dimer bridge having the formula X'—$R^{3''}$—X' linking the monomers.

$R^7$

In one embodiment, the compound is a dimer where the $R^7$ groups of each monomer form together a dimer bridge having the formula X'—$R^{3''}$—X' linking the monomers.

In one embodiment, $R^7$ is independently $OR^{7A}$, where $R^{7A}$ is independently optionally substituted $C_{1-4}$ alkyl.

In one embodiment, $R^{7A}$ is independently optionally substituted saturated $C_{1-6}$ alkyl or optionally substituted $C_{2-4}$ alkenyl.

In one embodiment, $R^{7A}$ is independently Me.

In one embodiment, $R^{7A}$ is independently $CH_2Ph$.

In one embodiment, $R^{7A}$ is independently allyl.

In one embodiment, $R^7$ and $R^8$ together form a group —O—$(CH_2)_p$—O—, where p is 1 or 2.

In one embodiment, $R^7$ and $R^6$ together form a group —O—$(CH_2)_p$—O—, where p is 1 or 2.

In one embodiment, $R^7$ or $R^8$ of formula (I) are bonded to $R^7$ or $R^8$ of formula (II) forming a dimer.

$R^6$

In one embodiment, $R^6$ is independently selected from H, $R^{1'}$, OH, $OR^{1'}$, SH, $SR^{1'}$, $NH_2$, $NHR^{1'}$, $NR^{1'}R^{3'}$, $NO_2$, $Me_3Sn$— and Halo.

In one embodiment, $R^6$ is independently H.

In one embodiment, $R^6$ is independently $R^{1'}$ or $OR^{1'}$.

$R^{5a}$ and $R^{5b}$

For the avoidance of doubt, where $R^{5b}$ is a linker connected to a cell binding agent, the cell binding agent is part of the group $R^{5b}$.

In certain embodiments of the invention, where the conjugate is a dimer comprising two monomers, wherein one monomer has a group $R^{5b}$ that is a linker connected to a cell binding agent, and the other monomer has a group $R^{5a}$ that is H, a capping/protecting group, a peptide, an optionally substituted linear, branched or cyclic alkyl, alkenyl or alkynyl having from 1 to 10 carbon atoms, a polyethylene glycol unit —$(CH_2CH_2O)_n$—$R^e$, an optionally substituted aryl having 6 to 18 carbon atoms, an optionally substituted 5- to 18-membered heteroaryl ring containing one or more heteroatoms independently selected from nitrogen, oxygen, and sulfur, and an optionally substituted 3- to 18-membered heterocyclic ring containing 1 to 6 heteroatoms independently selected from O, S, N and P. Thus, in this preferred embodiment, there is only a single link to the cell binding agent. Preferably, $R^{5a}$ is H.

In one embodiment, $R^{5a}$ in formula (I) is a protecting group $R^{cc}$, which is removable from the N10 position, such as enzymatically or hydrolytically cleavable in vivo.

In one embodiment, the group $R^{5b}$ is removable from the N10 position of the PBD/IBD moiety to leave an N10-C11 imine bond, a carbinolamine, a substituted carbinolamine, where $R^{4b}$ is a leaving group selected from —$OR^{6'}$, —$OCOR^{4'}$, —$OCOOR^{4'}$, —$OCONR^{4'}R^{5'}$, —$NR^{4'}R^{5'}$, —$NR^{4'}COR^{5'}$, —$NR^{4'}NR^{4'}R^{5'}$, an optionally substituted 5- or 6-membered nitrogen-containing heterocycle (e.g., piperidine, tetrahydropyrrole, pyrazole, morpholine), a guanidinum represented by —$NR^{4'}(C=NH)NR^{4'}R^{5'}$, an amino acid, or a peptide represented by —$NR^6COP'$, wherein P' is an amino acid or a polypeptide containing between 2 to 20 amino acid units, —$SR^{6'}$, —$SOR^{4'}$, —$SO_2M$, —$SO_3M$, —$OSO_3M$, a bisulfite adduct, halogen, cyano, an azido, a thiocarbinolamine, a substituted thiocarbinolamine, or a substituted carbinalamine, as illustrated below:

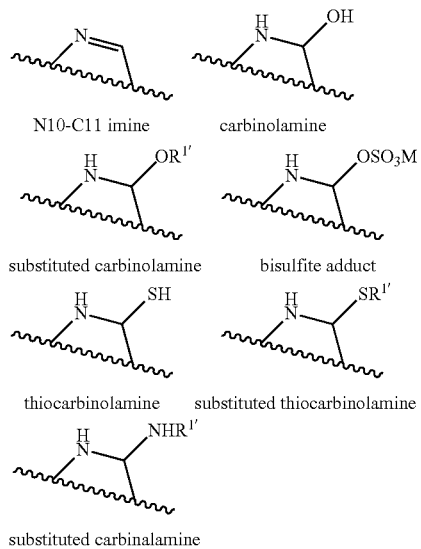

where $R^{1'}$ and M are as defined for the conjugates of the invention.

In one embodiment, the group $R^{5b}$ is removable from the N10 position of the PBD/IBD moiety to leave an N10-C11 imine bond.

In one embodiment, $R^{4b}$ is H and the group $R^{5b}$ is removable from the N10 position of the PBD/IBD moiety to leave a N10-C11 amine bond.

In some embodiments, the conjugate of the invention is a dimer compound comprising a monomer of formula (I) and a monomer of formula (II).

This application is particularly concerned with those $R^{5b}$ groups which have a carbamate link to the N10 position.

The linker attaches the Cell Binding Agent (CBA), e.g., antibody, to the PBD/IBD drug moiety D through covalent bond(s). The linker is a bifunctional or multifunctional moiety which can be used to link one or more drug moiety (D) and an antibody unit (Ab) to form antibody-drug conjugates (ADC). The linker (L) may be stable outside a cell, i.e., extracellular, or it may be cleavable by enzymatic activity, hydrolysis, or other metabolic conditions. Antibody-drug conjugates (ADC) can be conveniently prepared using a linker having reactive functionality for binding to the drug moiety and to the antibody. A cysteine thiol, or an amine, e.g., N-terminus or amino acid side chain such as lysine, of the antibody (Ab) can form a bond with a functional group of a linker or spacer reagent, PBD/IBD drug moiety (D) or drug-linker reagent (D-L).

Many functional groups on the linker attached to the N10 position of the PBD/IBD moiety may be useful to react with the cell binding agent. For example, ester, thioester, amide, thioamide, carbamate, thiocarbamate, urea, thiourea, ether, thioether, or disulfide linkages may be formed from reaction of the linker-PBD/IBD drug intermediates and the cell binding agent. The linkers of the ADC preferably prevent aggregation of ADC molecules and keep the ADC freely soluble in aqueous media and in a monomeric state.

The linkers of the ADC are preferably stable extracellularly. Before transport or delivery into a cell, the antibody-drug conjugate (ADC) is preferably stable and remains intact, i.e., the antibody remains linked to the drug moiety. The linkers are stable outside the target cell and may be cleaved at some efficacious rate inside the cell. An effective linker will: (i) maintain the specific binding properties of the antibody; (ii) allow intracellular delivery of the conjugate or drug moiety; (iii) remain stable and intact, i.e., not cleaved, until the conjugate has been delivered or transported to its targeted site; and (iv) maintain a cytotoxic, cell-killing effect or a cytostatic effect of the PBD/IBD drug moiety. Stability of the ADC may be measured by standard analytical techniques such as mass spectroscopy, HPLC, and the separation/analysis technique LC/MS.

Covalent attachment of the antibody and the drug moiety requires the linker to have two reactive functional groups, i.e., bivalency in a reactive sense. Bivalent linker reagents which are useful to attach two or more functional or biologically active moieties, such as peptides, nucleic acids, drugs, toxins, antibodies, haptens, and reporter groups are known, and methods have been described their resulting conjugates (Hermanson, G. T. (1996) *Bioconjugate Techniques*; Academic Press: New York, pp. 234-242).

In another embodiment, the linker may be substituted with groups which modulate aggregation, solubility or reactivity. For example, a sulfonate substituent may increase water solubility of the reagent and facilitate the coupling reaction of the linker reagent with the antibody or the drug moiety, or facilitate the coupling reaction of Ab-L with D, or D-L with Ab, depending on the synthetic route employed to prepare the ADC.

In one embodiment, $R^{5b}$ is a group:

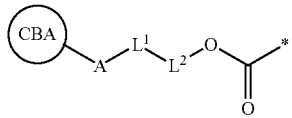

where the asterisk indicates the point of attachment to the N10 position, CBA is a cell binding agent, $L^1$ is a linker, A is a connecting group connecting $L^1$ to the cell binding agent, $L^2$ is a covalent bond or together with —OC(=O)— forms a self-immolative linker, and $L^1$ or $L^2$ is a cleavable linker.

$L^1$ is preferably the cleavable linker, such as an enzyme cleavable linker, and may be referred to as a trigger for activation of the linker for cleavage.

The nature of $L^1$ and $L^2$, where present, can vary widely. These groups are chosen on the basis of their cleavage characteristics, which may be dictated by the conditions at the site to which the conjugate is delivered. Those linkers that are cleaved by the action of enzymes are preferred, although linkers that are cleavable by changes in pH (e.g., acid or base labile), temperature or upon irradiation (e.g., photolabile) may also be used. Linkers that are cleavable under reducing or oxidizing conditions may also find use in the present invention.

$L^1$ may comprise a contiguous sequence of amino acids. The amino acid sequence may be the target substrate for enzymatic cleavage, thereby allowing release of $R^{5b}$ from the N10 position.

In one embodiment, $L^1$ is cleavable by the action of an enzyme. In one embodiment, the enzyme is an esterase or a peptidase.

In one embodiment, $L^2$ is present and together with —C(=O)O— forms a self-immolative linker.

In one embodiment, $L^2$ is a substrate for enzymatic activity, thereby allowing release of $R^{5b}$ from the N10 position.

In one embodiment, where $L^1$ is cleavable by the action of an enzyme and $L^2$ is present, the enzyme cleaves the bond between $L^1$ and $L^2$.

$L^1$ and $L^2$, if present, may be connected by a bond selected from: —C(=O)NH—, —C(=O)O—, —NHC(=O)—, —OC(=O)—, —OC(=O)O—, —NHC(=O)O—, —OC(=O)NH—, and —NHC(=O)NH—.

An amino group of $L^1$ that connects to $L^2$ may be the N-terminus of an amino acid or may be derived from an amino group of an amino acid side chain, for example a lysine amino acid side chain.

A carboxyl group of $L^1$ that connects to $L^2$ may be the C-terminus of an amino acid or may be derived from a carboxyl group of an amino acid side chain, for example a glutamic acid amino acid side chain.

A hydroxyl group of $L^1$ that connects to $L^2$ may be derived from a hydroxyl group of an amino acid side chain, for example a serine amino acid side chain.

The term "amino acid side chain" includes those groups found in: (i) naturally occurring amino acids such as alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine; (ii) minor amino acids such as ornithine and citrulline; (iii) unnatural amino acids, beta-amino acids, synthetic analogs and derivatives of naturally occurring amino acids; and (iv) all enantiomers, diastereomers, isomerically enriched, isotopically labelled (e.g., $^2$H, $^3$H, $^{14}$C, $^{15}$N), protected forms, and racemic mixtures thereof.

In one embodiment, —C(=O)O— and $L^2$ together form a self-immolative linker, such as the group shown below:

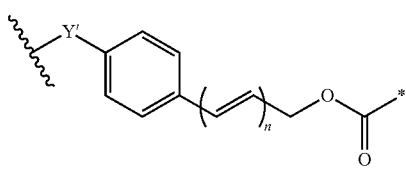

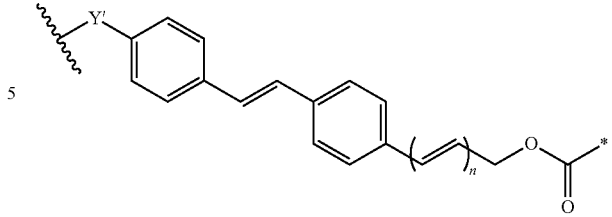

where the asterisk indicates the point of attachment to the N10 position, the wavy line indicates the point of attachment to the linker $L^1$, Y' is —N(H)—, —O—, —C(=O)N(H)— or —C(=O)O—, and n is 0 to 3. The phenylene ring is optionally substituted with one, two or three substituents as described herein. In one embodiment, the phenylene group is optionally substituted with halo, $NO_2$, $R^{1'}$ or $OR^{1'}$.

In one embodiment, Y' is NH.

In one embodiment, n is 0 or 1. Preferably, n is 0.

Where Y' is NH and n is 0, the self-immolative linker may be referred to as a p-aminobenzylcarbonyl linker (PABC).

The self-immolative linker will allow for release of the protected compound when a remote site is activated, proceeding along the lines shown below (for n=0):

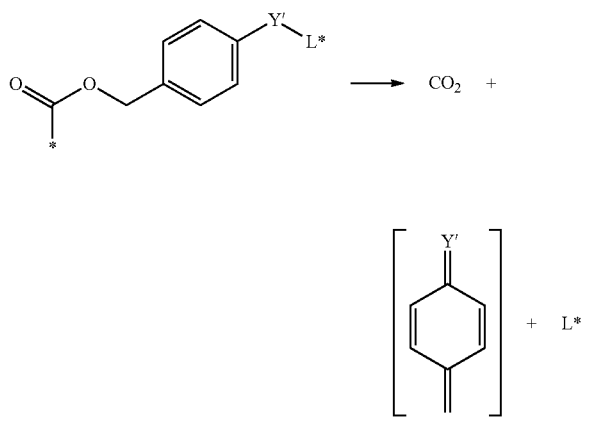

where L* is the activated form of the remaining portion of the linker. These groups have the advantage of separating the site of activation from the compound being protected. As described above, the phenylene group may be optionally substituted.

In one embodiment described herein, the group L* is a linker $L^1$ as described herein, which may include a dipeptide group.

In another embodiment, —C(=O)O— and $L^2$ together form a group selected from:

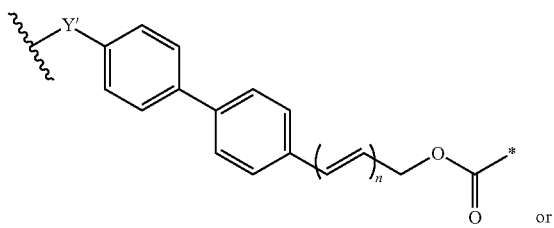

where the asterisk, the wavy line, Y', and n are as defined above. Each phenylene ring is optionally substituted with one, two or three substituents as described herein. In one embodiment, the phenylene ring having the Y' substituent is optionally substituted and the phenylene ring not having the Y' substituent is unsubstituted. In one embodiment, the phenylene ring having the Y' substituent is unsubstituted and the phenylene ring not having the Y' substituent is optionally substituted.

In another embodiment, —C(=O)O— and $L^2$ together form a group selected from:

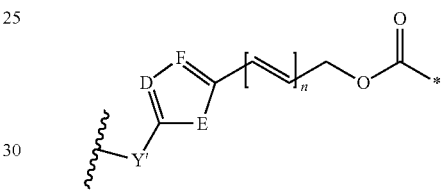

where the asterisk, the wavy line, Y', and n are as defined above, E is O, S or NR, D is N, CH, or CR, and F is N, CH, or CR, wherein R is H or an alkyl.

In one embodiment, D is N.

In one embodiment, D is CH.

In one embodiment, E is O or S.

In one embodiment, F is CH.

In a preferred embodiment, the linker is a cathepsin labile linker.

In one embodiment, $L^1$ comprises a dipeptide. The dipeptide may be represented as —NH—$X_1$—$X_2$—CO—, where —NH— and —CO— represent the N- and C-terminals of the amino acid groups $X_1$ and $X_2$ respectively. The amino acids in the dipeptide may be any combination of natural amino acids. Where the linker is a cathepsin labile linker, the dipeptide may be the site of action for cathepsin-mediated cleavage.

Additionally, for those amino acids groups having carboxyl or amino side chain functionality, for example Glu and Lys respectively, CO and NH may represent that side chain functionality.

In one embodiment, the group —$X_1$—$X_2$— in dipeptide, —NH—$X_1$—$X_2$—CO—, is selected from: -Phe-Lys-, -Val-Ala-, -Val-Lys-, -Ala-Lys-, -Val-Cit-, -Phe-Cit-, -Leu-Cit-, -Ile-Cit-, -Phe-Arg-, -Trp-Cit- where Cit is citrulline.

Preferably, the group —$X_1$—$X_2$— in dipeptide, —NH—$X_1$—$X_2$—CO—, is selected from: -Phe-Lys-, -Val-Ala-, -Val-Lys-, -Ala-Lys-, -Val-Cit-.

Most preferably, the group —$X_1$—$X_2$— in dipeptide, —NH—$X_1$—$X_2$—CO—, is -Phe-Lys- or -Val-Ala-.

Other dipeptide combinations may be used, including those described by Dubowchik et al., *Bioconjugate Chemistry*, 2002, 13, 855-869, which is incorporated herein by reference.

Additional dipeptides include: Lys-Lys, Phe-Ala, Phe-N$^9$-tosyl-Arg, Phe-N$^9$-nitro-Arg, Val-Arg, Arg-Val, Arg-Arg, Val-D-Cit, Val-D-Lys, Val-D-Arg, D-Val-Cit, D-Val-Lys, D-Val-Arg, D-Val-D-Cit, D-Val-D-Lys, D-Val-D-Arg, and D-Arg-D-Arg, where Cit is citrulline.

Alternatively, $L^1$ comprises a tripeptide —$X_1$—$X_2$—$X_3$—, wherein the tripeptide in $L^1$ as represented by —NH—$X_1$—$X_2$—$X_3$—CO—, and is selected from Gly-Gly-Gly, Phe-Phe-Lys, D-Phe-Phe-Lys, Gly-Phe-Lys, Leu-Ala-Leu, Ile-Ala-Leu and Val-Ala-Val.

Alternatively, $L^1$ comprises a tetrapeptide —$X_1$—$X_2$—$X_3$—$X_4$—, wherein the tetrapeptide in $L^1$ as represented by —NH—$X_1$—$X_2$—$X_3$—$X_4$—CO—, and is selected from Ala-Leu-Ala-Leu, β-Ala-Leu-Ala-Leu and Gly-Phe-Leu-Gly.

In one embodiment, the group —$X_2$—CO— is connected to $L^2$.

In one embodiment, the group —NH—$X_1$— is connected to A.

In one embodiment, the amino acid side chain is derivatized, where appropriate. For example, an amino group or carboxy group of an amino acid side chain may be derivatized. In one embodiment, an amino group $NH_2$ of a side chain amino acid, such as lysine, is a derivatized form selected from the group consisting of NHR and NRR'.

In one embodiment, a carboxy group COOH of a side chain amino acid, such as aspartic acid, is a derivatized form selected from the group consisting of COOR, $CONH_2$, CONHR and CONRR'.

In one embodiment, the amino acid side chain is chemically protected, where appropriate. The side chain protecting group may be a group as discussed below in relation to the group $R^L$. The present inventors have established that protected amino acid sequences are cleavable by enzymes. For example, it has been established that a dipeptide sequence comprising a Boc side chain-protected Lys residue is cleavable by cathepsin.

Protecting groups for the side chains of amino acids are well known in the art and are described in the Novabiochem Catalog. Additional protecting group strategies are set out in Protective Groups in Organic Synthesis, Greene and Wuts.

Possible side chain protecting groups are shown below for those amino acids having reactive side chain functionality: Arg: Z, Mtr, Tos; Asn: Trt, Xan; Asp: Bzl, t-Bu; Cys: Acm, Bzl, Bzl-OMe, Bzl-Me, Trt; Glu: Bzl, t-Bu; Gln: Trt, Xan; His: Boc, Dnp, Tos, Trt; Lys: Boc, Z—Cl, Fmoc, Z, Alloc; Ser: Bzl, TBDMS, TBDPS; Thr: Bz; Trp: Boc; Tyr: Bzl, Z, Z—Br.

In one embodiment, the side chain protection is selected to be orthogonal to a group provided as, or as part of, a capping group, where present. Thus, the removal of the side chain protecting group does not remove the capping group, or any protecting group functionality that is part of the capping group.

In other embodiments of the invention, the amino acids selected are those having no reactive side chain functionality. For example, the amino acids may be selected from: Ala, Gly, Ile, Leu, Met, Phe, Pro, and Val.

In one embodiment, the dipeptide is used in combination with a self-immolative linker. The self-immolative linker may be connected to —$X_2$—.

Where a self-immolative linker is present, —$X_2$— is connected directly to the self-immolative linker. Preferably the group —$X_2$—CO— is connected to Y, where Y is NH, thereby forming the group —$X_2$—CO—NH—.

—NH—$X_1$— is connected directly to A. A may comprise the functionality —CO— thereby to form an amide link with —$X_1$—.

In one embodiment, $L^1$ and $L^2$ together with —OC(=O)— comprise the group NH—$X_1$—$X_2$—CO-PABC-. The PABC group is connected directly to the N10 position. Preferably, the self-immolative linker and the dipeptide together form the group —NH-Phe-Lys-CO—NH-PABC-, which is illustrated below:

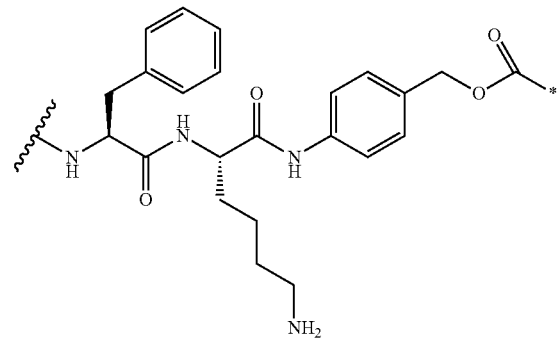 [SMILES: *N[C@@H](Cc1ccccc1)C(=O)N[C@@H](CCCCN)C(=O)Nc1ccc(COC(*)=O)cc1]

where the asterisk indicates the point of attachment to the N10 position, and the wavy line indicates the point of attachment to the remaining portion of the linker $L^1$ or the point of attachment to A. Preferably, the wavy line indicates the point of attachment to A. The side chain of the Lys amino acid may be protected, for example, with Boc, Fmoc, or Alloc, as described above.

Alternatively, the self-immolative linker and the dipeptide together form the group —NH-Val-Ala-CO—NH-PABC-, which is illustrated below:

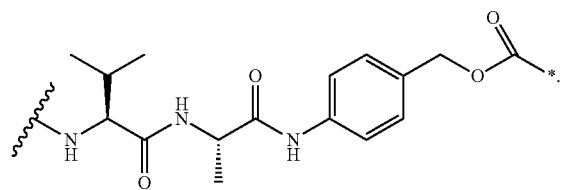

where the asterisk and the wavy line are as defined above.

Alternatively, the self-immolative linker and the dipeptide together form the group —NH-Val-Cit-CO—NH-PABC-, which is illustrated below:

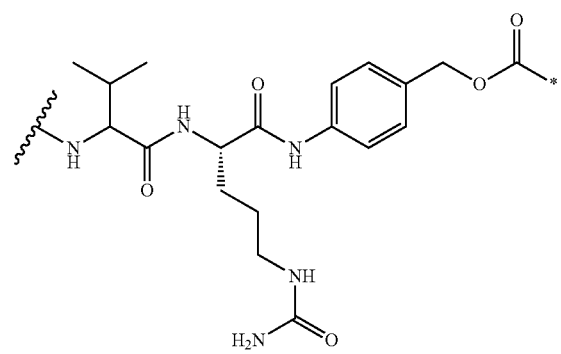 [SMILES: *NC(C(=O)N[C@@H](CCCNC(N)=O)C(=O)Nc1ccc(COC(*)=O)cc1)C(C)C]

where the asterisk and the wavy line are as defined above.

In some embodiments of the present invention, it may be preferred that if the PBD/IBD-drug moiety contains an unprotected imine bond, e.g, if moiety B is present, then the linker does not contain a free amino (H$_2$N—) group. Thus if the linker has the structure -A-L$^1$-L$^2$- then this would preferably not contain a free amino group. This preference is particularly relevant when the linker contains a dipeptide, for example as L$^1$; in this embodiment, it would be preferred that one of the two amino acids is not selected from lysine.

Without wishing to be bound by theory, the present inventors have found that the combination of an unprotected imine bond in the drug moiety and a free amino group in the linker can cause dimerization of the drug-linker moiety which may interfere with the conjugation of such a drug-linker moiety to an antibody. The cross-reaction of these groups may be accelerated in the case the free amino group is present as an ammonium ion (H$_3$N$^+$—), such as when a strong acid (e.g., TFA) has been used to deprotect the free amino group.

In one embodiment, A is a covalent bond. Thus, L$^1$ and the cell binding agent are directly connected. For example, where L$^1$ comprises a contiguous amino acid sequence, the N-terminus of the sequence may connect directly to the cell binding agent.

Thus, where A is a covalent bond, the connection between the cell binding agent and L$^1$ may be selected from: —C(=O)NH—, —C(=O)O—, —NHC(=O)—, —OC(=O)—, —OC(=O)O—, —NHC(=O)O—, —OC(=O)NH—, —NHC(=O)NH—, —C(=O)NHC(=O)—, —S—, —S—S—, —CH2C(=O)—, and =N—NH—.

An amino group of L$^1$ that connects to the cell binding agent may be the N-terminus of an amino acid or may be derived from an amino group of an amino acid side chain, for example a lysine amino acid side chain.

An carboxyl group of L$^1$ that connects to the cell binding agent may be the C-terminus of an amino acid or may be derived from a carboxyl group of an amino acid side chain, for example a glutamic acid amino acid side chain.

A hydroxyl group of L$^1$ that connects to the cell binding agent may be derived from a hydroxyl group of an amino acid side chain, for example a serine amino acid side chain.

A thiol group of L$^1$ that connects to the cell binding agent may be derived from a thiol group of an amino acid side chain, for example a serine amino acid side chain.

The comments above in relation to the amino, carboxyl, hydroxyl and thiol groups of L$^1$ also apply to the cell binding agent.

In one embodiment, L$^2$ together with —OC(=O)— represents:

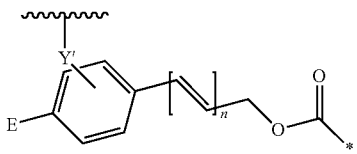

where the asterisk indicates the point of attachment to the N10 position, the wavy line indicates the point of attachment to L$^1$, n is 0 to 3, Y' is a covalent bond or a functional group, and E is an activatable group, for example by enzymatic action or light, thereby to generate a self-immolative unit. The phenylene ring is optionally further substituted with one, two or three substituents as described herein. In one embodiment, the phenylene group is optionally further substituted with halo, NO$_2$, R or OR. Preferably n is 0 or 1, most preferably 0.

E is selected such that the group is susceptible to activation, e.g., by light or by the action of an enzyme. E may be —NO$_2$ or glucuronic acid. The former may be susceptible to the action of a nitroreductase, the latter to the action of a β-glucoronidase.

In this embodiment, the self-immolative linker will allow for release of the protected compound when E is activated, proceeding along the lines shown below (for n=0):

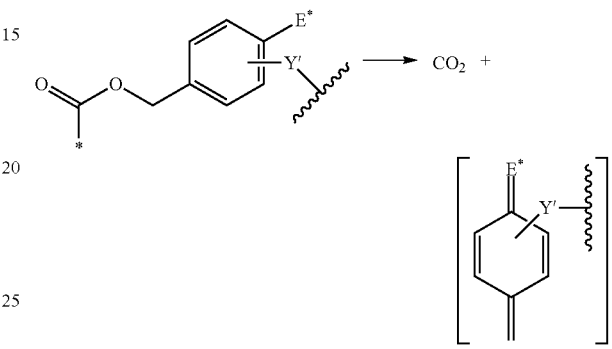

where the asterisk indicates the point of attachment to the N10 position, E* is the activated form of E, and Y' is as described above. These groups have the advantage of separating the site of activation from the compound being protected. As described above, the phenylene group may be optionally further substituted.

The group Y' may be a covalent bond to L$^1$.

The group Y' may be a functional group selected from: —C(=O)—, —NH—, —O—, —C(=O)NH—, —C(=O)O—, —NHC(=O)—, —OC(=O)—, —OC(=O)O—, —NHC(=O)O—, —OC(=O)NH—, —NHC(=O)NH—, —NHC(=O)NH, —C(=O)NHC(=O)—, and —S—.

Where L$^1$ is a dipeptide, it is preferred that Y' is —NH— or —C(=O)—, thereby to form an amide bond between L$^1$ and Y'. In this embodiment, the dipeptide sequence need not be a substrate for an enzymatic activity.

In another embodiment, A is a spacer group. Thus, L$^1$ and the cell binding agent are indirectly connected.

L$^1$ and A may be connected by a bond selected from: —C(=O)NH—, —C(=O)O—, —OC(=O)—, —NHC(=O)—, —OC(=O)O—, —NHC(=O)O—, —OC(=O)NH—, and —NHC(=O)NH—.

Preferably, the linker contains an electrophilic functional group for reaction with a nucleophilic functional group on the cell binding agent. Nucleophilic groups on antibodies include, but are not limited to: (i) N-terminal amine groups, (ii) side chain amine groups, e.g., lysine, (iii) side chain thiol groups, e.g., cysteine, and (iv) sugar hydroxyl or amino groups where the antibody is glycosylated. Amine, thiol, and hydroxyl groups are nucleophilic and capable of reacting to form covalent bonds with electrophilic groups on linker moieties and linker reagents including: (i) maleimide groups (ii) activated disulfides, (iii) active esters such as NHS (N-hydroxysuccinimide) esters, HOBt (N-hydroxybenzotriazole) esters, haloformates, and acid halides; (iv) alkyl and benzyl halides such as haloacetamides; and (v) aldehydes, ketones, carboxyl, and, some of which are exemplified as follows:

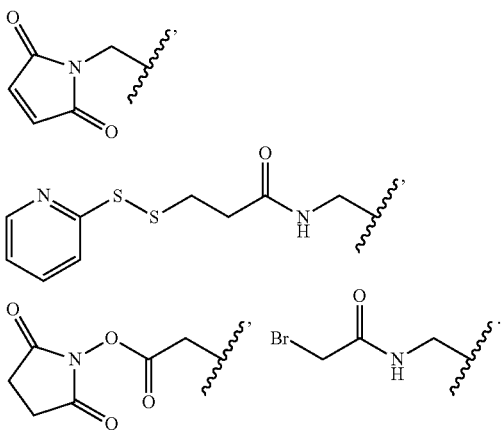

Certain antibodies have reducible interchain disulfides, i.e., cysteine bridges. Antibodies may be made reactive for conjugation with linker reagents by treatment with a reducing agent such as DTT (dithiothreitol). Each cysteine bridge will thus form, theoretically, two reactive thiol nucleophiles. Additional nucleophilic groups can be introduced into antibodies through the reaction of lysines with 2-iminothiolane (Traut's reagent) resulting in conversion of an amine into a thiol. Reactive thiol groups may be introduced into the antibody (or fragment thereof) by introducing one, two, three, four, or more cysteine residues (e.g., preparing mutant antibodies comprising one or more non-native cysteine amino acid residues). U.S. Pat. No. 7,521,541 teaches engineering antibodies by introduction of reactive cysteine amino acids. In some embodiments, a Linker has a reactive nucleophilic group which is reactive with an electrophilic group present on an antibody. Useful electrophilic groups on an antibody include, but are not limited to, aldehyde and ketone carbonyl groups. The heteroatom of a nucleophilic group of a Linker can react with an electrophilic group on an antibody and form a covalent bond to an antibody unit. Useful nucleophilic groups on a Linker include, but are not limited to, hydrazide, oxime, amino, hydroxyl, hydrazine, thiosemicarbazone, hydrazine carboxylate, and arylhydrazide. The electrophilic group on an antibody provides a convenient site for attachment to a Linker.

In one embodiment, the group A is:

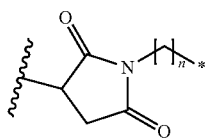

where the asterisk indicates the point of attachment to $L^1$, the wavy line indicates the point of attachment to the cell binding agent, and n is 0 to 6. In one embodiment, n is 5.

In one embodiment, the group A is:

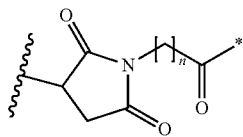

where the asterisk indicates the point of attachment to $L^1$, the wavy line indicates the point of attachment to the cell binding agent, and n is 0 to 6. In one embodiment, n is 5.

In one embodiment, the group A is:

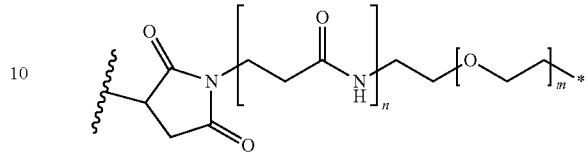

where the asterisk indicates the point of attachment to $L^1$, the wavy line indicates the point of attachment to the cell binding agent, n is 0 or 1, and m is 0 to 30. In a preferred embodiment, n is 1 and m is 0 to 10, 1 to 8, preferably 4 to 8, and most preferably 4 or 8. In another embodiment, m is 10 to 30, and preferably 20 to 30. Alternatively, m is 0 to 50. In this embodiment, m is preferably 10-40 and n is 1.

In one embodiment, the group A is:

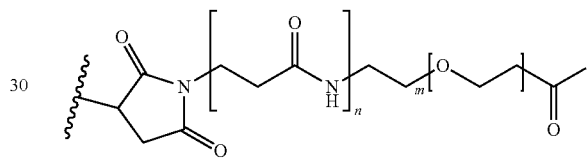

where the asterisk indicates the point of attachment to $L^1$, the wavy line indicates the point of attachment to the cell binding agent, n is 0 or 1, and m is 0 to 30. In a preferred embodiment, n is 1 and m is 0 to 10, 1 to 8, preferably 4 to 8, and most preferably 4 or 8. In another embodiment, m is 10 to 30, and preferably 20 to 30. Alternatively, m is 0 to 50. In this embodiment, m is preferably 10-40 and n is 1.

In one embodiment, the group A is:

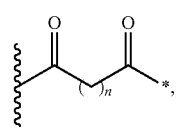

where the asterisk indicates the point of attachment to $L^1$, the wavy line indicates the point of attachment to the CBA and the CBA, and n is 1 to 6.

In one embodiment, the group A is:

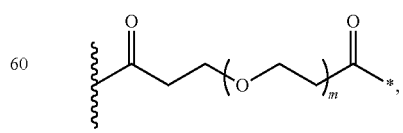

where the asterisk indicates the point of attachment to $L^1$, the wavy line indicates the point of attachment to the CBA and the CBA, and m is 1 to 30.

In one embodiment, the group A is:

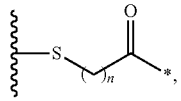

where the asterisk indicates the point of attachment to $L^1$, the wavy line indicates the point of attachment to the CBA and the CBA, and n is 2 to 6.

In one embodiment, the group A is:

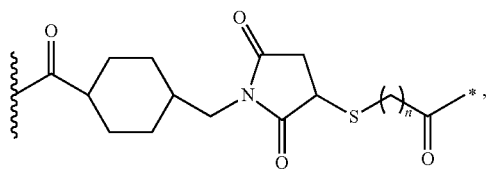

where the asterisk indicates the point of attachment to $L^1$, the wavy line indicates the point of attachment to the CBA and the CBA, and n is 2 to 6.

In one embodiment, the connection between the cell binding agent and A is through a thiol residue of the cell binding agent and a maleimide group of A (e.g., the cell binding agent is connected to A through a thioether bond formed from a cysteine thiol residue of the cell binding agent and a malemide group of A).

In one embodiment, the connection between the cell binding agent and A is:

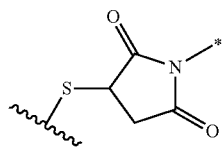 [SMILES: *SC1CC(=O)N(C)C1=O]

where the asterisk indicates the point of attachment to the remaining portion of A and the wavy line indicates the point of attachment to the remaining portion of the cell binding agent. In this embodiment, the S atom is typically derived from the cell binding agent.

In each of the embodiments above, an alternative functionality may be used in place of the maleimide-derived group shown below:

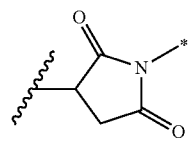 [SMILES: *C1CC(=O)N(C)C1=O]

where the wavy line indicates the point of attachment to the cell binding agent as before, and the asterisk indicates the bond to the remaining portion of the A group.

In one embodiment, the maleimide-derived group is replaced with the group:

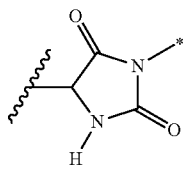 [SMILES: *C1NC(=O)N(C)C1=O]

where the wavy line indicates point of attachment to the cell binding agent, and the asterisk indicates the bond to the remaining portion of the A group.

In one embodiment, the maleimide-derived group is replaced with a group, which optionally together with the cell binding agent, is selected from: —C(=O)NH—, —C(=O)O—, —NHC(=O)—, —OC(=O)—, —OC(=O)O—, —NHC(=O)O—, —OC(=O)NH—, —NHC(=O)NH—, —NHC(=O)NH, —C(=O)NHC(=O)—, —S—, —S—S—, —CH2C(=O)—, —C(=O)CH2-, =N—NH—, and —NH—N=.

In one embodiment, the maleimide-derived group is replaced with a group, which optionally together with the cell binding agent, is selected from:

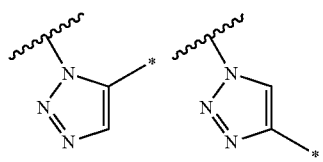

where the wavy line indicates either the point of attachment to the cell binding agent or the bond to the remaining portion of the A group, and the asterisk indicates the other of the point of attachment to the cell binding agent or the bond to the remaining portion of the A group.

In one embodiment, the cell binding agent is connected to A through an amide bond formed from a lysine residue of the cell binding agent and a carboxyl group of A.

Other groups suitable for connecting $L^1$ to the cell binding agent are described in WO 2005/082023.

The group $R^{5b}$ is derivable from the group $R^L$. The group $R^L$ may be converted to a group $R^{5b}$ by connection of a cell binding agent to a functional group of $R^L$. Other steps may be taken to convert $R^L$ to $R^{5b}$. These steps may include the removal of protecting groups, where present, or the installation of an appropriate functional group.

Additional means to conjugate compounds of the invention either to the free Cys residues of the CBA, or to cysteine residues obtained by reduction of one or more native disulfide bonds of the CBA, are described below, in U.S. Pat. No. 7,939,630, S. Balan et al. (*BioConjugate Chem.*, 18:61-76, 2007), and, Smith et al. (*J. Am. Chem. Soc.*, 132:1960-1965, 2010). All incorporated herein by reference.

For example, a cell binding agent (CBA) can be reacted with the reagent A to give a conjugate B

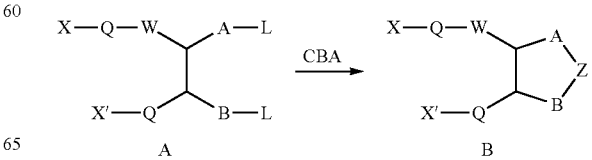

wherein X and X' are each selected from a cytotoxic agent directly attached to Q, a cytotoxic agent attached to Q through the intermediacy of a PEG unit bearing between 1 to 100 ethyleneoxy (—CH$_2$H$_2$O—) units and H, provided that both X and X' are not H at the same time; Q is a linking group; W is selected from a keto group, an ester group, a sulfone group; A is a C$_{1-5}$ alkylene or alkenylene; B is a bond or a C$_{1-5}$ alkylene or alkenylene; Z is a cell binding agent linked between A and B through two thiol groups; W' is selected from the group consisting of a keto group, an ester group, and a sulfone; L is independently a leaving group; CBA represents a cell binding agent, preferably a monoclonal antibody. The cytotoxic agent is selected from pyrrolobenzodiazepine or indolinobenzodiazepine compounds disclosed herein.

A cell binding agent bearing cysteine residues (such as an antibody or an antigen-binding portion thereof) can also be linked to a pyrrolobenzodiazepine or indolinobenzodiazepine compounds described herein by the scheme shown below:

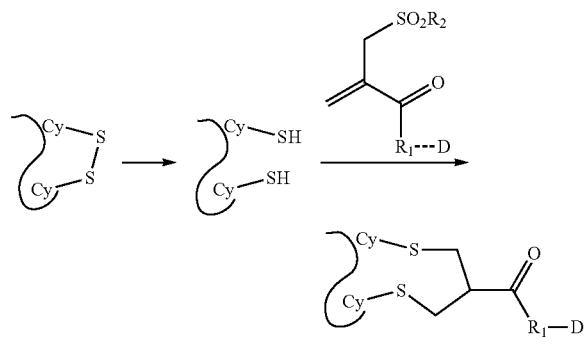

Wherein CySH represents a cysteine residue on the cell binding agent, such as a (monoclonal) antibody or an antigen-binding portion thereof; D represents a pyrrolobenzodiazepine or indolinobenzodiazepine compound linked directly to R$_1$ via a cleavable or non-cleavable linker, or through the intermediacy of a PEG unit bearing between 1 to 100 ethyleneoxy (—CH$_2$CH$_2$O—)$_n$ units to R$_1$; R$_1$ and R$_2$ are independently selected from alkylene bearing 1 to 5 carbon atoms, phenyl or substituted phenyl, wherein the substituent is alkyl bearing 1 to 4 carbon atoms, methoxy, halogen or a nitro group.

Furthermore, a cell binding agent bearing cysteine residues can also be linked via bromomaleimido or dibromomaleimido reagent to a pyrrolobenzodiazepine or indolinobenzodiazepine compounds described herein by the scheme shown below:

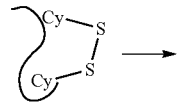

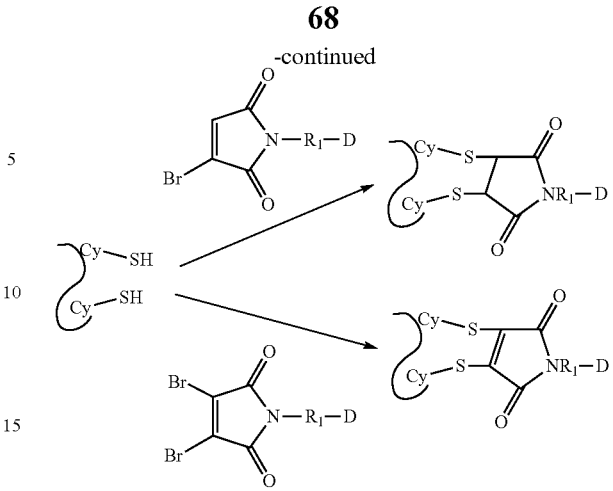

Wherein CySH represents a cysteine residue on the cell binding agent, such as a (monoclonal) antibody or an antigen-binding portion thereof; D represents a pyrrolobenzodiazepine or indolinobenzodiazepine compound linked directly to N via a cleavable or non-cleavable linker, or through the intermediacy of an optional PEG unit R$_1$ bearing between 1 to 100 ethyleneoxy (—CH$_2$CH$_2$O—)$_n$.

R$^{4a}$ and R$^{4b}$ (e.g., QR$^{11'}$)

In one embodiment, the group R$^{4a}$ is selected from —H, an oxo group, an optionally substituted linear, branched or cyclic alkyl, alkenyl or alkynyl having from 1 to 10 carbon atoms, an optionally substituted 6- to 18-membered aryl, an optionally substituted 5- to 18-membered heteroaryl ring containing one or more heteroatoms independently selected from nitrogen, oxygen, or sulfur, and an optionally substituted 3- to 18-membered heterocyclic ring having 1 to 6 heteroatoms. Preferably, R$^{4a}$ is H. Preferably, R$^{4a}$ is not a leaving group, and the C11 position to which R$^{4a}$ is attached forms an amine bond with N10, to which group R$^{5a}$ is attached. Preferably, both R$^{4a}$ and R$^{5a}$ are H.

In one embodiment, the group R$^{4b}$ may be —H or a leaving group selected from —OR$^{6'}$, —OCOR$^{4'}$, —OCOOR$^{4'}$, —OCONR$^{4'}$R$^{5'}$, —NR$^{4'}$R$^{5'}$, —NR$^{4'}$COR$^{5'}$, —NR$^{4'}$NR$^{4'}$R$^{5'}$, an optionally substituted 5- or 6-membered nitrogen-containing heterocycle (e.g., piperidine, tetrahydropyrrole, pyrazole, morpholine), a guanidinum represented by —NR$^{4'}$(C=NH)NR$^{4'}$R$^{5}$, an amino acid, or a peptide represented by —NR$^{6'}$COP', wherein P' is an amino acid or a polypeptide containing between 2 to 20 amino acid units, —SR$^{6'}$, —SOR$^{4'}$, —SO$_2$M, —SO$_3$M, —OSO$_3$M, halogen, cyano and an azido.

In one embodiment, the group R$^{4b}$ may also be QR$^{11'}$.

In one embodiment, Q is selected from O, S, or N(H). Preferably, Q is O.

In one embodiment, R$^{11'}$ is either H, or R$^{1'}$ or, where Q is O, R$^{11'}$ is SO$_3$M, where M is a metal cation.

In one embodiment, R$^{11'}$ is H.

In one embodiment, R$^{11'}$ is R$^{1'}$.

In one embodiment, where Q is O, R$^{11'}$ is SO$_3$M, where M is a metal cation. The cation may be Na$^+$.

R$^L$

In one embodiment, R$^L$ is a linker for connection to a cell binding agent.

In one embodiment, the linker is provided with a functional group to form a connection to a cell binding agent. This application is particularly concerned with those R$^L$ groups which have a carbamate link to the N10 position. The discussion of the linking group in $R^{5b}$ above is also relevant to their immediate precursors here.

$R^L$ is different from $R^{cc}$, which is not suitable for reaction with a cell binding agent. However, in some embodiments, $R^{cc}$ may be converted into a group $R^L$, for example, by appropriate manipulation of the protecting groups and other functionalities that are, or form part of, $R^{cc}$.

In one embodiment, $R^L$ is a group:

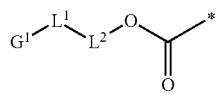

where the asterisk indicates the point of attachment to the N10 position, $G^1$ is a functional group to form a connection to a cell binding agent, $L^1$ is a linker, $L^2$ is a covalent bond or together with —OC(=O)— forms a self-immolative linker, and $L^1$ or $L^2$ is a cleavable linker.

$L^1$ and $L^2$ are as defined above in relation to $R^{5b}$. References to connection to A can be construed here as referring to a connection to $G^1$.

In one embodiment, where $L^1$ comprises an amino acid, the side chain of that amino acid may be protected. Any suitable protecting group may be used. In one embodiment, the side chain protecting groups are removable with other protecting groups in the compound, where present. In other embodiments, the protecting groups may be orthogonal to other protecting groups in the molecule, where present.

Suitable protecting groups for amino acid side chains include those groups described in the Novabiochem Catalog 2006/2007. Protecting groups for use in a cathepsin labile linker are also discussed in Dubowchik et al. Both incorporated herein by reference.

In certain embodiments of the invention, the group $L^1$ includes a Lys amino acid residue. The side chain of this amino acid may be protected with a Boc or Alloc protected group. A Boc protecting group is most preferred.

The functional group $G^1$ forms a connecting group A upon reaction with a cell binding agent.

In one embodiment, the functional group $G^1$ is or comprises an amino, carboxylic acid, reactive carboxylic ester, hydroxyl, thiol, or maleimide group for reaction with an appropriate group on the cell binding agent. In a preferred embodiment, $G^1$ comprises a maleimide group.

In one embodiment, the group $G^1$ is an alkyl maleimide group. This group is suitable for reaction with thiol groups, particularly cysteine thiol groups, present in the cell binding agent, for example present in an antibody.

In one embodiment, the group $G^1$ is:

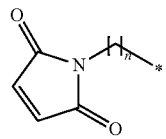

where the asterisk indicates the point of attachment to L and n is 0 to 6. In one embodiment, n is 5.

In one embodiment, the group $G^1$ is:

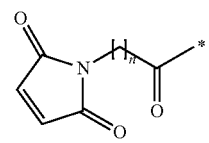

where the asterisk indicates the point of attachment to $L^1$ and n is 0 to 6. In one embodiment, n is 5.

In one embodiment, the group $G^1$ is:

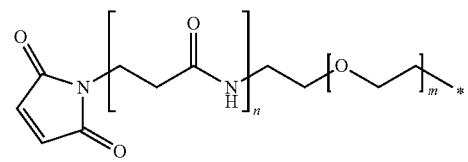

where the asterisk indicates the point of attachment to $L^1$, n is 0 or 1, and m is 0 to 30. In a preferred embodiment, n is 1 and m is 0 to 10, 1 to 2, preferably 4 to 8, and most preferably 4 or 8. Alternatively, m is 0 to 50. In this embodiment, m is preferably 10-40 and n is 1.

In one embodiment, the group $G^1$ is:

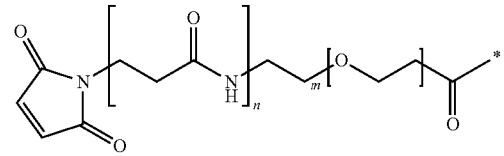

where the asterisk indicates the point of attachment to $L^1$, n is 0 or 1, and m is 0 to 30. In a preferred embodiment, n is 1 and m is 0 to 10, 1 to 8, preferably 4 to 8, and most preferably 4 or 8. Alternatively, m is 0 to 50. In this embodiment, m is preferably 10-40 and n is 1.

In each of the embodiments above, an alternative functionality may be used in place of the maleimide group shown below:

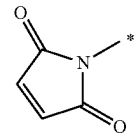

where asterisk indicates the bond to the remaining portion of the $G^1$ group.

In one embodiment, the maleimide-derived group is replaced with the group:

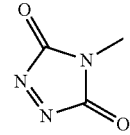

where the asterisk indicates the bond to the remaining portion of the $G^1$ group.

In one embodiment, the maleimide group is replaced with a group selected from: —C(=O)OH, —OH, —NH$_2$, —SH, —C(=O)CH$_2$D, where D is Cl, Br or I, —CHO, —NHNH$_2$, —C≡CH, and —N$_3$ (azide).

In one embodiment, where L$^1$ is present, G$^1$ is —NH$_2$, —NHMe, —COOH, —OH or —SH.

In one embodiment, where L$^1$ is present, G$^1$ is —NH$_2$ or —NHMe. Either group may be the N-terminal of an L$^1$ amino acid sequence.

In one embodiment, where L$^1$ is present, G$^1$ is —NH$_2$, and L$^1$ is an amino acid sequence —X$_1$—X$_2$—, as defined above in relation to R$^{5b}$.

In one embodiment, where L$^1$ is present, G$^1$ is COOH. This group may be the C-terminal of an L$^1$ amino acid sequence.

In one embodiment, where L$^1$ is present, G$^1$ is a reactive ester group. A reactive ester group can readily form an amide bond with an amine group on the cell-binding agent. Exemplary reactive ester groups include, but are not limited to, N-hydroxysuccinimide ester, N-hydroxy sulfosuccinimide ester, nitrophenyl (e.g., 2 or 4-nitrophenyl) ester, dinitrophenyl (e.g., 2,4-dinitrophenyl) ester, sulfo-tetraphenyl (e.g., 4-sulfo-2,3,5,6-tetrafluorophenyl) ester, and pentafluorophenyl ester.

In one embodiment, where L$^1$ is present, G$^1$ is OH.

In one embodiment, where L$^1$ is present, G$^1$ is SH.

The group G$^1$ may be convertible from one functional group to another. In one embodiment, where L$^1$ is present, G$^1$ is —NH$_2$. This group is convertible to another group G$^1$ comprising a maleimide group. For example, the group —NH$_2$ may be reacted with an acids or an activated acid (e.g., N-succinimide forms) of those G$^1$ groups comprising maleimide shown above.

The group G$^1$ may therefore be converted to a functional group that is more appropriate for reaction with a cell binding agent.

In other embodiments, R$^L$ is a group that is a precursor to the linker that is provided with a functional group.

As noted above, in one embodiment, where L$^1$ is present, G$^1$ is —NH$_2$, —NHMe, —COOH, —OH or —SH. In a further embodiment, these groups are provided in a chemically protected form. The chemically protected form is therefore a precursor to the linker that is provided with a functional group.

In one embodiment, G$^1$ is —NH$_2$ in a chemically protected form. The group may be protected with a carbamate protecting group. The carbamate protecting group may be selected from the group consisting of: Alloc, Fmoc, Boc, Troc, Teoc, Cbz and PNZ.

Preferably, where G$^1$ is —NH$_2$, it is protected with an Alloc or Fmoc group.

In one embodiment, where G$^1$ is —NH$_2$, it is protected with an Fmoc group.

In one embodiment, the protecting group is the same as the carbamate protecting group of the capping group.

In one embodiment, the protecting group is not the same as the carbamate protecting group of the capping group. In this embodiment, it is preferred that the protecting group is removable under conditions that do not remove the carbamate protecting group of the capping group.

The chemical protecting group may be removed to provide a functional group to form a connection to a cell binding agent. Optionally, this functional group may then be converted to another functional group as described above.

In one embodiment, the active group is an amine. This amine is preferably the N-terminal amine of a peptide, and may be the N-terminal amine of the preferred dipeptides of the invention.

The active group may be reacted to yield the functional group that is intended to form a connection to a cell binding agent.

In other embodiments, the linker is a precursor to the linker having an active group. In this embodiment, the linker/precursor comprises the active group, which is protected by way of a protecting group. The protecting group may be removed to provide the linker having an active group.

Where the active group is an amine, the protecting group may be an amine protecting group, such as those described in Green and Wuts (incorporated herein).

The protecting group is preferably orthogonal to other protecting groups, where present, in the group R$^L$.

In one embodiment, the protecting group is orthogonal to the capping group. Thus, the active group protecting group is removable whilst retaining the capping group. In other embodiments, the protecting group and the capping group is removable under the same conditions as those used to remove the capping group.

In one embodiment, R$^L$ is:

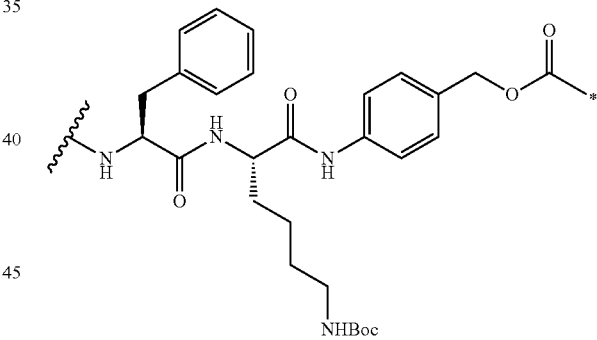

where the asterisk indicates the point of attachment to the N10 position, and the wavy line indicates the point of attachment to the remaining portion of the linker L$^1$ or the point of attachment to G$^1$. Preferably, the wavy line indicates the point of attachment to G$^1$.

In one embodiment, R$^L$ is:

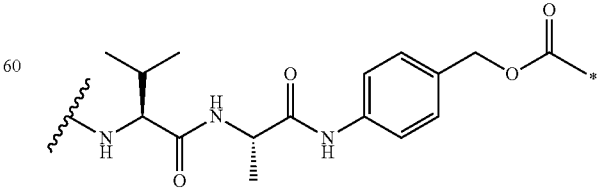

where the asterisk and the wavy line are as defined above.

In one embodiment, $R^L$ is:

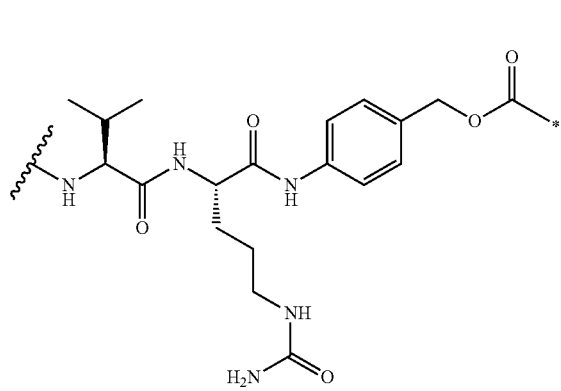 [SMILES: *N[C@H](C(=O)N[C@@H](CCCNC(N)=O)C(=O)Nc1ccc(COC(C)=O)cc1)C(C)C]

where the asterisk and the wavy line are as defined above.

Other functional groups suitable for use in forming a connection between $L^1$ and the cell binding agent are described in WO 2005/082023 (incorporated herein).

Linkers can include protease-cleavable peptidic moieties comprising one or more amino acid units. Peptide linker reagents may be prepared by solid phase or liquid phase synthesis methods (E. Schroder and K. Lubke, *The Peptides*, 1:76-136 (1965) Academic Press) that are well known in the field of peptide chemistry, including t-BOC chemistry (Geiser et al. "Automation of solid-phase peptide synthesis" in *Macromolecular Sequencing and Synthesis*, Alan R. Liss, Inc., 1988:199-218) and Fmoc/HBTU chemistry (Fields, G. and Noble, R. (1990) "Solid phase peptide synthesis utilizing 9-fluoroenylmethoxycarbonyl amino acids," *Int. J. Peptide Protein Res.*, 35:161-214), on an automated synthesizer such as the Rainin Symphony Peptide Synthesizer (Protein Technologies, Inc., Tucson, Ariz.), or Model 433 (Applied Biosystems, Foster City, Calif.).

Exemplary amino acid linkers include a dipeptide, a tripeptide, a tetrapeptide or a pentapeptide. Exemplary dipeptides include: valine-citrulline (vc or val-cit), alanine-phenylalanine (af or ala-phe). Exemplary tripeptides include: glycine-valine-citrulline (gly-val-cit) and glycine-glycine-glycine (gly-gly-gly). Amino acid residues which comprise an amino acid linker component include those occurring naturally, as well as minor amino acids and non-naturally occurring amino acid analogs, such as citrulline. Amino acid linker components can be designed and optimized in their selectivity for enzymatic cleavage by a particular enzymes, for example, a tumor-associated protease, cathepsin B, C and D, or a plasmin protease.

Amino acid side chains include those occurring naturally, as well as minor amino acids and non-naturally occurring amino acid analogs, such as citrulline. Amino acid side chains include hydrogen, methyl, isopropyl, isobutyl, sec-butyl, benzyl, p-hydroxybenzyl, —$CH_2OH$, —$CH(OH)$ $CH_3$, —$CH_2CH_2SCH_3$, —$CH_2CONH_2$, —$CH_2COOH$, —$CH_2CH_2CONH_2$, —$CH_2CH_2COOH$, —$(CH_2)_3NHC$ (=$NH)NH_2$, —$(CH_2)_3NH_2$, —$(CH_2)_3NHCOCH_3$, —$(CH_2)_3NHCHO$, —$(CH_2)_4NHC$(=$NH)NH_2$, —$(CH_2)_4$ $NH_2$, —$(CH_2)_4NHCOCH_3$, —$(CH_2)_4NHCHO$, —$(CH_2)_3$ $NHCONH_2$, —$(CH_2)_4NHCONH_2$, —$CH_2CH_2CH(OH)$ $CH_2NH_2$, 2-pyridylmethyl-, 3-pyridylmethyl-, 4-pyridylmethyl-, phenyl, cyclohexyl, as well as the following structures:

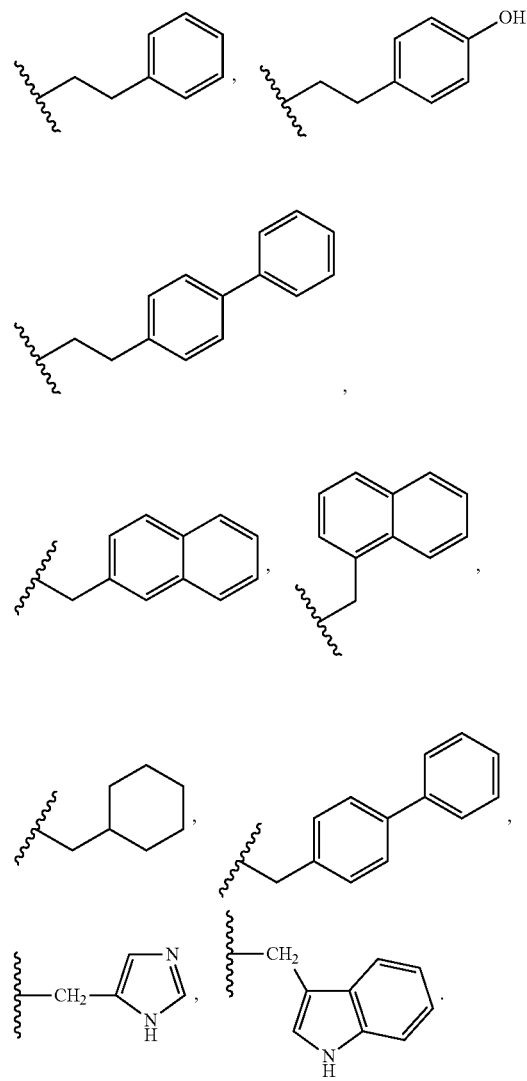

When the amino acid side chains include other than hydrogen (glycine), the carbon atom to which the amino acid side chain is attached is chiral. Each carbon atom to which the amino acid side chain is attached is independently in the (S) or (R) configuration, or a racemic mixture. Drug-linker reagents may thus be enantiomerically pure, racemic, or diastereomeric.

In exemplary embodiments, amino acid side chains are selected from those of natural and non-natural amino acids, including alanine, 2-amino-2-cyclohexylacetic acid, 2-amino-2-phenylacetic acid, arginine, asparagine, aspartic acid, cysteine, glutamine, glutamic acid, glycine, histidine, isoleucine, leucine, lysine, methionine, norleucine, phenylalanine, proline, serine, threonine, tryptophan, tyrosine, valine, γ-aminobutyric acid, α,α-dimethyl γ-aminobutyric acid, β,β-dimethyl γ-aminobutyric acid, ornithine, and citrulline (Cit).

An exemplary valine-citrulline (val-cit or vc) dipeptide linker reagent useful for constructing a linker-PBD/IBD drug moiety intermediate for conjugation to a cell binding agent, e.g., an antibody, having a para-aminobenzylcarbamoyl (PAB) self-immolative spacer has the structure:

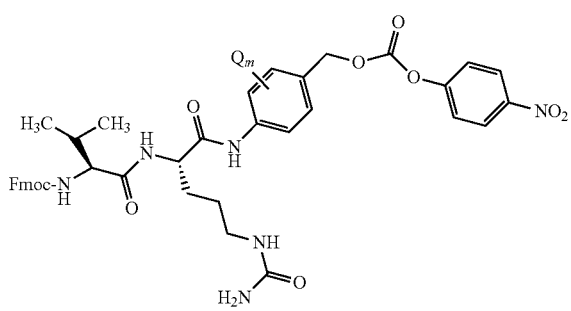

where Q is C1-C8 alkyl, —O—(C1-C8 alkyl), -halogen, —NO₂ or —CN; and m is an integer ranging from 0-4.

An exemplary phe-lys(Mtr) dipeptide linker reagent having a p-aminobenzyl group can be prepared according to Dubowchik et al. (1997) *Tetrahedron Letters*, 38:5257-5260, and has the structure:

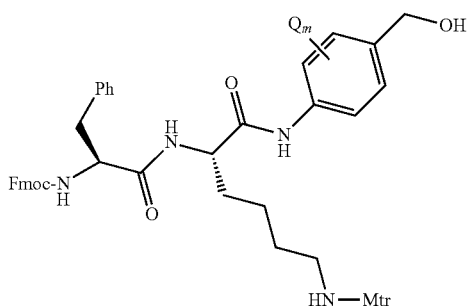

where Mtr is mono-4-methoxytrityl, Q is C1-C8 alkyl, —O—(C1-C8 alkyl), -halogen, —NO₂ or —CN; and m is an integer ranging from 0-4.

The "self-immolative linker" PAB (para-aminobenzyloxycarbonyl), attaches the drug moiety to the antibody in the antibody drug conjugate (Carl et al. (1981) *J. Med. Chem.* 24:479-480; Chakravarty et al. (1983) *J. Med. Chem.* 26:638-644; U.S. Pat. No. 6,214,345; US 2003/0130189; US 2003/0096743; U.S. Pat. No. 6,759,509; US 2004/0052793; U.S. Pat. No. 6,218,519; U.S. Pat. No. 6,835,807; U.S. Pat. No. 6,268,488; US 2004/0018194; WO 98/13059; US 2004/0052793; U.S. Pat. No. 6,677,435; U.S. Pat. No. 5,621,002; US 2004/0121940; WO 2004/032828, all incorporated herein). Other examples of self-immolative spacers besides PAB include, but are not limited to: (i) aromatic compounds that are electronically similar to the PAB group such as 2-aminoimidazol-5-methanol derivatives (Hay et al. (1999) *Bioorg. Med. Chem. Lett.*, 9:2237), thiazoles (U.S. Pat. No. 7,375,078), multiple, elongated PAB units (de Groot et al. (2001) *J. Org. Chem.*, 66:8815-8830); and ortho or para-aminobenzylacetals; and (ii) homologated styryl PAB analogs (U.S. Pat. No. 7,223,837). Spacers can be used that undergo cyclization upon amide bond hydrolysis, such as substituted and unsubstituted 4-aminobutyric acid amides (Rodrigues et al. (1995) *Chemistry Biology* 2:223), appropriately substituted bicyclo[2.2.1] and bicyclo[2.2.2] ring systems (Storm et al. (1972) *J. Amer. Chem. Soc.*, 94:5815) and 2-aminophenylpropionic acid amides (Amsberry et al. (1990) *J. Org. Chem.*, 55:5867). Elimination of amine-containing drugs that are substituted at glycine (Kingsbury et al. (1984) *J. Med. Chem.*, 27:1447) are also examples of self-immolative spacers useful in ADC.

In one embodiment, a valine-citrulline dipeptide PAB analog reagent has a 2,6 dimethyl phenyl group and has the structure:

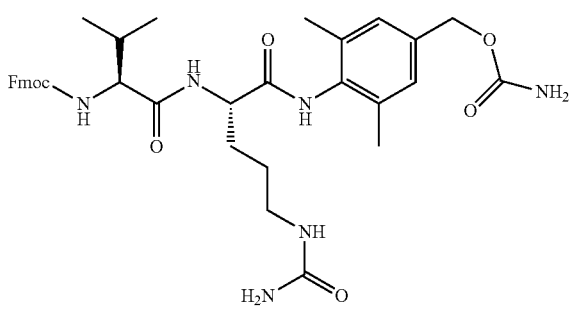

Linker reagents useful for the antibody drug conjugates of the invention include, but are not limited to: BMPEO, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate), and bis-maleimide reagents: DTME, BMB, BMDB, BMH, BMOE, 1,8-bis-maleimidodiethyleneglycol (BM(PEO)₂), and 1,11-bis-maleimidotriethyleneglycol (BM(PEO)₃), which are commercially available from Pierce Biotechnology, Inc., ThermoScientific, Rockford, Ill., and other reagent suppliers. Bis-maleimide reagents allow the attachment of a free thiol group of a cysteine residue of an antibody to a thiol-containing drug moiety, label, or linker intermediate, in a sequential or concurrent fashion. Other functional groups besides maleimide, which are reactive with a thiol group of an antibody, PBD drug moiety, or linker intermediate include iodoacetamide, bromoacetamide, vinyl pyridine, disulfide, pyridyl disulfide, isocyanate, and isothiocyanate.

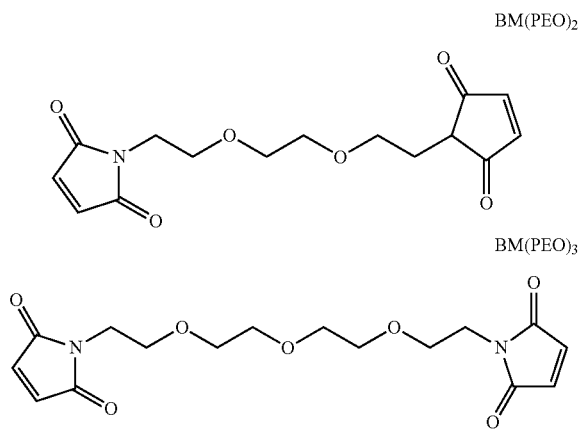 [SMILES: O=C1C=CC(=O)C1CCOCCOCCN1C(=O)C=CC1=O ; O=C1C=CC(=O)N1CCOCCOCCOCCN1C(=O)C=CC1=O]

Other embodiments of linker reagents are: N-succinimidyl-4-(2-pyridylthio)pentanoate (SPP), N-succinimidyl-3-(2-pyridyldithio) propionate (SPDP, Carlsson et al. (1978) *Biochem. J.*, 173:723-737), N-succinimidyl-4-(2-pyridyldithio)butanoate (SPDB), succinimidyl-4-(N-maleimidomethyl)cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis(p-azidobenzoyl)hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). Useful linker reagents can also be obtained via other commercial sources, such as Molecular Biosciences Inc. (Boulder, Colo.), or synthesized in accordance with procedures described in Toki et al. (2002) *J. Org. Chem.* 67:1866-1872; U.S. Pat. No. 6,214,345; WO 02/088172; US 2003130189; US 2003/096743; WO 03/026577; WO 03/043583; and WO 04/032828. Incorporated herein.

The Linker may be a dendritic type linker for covalent attachment of more than one drug moiety through a branching, multifunctional linker moiety to an antibody (US 2006/116422; US 2005/271615; de Groot et al. (2003) *Angew. Chem. Int. Ed.,* 42:4490-4494; Amir et al. (2003) *Angew. Chem. Int. Ed.,* 42:4494-4499; Shamis et al. (2004) *J. Am. Chem. Soc.,* 126:1726-1731; Sun et al. (2002) *Bioorganic & Medicinal Chemistry Letters,* 12:2213-2215; Sun et al. (2003) *Bioorganic & Medicinal Chemistry,* 11:1761-1768; King et al. (2002) *Tetrahedron Letters,* 43:1987-1990). Dendritic linkers can increase the molar ratio of drug to antibody, i.e., loading, which is related to the potency of the ADC. Thus, where an antibody bears only one reactive cysteine thiol group, a multitude of drug moieties may be attached through a dendritic or branched linker.

One exemplary embodiment of a dendritic type linker has the structure:

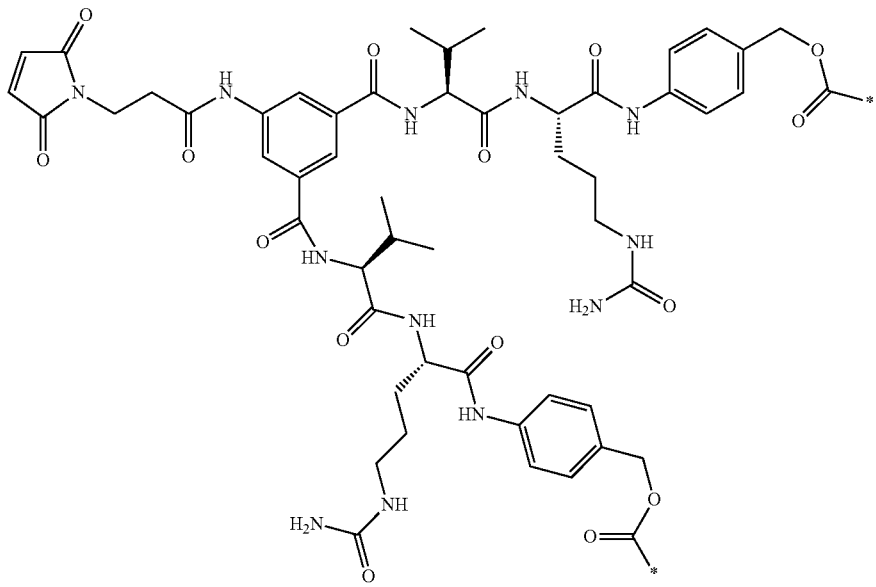 [SMILES: *C(=O)OCc1ccc(NC(=O)[C@H](CCCNC(N)=O)NC(=O)[C@@H](NC(=O)c2cc(NC(=O)CCN3C(=O)C=CC3=O)cc(C(=O)N[C@H](C(=O)N[C@@H](CCCNC(N)=O)C(=O)Nc3ccc(COC(*)=O)cc3)C(C)C)c2)C(C)C)cc1]

where the asterisk indicate the point of attachment to the N10 position of a PBD moiety.

$R^{4'}$, $R^{5'}$, and $R^{6'}$ $R^{4'}$ and $R^{5'}$ are each independently selected from —H, —OH, —OR$^{6'}$, —NHR$^{6'}$, —NR$^{6'}$2, —COR$^{6'}$, an optionally substituted linear, branched or cyclic alkyl, alkenyl or alkynyl having from 1 to 10 carbon atoms, a polyethylene glycol unit —(CH$_2$CH$_2$O)$_n$—R$^b$, or an optionally substituted 3-18-membered heterocyclic ring having 1 to 6 heteroatoms independently selected from O, S, N or P.

$R^{6'}$, for each occurrence, is independently selected from the group consisting of —H, an optionally substituted linear, branched or cyclic alkyl, alkenyl or alkynyl having from 1 to 10 carbon atoms, a polyethylene glycol unit —(CH$_2$CH$_2$O)$_n$—R$^b$, an optionally substituted aryl having 6 to 18 carbon atoms, an optionally substituted 5- to 18-membered heteroaryl ring containing one or more heteroatoms independently selected from nitrogen, oxygen, or sulfur, and an optionally substituted 3- to 18-membered heterocyclic ring containing 1 to 6 heteroatoms independently selected from O, S, N or P.

$R^a$ is independently selected from —R$^{1'}$, —CO$_2$R$^{1'}$, —COR$^{1'}$, —CHO, —CO$_2$H, or halo.

$R^b$ is —H or a substituted or unsubstituted linear or branched alkyl having 1 to 4 carbon atoms.

M is H or a pharmaceutically acceptable cation, such as; and n is an integer from 1 to 24.

$R^{10}$, $R^{11}$, $R^{12}$, and $R^{13}$

In one embodiment, $R^{10}$, $R^{11}$, $R^{12}$, $R^{13}$ are each independently selected from H, NR$^{4'}$R$^{5'}$, NR$^{4'}$(C=O)R$^{6'}$, OR$^{6'}$, SR$^{6'}$, NO$_2$.

In one embodiment, $R^{10}$, $R^{11}$, $R^{12}$, and $R^{13}$ are each —H.

Cell Binding Agent

A cell binding agent may be of any kind, and include peptides and non-peptides. These can include antibodies or a fragment of an antibody that contains at least one binding site, lymphokines, hormones, growth factors, nutrient-transport molecules, or any other cell binding molecule or substance.

The term "antibody" herein is used in the broadest sense and specifically covers monoclonal antibodies, polyclonal antibodies, dimers, multimers, multispecific antibodies (e.g., bispecific antibodies), and antibody fragments, so long as they exhibit the desired biological activity (Miller et al. (2003) *Jour. of Immunology* 170:4854-4861). Antibodies may be murine, human, humanized, chimeric, or derived from other species. An antibody is a protein generated by the immune system that is capable of recognizing and binding to a specific antigen. (Janeway, C., Travers, P., Walport, M., Shlomchik (2001) *Immuno Biology,* 5th Ed., Garland Publishing, New York). A target antigen generally has numerous binding sites, also called epitopes, recognized by CDRs on multiple antibodies. Each antibody that specifically binds to a different epitope has a different structure. Thus, one antigen may have more than one corresponding antibody. An antibody includes a full-length immunoglobulin molecule or an immunologically active portion of a full-length immunoglobulin molecule, i.e., a molecule that contains an antigen binding site that immunospecifically binds an antigen of a target of interest or part thereof, such targets including but not limited to, cancer cell or cells that produce autoimmune antibodies associated with an autoimmune disease. The immunoglobulin can be of any type (e.g., IgG, IgE, IgM, IgD, and IgA), class (e.g., IgG1, IgG2, IgG3, IgG4, IgA1 and IgA2) or subclass of immunoglobulin molecule. The immunoglobulins can be derived from any species, including human, murine, or rabbit origin.

"Antibody fragments" comprise a portion of a full length antibody, generally the antigen binding or variable region thereof. Examples of antibody fragments include Fab, Fab', F(ab')$_2$, and Fv fragments; diabodies; linear antibodies; fragments produced by a Fab expression library, anti-idiotypic (anti-Id) antibodies, CDR (complementary determining region), and epitope-binding fragments of any of the above which immunospecifically bind to cancer cell antigens, viral antigens or microbial antigens, single-chain antibody molecules; and multispecific antibodies formed from antibody fragments.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al. (1975) *Nature* 256:495, or may be made by recombinant DNA methods (see, U.S. Pat. No. 4,816,567). The monoclonal antibodies may also be isolated from phage antibody libraries using the techniques described in Clackson et al. (1991) *Nature*, 352:624-628; Marks et al. (1991) *J. Mol. Biol.*, 222:581-597.

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al. (1984) *Proc. Natl. Acad. Sci. USA*, 81:6851-6855). Chimeric antibodies include "primatized" antibodies comprising variable domain antigen-binding sequences derived from a non-human primate (e.g., Old World Monkey or Ape) and human constant region sequences.

An "intact antibody" herein is one comprising a VL and VH domains, as well as a light chain constant domain (CL) and heavy chain constant domains, CH1, CH2 and CH3. The constant domains may be native sequence constant domains (e.g., human native sequence constant domains) or amino acid sequence variant thereof. The intact antibody may have one or more "effector functions" which refer to those biological activities attributable to the Fc region (a native sequence Fc region or amino acid sequence variant Fc region) of an antibody. Examples of antibody effector functions include Clq binding; complement dependent cytotoxicity; Fc receptor binding; antibody-dependent cell-mediated cytotoxicity (ADCC); phagocytosis; and down regulation of cell surface receptors such as B cell receptor and BCR.

Depending on the amino acid sequence of the constant domain of their heavy chains, intact antibodies can be assigned to different "classes." There are five major classes of intact antibodies: IgA, IgD, IgE, IgG, and IgM, and several of these may be further divided into "subclasses" (isotypes), e.g., IgG1, IgG2, IgG3, IgG4, IgA, and IgA2. The heavy-chain constant domains that correspond to the different classes of antibodies are called α, δ, ε, γ, and μ, respectively. The subunit structures and three-dimensional configurations of different classes of immunoglobulins are well known.

In one embodiment, the Ab is a cysteine-engineered antibody.

Examples of cell binding agents include those agents described for use in WO 2007/085930, which is incorporated herein.

The cell binding agent may be, or comprise, a polypeptide. The polypeptide may be a cyclic polypeptide. The cell binding agent may be antibody. Thus, in one embodiment, the present invention provides an antibody-drug conjugate (ADC).

Drug Loading

The drug loading is the average number of PBD drugs per antibody. Drug loading may range from 1 to 8 drugs (D) per antibody (Ab), i.e., where 1, 2, 3, 4, 5, 6, 7, and 8 drug moieties are covalently attached to the antibody. Compositions of ADC include collections of antibodies conjugated with a range of drugs, from 1 to 8. The average number of drugs per antibody in preparations of ADC from conjugation reactions may be characterized by conventional means such as mass spectroscopy, ELISA assay, electrophoresis, and HPLC. The quantitative distribution of ADC in terms of p may also be determined. By ELISA, the averaged value of p in a particular preparation of ADC may be determined (Hamblett et al. (2004) *Clin. Cancer Res.* 10:7063-7070; Sanderson et al. (2005) *Clin. Cancer Res.* 11:843-852). However, the distribution of p (drug) values is not discernible by the antibody-antigen binding and detection limitation of ELISA. Also, ELISA assay for detection of antibody-drug conjugates does not determine where the drug moieties are attached to the antibody, such as the heavy chain or light chain fragments, or the particular amino acid residues. In some instances, separation, purification, and characterization of homogeneous ADC where p is a certain value from ADC with other drug loadings may be achieved by means such as reverse phase HPLC or electrophoresis.

For some antibody-drug conjugates, p may be limited by the number of attachment sites on the antibody. For example, an antibody may have only one or several cysteine thiol groups, or may have only one or several sufficiently reactive thiol groups through which a linker may be attached. Higher drug loading, e.g., p>5, may cause aggregation, insolubility, toxicity, or loss of cellular permeability of certain antibody-drug conjugates.

Typically, fewer than the theoretical maximum of drug moieties are conjugated to an antibody during a conjugation reaction. An antibody may contain, for example, many lysine residues that do not react with the drug-linker intermediate (D-L) or linker reagent. Only the most reactive lysine groups may react with an amine-reactive linker reagent. Also, only the most reactive cysteine thiol groups may react with a thiol-reactive linker reagent. Generally, antibodies do not contain many, if any, free and reactive cysteine thiol groups which may be linked to a drug moiety. Most cysteine thiol residues in the antibodies of the compounds exist as disulfide bridges and must be reduced with a reducing agent such as dithiothreitol (DTT) or TCEP, under partial or total reducing conditions. The loading (drug/antibody ratio) of an ADC may be controlled in several different manners, including: (i) limiting the molar excess of drug-linker intermediate (D-L) or linker reagent relative to antibody, (ii) limiting the conjugation reaction time or temperature, and (iii) partial or limiting reductive conditions for cysteine thiol modification.

Cysteine amino acids may be engineered at reactive sites in an antibody and which do not form intrachain or intermolecular disulfide linkages (Junutula et al., 2008b *Nature Biotech.*, 26(8):925-932; Dornan et al. (2009) *Blood*, 114 (13):2721-2729; U.S. Pat. No. 7,521,541; U.S. Pat. No. 7,723,485; WO 2009/052249). The engineered cysteine thiols may react with linker reagents or the drug-linker reagents of the present invention which have thiol-reactive, electrophilic groups such as maleimide or alpha-halo amides to form ADC with cysteine engineered antibodies and the PBD drug moieties. The location of the drug moiety can thus be designed, controlled, and known. The drug loading can be controlled since the engineered cysteine thiol groups typically react with thiol-reactive linker reagents or drug-linker reagents in high yield. Engineering an IgG antibody to introduce a cysteine amino acid by substitution at a single site on the heavy or light chain gives two new cysteines on the symmetrical antibody. A drug loading near 2 can be achieved and near homogeneity of the conjugation product ADC.

Where more than one nucleophilic or electrophilic group of the antibody reacts with a drug-linker intermediate, or linker reagent followed by drug moiety reagent, then the resulting product is a mixture of ADC compounds with a distribution of drug moieties attached to an antibody, e.g., 1, 2, 3, etc. Liquid chromatography methods such as polymeric reverse phase (PLRP) and hydrophobic interaction (HIC) may separate compounds in the mixture by drug loading value. Preparations of ADC with a single drug loading value (p) may be isolated, however, these single loading value ADCs may still be heterogeneous mixtures because the drug moieties may be attached, via the linker, at different sites on the antibody.

Thus the antibody-drug conjugate compositions of the invention include mixtures of antibody-drug conjugate compounds where the antibody has one or more drug moieties and where the drug moieties may be attached to the antibody at various amino acid residues.

In one embodiment, the average number of monomer or dimer pyrrolobenzodiazepine groups per cell binding agent is in the range 1 to 20. In some embodiments the range is selected from 1 to 8, 2 to 8, 2 to 6, 2 to 4, and 4 to 8.

Thus in one embodiment, the conjugate has the formula: Ab-(D)$_p$, where Ab is an antibody attached to the dimer compound of the invention as a drug moiety (D), and p is an integer from 1 to about 20, or 1 to 8, 2 to 8, 2 to 6, 2 to 4, and 4 to 8. In one embodiment, p is 1, 2, 3, or 4.

In one embodiment, the conjugate comprises a mixture of the antibody-drug conjugate compounds, wherein the average drug loading per antibody in the mixture of antibody-drug conjugate compound is about 2 to about 5.

In some embodiments, there is one monomer or dimer PBD/IBD groups per CBA.

Peptides

In one embodiment, the cell binding agent is a linear or cyclic peptide comprising 4-20, preferably 6-20, contiguous amino acid residues. In this embodiment, it is preferred that one cell binding agent is linked to one monomer or dimer pyrrolobenzodiazepine or indolinobenzodiazepine compound.

In one embodiment the cell binding agent comprises a peptide that binds integrin αvβ6. The peptide may be selective for αvβ6 over XYS.

In one embodiment the cell binding agent comprises the A20FMDV-Cys polypeptide. The A20FMDV-Cys has the sequence: NAVPNLRGDLQVLAQKVARTC. Alternatively, a variant of the A20FMDV-Cys sequence may be used wherein one, two, three, four, five, six, seven, eight, nine or ten amino acid residues is substituted with another amino acid residue.

In one embodiment the antibody is a monoclonal antibody; chimeric antibody; humanized antibody; fully human antibody; or a single chain antibody. One embodiment the antibody is a fragment of one of these antibodies having biological activity. Examples of such fragments include Fab, Fab', F(ab')$_2$ and Fv fragments.

In these embodiments, each antibody may be linked to one or several monomer or dimer pyrrolobenzodiazepine groups. The preferred ratios of pyrrolobenzodiazepine to cell binding agent are given above.

The antibody may be a domain antibody (DAB).

In one embodiment, the antibody is a monoclonal antibody.

Antibodies for use in the present invention include those antibodies described in WO 2005/082023 which is incorporated herein. Particularly preferred are those antibodies for tumor-associated antigens. Examples of those antigens known in the art include, but are not limited to, those tumor-associated antigens set out in WO 2005/082023. See, for instance, pages 41-55.

The conjugates of the invention are designed to target tumor cells via their cell surface antigens. The antigens are usually normal cell surface antigens which are either over-expressed or expressed at abnormal times. Ideally the target antigen is expressed only on proliferative cells (preferably tumor cells), however this is rarely observed in practice. As a result, target antigens are usually selected on the basis of differential expression between proliferative and healthy tissue.

Antibodies have been raised to target specific tumor related antigens including: Cripto, CD30, CD19, CD33, Glycoprotein NMB, CanAg, Her2 (ErbB2/Neu), CD56 (NCAM), CD22 (Siglec2), CD33 (Siglec3), CD79, CD138, PSCA, PSMA (prostate specific membrane antigen), BCMA, CD20, CD70, E-selectin, EphB2, Melanotransferin, Muc16 and TMEFF2. Thus CBA of the invention may utilize any art recognized antibodies or antigen-binding fragment thereof against tumor-associated antigens.

In one embodiment, the Ab is an antibody which binds to an ErbB receptor.

In one embodiment, the Ab is trastuzumab.

In one embodiment, the Ab is an anti-HER$^2$, an anti-Steap1, or an anti-CD22 antibody.

Tumor-associated antigens (TAA) are known in the art, and can be prepared for use in generating antibodies using methods and information which are well known in the art. In attempts to discover effective cellular targets for cancer diagnosis and therapy, researchers have sought to identify transmembrane or otherwise tumor-associated polypeptides that are specifically expressed on the surface of one or more particular type(s) of cancer cell as compared to on one or more normal non-cancerous cell(s). Often, such tumor-associated polypeptides are more abundantly expressed on the surface of the cancer cells as compared to on the surface of the non-cancerous cells. The identification of such tumor-associated cell surface antigen polypeptides has given rise to the ability to specifically target cancer cells for destruction via antibody-based therapies.

Examples of TAA include, but are not limited to, TAA (1)-(36) listed below. For convenience, information relating to these antigens, all of which are known in the art, is listed below and includes names, alternative names, GenBank accession numbers and primary reference(s), following nucleic acid and protein sequence identification conventions of the National Center for Biotechnology Information (NCBI). Nucleic acid and protein sequences corresponding to TAA (1)-(36) are available in public databases such as GenBank. Tumor-associated antigens targeted by antibodies include all amino acid sequence variants and isoforms possessing at least about 70%, 80%, 85%, 90%, or 95% sequence identity relative to the sequences identified in the cited references, or which exhibit substantially the same biological properties or characteristics as a TAA having a sequence found in the cited references. For example, a TAA having a variant sequence generally is able to bind specifically to an antibody that binds specifically to the TAA with the corresponding sequence listed. The sequences and disclosure in the reference specifically recited herein are expressly incorporated by reference.

Tumor-Associated Antigens (1)-(36):

(1) BMPR1B (bone morphogenetic protein receptor-type IB, GenBank accession no. NM-001203);

(2) E16 (LAT1, SLC7A5, GenBank accession no. NM-003486);

(3) STEAP1 (six transmembrane epithelial antigen of prostate, GenBank accession no. NM-012449);

(4) 0772P (CA125, MUC16, GenBank accession no. AF361486);

(5) MPF (MPF, MSLN, SMR, megakaryocyte potentiating factor, mesothelin, GenBank accession no. NM-005823);

(6) Napi3b (NAPI-3B, NPTIIb, SLC34A2, solute carrier family 34 (sodium phosphate), member 2, type II sodium-dependent phosphate transporter 3b, GenBank accession no. NM-006424);

(7) Sema 5b (FLJ10372, KIAA1445, Mm.42015, SEMA5B, SEMAG, Semaphorin 5b Hlog, sema domain, seven thrombospondin repeats (type 1 and type 1-like), transmembrane domain (TM) and short cytoplasmic domain, (semaphorin) 5B, GenBank accession no. AB040878);

(8) PSCA hlg (2700050C12Rik, C530008016Rik, RIKEN cDNA 2700050C12, RIKEN cDNA 2700050C12 gene, GenBank accession no. AY358628);

(9) ETBR (Endothelin type B receptor, GenBank accession no. AY275463);

(10) MSG783 (RNF124, hypothetical protein FLJ20315, GenBank accession no. NM-017763);

(11) STEAP2 (HGNC-8639, IPCA-1, PCANAP1, STAMPI, STEAP2, STMP, prostate cancer associated gene 1, prostate cancer associated protein 1, six transmembrane epithelial antigen of prostate 2, six transmembrane prostate protein, GenBank accession no. AF455138);

(12) TrpM4 (BR22450, FLJ20041, TRPM4, TRPM4B, transient receptor potential cation channel, subfamily M, member 4, GenBank accession no. NM-017636);

(13) CRIPTO (CR, CR1, CRGF, CRIPTO, TDGF1, teratocarcinoma-derived growth factor, GenBank accession no. NP-003203 or NM-003212);

(14) CD21 (CR$^2$ (Complement receptor 2) or C3DR (C3d/Epstein Barr virus receptor) or Hs.73792 GenBank accession no. M26004);

(15) CD79b (CD79B, CD79β, IGb (immunoglobulin-associated beta), B29, GenBank accession no. NM-000626 or 11038674);

(16) FcRH2 (IFGP4, IRTA4, SPAP1A (SH2 domain containing phosphatase anchor protein 1a), SPAP1B, SPAP1C, GenBank accession no. NM-030764, AY358130);

(17) HER2 (ErbB2, GenBank accession no. M11730);

(18) NCA (CEACAM6, GenBank accession no. M18728);

(19) MDP (DPEP1, GenBank accession no. BC017023);

(20) IL20R.alpha. (IL20Ra, ZCYTOR7, GenBank accession no. AF184971);

(21) Brevican (BCAN, BEHAB, GenBank accession no. AF229053);

(22) EphB2R (DRT, ERK, HekS, EPHT3, Tyro5, GenBank accession no. NM-004442);

(23) ASLG659 (B7h, GenBank accession no. AX092328);

(24) PSCA (Prostate stem cell antigen precursor, GenBank accession no. AJ297436);

(25) GEDA (GenBank accession No. AY260763);

(26) BAFF-R (B cell-activating factor receptor, BLyS receptor 3, BR3, GenBank accession No. AF116456);

(27) CD22 (B-cell receptor CD22-B isoform, BL-CAM, Lyb-8, Lyb8, SIGLEC-2, FLJ22814, GenBank accession No. AK026467);

(28) CD79a (CD79A, CD79a, immunoglobulin-associated alpha, a B cell-specific protein that covalently interacts with Ig beta (CD79B) and forms a complex on the surface with Ig M molecules, transduces a signal involved in B-cell differentiation), pI: 4.84, MW: 25028 TM: 2 [P] Gene Chromosome: 19q13.2, GenBank accession No. NP-001774.10);

(29) CXCR5 (Burkitt's lymphoma receptor 1, a G protein-coupled receptor that is activated by the CXCL13 chemokine, functions in lymphocyte migration and humoral defense, plays a role in HIV-2 infection and perhaps development of AIDS, lymphoma, myeloma, and leukemia); 372 aa, pI: 8.54 MW: 41959 TM: 7 [P] Gene Chromosome: 11q23.3, GenBank accession No. NP-001707.1);

(30) HLA-DOB (Beta subunit of MHC class II molecule (Ia antigen) that binds peptides and presents them to CD4+T lymphocytes); 273 aa, pI: 6.56, MW: 30820.TM: 1 [P] Gene Chromosome: 6p21.3, GenBank accession No. NP-002111.1);

(31) P2X5 (Purinergic receptor P2X ligand-gated ion channel 5, an ion channel gated by extracellular ATP, may be involved in synaptic transmission and neurogenesis, deficiency may contribute to the pathophysiology of idiopathic detrusor instability); 422 aa), pI: 7.63, MW: 47206 TM: 1 [P] Gene Chromosome: 17p13.3, GenBank accession No. NP-002552.2);

(32) CD72 (B-cell differentiation antigen CD72, Lyb-2); 359 aa, pI: 8.66, MW: 40225, TM: 1 [P] Gene Chromosome: 9p13.3, GenBank accession No. NP-001773.1);

(33) LY64 (Lymphocyte antigen 64 (RP105), type I membrane protein of the leucine rich repeat (LRR) family, regulates B-cell activation and apoptosis, loss of function is associated with increased disease activity in patients with systemic lupus erythematosis); 661 aa, pI: 6.20, MW: 74147 TM: 1 [P] Gene Chromosome: 5q12, GenBank accession No. NP-005573.1);

(34) FcRH1 (Fc receptor-like protein 1, a putative receptor for the immunoglobulin Fc domain that contains C2 type Ig-like and ITAM domains, may have a role in B-lymphocyte differentiation); 429 aa, pI: 5.28, MW: 46925 TM: 1 [P] Gene Chromosome: 1q21-1q22, GenBank accession No. NP-443170.1);

(35) IRTA2 (Immunoglobulin superfamily receptor translocation associated 2, a putative immunoreceptor with possible roles in B cell development and lymphomagenesis; deregulation of the gene by translocation occurs in some B cell malignancies); 977 aa, pI: 6.88, MW: 106468, TM: 1 [P] Gene Chromosome: 1q21, GenBank accession Nos. Human: AF343662, AF343663, AF343664, AF343665, AF369794, AF397453, AK090423, AK090475, AL834187, AY358085; Mouse: AK089756, AY158090, AY506558; NP-112571.1; or

(36) TENB2 (TMEFF2, tomoregulin, TPEF, HPP1, TR, putative transmembrane proteoglycan, related to the EGF/heregulin family of growth factors and follistatin); 374 aa, NCBI Accession: AAD55776, AAF91397, AAG49451, NCBI RefSeq: NP-057276; NCBI Gene: 23671; OMIM: 605734; SwissProt Q9UIK5; GenBank accession No. AF179274; AY358907, CAF85723, CQ782436.

Other related or similar TAA's corresponding to the above listed TAA's can be found in scientific or patent literature, see US 2011-0256157 A1 (incorporated herein by reference).

The parent antibody may also be a fusion protein comprising an albumin-binding peptide (ABP) sequence (Denn is et al. (2002) "Albumin Binding As A General Strategy For Improving The Pharmacokinetics of Proteins," *J. Biol. Chem.* 277:35035-35043; WO 01/45746). Antibodies of the invention include fusion proteins with ABP sequences taught by: (i) Denn is et al. (2002) *J. Biol. Chem.* 277:35035-35043 at Tables III and IV, page 35038; (ii) US 2004/0001827 at [0076]; and (iii) WO 01/45746 at pages 12-13, and all of which are incorporated herein by reference.

In one embodiment, the antibody has been raised to target specific the tumor related antigen αvβ6.

The cell binding agent is connected to the linker. In one embodiment, the cell binding agent is connected to A, where present, of the linker.

In one embodiment, the connection between the cell binding agent and the linker is through a thioether bond.

In one embodiment, the connection between the cell binding agent and the linker is through a disulfide bond.

In one embodiment, the connection between the cell binding agent and the linker is through an amide bond.

In one embodiment, the connection between the cell binding agent and the linker is through an ester bond.

In one embodiment, the connection between the cell binding agent and the linker is formed between a thiol group of a cysteine residue of the cell binding agent and a maleimide group of the linker.

The cysteine residues of the cell binding agent may be available for reaction with the functional group of $R^L$ to form a connection. In other embodiments, for example where the cell binding agent is an antibody, the thiol groups of the antibody may participate in interchain disulfide bonds. These interchain bonds may be converted to free thiol groups by e.g., treatment of the antibody with DTT prior to reaction with the functional group of $R^L$.

The cell binding agent may be labelled, for example to aid detection or purification of the agent either prior to incorporation as a conjugate, or as part of the conjugate. The label may be a biotin label. In another embodiment, the cell binding agent may be labelled with a radioisotope.

$R^{1'}$ and $R^{3'}$

In one embodiment, $R^{1'}$ is independently selected from optionally substituted $C_{1-12}$ alkyl, $C_{3-20}$ heterocyclyl and $C_{5-20}$ aryl groups. These groups are each defined in the substituents section below.

In one embodiment, $R^{1'}$ is independently optionally substituted $C_{1-12}$ alkyl.

In one embodiment, $R^{1'}$ is independently optionally substituted $C_{3-20}$ heterocyclyl.

In one embodiment, $R^{1'}$ is independently optionally substituted $C_{5-20}$ aryl.

Described above in relation to $R^2$ or $R^{2'}$ are various embodiments relating to preferred alkyl and aryl groups and the identity and number of optional substituents. The preferences set out for $R^2$ or $R^{2'}$ as it applies to $R^{1'}$ are applicable, where appropriate, to all other groups $R^{1'}$, for examples where $R^6$, $R^7$, $R^8$ or $R^9$ is $R^{1'}$.

The preferences for $R^{1'}$ apply also to $R^{3'}$.

In some embodiments of the invention there is provided a compound having a substituent group —$NR^{1'}R^{3'}$. In one embodiment, $R^{1'}$ and $R^{3'}$ together with the nitrogen atom to which they are attached form an optionally substituted 4-, 5-, 6- or 7-membered heterocyclic ring. The ring may contain a further heteroatom, for example N, O or S.

In one embodiment, the heterocyclic ring is itself substituted with a group $R^{1'}$. Where a further N heteroatom is present, the substituent may be on the N heteroatom.

$R^{3''}$ $R^{3''}$ is a $C_{3-12}$ alkylene group, which chain may be interrupted by one or more heteroatoms, e.g., O, S, N(H), NMe and/or aromatic rings, e.g., benzene or pyridine, which rings are optionally substituted.

In one embodiment, $R^{3''}$ is a $C_{3-12}$ alkylene group, which chain may be interrupted by one or more heteroatoms and/or aromatic rings, e.g., benzene or pyridine.

In one embodiment, the alkylene group is optionally interrupted by one or more heteroatoms selected from O, S, and NMe and/or aromatic rings, which rings are optionally substituted. In one embodiment, the aromatic ring is a $C_{5-20}$ arylene group, where arylene pertains to a divalent moiety obtained by removing two hydrogen atoms from two aromatic ring atoms of an aromatic compound, which moiety has from 5 to 20 ring atoms.

In one embodiment, $R^{3''}$ is a $C_{3-12}$ alkylene group, which chain may be interrupted by one or more heteroatoms, e.g., O, S, N(H), NMe and/or aromatic rings, e.g., benzene or pyridine, which rings are optionally substituted by $NH_2$.

In one embodiment, $R^{3'''}$ is a $C_{3-12}$ alkylene group.

In one embodiment, $R^{3'''}$ is selected from a $C_3$, $C_5$, $C_7$, $C_9$ and a $C_{11}$ alkylene group.

In one embodiment, $R^{3'''}$ is selected from a $C_3$, $C_5$ and a $C_7$ alkylene group.

In one embodiment, $R^{3'''}$ is selected from a $C_3$ and a $C_5$ alkylene group.

In one embodiment, $R^{3'''}$ is a $C_3$ alkylene group.
In one embodiment, $R^{3'''}$ is a $C_4$ alkylene group.
In one embodiment, $R^{3'''}$ is a $C_5$ alkylene group.

The alkylene groups listed above may be optionally interrupted by one or more heteroatoms and/or aromatic rings, e.g., benzene or pyridine, which rings are optionally substituted.

The alkylene groups listed above may be optionally interrupted by one or more heteroatoms and/or aromatic rings, e.g., benzene or pyridine.

The alkylene groups listed above may be unsubstituted linear aliphatic alkylene groups.

X'

In one embodiment, X' is selected from O, S, or N(H).
Preferably, X' is O.

Conjugates

In one embodiment, the conjugate is a dimer with one monomer being of formula (IIIa) or (IIIb), and the other monomer being of formula (IVa) or (IVb).

In one embodiment, the conjugate is a dimer with a monomer of formula (IIIa) and a monomer of formula (IVa), with the structure shown below:

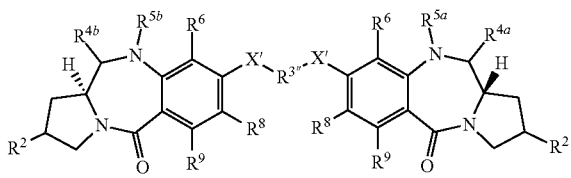

where $R^2$, $R^6$, $R^8$, $R^9$, $R^{4a}$, $R^{5a}$, $R^{4b}$, $R^{5b}$, X' and $R^{3'''}$ are as defined above for the dimer with a monomer of formula (IIIa) and a monomer of formula (IVa). In one embodiment, $R^{4b}$ is $QR^{11'}$ as defined herein.

In a related embodiment, $R^{5a}$ is a capping group $R^{cc}$, and optionally, $R^{4b}$ is $QR^{11'}$, and the conjugate has the following structure:

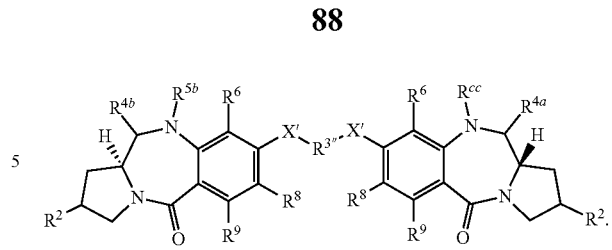

In one embodiment, the conjugate is a dimer with a monomer of formula (IIIb) and a monomer of formula (IVb), with the structure shown below:

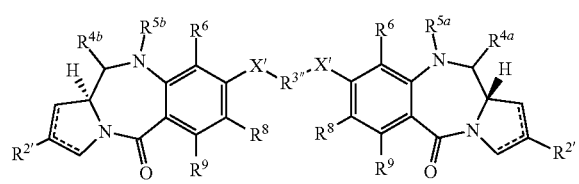

where $R^{2'}$, $R^6$, $R^8$, $R^9$, $R^{4a}$, $R^{5a}$, $R^{4b}$, $R^{5b}$, X' and $R^{3'''}$ are as defined above for the dimer with a monomer of formula (IIIb) and a monomer of formula (IVb). In one embodiment, $R^{4b}$ is $QR^{11'}$ as defined herein.

In a related embodiment, $R^{5a}$ is a capping group $R^{cc}$, and optionally, $R^{4b}$ is $QR^{11'}$, and the conjugate has the following structure:

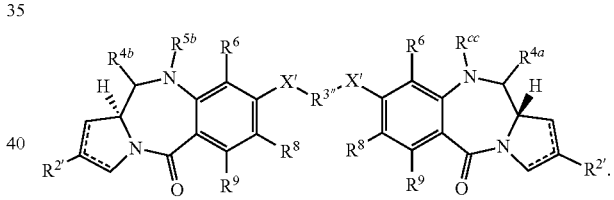

In one embodiment, the conjugate is a dimer with a monomer of formula (V) and a monomer of formula (VI), with the structure shown below:

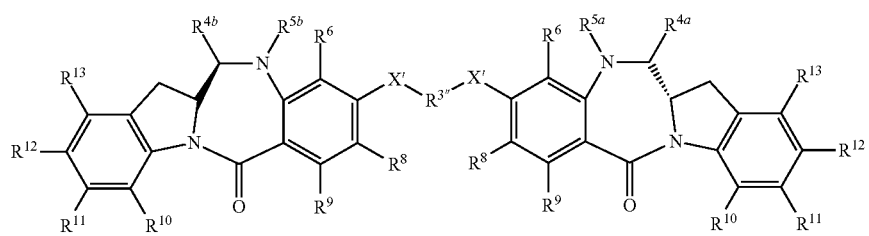

where $R^{10}$-$R^{13}$, $R^6$, $R^8$, $R^9$, $R^{4a}$, $R^{5a}$, $R^{4b}$, $R^{5b}$, X' and $R^{3'''}$ are as defined above for the dimer with a monomer of formula (V) and a monomer of formula (VI). In one embodiment, $R^{4b}$ is $QR^{11'}$ as defined herein.

In a related embodiment, $R^{5a}$ is a capping group $R^{cc}$, and optionally, $R^{4b}$ is $QR^{11'}$, and the conjugate has the following structure:

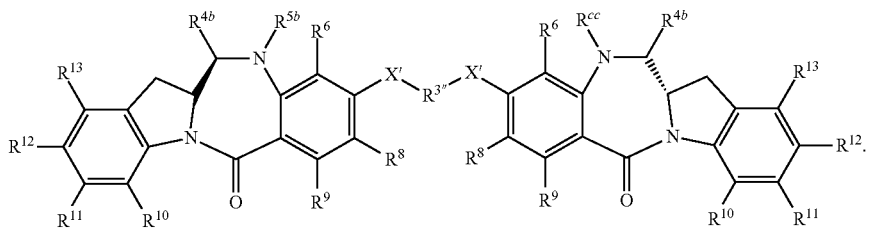

In one embodiment, the conjugate is a dimer with a monomer of formula (VII) and a monomer of formula (VIII), with the structure shown below:

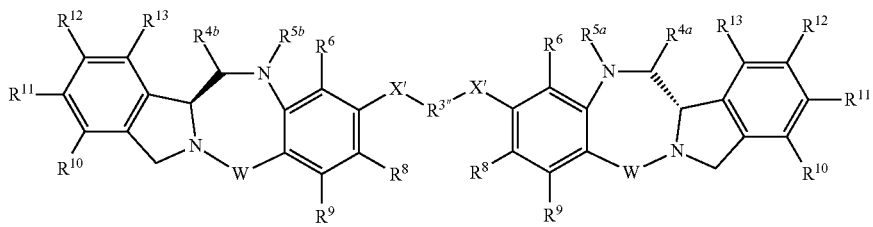

where $R^{10}$-$R^{13}$, $R^6$, $R^8$, $R^9$, $R^{4a}$, $R^{5a}$, $R^{4b}$, $R^{5b}$, X' and $R^{3''}$ are as defined above for the dimer with a monomer of formula (VII) and a monomer of formula (VIII). In one embodiment, $R^{4b}$ is $QR^{11'}$ as defined herein.

In a related embodiment, $R^{5a}$ is a capping group $R^{cc}$, and optionally, $R^{4b}$ is $QR^{11'}$, and the conjugate has the following structure:

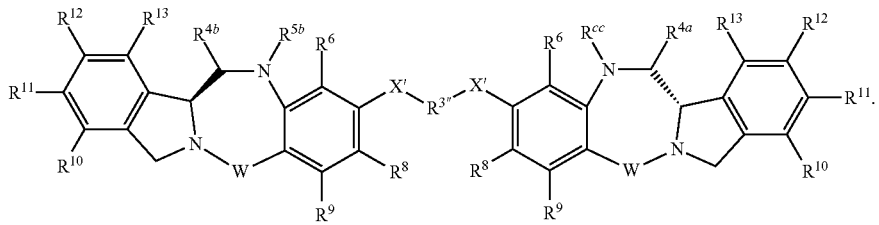

$R^{cc}$—Capping Group

The conjugate of the first aspect of the invention may have a capping group $R^{cc}$ at the N10 position.

In one embodiment, where the conjugate is a dimer, the group $R^{5a}$ in one of the monomer units may be a capping group $R^{cc}$, and the other monomer has a group $R^{5b}$ at the corresponding N10 position.

In one embodiment, the group $R^L$ in one of the monomer units of a dimer is a linker with a reactive group for connection to a cell binding agent, while the other monomer has a capping group $R^{cc}$ at the corresponding N10 position.

In one embodiment, the group $R^L$ in one of the monomer units of a dimer is the capping group $R^{cc}$, wherein $R^{cc}$ is a protecting group, the removal of which exposes a linker with a reactive group for connection to a cell binding agent.

In one embodiment, $R^{cc}$ may be a protecting group that is removable to leave an N10-C11 imine bond, a carbinolamine, a substituted cabinolamine, or, where $R^{4b}$ or $QR^{11'}$ is —$OSO_3M$, a bisulfite adduct. In one embodiment, $R^{cc}$ is a protecting group that is removable to leave an N10-C11 imine bond.

Where the group $R^{cc}$ is intended to be removable, it is removable under the same conditions as those required for the removal of the group $R^{5b}$, for example to yield an N10-C11 imine bond, a carbinolamine and so on. The capping group acts as a protecting group for the intended functionality at the N10 position. The capping group is intended not to be reactive towards a cell binding agent. For example, $R^{cc}$ is not the same as $R^L$.

Compounds having a capping group may be used as intermediates in the synthesis of dimers having an imine monomer. Alternatively, the capping group may be referred to as a therapeutically removable nitrogen protecting group, as defined in WO 00/12507, incorporated herein by reference.

In one embodiment, where the group $R^{cc}$ is intended to be removable, it is removable under the conditions that cleave the $R^L$ group or the $R^{5b}$ group. Thus, in this embodiment, the capping group may be cleavable by the action of an enzyme.

In an alternative embodiment, the capping group is removable prior to the connection of the linker $R^L$ to the cell binding agent (e.g., removing the capping group as a protecting group to create a linker group $R^L$). In this embodiment, the capping group is removable under conditions that do not cleave the linker $R^L$.

Thus the capping group may be used as part of a protecting group strategy to ensure that only one of the monomer units in a dimer is connected to a cell binding agent.

The capping group $R^{cc}$ may be an N10 protecting group, such as those groups described in WO 00/12507 (incorporated herein). In one embodiment, $R^{cc}$ is a therapeutically removable nitrogen protecting group, as defined in WO 00/12507.

In one embodiment, $R^{cc}$ is a carbamate protecting group.

In one embodiment, the carbamate protecting group is selected from: Alloc, Fmoc, Boc, Troc, Teoc, Psec, Cbz and PNZ.

Optionally, the carbamate protecting group is further selected from Moc.

In one embodiment, $R^{cc}$ is a linker group $R^L$ lacking the functional group for connection to the cell binding agent.

This application is particularly concerned with those $R^{cc}$ groups which are carbamates.

In one embodiment, $R^{cc}$ is a group:

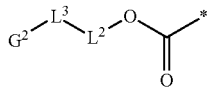

where the asterisk indicates the point of attachment to the N10 position, $G^2$ is a terminating group, $L^3$ is a covalent bond or a cleavable linker $L^1$, $L^2$ is a covalent bond or together with OC(=O) forms a self-immolative linker.

Where $L^3$ and $L^2$ are both covalent bonds, $G^2$ and OC(=O) together form a carbamate protecting group as defined above.

$L^1$ is as defined above in relation to $R^{5b}$. $L^2$ is as defined above in relation to $R^{5b}$.

Various terminating groups are described below, including those based on well-known protecting groups.

In one embodiment $L^3$ is a cleavable linker $L^1$, and $L^2$, together with OC(=O), forms a self-immolative linker. In this embodiment, $G^2$ is Ac (acetyl) or Moc, or a carbamate protecting group selected from: Alloc, Fmoc, Boc, Troc, Teoc, Psec, Cbz and PNZ.

Optionally, the carbamate protecting group is further selected from Moc.

In another embodiment, $G^2$ is an acyl group —C(=O)$G^3$, where $G^3$ is selected from alkyl (including cycloalkyl, alkenyl and alkynyl), heteroalkyl, heterocyclyl and aryl (including heteroaryl and carboaryl). These groups may be optionally substituted. The acyl group together with an amino group of $L^3$ or $L^2$, where appropriate, may form an amide bond. The acyl group together with a hydroxy group of $L^3$ or $L^2$, where appropriate, may form an ester bond.

In one embodiment, $G^3$ is heteroalkyl. The heteroalkyl group may comprise polyethylene glycol. The heteroalkyl group may have a heteroatom, such as O or N, adjacent to the acyl group, thereby forming a carbamate or carbonate group, where appropriate, with a heteroatom present in the group $L^3$ or $L^2$, where appropriate.

In one embodiment, $G^3$ is selected from $NH_2$, $NHR^{1'}$ and $NR^{1'}R^{3'}$. Preferably, $G^3$ is $NR^{1'}R^{3'}$.

In one embodiment $G^2$ is the group:

where the asterisk indicates the point of attachment to $L^3$, n is 0 to 6 and $G^4$ is selected from OH, $OR^{1'}$, SH, $SR^{1'}$, $COOR^{1'}$, $CONH_2$, $CONHR^{1'}$, $CONR^{1'}R^{3'}$, $NH_2$, $NHR^{1'}$, $NR^{1'}R^{3'}$, $NO_2$, and halo. The groups OH, SH, $NH_2$ and $NHR^{1'}$ are protected. In one embodiment, n is 1 to 6, and preferably n is 5. In one embodiment, $G^4$ is $OR^{1'}$, $SR^{1'}$, $COOR^{1'}$, $CONH_2$, $CONHR^{1'}$, $CONR^{1'}R^{3'}$, and $NR^{1'}R^{3'}$. In one embodiment, $G^4$ is $OR^{1'}$, $SR^{1'}$, and $NR^{1'}R^{3'}$. Preferably $G^4$ is selected from $OR^{1'}$ and $NR^{1'}R^{3'}$, most preferably $G^4$ is $OR^{1'}$. Most preferably $G^4$ is OMe.

In one embodiment, the group $G^2$ is:

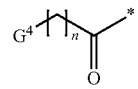

where the asterisk indicates the point of attachment to $L^3$, and n and $G^4$ are as defined above.

In one embodiment, the group $G^2$ is:

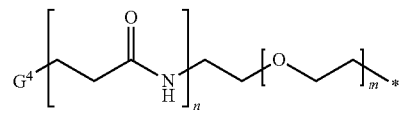

where the asterisk indicates the point of attachment to $L^3$, n is 0 or 1, m is 0 to 50, and $G^4$ is selected from OH, $OR^{1'}$, SH, $SR^{1'}$, $COOR^{1'}$, $CONH_2$, $CONHR^{1'}$, $CONR^{1'}R^{3'}$, $NH_2$, $NHR^{1'}$, $NR^{1'}R^{3'}$, $NO_2$, and halo. In a preferred embodiment, n is 1 and m is 0 to 10, 1 to 2, preferably 4 to 8, and most preferably 4 or 8. In another embodiment, n is 1 and m is 10 to 50, preferably 20 to 40. The groups OH, SH, $NH_2$ and $NHR^{1'}$ are protected. In one embodiment, $G^4$ is $OR^{1'}$, $SR^{1'}$, $COOR^{1'}$, $CONH_2$, $CONHR^{1'}$, $CONR^{1'}R^{3'}$, and $NR^{1'}R^{3'}$. In one embodiment, $G^4$ is $OR^{1'}$, $SR^{1'}$, and $NR^{1'}R^{3'}$. Preferably $G^4$ is selected from $OR^{1'}$ and $NR^{1'}R^{3'}$, most preferably $G^4$ is $OR^{1'}$. Preferably $G^4$ is OMe.

In one embodiment, the group $G^2$ is:

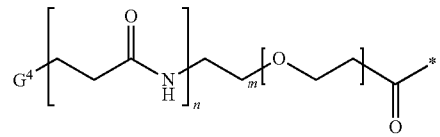

where the asterisk indicates the point of attachment to $L^3$, and n, m and $G^4$ are as defined above.

In one embodiment, the group $G^2$ is:

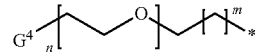

where n is 1-20, m is 0-6, and $G^4$ is selected from OH, $OR^{1'}$, SH, $SR^{1'}$, $COOR^{1'}$, $CONH_2$, $CONHR^{1'}$, $CONR^{1'}R^{3'}$, $NH_2$, $NHR^{1'}$, $NR^{1'}R^{3'}$, $NO_2$, and halo. In one embodiment, n is 1-10. In another embodiment, n is 10 to 50, preferably 20 to 40. In one embodiment, n is 1. In one embodiment, m is 1. The groups OH, SH, NH2 and $NHR^{1'}$ are protected. In one embodiment, $G^4$ is $OR^{1'}$, $SR^{1'}$, $COOR^{1'}$, $CONH_2$, $CONHR^{1'}$, $CONR^{1'}R^{3'}$, and $NR^{1'}R^{3'}$. In one embodiment, $G^4$ is $OR^{1'}$, $SR^{1'}$, and $NR^{1'}R^{3'}$. Preferably $G^4$ is selected from $OR^{1'}$ and $NR^{1'}R^{3'}$, most preferably $G^4$ is $OR^{1'}$. Preferably $G^4$ is OMe.

In one embodiment, the group $G^2$ is:

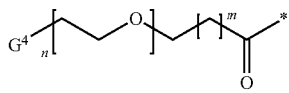

where the asterisk indicates the point of attachment to $L^3$, and n, m and $G^4$ are as defined above.

In each of the embodiments above, $G^4$ may be OH, SH, $NH_2$ and $NHR^{1'}$. These groups are preferably protected.

In one embodiment, OH is protected with Bzl, TBDMS, or TBDPS.

In one embodiment, SH is protected with Acm, Bzl, Bzl-OMe, Bzl-Me, or Trt.

In one embodiment, $NH_2$ or $NHR^{1'}$ are protected with Boc, Moc, Z—Cl, Fmoc, Z, or Alloc.

In one embodiment, the group $G^2$ is present in combination with a group $L^3$, which group is a dipeptide.

The capping group is not intended for connection to the cell binding agent. Thus, the other monomer present in the dimer serves as the point of connection to the cell binding agent via a linker. Accordingly, it is preferred that the functionality present in the capping group is not available for reaction with a cell binding agent. Thus, reactive functional groups such as OH, SH, $NH_2$, COOH are preferably avoided. However, such functionality may be present in the capping group if protected, as described above.

In the preparation of the compounds of the invention the capping group may be used to prepare a linker $R^L$.

An exemplary embodiment of an antibody-drug conjugate (ADC) compound comprises an antibody (Ab), and a PBD drug moiety (PBD) wherein the antibody is attached by a linker moiety (L) to PBD; the composition having the formula:

Ab-(L-PBD)$_p$ where p is an integer from 1 to about 8, and represents the drug loading. If Ab is a cysteine engineered antibody, the number of drug moieties which may be conjugated via a thiol reactive linker moiety to an antibody molecule is limited by the number of cysteine residues which are introduced by the methods described herein. Exemplary ADC therefore comprise antibodies which have 1, 2, 3, or 4 engineered cysteine amino acids.

Preferred Compounds

In one embodiment, the conjugate is a dimer wherein each of the monomers has a C2 methylene group i.e., $=CH_2$. It is preferred that the cell binding agent is an antibody.

In another embodiment, the conjugate is a dimer wherein each of the monomers has a C2 aryl group, i.e., each $R^2$ or $R^{2'}$ is optionally substituted $C_{5-20}$ aryl. It is preferred that the cell binding agent is an antibody.

C2 Alkylene

In one embodiment, the conjugate is a compound:

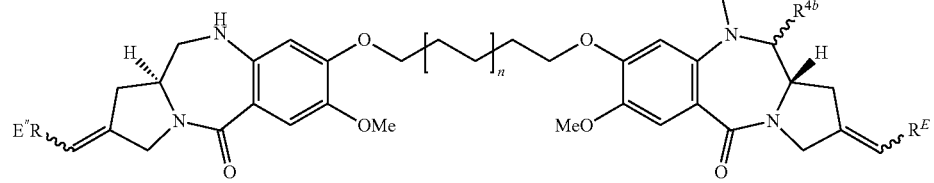

wherein CBA is a cell binding agent such as an antibody or a cyclic or linear peptide, and n is 0 or 1. $L^1$ and $L^2$ are as previously defined, and $R^E$ and $R^{E''}$ are each independently selected from H or $R^a$. $R^{4b}$ is as described above. In a specific embodiment, X is —H, —$OR^{6'}$, —$SO_3M$, or —$OSO_3M$, wherein $R^{6'}$ and M are as described above. In another specific embodiment, X is —H. Alternatively, X is —OH.

In one embodiment, the conjugate is a compound:

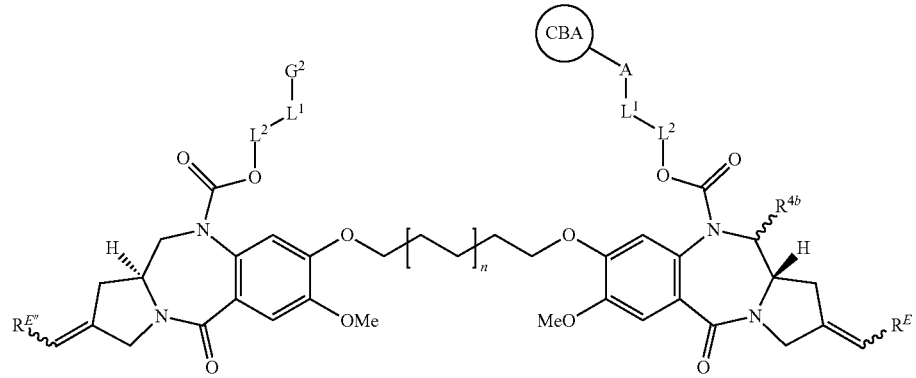

wherein CBA is a cell binding agent such as an antibody or a cyclic or linear peptide, and n is 0 or 1. $L^1$, $L^2$ and $G^2$ are as previously defined, and $R^E$ and $R^{E''}$ are each independently selected from H or $R^a$. $R^{4b}$ is as described above. In a specific embodiment, X is —H, —$OR^{6'}$, —$SO_3M$, or —$OSO_3M$, wherein $R^{6'}$ and M are as described above. In another specific embodiment, X is —H. Alternatively, X is —OH.

In one embodiment, the conjugate is a compound:

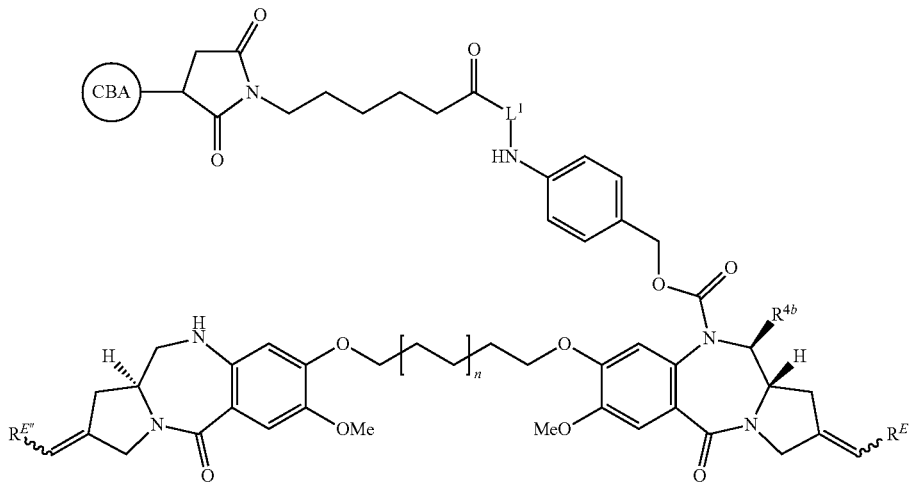

wherein CBA is a cell binding agent such as an antibody or a cyclic or linear peptide, and n is 0 or 1. $L^1$ is as previously defined, and $R^E$ and $R^{E''}$ are each independently selected from H or $R^a$. $R^{4b}$ is as described above. In a specific embodiment, $R^{4b}$ is —H, —$OR^{6'}$, —$SO_3M$, or —$OSO_3M$, wherein $R^{6'}$ and M are as described above. In another specific embodiment, $R^{4b}$ is —H. Alternatively, $R^{4b}$ is —OH.

In one embodiment, the conjugate is a compound:

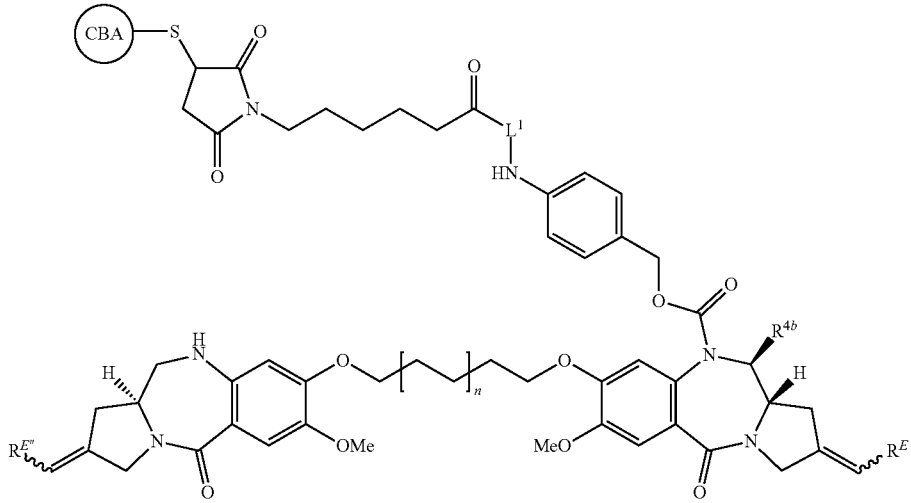

wherein CBA is a cell binding agent such as an antibody or a cyclic or linear peptide, and n is 0 or 1. $L^1$ is as previously defined, and $R^E$ and $R^{E''}$ are each independently selected from H or $R^a$. $R^{4b}$ is as described above. In a specific embodiment, $R^{4b}$ is —H, —$OR^{6'}$, —$SO_3M$, or —$OSO_3M$, wherein $R^{6'}$ and M are as described above. In another specific embodiment, $R^{4b}$ is —H. Alternatively, $R^{4b}$ is —OH.

In one embodiment, the conjugate is a compound:

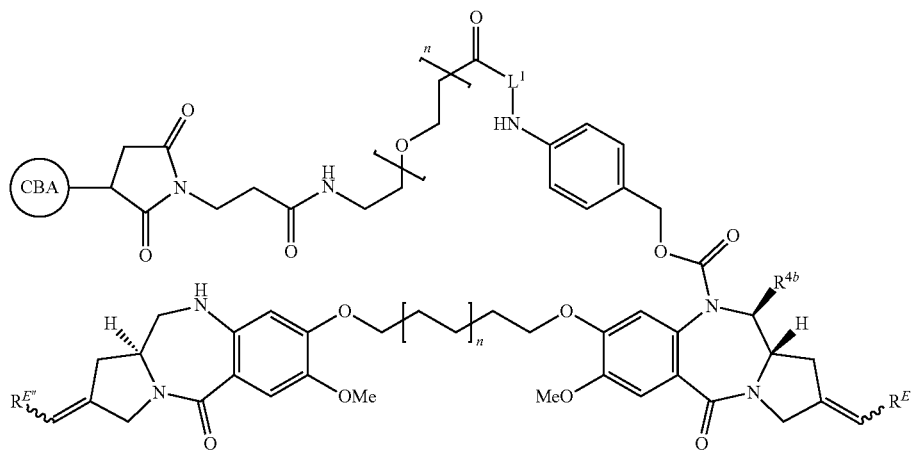

wherein CBA is a cell binding agent such as an antibody or a cyclic or linear peptide, and n is 0 or 1. $L^1$ is as previously defined, and $R^E$ and $R^{E''}$ are each independently selected from H or $R^a$. $R^{4b}$ is as described above. In a specific embodiment, $R^{4b}$ is —H, —$OR^{6'}$, —$SO_3M$, or —$OSO_3M$, wherein $R^{6'}$ and M are as described above. In another specific embodiment, $R^{4b}$ is —H. Alternatively, $R^{4b}$ is —OH.

In one embodiment, the conjugate is a compound:

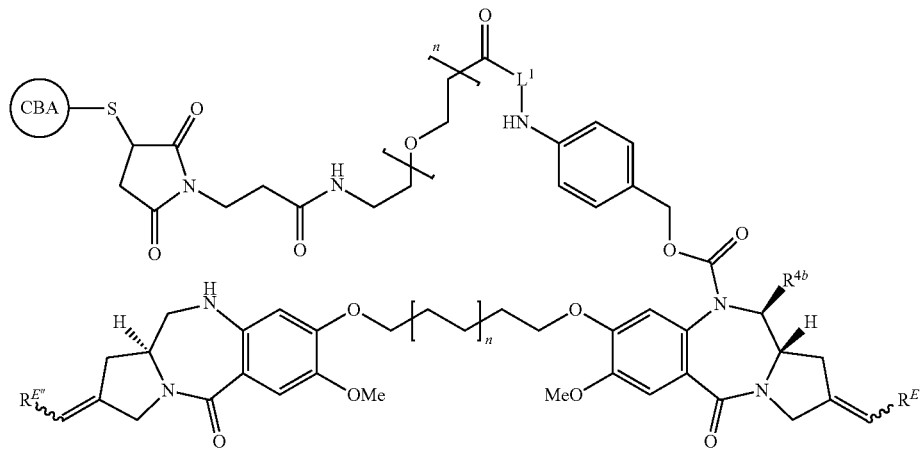

wherein CBA is a cell binding agent such as an antibody or a cyclic or linear peptide, and n is 0 or 1. $L^1$ is as previously defined, and $R^E$ and $R^{E''}$ are each independently selected from H or $R^a$. $R^{4b}$ is as described above. In a specific embodiment, $R^{4b}$ is —H, —$OR^{6'}$, —$SO_3M$, or —$OSO_3M$, wherein $R^{6'}$ and M are as described above. In another specific embodiment, $R^{4b}$ is —H. Alternatively, $R^{4b}$ is —OH.

For each of the compounds above, the following preferences may apply, where appropriate: n is 0; n is 1; $R^E$ is H; $R^E$ is $R^a$, where $R^a$ is optionally substituted alkyl; $R^E$ is $R^a$, where $R^a$ is methyl; CBA is an antibody; CBA is a cyclic peptide; L is or comprises a dipeptide; $L^1$ is ($H_2N$)-Val-Ala-(CO) or ($H_2N$)-Phe-Lys-(CO), where ($H_2N$) and (CO) indicate the respective N and C terminals; $L^2$ is p-aminobenzylene; $G^2$ is selected from Alloc, Fmoc, Boc, Troc, Teoc, Psec, Cbz and PNZ.

The following preferences may also apply in addition to the preferences above:

$G^2$ is:

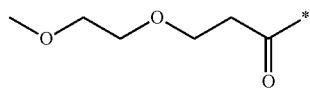

where the asterisk indicates the point of attachment to the N terminal of $L^1$;

A is:

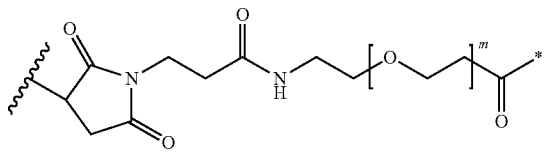

where the asterisk indicates the point of attachment to the N terminal of $L^1$, the wavy line indicates the point of attachment to the cell binding agent and m is 4 or 8;

A is:

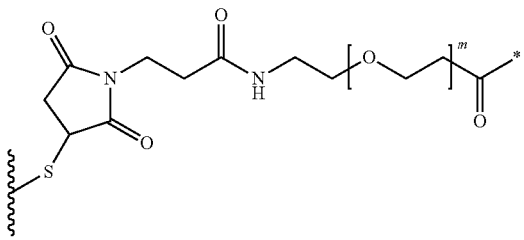

where the asterisk indicates the point of attachment to the N terminal of $L^1$, the wavy line indicates the point of attachment to the cell binding agent, and m is 4 or 8.

In a particularly preferred embodiment, n is 1; $R^E$ is H; CBA is an antibody; $L^1$ is $(H_2N)$-Val-Ala-(CO) or $(H_2N)$-Phe-Lys-(CO), where $(H_2N)$ and (CO) indicate the respective N and C terminals; $L^2$ is p-aminobenzylene;

$G^2$ is:

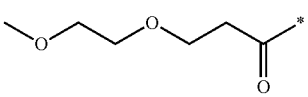 [SMILES: *C(=O)CCOCCOC]

where the asterisk indicates the point of attachment to the N terminal of L; and A is:

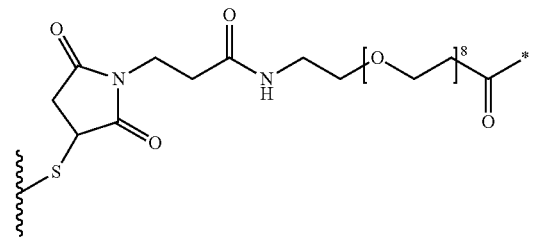

where the asterisk indicates the point of attachment to the N terminal of $L^1$, and the wavy line indicates the point of attachment to the cell binding agent.

C2 Aryl

In one embodiment, the conjugate is a compound:

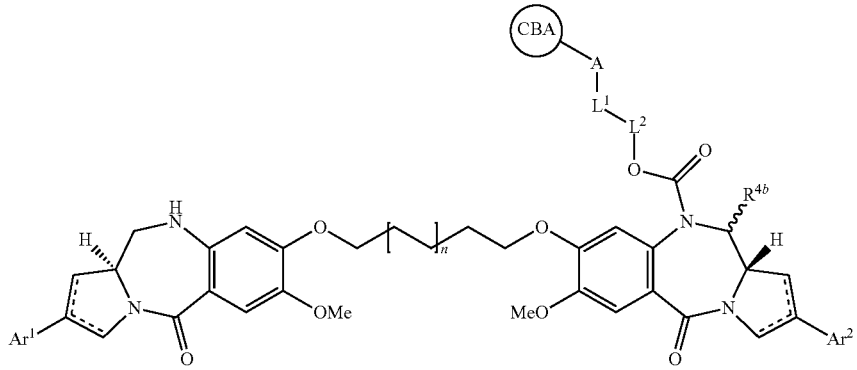

wherein CBA is a cell binding agent such as an antibody or a cyclic or linear peptide, $L^1$ and $L^2$ are as previously defined $Ar^1$ and $Ar^2$ are each independently optionally substituted $C_{5-20}$ aryl, and n is 0 or 1. $Ar^1$ and $Ar^2$ may be the same or different. $R^{4b}$ is as described above. In a specific embodiment, $R^{4b}$ is —H, —$OR^{6'}$, —$SO_3M$, or —$OSO_3M$, wherein $R^{6'}$ and M are as described above. In another specific embodiment, $R^{4b}$ is —H. Alternatively, $R^{4b}$ is —OH.

In one embodiment, the conjugate is a compound:

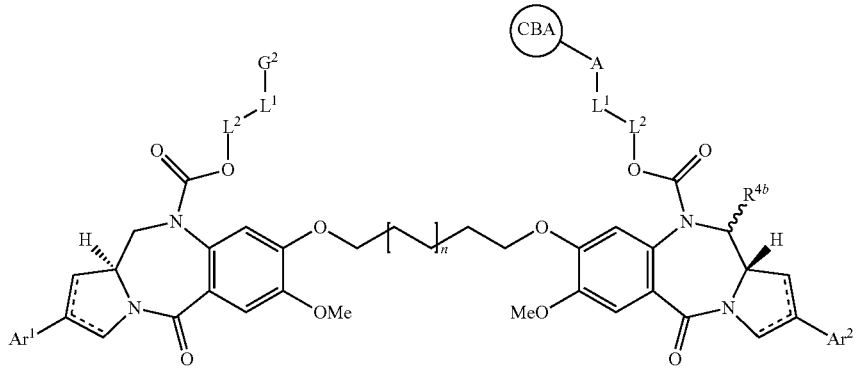

wherein CBA is a cell binding agent such as an antibody or a cyclic or linear peptide, $L^1$, $L^2$ and G2 are as previously defined, $Ar^1$ and $Ar^2$ are each independently optionally substituted $C_{5-20}$ aryl, and n is 0 or 1. $R^{4b}$ is as described above. In a specific embodiment, $R^{4b}$ is —H, —$OR^{6'}$, —$SO_3M$, or —$OSO_3M$, wherein $R^{6'}$ and M are as described above. In another specific embodiment, $R^{4b}$ is —H. Alternatively, $R^{4b}$ is —OH.

In one embodiment, the conjugate is a compound:

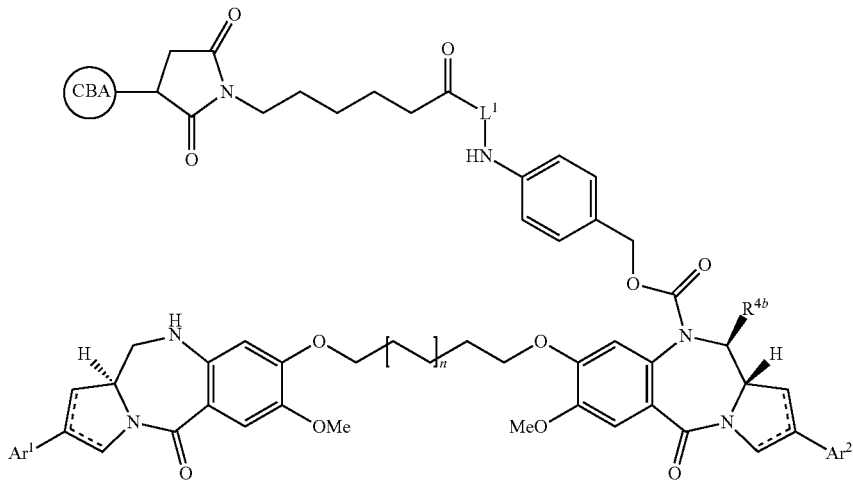

30 wherein CBA is a cell binding agent such as an antibody or a cyclic or linear peptide, $L^1$ is as previously defined, $Ar^1$ and $Ar^2$ are each independently optionally substituted $C_{5-20}$ aryl, and n is 0 or 1. $R^{4b}$ is as described above. In a specific embodiment, $R^{4b}$ is —H, —$OR^{6'}$—$SO_3M$, or —$OSO_3M$, wherein $R^{6'}$ and M are as described above. In another specific embodiment, $R^{4b}$ is —H. Alternatively, $R^{4b}$ is —OH.

In one embodiment, the conjugate is a compound:

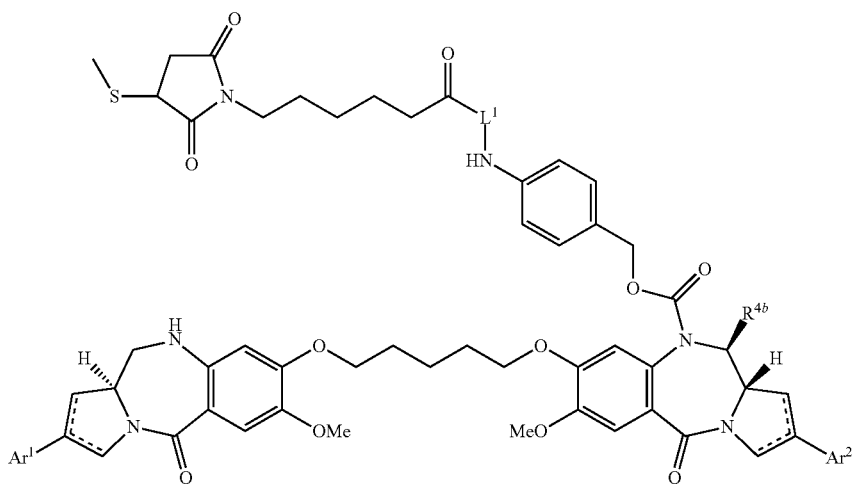

wherein CBA is a cell binding agent such as an antibody or a cyclic or linear peptide, $L^1$ is as previously defined, $Ar^1$ and $Ar^2$ are each independently optionally substituted $C_{5-20}$ aryl, and n is 0 or 1. $R^{4b}$ is as described above. In a specific embodiment, $R^{4b}$ is —H, —$OR^{6'}$—$SO_3M$, or —$OSO_3M$, wherein $R^{6'}$ and M are as described above. In another specific embodiment, $R^{4b}$ is —H. Alternatively, $R^{4b}$ is —OH.

In one embodiment, the conjugate is a compound:

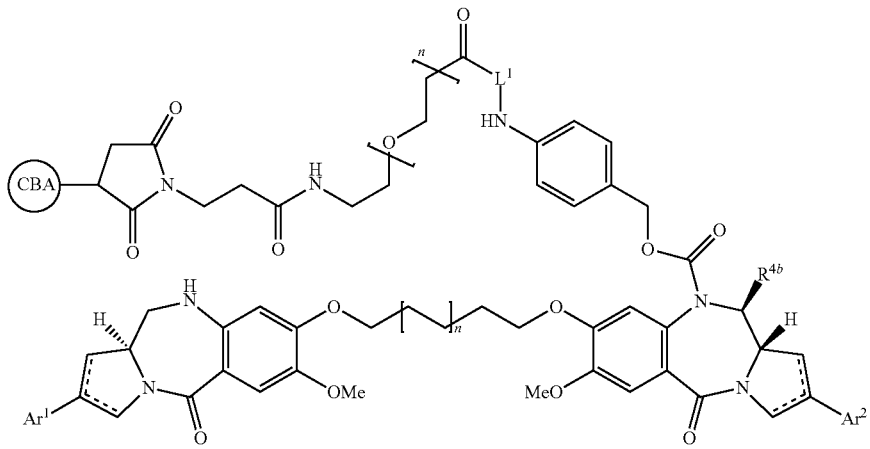

wherein CBA is a cell binding agent such as an antibody or a cyclic or linear peptide, and n is 0 or 1. $L^1$ is as previously defined, $Ar^1$ and $Ar^2$ are each independently optionally substituted $C_{5-20}$ aryl, and n is 0 or 1. $R^{4b}$ is as described above. In a specific embodiment, $R^{4b}$ is —H, —$OR^{6'}$, —$SO_3M$, or —$OSO_3M$, wherein $R^{6'}$ and M are as described above. In another specific embodiment, $R^{4b}$ is —H. Alternatively, $R^{4b}$ is —OH.

In one embodiment, the conjugate is a compound:

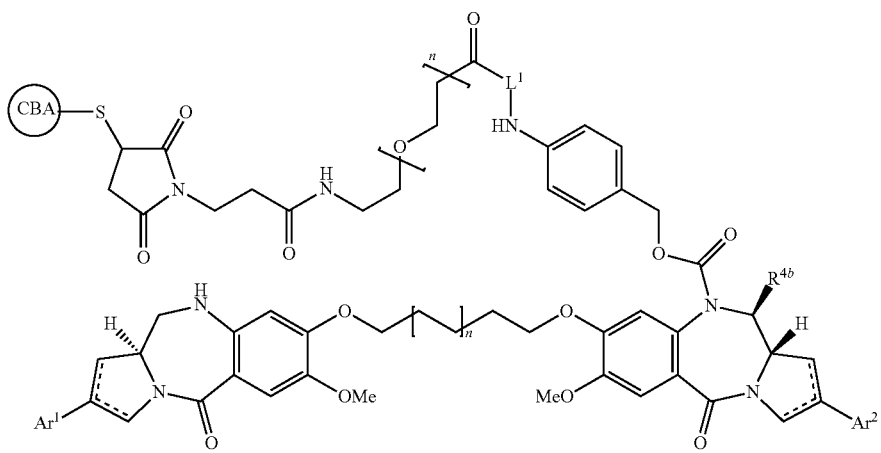

wherein CBA is a cell binding agent such as an antibody or a cyclic or linear peptide, and n is 0 or 1. $L^1$ is as previously defined, $Ar^1$ and $Ar^2$ are each independently optionally substituted $C_{5-20}$ aryl, and n is 0 or 1. $R^{4b}$ is as described above. In a specific embodiment, $R^{4b}$ is —H, —$OR^{6'}$, —$SO_3M$, or —$OSO_3M$, wherein $R^{6'}$ and M are as described above. In another specific embodiment, $R^{4b}$ is —H. Alternatively, $R^{4b}$ is —OH.

In one embodiment, $Ar^1$ and $Ar^2$ in each of the embodiments above are each independently selected from optionally substituted phenyl, furanyl, thiophenyl and pyridyl.

In one embodiment, $Ar^1$ and $Ar^2$ in each of the embodiments above is optionally substituted phenyl.

In one embodiment, $Ar^1$ and $Ar^2$ in each of the embodiments above is optionally substituted thiophen-2-yl or thiophen-3-yl.

In one embodiment, $Ar^1$ and $Ar^2$ in each of the embodiments above is optionally substituted quinolinyl or isoquinolinyl.

The quinolinyl or isoquinolinyl group may be bound to the PBD/IBD core through any available ring position. For example, the quinolinyl may be quinolin-2-yl, quinolin-3-yl, quinolin-4yl, quinolin-5-yl, quinolin-6-yl, quinolin-7-yl and quinolin-8-yl. Of these quinolin-3-yl and quinolin-6-yl may be preferred. The isoquinolinyl may be isoquinolin-1-yl, isoquinolin-3-yl, isoquinolin-4yl, isoquinolin-5-yl, isoquinolin-6-yl, isoquinolin-7-yl and isoquinolin-8-yl. Of these isoquinolin-3-yl and isoquinolin-6-yl may be preferred.

C2 Vinyl

In one embodiment, the conjugate is a compound:

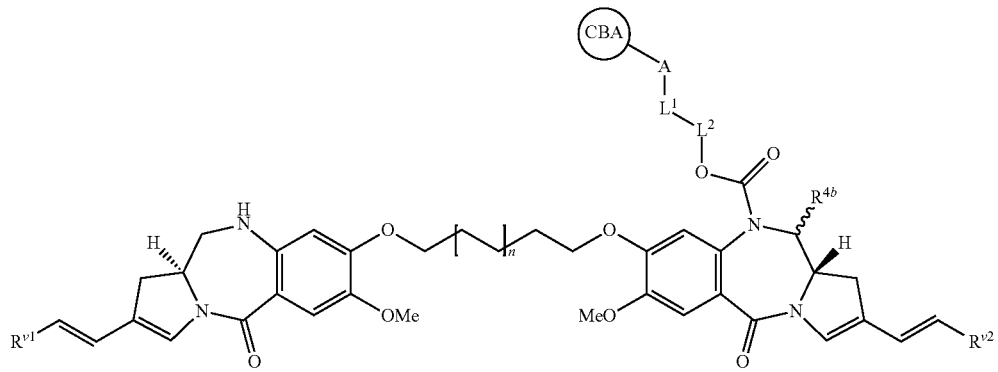

wherein CBA is a cell binding agent such as an antibody or a cyclic or linear peptide, $L^1$ and $L^2$ are as previously defined, $R^{V1}$ and $R^{V2}$ are independently selected from H, methyl, ethyl and phenyl (which phenyl may be optionally substituted with fluoro, particularly in the 4 position) and C5-6 heterocyclyl, and n is 0 or 1. $R^{V1}$ and $R^{V2}$ may be the same or different. $R^{4b}$ is as described above. In a specific embodiment, $R^{4b}$ is —H, —OR$^{6'}$, —SO$_3$M, or —OSO$_3$M, wherein $R^{6'}$ and M are as described above. In another specific embodiment, $R^{4b}$ is —H. Or, $R^{4b}$ is —OH.

In one embodiment, the conjugate is a compound:

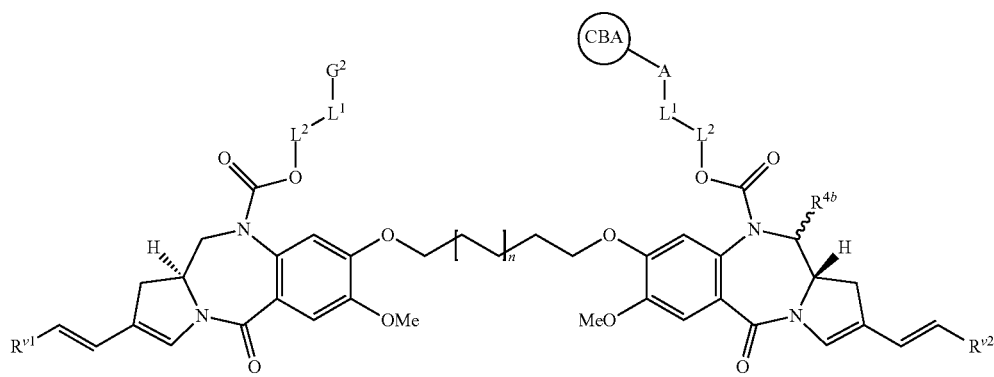

wherein CBA is a cell binding agent such as an antibody or a cyclic or linear peptide, $L^1$, $L^2$ and G2 are as previously defined, $R^{V1}$ and $R^{V2}$ are independently selected from H, methyl, ethyl and phenyl (which phenyl may be optionally substituted with fluoro, particularly in the 4 position) and $C_{5-6}$ heterocyclyl, and n is 0 or 1. $R^{V1}$ and $R^{V2}$ may be the same or different. $R^{4b}$ is as described above. In a specific embodiment, $R^{4b}$ is —H, —OR$^{6'}$—SO$_3$M, or —OSO$_3$M, wherein $R^{6'}$ and M are as described above. In another specific embodiment, $R^{4b}$ is —H. Alternatively, $R^{4b}$ is —OH.

In one embodiment, the conjugate is a compound:

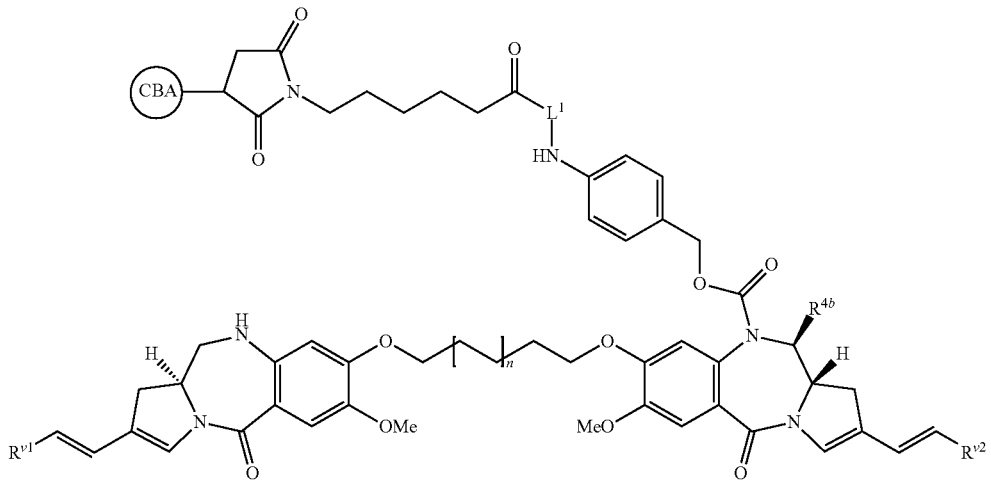

wherein CBA is a cell binding agent such as an antibody or a cyclic or linear peptide, $L^1$ is as previously defined, $R^{v1}$ and $R^{v2}$ are independently selected from H, methyl, ethyl and phenyl (which phenyl may be optionally substituted with fluoro, particularly in the 4 position) and $C_{5-6}$ heterocyclyl, and n is 0 or 1. $R^{v1}$ and $R^{v2}$ may be the same or different. $R^{4b}$ is as described above. In a specific embodiment, $R^{4b}$ is —H, —$OR^{6'}$, —$SO_3M$, or —$OSO_3M$, wherein $R^{6'}$ and M are as described above. In another specific embodiment, $R^{4b}$ is —H. Alternatively, $R^{4b}$ is —OH.

In one embodiment, the conjugate is a compound:

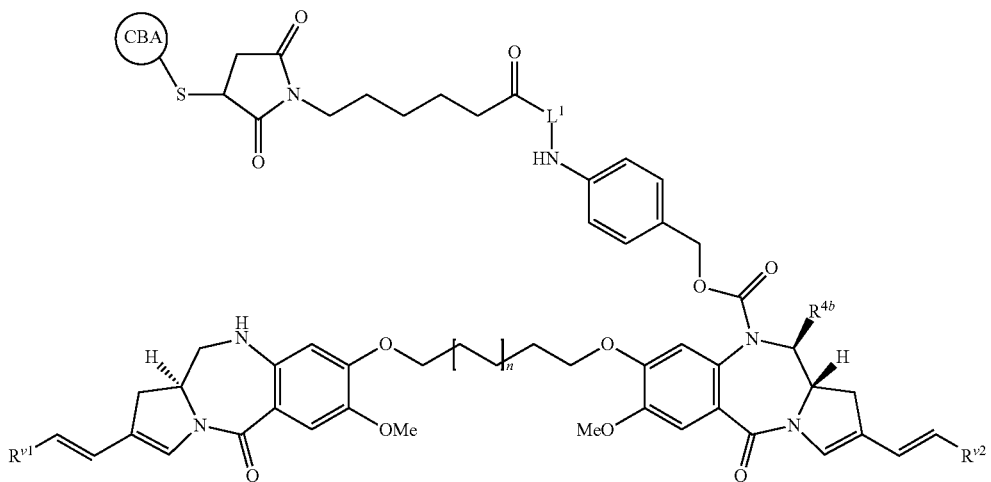

wherein CBA is a cell binding agent such as an antibody or a cyclic or linear peptide, $L^1$ is as previously defined, $R^{v1}$ and $R^{v2}$ are independently selected from H, methyl, ethyl and phenyl (which phenyl may be optionally substituted with fluoro, particularly in the 4 position) and $C_{5-6}$ heterocyclyl, and n is 0 or 1. $R^{v1}$ and $R^{v2}$ may be the same or different. $R^{4b}$ is as described above. In a specific embodiment, $R^{4b}$ is —H, —$OR^{6'}$, —$SO_3M$, or —$OSO_3M$, wherein $R^{6'}$ and M are as described above. In another specific embodiment, $R^{4b}$ is —H. Alternatively, $R^{4b}$ is —OH.

In one embodiment, the conjugate is a compound:

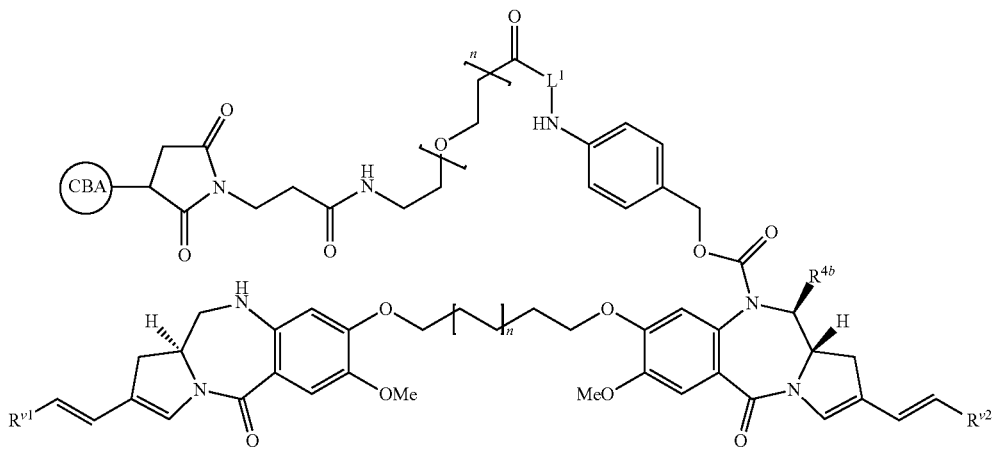

wherein CBA is a cell binding agent such as an antibody or a cyclic or linear peptide, and n is 0 or 1. $L^1$ is as previously defined, $R^{V1}$ and $R^{V2}$ are independently selected from H, methyl, ethyl and phenyl (which phenyl may be optionally substituted with fluoro, particularly in the 4 position) and C5-6 heterocyclyl, and n is 0 or 1. $R^{V1}$ and $R^{V2}$ may be the same or different. $R^{4b}$ is as described above. In a specific embodiment, $R^{4b}$ is —H, —OR$^{6'}$, —SO$_3$M, or —OSO$_3$M, wherein $R^{6'}$ and M are as described above. In another specific embodiment, $R^{4b}$ is —H. Alternatively, $R^{4b}$ is —OH.

In one embodiment, the conjugate is a compound:

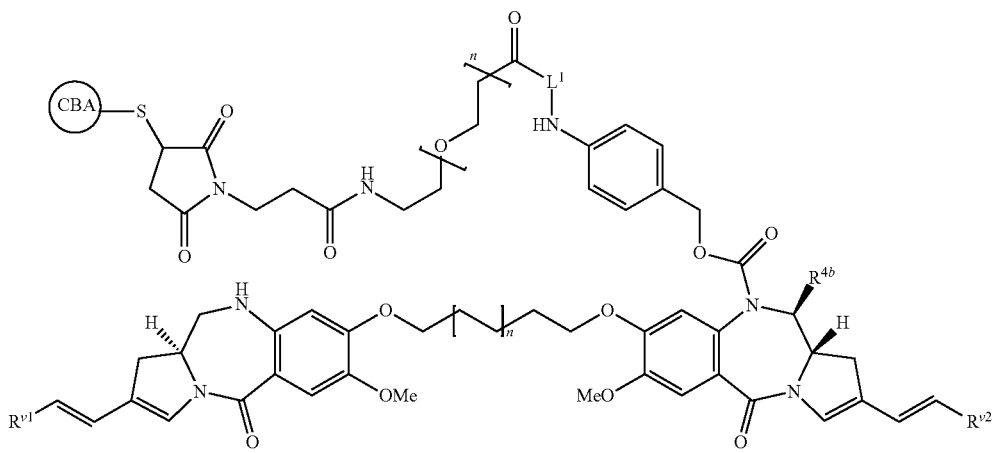

wherein CBA is a cell binding agent such as an antibody or a cyclic or linear peptide, and n is 0 or 1. $L^1$ is as previously defined, RV1 and RV2 are independently selected from H, methyl, ethyl and phenyl (which phenyl may be optionally substituted with fluoro, particularly in the 4 position) and $C_{5-6}$ heterocyclyl, and n is 0 or 1. $R^{V1}$ and $R^{V2}$ may be the same or different. $R^{4b}$ is as described above. In a specific embodiment, $R^{4b}$ is —H, —OR$^{6'}$—SO$_3$M, or —OSO$_3$M, wherein $R^{6'}$ and M are as described above. In another specific embodiment, $R^{4b}$ is —H. Alternatively, $R^{4b}$ is —OH.

In some of the above embodiments, $R^{V1}$ and $R^{V2}$ may be independently selected from H, phenyl, and 4-fluorophenyl.

Other preferred conjugates are listed in the Summary.

Preferred Intermediates

The present invention also provides intermediates for use in the preparation of the conjugate compounds described herein.

Preferred intermediates are described below, and correspond closely to the preferred conjugates described above.

In one embodiment, the intermediate is a compound:

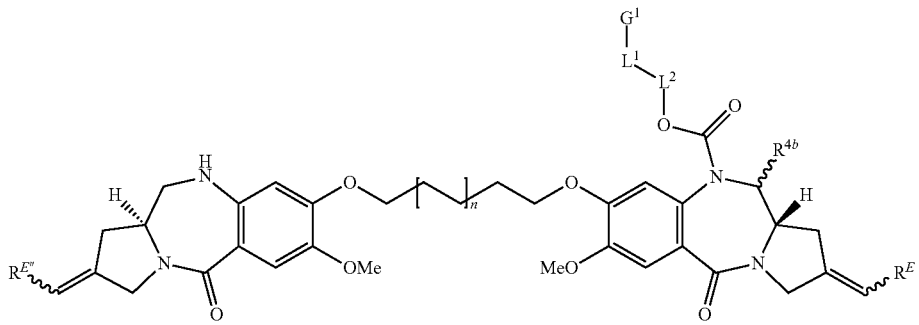

wherein n is 0 or 1, $G^1$, $L^1$ and $L^2$ are as previously defined, and $R^E$ and $R^{E''}$ are each independently selected from H or $R^a$. $R^{4b}$ is as described above. In a specific embodiment, $R^{4b}$ is —H, —$OR^{6'}$, —$SO_3M$, or —$OSO_3M$, wherein $R^{6'}$ and M are as described above. In another specific embodiment, $R^{4b}$ is —H. Alternatively, $R^{4b}$ is —OH.

In one embodiment, the intermediate is a compound:

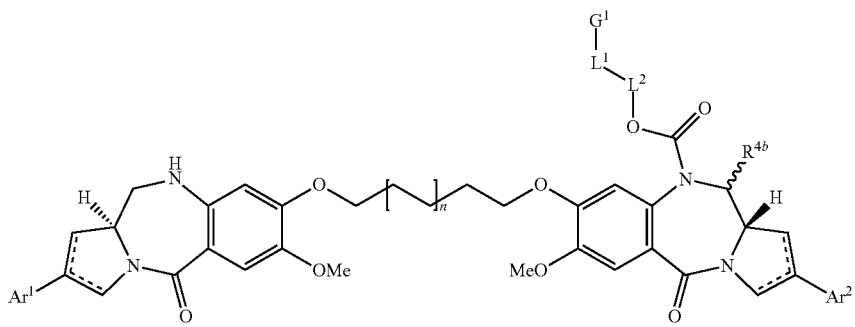

wherein $G^1$, $L^1$ and $L^2$ are as previously defined $Ar^1$ and $Ar^2$ are each independently optionally substituted $C_{5-20}$ aryl, and n is 0 or 1. $Ar^1$ and $Ar^2$ may be the same or different. $R^{4b}$ is as described above. In a specific embodiment, $R^{4b}$ is —H, —$OR^{6'}$, —$SO_3M$, or —$OSO_3M$, wherein $R^{6'}$ and M are as described above. In another specific embodiment, $R^{4b}$ is —H. Or, $R^{4b}$ is —OH.

In one embodiment, the intermediate is a compound:

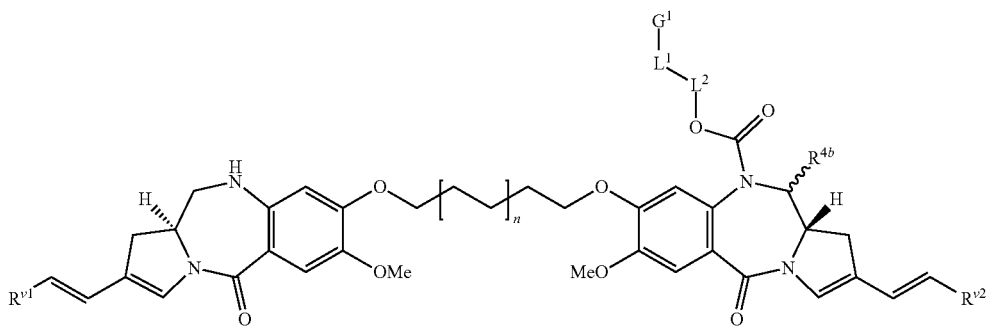

wherein $G^1$, L and $L^2$ are as previously defined, $R^{V1}$ and $R^{V2}$ are independently selected from H, methyl, ethyl and phenyl (which phenyl may be optionally substituted with fluoro, particularly in the 4 position) and $C_{5-6}$ heterocyclyl, and n is 0 or 1. $R^{V1}$ and $R^{V2}$ may be the same or different. $R^{4b}$ is as described above. In a specific embodiment, $R^{4b}$ is —H, —$OR^{6'}$, —$SO_3M$, or —$OSO_3M$, wherein $R^{6'}$ and M are as described above. In another specific embodiment, $R^{4b}$ is —H. Alternatively, $R^{4b}$ is —OH.

In one embodiment, the intermediate is a compound:

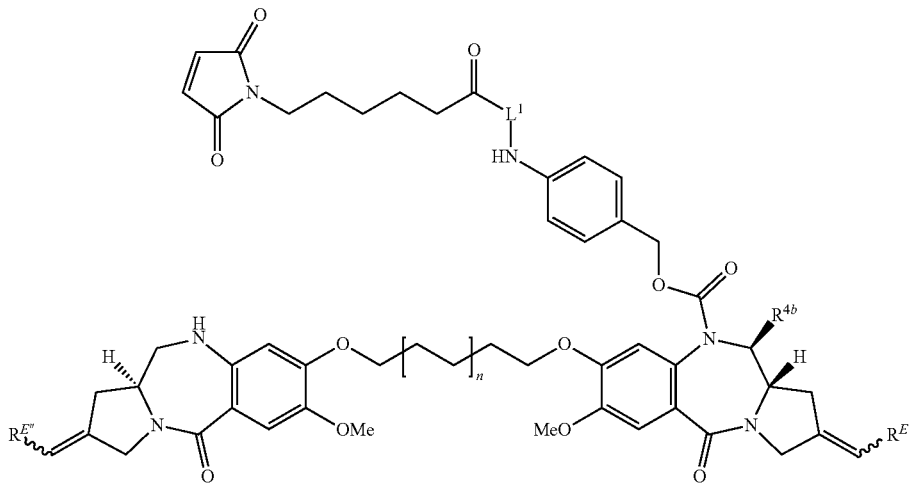

wherein n is 0 or 1, $L^1$ is as previously defined, and $R^E$ and $R^{E''}$ are each independently selected from H or $R^a$. $R^{4b}$ is as described above. In a specific embodiment, $R^{4b}$ is —H, —$OR^{6'}$, —$SO_3M$, or —$OSO_3M$, wherein $R^{6'}$ and M are as described above. In another specific embodiment, $R^{4b}$ is —H. Alternatively, $R^{4b}$ is —OH.

In one embodiment, the intermediate is a compound:

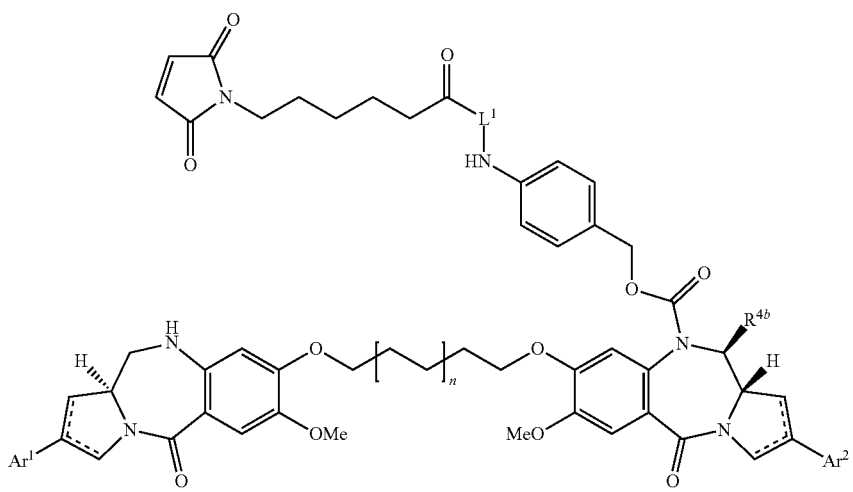

wherein $L^1$ is as previously defined, $Ar^1$ and $Ar^2$ are each independently optionally substituted $C_{5-20}$ aryl, and n is 0 or 1. $R^{4b}$ is as described above. In a specific embodiment, $R^{4b}$ is —H, —$OR^{6'}$, —$SO_3M$, or —$OSO_3M$, wherein $R^{6'}$ and M are as described above. In another specific embodiment, $R^{4b}$ is —H. Alternatively, $R^{4b}$ is —OH.

In one embodiment, the intermediate is a compound:

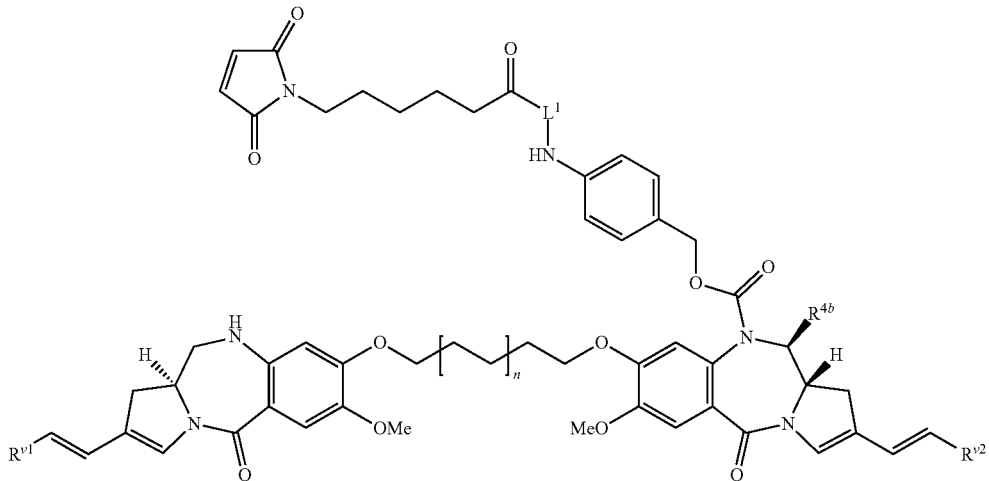

wherein $L^1$ is as previously defined, and $R^{V1}$ and $R^{V2}$ are independently selected from H, methyl, ethyl and phenyl (which phenyl may be optionally substituted with fluoro, particularly in the 4 position) and $C_{5-6}$ heterocyclyl, and n is 0 or 1. $R^{V1}$ and $R^{V2}$ may be the same or different. $R^{4b}$ is as described above. In a specific embodiment, $R^{4b}$ is —H, —$OR^{6'}$, —$SO_3M$, or —$OSO_3M$, wherein $R^{6'}$ and M are as described above. In another specific embodiment, $R^{4b}$ is —H. Alternatively, $R^{4b}$ is —OH.

In one embodiment, the intermediate is a compound:

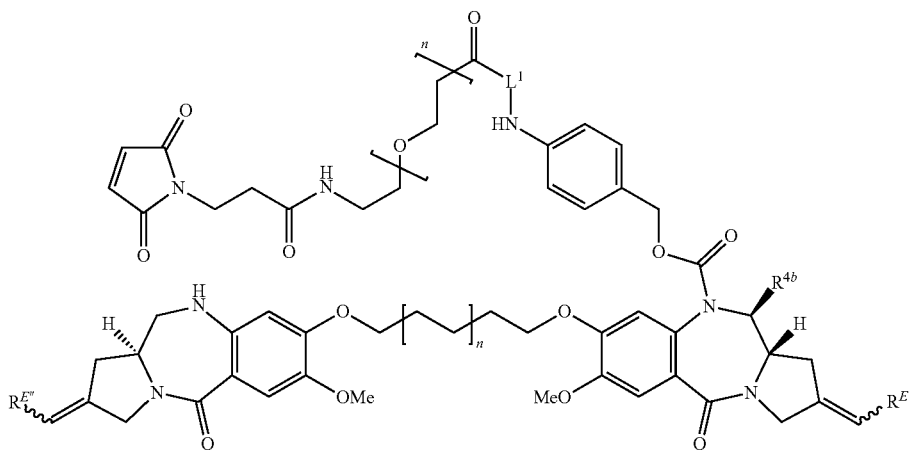

wherein n is 0 or 1, $L^1$ is as previously defined, and $R^E$ and $R^{E''}$ are each independently selected from H or $R^a$. $R^{4b}$ is as described above. In a specific embodiment, $R^{4b}$ is —H, —$OR^{6'}$, —$SO_3M$, or —$OSO_3M$, wherein $R^{6'}$ and M are as described above. In another specific embodiment, $R^{4b}$ is —H. Alternatively, $R^{4b}$ is —OH.

In one embodiment, the intermediate is a compound:

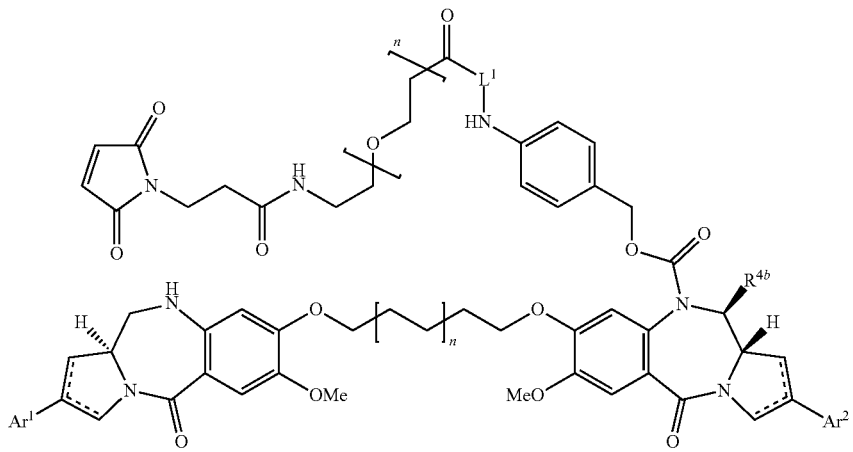

wherein n is 0 or 1, $L^1$ is as previously defined, $Ar^1$ and $Ar^2$ are each independently optionally substituted $C_{5\text{-}20}$ aryl, and n is 0 or 1. $R^{4b}$ is as described above. In a specific embodiment, $R^{4b}$ is —H, —$OR^{6'}$, —$SO_3M$, or —$OSO_3M$, wherein $R^{6'}$ and M are as described above. In another specific embodiment, $R^{4b}$ is —H. Alternatively, $R^{4b}$ is —OH.

In one embodiment, the intermediate is a compound:

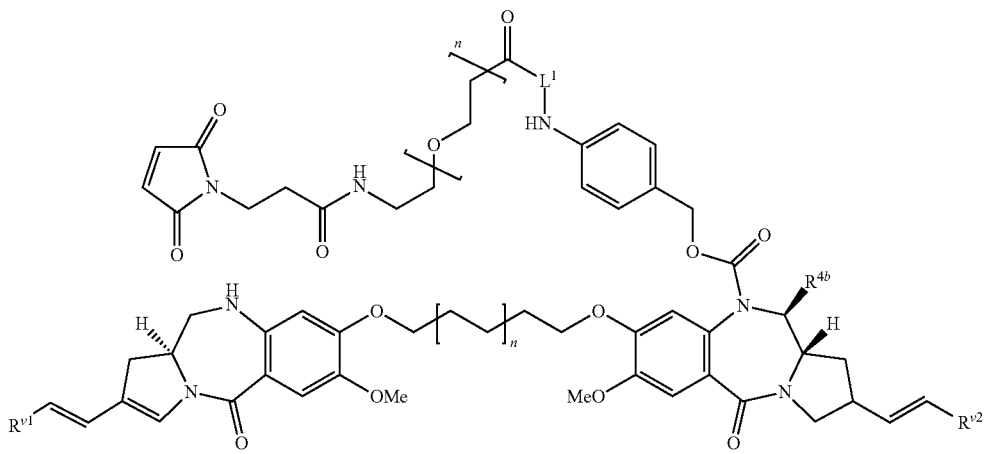

wherein $L^1$ is as previously defined, $R^{V1}$ and $R^{V2}$ are independently selected from H, methyl, ethyl and phenyl (which phenyl may be optionally substituted with fluoro, particularly in the 4 position) and $C_{5\text{-}6}$ heterocyclyl, and n is 0 or 1. $R^{V1}$ and $R^{V2}$ may be the same or different. $R^{4b}$ is as described above. In a specific embodiment, $R^{4b}$ is —H, —$OR^{6'}$—$SO_3M$, or —$OSO_3M$, wherein $R^{6'}$ and M are as described above. In another specific embodiment, $R^{4b}$ is —H. Alternatively, $R^{4b}$ is —OH.

Other preferred compounds are listed in the Summary.

Substituents

The phrase "optionally substituted" as used herein, pertains to a parent group which may be unsubstituted or which may be substituted.

Unless otherwise specified, the term "substituted" as used herein, pertains to a parent group which bears one or more substituents. The term "substituent" is used herein in the conventional sense and refers to a chemical moiety which is covalently attached to, or if appropriate, fused to, a parent group. A wide variety of substituents are well known, and methods for their formation and introduction into a variety of parent groups are also well known. See, for example, those as defined in US 2011/0256157 A1 (all definitions therein, especially definitions for "substituents," are incorporated herein by reference).

In a preferred embodiment, the substituents described herein (which include optional substituents) are limited to those groups that are not reactive to a cell binding agent. The link to the cell binding agent in the present case is formed from the N10 position of the PBD/IBD compound through a linker group (comprising, for example, $L^1$, $L^2$ and A) to the cell binding agent. Reactive functional groups located at other parts of the PBD/IBD structure may be capable of forming additional bonds to the cell binding agent (this may be referred to as crosslinking). These additional bonds may alter transport and biological activity of the conjugate. Therefore, in some embodiment, the additional substituents are limited to those lacking reactive functionality.

In one embodiment, the substituents are selected from the group consisting of $R^{1'}$, $OR^{1'}$, $SR^{1'}$, $NR^{1'}R^{3'}$, $NO_2$, halo, $CO_2R^{1'}$, $COR^{1'}$, $CONH_2$, $CONHR^{1'}$, and $CONR^{1'}R^{3'}$.

Any one of the embodiment mentioned above may be applied to any one of the substituents described herein. Alternatively, the substituents may be selected from one or more of the groups listed below.

Examples of substituents are described in more detail below.

Alkyl: The term "alkyl" as used herein, pertains to a monovalent moiety obtained by removing a hydrogen atom from a carbon atom of a hydrocarbon compound having a given number of carbon atoms, which may include cycloalkyl. Exemplary alkyl include $(C_{1-12})$alkyl, $(C_{1-6})$alkyl, $(C_{1-4})$alkyl, $(C_{1-3})$alkyl, $(C_{3-10})$cycloalkyl, $(C_{3-6})$cycloalkyl, etc.

An alkyl group may optionally be interrupted by one or more heteroatoms selected from O, N(H) and S. Such groups may be referred to as "heteroalkyl."

The terminal of a heteroalkyl group may be the primary form of a heteroatom, e.g., —OH, —SH or —NH$_2$. In a preferred embodiment, the terminal is —CH$_3$.

Alkenyl: The term "alkenyl" as used herein pertains to an alkyl group having one or more carbon-carbon double bonds.

Alkynyl: The term "alkynyl" as used herein pertains to an alkyl group having one or more carbon-carbon triple bonds.

Cycloalkyl: The term "cycloalkyl" as used herein, pertains to an alkyl group which is also a cyclyl group; that is, a monovalent moiety obtained by removing a hydrogen atom from an alicyclic ring atom of a cyclic hydrocarbon (carbocyclic) compound, which moiety may have from 3 to 7 carbon atoms, including from 3 to 7 ring atoms.

$C_{3-20}$ heterocyclyl: The term "$C_{3-20}$ heterocyclyl" as used herein, pertains to a monovalent moiety obtained by removing a hydrogen atom from a ring atom of a heterocyclic compound, which moiety has from 3 to 20 ring atoms, of which from 1 to 10 are ring heteroatoms. Preferably, each ring has from 3 to 7 ring atoms, of which from 1 to 4 are ring heteroatoms.

Examples of substituted monocyclic heterocyclyl groups include those derived from saccharides, in cyclic form, for example, furanoses ($C_5$), such as arabinofuranose, lyxofuranose, ribofuranose, and xylofuranse, and pyranoses ($C_6$), such as allopyranose, altropyranose, glucopyranose, mannopyranose, gulopyranose, idopyranose, galactopyranose, and talopyranose.

The term "$C_{5-20}$ aryl," as used herein, pertains to a monovalent moiety obtained by removing a hydrogen atom from an aromatic ring atom of an aromatic compound, which moiety has from 3 to 20 ring atoms. Preferably, each ring has from 5 to 7 ring atoms. In one embodiment, the aryl is an optionally substituted phenyl group.

The ring atoms may be all carbon atoms, as in "carboaryl groups."

Aryl groups may comprise fused rings, at least one of which is an aromatic ring. Alternatively, the ring atoms may include one or more heteroatoms, as in "heteroaryl groups." The above groups, whether alone or part of another substituent, may themselves optionally be substituted with one or more groups selected from themselves and the additional substituents listed below: halo, hydroxy, ether —OR, acetal —CH(OR$^1$)(OR$^2$), hemiacetal: —CH(OH)(OR$^1$), ketal —CR(OR$^1$)(OR$^2$), hemiketal —CR(OH)(OR$^1$), oxo (keto,-one): =O; thione (thioketone): =S; imino (imine) =NR, formyl (carbaldehyde, carboxaldehyde) —C(=O)H, acyl (keto) —C(=O)R, —C(=O)OH, —C(=S)SH, —C(=O)SH, —C(=S)OH, —C(=NH)OH, —C(=NOH)OH, —C(=O)OR, —OC(=O)R, —OC(=O)OR, —NR$^1$R$^2$.

Amino groups may be primary (—NH$_2$), secondary (—NHR$^1$), or tertiary (—NHR$^1$R$^2$), and in cationic form, may be quaternary (—$^+$NR$^1$R$^2$R$^3$) —C(=O)NR$^1$R$^2$, —C(=S)NR$^1$R$^2$, —NR$^1$C(=O)R$^2$, wherein R$^1$ and R$^2$ may together form a cyclic structure, as in, for example, succinimidyl, maleimidyl, and phthalimidyl:

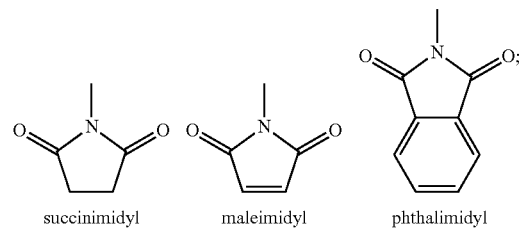

succinimidyl    maleimidyl    phthalimidyl

—OC(=O)NR$^1$R$^2$, —N(R$^1$)CONR$^2$R$^3$, —NH—C(=NH)NH$_2$, tetrazolyl: a five membered aromatic ring having four nitrogen atoms and one carbon atom,

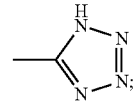

Imino: =NR, Amidine (amidino): —C(=NR)NR$^2$, Nitro: —NO$_2$, Nitroso: —NO, Azido: —N$_3$, Cyano (nitrile, carbonitrile): —CN, Isocyano: —NC, Cyanato: —OCN, Isocyanato: —NCO, Thiocyano (thiocyanato): —SCN, Isothiocyano (isothiocyanato): —NCS, Sulfhydryl (thiol, mercapto): —SH, Thioether (sulfide): —SR, disulfide: —SS—R, sulfine (sulfinyl, sulfoxide): —S(=O)R, sulfone (sulfonyl): —S(=O)$_2$R, sulfinic acid (sulfino): —S(=O)OH, —SO$_2$H, sulfonic acid (sulfo): —S(=O)$_2$OH, —SO$_3$H, sulfinate (sulfinic acid ester): —S(=O)OR, sulfonate (sulfonic acid ester): —S(=O)$_2$OR, sulfinyloxy: —OS(=O)R, sulfonyloxy: —OS(=O)$_2$R, sulfate: —OS(=O)$_2$OR, sulfamyl (sulfamoyl; sulfinic acid amide; sulfinamide): —S(=O)NR$^1$R$^2$, sulfonamido (sulfinamoyl; sulfonic acid amide; sulfonamide): —S(=O)$_2$NR$^1$R$^2$, sulfamino: —NR$^1$S(=O)$_2$OH, sulfonamino: —NR$^1$S(=O)$_2$R, sulfinamino: —NR$^1$S(=O)R, phosphino (phosphine): —PR$^2$, phospho: —P(=O)$_2$, phosphinyl (phosphine oxide): —P(=O)R$^2$, phosphonic acid (phosphono): —P(=O)(OH)$_2$, phosphonate (phosphono ester): —P(=O)(OR)$_2$, phosphoric acid (phosphonooxy): —OP(=O)(OH)$_2$, phosphate (phosphonooxy ester): —OP(=O)(OR)$_2$, phosphorous acid: —OP(OH)$_2$, phosphite: —OP(OR)$_2$, phosphoramidite: —OP(OR$^1$)—NR$^2$$_2$, phosphoramidate: —OP(=O)(OR)—NR$^2$$_2$.

Includes Other Forms

Unless otherwise specified, included in the above are the well-known ionic, salt, solvate, and protected forms of these substituents. For example, a reference to carboxylic acid (—COOH) also includes the anionic (carboxylate) form (—COO), a salt or solvate thereof, as well as conventional protected forms. Similarly, a reference to an amino group includes the protonated form (—N$^+$HR$^1$R$^2$), a salt or solvate of the amino group, for example, a hydrochloride salt, as well as conventional protected forms of an amino group. Similarly, a reference to a hydroxyl group also includes the anionic form (—O—), a salt or solvate thereof, as well as conventional protected forms.

Salts

It may be convenient or desirable to prepare, purify, and/or handle a corresponding salt of the active compound, for example, a pharmaceutically-acceptable salt. Examples of pharmaceutically acceptable salts are discussed in Berge et al., *J. Pharm. Sci.* 66:1-19 (1977).

For example, if the compound is anionic, or has a functional group which may be anionic (e.g., —COOH may be —COO), then a salt may be formed with a suitable cation. Examples of suitable inorganic cations include, but are not limited to, alkali metal ions such as $Na^+$ and $K^+$, alkaline earth cations such as $Ca^{2+}$ and $Mg^{2+}$, and other cations such as $Al^{+3}$. Examples of suitable organic cations include, but are not limited to, ammonium ion (i.e., $NH^{4+}$) and substituted ammonium ions (e.g., $NH^3R^+$, $NH2R^{2+}$, $NHR^{3+}$, $NR^{4+}$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)^{4+}$.

If the compound is cationic, or has a functional group which may be cationic (e.g., —$NH_2$ may be —$NH^{3+}$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, trifluoroacetic acid and valeric. Examples of suitable polymeric organic anions include, but are not limited to, those derived from the following polymeric acids: tannic acid, carboxymethyl cellulose.

Solvates

It may be convenient or desirable to prepare, purify, and/or handle a corresponding solvate of the active compound. The term "solvate" is used herein in the conventional sense to refer to a complex of solute (e.g., active compound, salt of active compound) and solvent. If the solvent is water, the solvate may be conveniently referred to as a hydrate, for example, a mono-hydrate, a di-hydrate, a tri-hydrate, etc.

The invention includes compounds where a solvent adds across the imine bond of the PBD/IBD moiety, which is illustrated below where the solvent is water or an alcohol (RAOH, where RA is $C_{1-4}$ alkyl):

These forms can be called the carbinolamine and carbinolamine ether forms of the PBD (as described in the section relating to $R^5$ above). The balance of these equilibria depends on the conditions in which the compounds are found, as well as the nature of the moiety itself.

These particular compounds may be isolated in solid form, for example, by lyophilization.

Isomers

Certain compounds of the invention may exist in one or more particular geometric, optical, enantiomeric, diastereomeric, epimeric, atropic, stereoisomeric, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g., melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., McGraw-Hill *Dictionary of Chemical Terms* (1984) McGraw-Hill Book Company, New York; and Eliel, E. and Wilen, S., *Stereochemistry of Organic Compounds*, John Wiley & Sons, Inc., New York, 1994. The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the

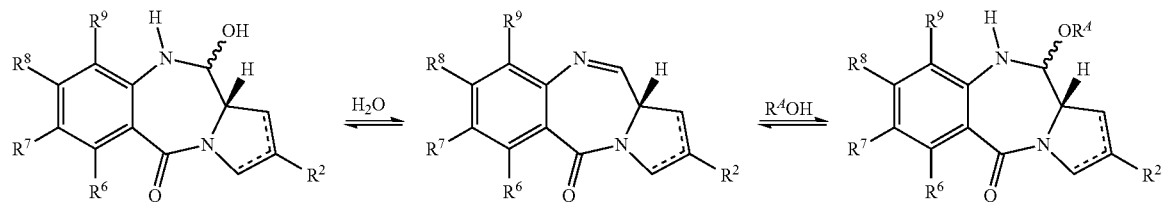

compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

Note that, except as discussed below for tautomeric forms, specifically excluded from the term "isomers," as used herein, are structural (or constitutional) isomers (i.e., isomers which differ in the connections between atoms rather than merely by the position of atoms in space). For example, a reference to a methoxy group, —OCH$_3$, is not to be construed as a reference to its structural isomer, a hydroxymethyl group, —CH$_2$OH. Similarly, a reference to ortho-chlorophenyl is not to be construed as a reference to its structural isomer, meta-chlorophenyl. However, a reference to a class of structures may well include structurally isomeric forms falling within that class (e.g., C$^{1-7}$ alkyl includes n-propyl and iso-propyl; butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, N-nitroso/hyroxyazo, and nitro/aci-nitro.

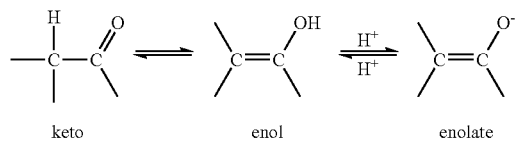

keto    enol    enolate

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

Note that specifically included in the term "isomer" are compounds with one or more isotopic substitutions. For example, H may be in any isotopic form, including $^1$H, $^2$H (D), and $^3$H (T); C may be in any isotopic form, including $^{12}$C, $^{13}$C, and $^{14}$C; O may be in any isotopic form, including $^{16}$O and $^{18}$O; and the like.

Examples of isotopes that can be incorporated into compounds of the invention include isotopes of hydrogen, carbon, nitrogen, oxygen, phosphorous, fluorine, and chlorine, such as, but not limited to $^2$H (deuterium, D), $^3$H (tritium), $^{11}$C, $^{13}$C $^{14}$C, $^{15}$N, $^{18}$F, $^{31}$P, $^{32}$P, $^{35}$S, $^{36}$Cl, and $^{125}$I. Various isotopically labeled compounds of the present invention, for example those into which radioactive isotopes such as $^3$H, $^{13}$C, and $^{14}$C are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays, or in radioactive treatment of patients. Deuterium labelled or substituted therapeutic compounds of the invention may have improved DMPK (drug metabolism and pharmacokinetics) properties, relating to distribution, metabolism, and excretion (ADME). Substitution with heavier isotopes such as deuterium may afford certain therapeutic advantages resulting from greater metabolic stability, for example increased in vivo half-life or reduced dosage requirements. An $^{18}$F labeled compound may be useful for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent. Further, substitution with heavier isotopes, particularly deuterium (i.e., $^2$H or D) may afford certain therapeutic advantages resulting from greater metabolic stability, for example increased in vivo half-life or reduced dosage requirements or an improvement in therapeutic index. It is understood that deuterium in this context is regarded as a substituent. The concentration of such a heavier isotope, specifically deuterium, may be defined by an isotopic enrichment factor. In the compounds of this invention any atom not specifically designated as a particular isotope is meant to represent any stable isotope of that atom.

Unless otherwise specified, a reference to a particular compound includes all such isomeric forms, including (wholly or partially) racemic and other mixtures thereof. Methods for the preparation (e.g., asymmetric synthesis) and separation (e.g., fractional crystallization and chromatographic means) of such isomeric forms are either known in the art or are readily obtained by adapting the methods taught herein, or known methods, in a known manner.

Use

The conjugates of the invention may be used to provide a PBD/IBD compound at a target location.

The target location is preferably a proliferative cell population. The antibody is an antibody for an antigen present in a proliferative cell population.

In one embodiment the antigen is absent or present at a reduced level in a non-proliferative cell population compared to the amount of antigen present in the proliferative cell population, for example a tumor cell population.

At the target location the linker may be cleaved so as to release a compound of formula (D). Thus, the conjugate may be used to selectively provide a compound of formula (D) to the target location.

The linker may be cleaved by an enzyme present at the target location.

The target location may be in vitro, in vivo or ex vivo.

The antibody-drug conjugate (ADC) compounds of the invention include those with utility for anticancer activity. In particular, the compounds include an antibody conjugated, i.e., covalently attached by a linker, to a PBD/IBD drug moiety, i.e., toxin. When the drug is not conjugated to an antibody, the PBD/IBD drug has a cytotoxic effect. The biological activity of the PBD/IBD drug moiety is thus modulated by conjugation to an antibody. The antibody-drug conjugates (ADC) of the invention selectively deliver an effective dose of a cytotoxic agent to tumor tissue whereby greater selectivity, i.e., a lower efficacious dose, may be achieved.

Thus, in one aspect, the present invention provides a conjugate compound as described herein for use in therapy.

In a further aspect there is also provides a conjugate compound as described herein for use in the treatment of a proliferative disease. A second aspect of the present invention provides the use of a conjugate compound in the manufacture of a medicament for treating a proliferative disease.

One of ordinary skill in the art is readily able to determine whether or not a candidate conjugate treats a proliferative condition for any particular cell type. For example, assays which may conveniently be used to assess the activity offered by a particular compound are described in the examples below.

The term "proliferative disease" pertains to an unwanted or uncontrolled cellular proliferation of excessive or abnormal cells which is undesired, such as, neoplastic or hyperplastic growth, whether in vitro or in vivo.

Examples of proliferative conditions include, but are not limited to, benign, pre-malignant, and malignant cellular proliferation, including but not limited to, neoplasms and tumors (e.g., histocytoma, glioma, astrocyoma, osteoma), cancers (e.g., lung cancer, small cell lung cancer, gastrointestinal cancer, bowel cancer, colon cancer, breast carinoma, ovarian carcinoma, prostate cancer, testicular cancer, liver cancer, kidney cancer, bladder cancer, pancreas cancer, brain cancer, sarcoma, osteosarcoma, Kaposi's sarcoma, melanoma), leukemias, psoriasis, bone diseases, fibroproliferative disorders (e.g., of connective tissues), and atherosclerosis. Cancers of particular interest include, but are not limited to, leukemias and ovarian cancers.

Any type of cell may be treated, including but not limited to, lung, gastrointestinal (including, e.g., bowel, colon), breast (mammary), ovarian, prostate, liver (hepatic), kidney (renal), bladder, pancreas, brain, and skin.

In one embodiment, the treatment is of a pancreatic cancer.

In one embodiment, the treatment is of a tumor having αvβ6 integrin on the surface of the cell.

It is contemplated that the antibody-drug conjugates (ADC) of the present invention may be used to treat various diseases or disorders, e.g., characterized by the overexpression of a tumor antigen. Exemplary conditions or hyperproliferative disorders include benign or malignant tumors; leukemia, haematological, and lymphoid malignancies. Others include neuronal, glial, astrocytal, hypothalamic, glandular, macrophagal, epithelial, stromal, blastocoelic, inflammatory, angiogenic and immunologic, including autoimmune, disorders. Generally, the disease or disorder to be treated is a hyperproliferative disease such as cancer. Examples of cancer to be treated herein include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

Autoimmune diseases for which the ADC compounds may be used in treatment include rheumatologic disorders (such as, for example, rheumatoid arthritis, Sjogren's syndrome, scleroderma, lupus such as SLE and lupus nephritis, polymyositis/dermatomyositis, cryoglobulinemia, anti-phospholipid antibody syndrome, and psoriatic arthritis), osteoarthritis, autoimmune gastrointestinal and liver disorders (such as, for example, inflammatory bowel diseases (e.g., ulcerative colitis and Crohn's disease), autoimmune gastritis and pernicious anemia, autoimmune hepatitis, primary biliary cirrhosis, primary sclerosing cholangitis, and celiac disease), vasculitis (such as, for example, ANCA-associated vasculitis, including Churg-Strauss vasculitis, Wegener's granulomatosis, and polyarteriitis), autoimmune neurological disorders (such as, for example, multiple sclerosis, opsoclonus myoclonus syndrome, myasthenia gravis, neuromyelitis optica, Parkinson's disease, Alzheimer's disease, and autoimmune polyneuropathies), renal disorders (such as, for example, glomerulonephritis, Goodpasture's syndrome, and Berger's disease), autoimmune dermatologic disorders (such as, for example, psoriasis, urticaria, hives, pemphigus vulgaris, bullous pemphigoid, and cutaneous lupus erythematosus), hematologic disorders (such as, for example, thrombocytopenic purpura, thrombotic thrombocytopenic purpura, post-transfusion purpura, and autoimmune hemolytic anemia), atherosclerosis, uveitis, autoimmune hearing diseases (such as, for example, inner ear disease and hearing loss), Behcet's disease, Raynaud's syndrome, organ transplant, and autoimmune endocrine disorders (such as, for example, diabetic-related autoimmune diseases such as insulin-dependent diabetes mellitus (IDDM), Addison's disease, and autoimmune thyroid disease (e.g., Graves' disease and thyroiditis)). More preferred such diseases include, for example, rheumatoid arthritis, ulcerative colitis, ANCA-associated vasculitis, lupus, multiple sclerosis, Sjogren's syndrome, Graves' disease, IDDM, pernicious anemia, thyroiditis, and glomerulonephritis.

Biological Activity

Various biological activity assays that may be useful in the instant invention can be found in US 2011-0256157 A1. The following assays are specifically incorporated herein by reference: in vitro cell proliferation assays, and in vivo efficacy measurement.

Methods of Treatment

Various methods of treatment, including combination treatment using the compounds/conjugates of the invention in combination with one or more therapeutic agents useful for treating a specific condition, can be found in US 2011-0256157 A1 (incorporated by reference).

Formulations

While it is possible for the conjugate compound to be used (e.g., administered) alone, it is often preferable to present it as a composition or formulation.

In one embodiment, the composition is a pharmaceutical composition (e.g., formulation, preparation, medicament) comprising a conjugate compound, as described herein, and a pharmaceutically acceptable carrier, diluent, or excipient.

In one embodiment, the composition is a pharmaceutical composition comprising at least one conjugate compound, as described herein, together with one or more other pharmaceutically acceptable ingredients well known to those skilled in the art, including, but not limited to, pharmaceutically acceptable carriers, diluents, excipients, adjuvants, fillers, buffers, preservatives, anti-oxidants, lubricants, stabilisers, solubilisers, surfactants (e.g., wetting agents), masking agents, coloring agents, flavouring agents, and sweetening agents.

In one embodiment, the composition further comprises other active agents, for example, other therapeutic or prophylactic agents.

Suitable carriers, diluents, excipients, etc. can be found in standard pharmaceutical texts. See, for example, Handbook of Pharmaceutical Additives, 2nd Edition (eds. M. Ash and I. Ash), 2001 (Synapse Information Resources, Inc., Endicott, N.Y., USA), Remington's Pharmaceutical Sciences, 20th edition, pub. Lippincott, Williams & Wilkins, 2000; and Handbook of Pharmaceutical Excipients, 2nd edition, 1994.

Another aspect of the present invention pertains to methods of making a pharmaceutical composition comprising admixing at least one [$^{11}$C]-radiolabelled conjugate or conjugate-like compound, as defined herein, together with one or more other pharmaceutically acceptable ingredients well known to those skilled in the art, e.g., carriers, diluents, excipients, etc. If formulated as discrete units (e.g., tablets, etc.), each unit contains a predetermined amount (dosage) of the active compound.

The term "pharmaceutically acceptable," as used herein, pertains to compounds, ingredients, materials, compositions, dosage forms, etc., which are, within the scope of sound medical judgment, suitable for use in contact with the tissues of the subject in question (e.g., human) without excessive toxicity, irritation, allergic response, or other problem or complication, commensurate with a reasonable benefit/risk ratio. Each carrier, diluent, excipient, etc. must also be "acceptable" in the sense of being compatible with the other ingredients of the formulation.

The formulations may be prepared by any methods well known in the art of pharmacy. Such methods include the step of bringing into association the active compound with a carrier which constitutes one or more accessory ingredients. In general, the formulations are prepared by uniformly and intimately bringing into association the active compound with carriers (e.g., liquid carriers, finely divided solid carrier, etc.), and then shaping the product, if necessary.

The formulation may be prepared to provide for rapid or slow release; immediate, delayed, timed, or sustained release; or a combination thereof.

Formulations suitable for parenteral administration (e.g., by injection), include aqueous or non-aqueous, isotonic, pyrogen-free, sterile liquids (e.g., solutions, suspensions), in which the active ingredient is dissolved, suspended, or otherwise provided (e.g., in a liposome or other microparticulate). Such liquids may additional contain other pharmaceutically acceptable ingredients, such as anti-oxidants, buffers, preservatives, stabilisers, bacteriostats, suspending agents, thickening agents, and solutes which render the formulation isotonic with the blood (or other relevant bodily fluid) of the intended recipient. Examples of excipients include, for example, water, alcohols, polyols, glycerol, vegetable oils, and the like. Examples of suitable isotonic carriers for use in such formulations include Sodium Chloride Injection, Ringer's Solution, or Lactated Ringer's Injection. Typically, the concentration of the active ingredient in the liquid is from about 1 ng/ml to about 10 μg/ml, for example from about 10 ng/ml to about 1 μg/ml. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets.

Dosage

It will be appreciated by one of skill in the art that appropriate dosages of the conjugate compound, and compositions comprising the conjugate compound, can vary from patient to patient. Determining the optimal dosage will generally involve the balancing of the level of therapeutic benefit against any risk or deleterious side effects. The selected dosage level will depend on a variety of factors including, but not limited to, the activity of the particular compound, the route of administration, the time of administration, the rate of excretion of the compound, the duration of the treatment, other drugs, compounds, and/or materials used in combination, the severity of the condition, and the species, sex, age, weight, condition, general health, and prior medical history of the patient. The amount of compound and route of administration will ultimately be at the discretion of the physician, veterinarian, or clinician, although generally the dosage will be selected to achieve local concentrations at the site of action which achieve the desired effect without causing substantial harmful or deleterious side-effects.

Administration can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell(s) being treated, and the subject being treated. Single or multiple administrations can be carried out with the dose level and pattern being selected by the treating physician, veterinarian, or clinician.

In general, a suitable dose of the active compound is in the range of about 100 ng to about 25 mg (more typically about 1 μg to about 10 mg) per kilogram body weight of the subject per day. Where the active compound is a salt, an ester, an amide, a prodrug, or the like, the amount administered is calculated on the basis of the parent compound and so the actual weight to be used is increased proportionately.

In one embodiment, the active compound is administered to a human patient according to the following dosage regime: about 100 mg, 3 times daily.

In one embodiment, the active compound is administered to a human patient according to the following dosage regime: about 150 mg, 2 times daily.

In one embodiment, the active compound is administered to a human patient according to the following dosage regime: about 200 mg, 2 times daily.

However in one embodiment, the conjugate compound is administered to a human patient according to the following dosage regime: about 50 or about 75 mg, 3 or 4 times daily.

In one embodiment, the conjugate compound is administered to a human patient according to the following dosage regime: about 100 or about 125 mg, 2 times daily.

The dosage amounts described above may apply to the conjugate (including the PBD/IBD moiety and the linker to the antibody) or to the effective amount of PBD/IBD compound provided, for example the amount of compound that is releasable after cleavage of the linker.

For the prevention or treatment of disease, the appropriate dosage of an ADC of the invention will depend on the type of disease to be treated, as defined above, the severity and course of the disease, whether the molecule is administered for preventive or therapeutic purposes, previous therapy, the patient's clinical history and response to the antibody, and the discretion of the attending physician. The molecule is suitably administered to the patient at one time or over a series of treatments. Depending on the type and severity of the disease, about 1 μg/kg to 15 mg/kg (e.g., 0.1-20 mg/kg) of molecule is an initial candidate dosage for administration to the patient, whether, for example, by one or more separate administrations, or by continuous infusion. A typical daily dosage might range from about 1 μg/kg to 100 mg/kg or more, depending on the factors mentioned above. An exemplary dosage of ADC to be administered to a patient is in the range of about 0.1 to about 10 mg/kg of patient weight. For repeated administrations over several days or longer, depending on the condition, the treatment is sustained until a desired suppression of disease symptoms occurs. An exemplary dosing regimen comprises a course of administering an initial loading dose of about 4 mg/kg, followed by additional doses every week, two weeks, or three weeks of an ADC. Other dosage regimens may be useful. The progress of this therapy is easily monitored by conventional techniques and assays.

Treatment

The term "treatment," as used herein in the context of treating a condition, pertains generally to treatment and therapy, whether of a human or an animal (e.g., in veterinary applications), in which some desired therapeutic effect is achieved, for example, the inhibition of the progress of the condition, and includes a reduction in the rate of progress, a halt in the rate of progress, regression of the condition, amelioration of the condition, and cure of the condition. Treatment as a prophylactic measure (i.e., prophylaxis, prevention) is also included.

The term "therapeutically-effective amount," as used herein, pertains to that amount of an active compound, or a material, composition or dosage from comprising an active compound, which is effective for producing some desired therapeutic effect, commensurate with a reasonable benefit/risk ratio, when administered in accordance with a desired treatment regimen.

Similarly, the term "prophylactically-effective amount," as used herein, pertains to that amount of an active compound, or a material, composition or dosage from comprising an active compound, which is effective for producing some desired prophylactic effect, commensurate with a reasonable benefit/risk ratio, when administered in accordance with a desired treatment regimen.

Preparation of Antibody Drug Conjugates

Antibody drug conjugates may be prepared by several routes, employing organic chemistry reactions, conditions, and reagents known to those skilled in the art, including: (1) reaction of a nucleophilic group or an electrophilic group of an antibody with a bivalent linker reagent, to form antibody-linker intermediate Ab-L, via a covalent bond, followed by reaction with an activated drug moiety reagent; and (2) reaction of a drug moiety reagent with a linker reagent, to form drug-linker reagent D-L, via a covalent bond, followed by reaction with the nucleophilic group or an electrophilic group of an antibody. Conjugation methods (1) and (2) may be employed with a variety of antibodies, and linkers to prepare the antibody-drug conjugates of the invention.

Nucleophilic groups on antibodies include, but are not limited to: (i) N-terminal amine groups, (ii) side chain amine groups, e.g., lysine, (iii) side chain thiol groups, e.g., cysteine, and (iv) sugar hydroxyl or amino groups where the antibody is glycosylated. Amine, thiol, and hydroxyl groups are nucleophilic and capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups. Certain antibodies have reducible interchain disulfides, i.e., cysteine bridges. Antibodies may be made reactive for conjugation with linker reagents by treatment with a reducing agent such as DTT (Cleland's reagent, dithiothreitol) or TCEP (tris(2-carboxyethyl)phosphine hydrochloride; Getz et al. (1999) *Anal.* *Biochem.* 273:73-80; Soltec Ventures, Beverly, Mass.). Each cysteine disulfide bridge will thus form, theoretically, two reactive thiol nucleophiles. Additional nucleophilic groups can be introduced into antibodies through the reaction of lysines with 2-iminothiolane (Traut's reagent) resulting in conversion of an amine into a thiol.

Antibody-drug conjugates may also be produced by modification of the antibody to introduce electrophilic moieties, which can react with nucleophilic substituents on the linker reagent. The sugars of glycosylated antibodies may be oxidized, e.g., with periodate oxidizing reagents, to form aldehyde or ketone groups which may react with the amine group of linker reagents or drug moieties. The resulting imine Schiff base groups may form a stable linkage, or may be reduced, e.g., by borohydride reagents to form stable amine linkages. In one embodiment, reaction of the carbohydrate portion of a glycosylated antibody with either galactose oxidase or sodium meta-periodate may yield carbonyl (aldehyde and ketone) groups in the protein that can react with appropriate groups on the drug (Hermanson, G. T. (1996) *Bioconjugate Techniques*; Academic Press, New York, p 234-242). In another embodiment, proteins containing N-terminal serine or threonine residues can react with sodium meta-periodate, resulting in production of an aldehyde in place of the first amino acid (Geoghegan & Stroh, (1992) *Bioconjugate Chem.* 3:138-146; U.S. Pat. No. 5,362,852). Such aldehyde can be reacted with a drug moiety or linker nucleophile.

Likewise, nucleophilic groups on a drug moiety include, but are not limited to: amine, thiol, hydroxyl, hydrazide, oxime, hydrazine, thiosemicarbazone, hydrazine carboxylate, and arylhydrazide groups capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups. Reactive nucleophilic groups may be introduced on the anthracycline derivative compounds by standard functional group interconversions. For example, hydroxyl groups may be converted to thiol groups by Mitsunobu-type reactions, to form thiol-modified drug compounds.

The Subject/Patient

The subject/patient may be an animal, mammal, a placental mammal, a marsupial (e.g., kangaroo, wombat), a monotreme (e.g., duckbilled platypus), a rodent (e.g., a guinea pig, a hamster, a rat, a mouse), murine (e.g., a mouse), a lagomorph (e.g., a rabbit), avian (e.g., a bird), canine (e.g., a dog), feline (e.g., a cat), equine (e.g., a horse), porcine (e.g., a pig), ovine (e.g., a sheep), bovine (e.g., a cow), a primate, simian (e.g., a monkey or ape), a monkey (e.g., marmoset, baboon), an ape (e.g., gorilla, chimpanzee, orangutan, gibbon), or a human.

Furthermore, the subject/patient may be any of its forms of development, for example, a foetus. In one preferred embodiment, the subject/patient is a human.

In one embodiment, the patient is a population where each patient has a tumor having $\alpha v \beta 6$ integrin on the surface of the cell.

Synthesis

The compounds (monomer, dimer) and conjugates of the invention can be synthesized using methods substantially the same as those in US 2011/0256157 A1.

Exemplary synthesis schemes for certain representative compounds and conjugates of the invention are provided in FIGS. 1-7, and further described below in the Examples.

Example 1

Figure 1:
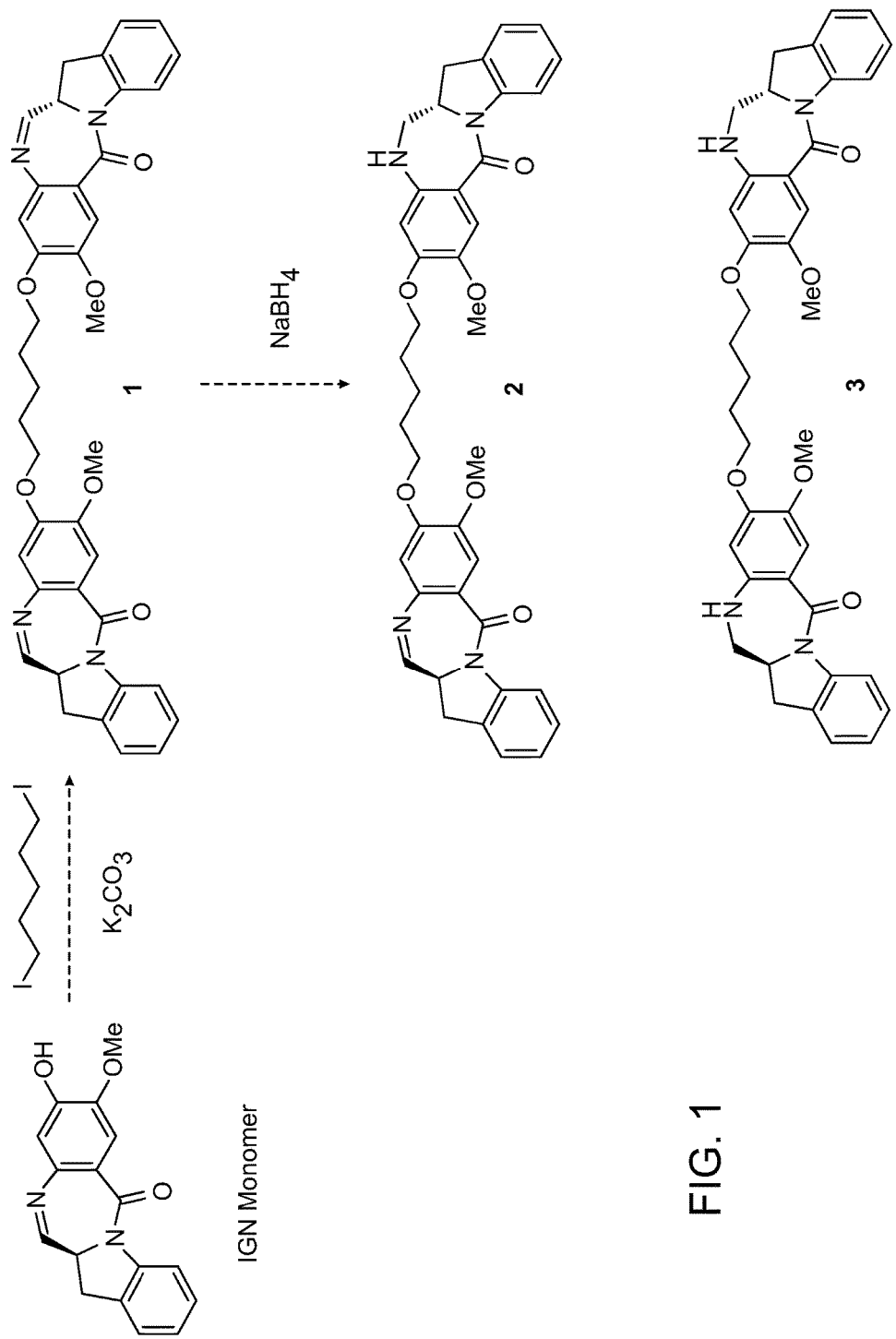
FIGS. 1, 2A, 2B, 2C, 3A, 3B, 4A, 4B, 4C, 5A, 5B, 5C, 5D, 6A, 6B, 7A and 7B show exemplary synthesis schemes for certain compounds and conjugates of the present invention.

The first step in the synthesis of PBD or IBD dimers from the respective monomers can be conducted through a variety of synthetic pathways, such as those disclosed in the art: see for example U.S. Pat. No. 8,163,736 and U.S. Patent Application Publications US 2010-0316656; US 2009-0036431; UA 2010-0203007; US 2011-0256157, and PCT publication WO 2011-130613. As shown in FIG. 1 the first step involves the union of two PBD or IBD monomer units, such as the IGN monomer, with a short spacer using potassium carbonate in an appropriate solvent such as acetone, DMA or DMF. In particular, one could use 1,5-diiodopentane or pentane 1,5-dimethanesulfonate to generate the desired bis-imine compound 1.

Fully reduced (diamines) or partially reduced (mono-imines) of PBD or IBD dimers, such as those disclosed herein, can be obtained by reduction of di-imine dimers, such as 1, with substoichiometric amounts of sodium borohydride to give both the mono-reduced dimer 2 and the fully reduced dimer 3. Other reducing agents known to one skilled in the art (see for example: *Handbook of reagents for organic synthesis, Oxidizing and Reducing agents*, S. D. Burke & R. L. Danheiser Eds (1999) John Wiley & Sons, New York) such as sodium triacetoxy borohydride, sodium cyanoborohydride, sodium in ethanol, dibutylchlorotin hydride, lithium aluminum hydride, lithium trimethoxyaluminum hydride, lithium t-butoxyaluminum hydride. or lithium borohydride, may also be used.

Example 2

Figure 2A:
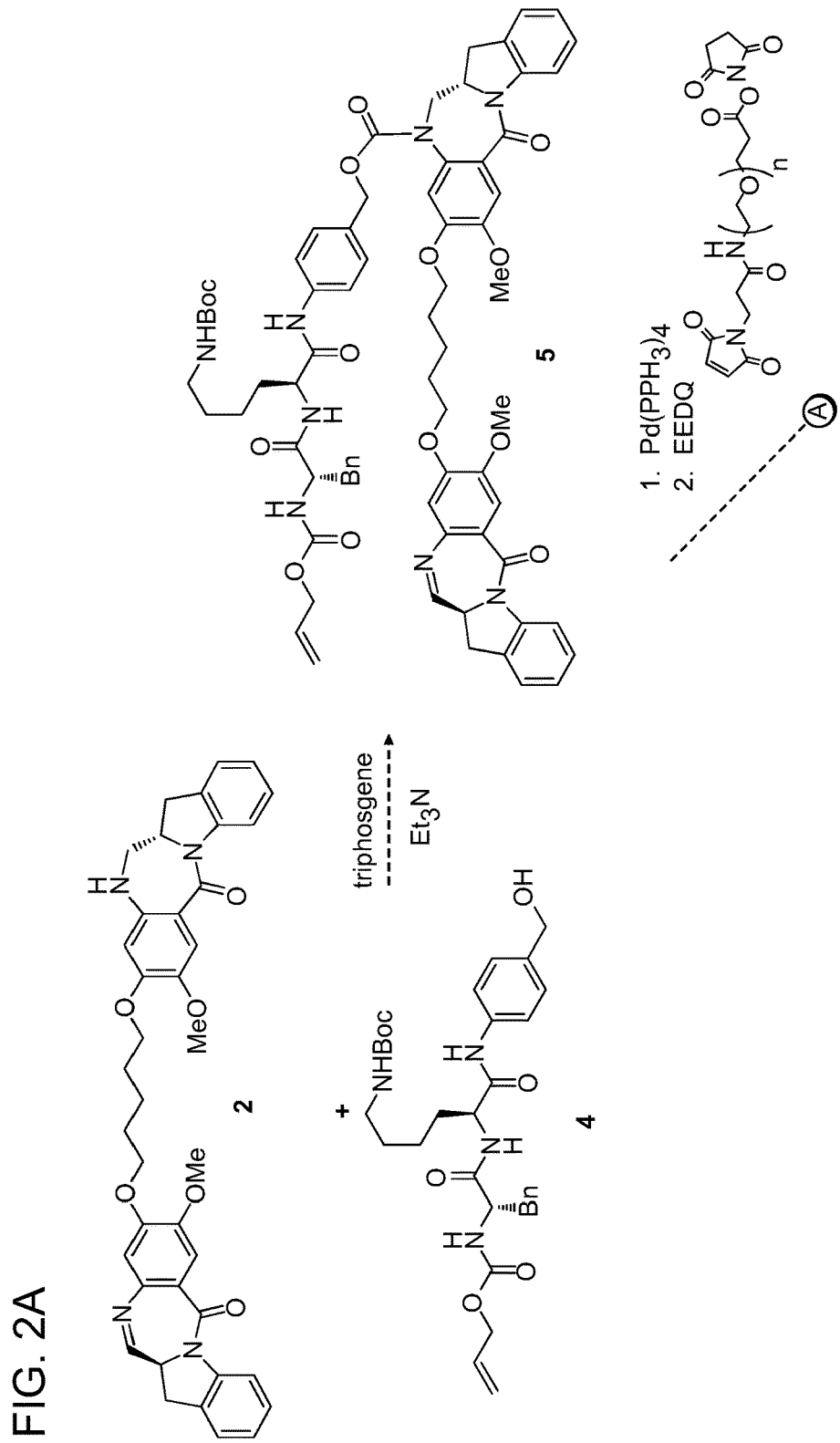
Figure 2B:
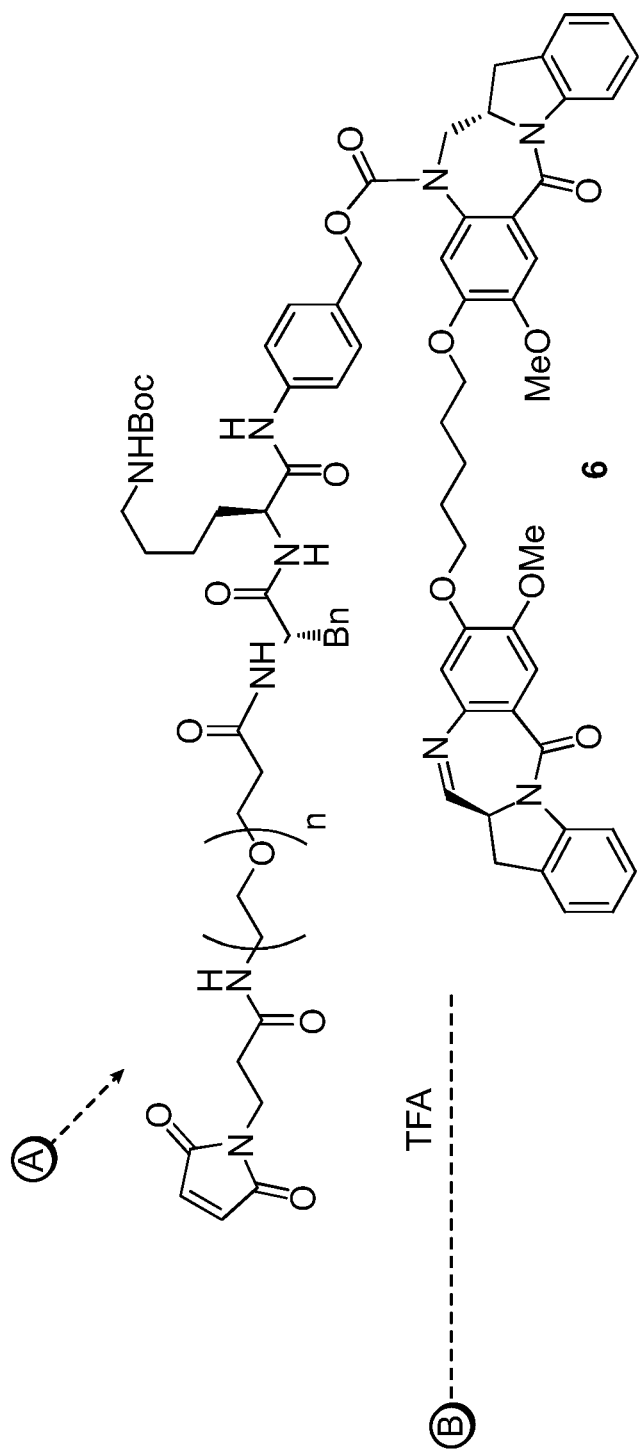
Figure 2C:
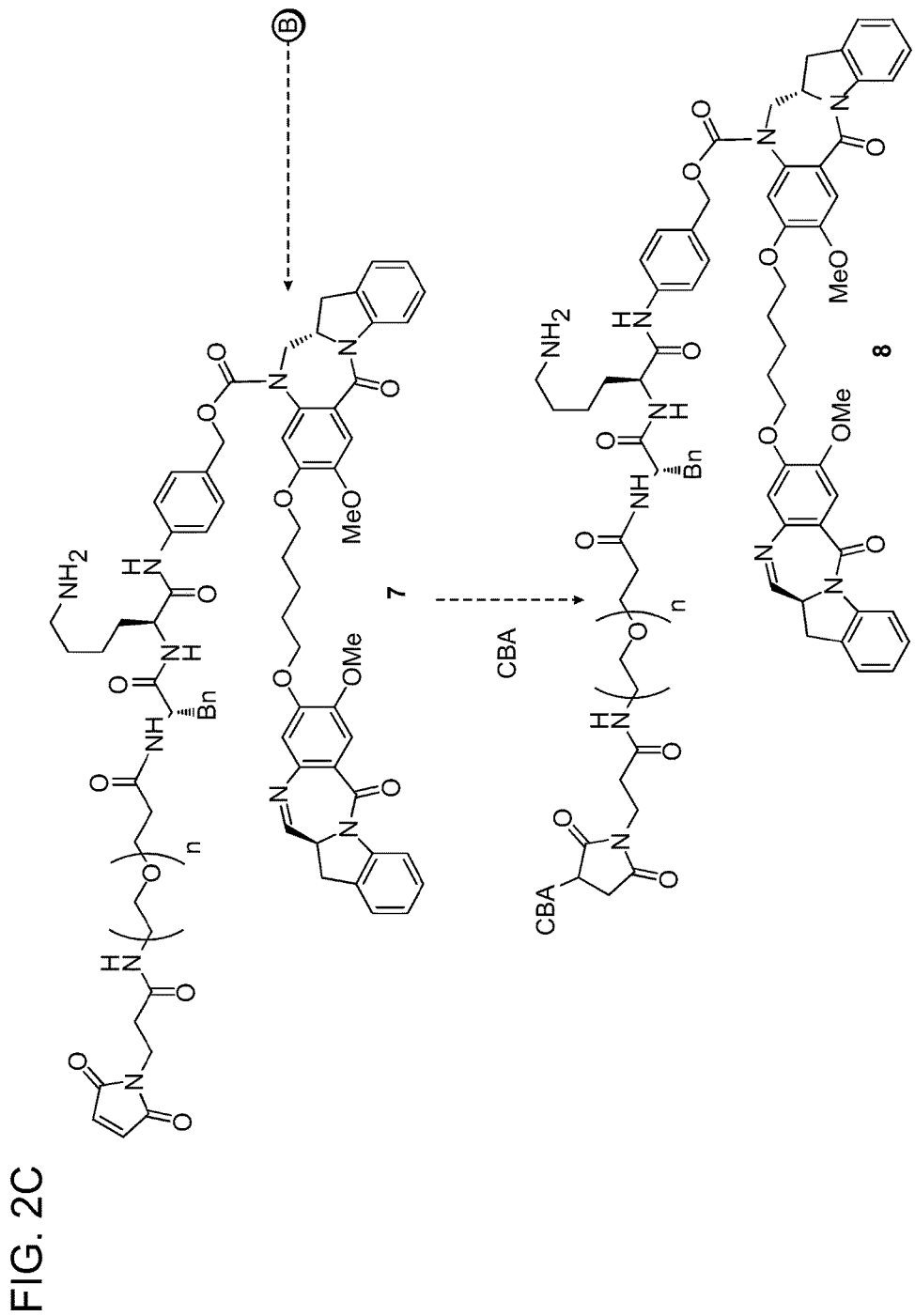

Cell binding agent conjugates of IBD mono-imine dimers of the invention are prepared as shown in FIG. 2. Treatment of the mono-reduced dimer 2 with triphosgene under basic conditions followed by the addition of a substituted amino benzyl alcohol such as 4 effects reaction at the amino position, giving coupled dimer 5 as shown in FIG. 2. Removal of the Alloc protecting group with Pd(PPH$_3$)$_4$ to generate the free amine followed by coupling with EEDQ and a maleimide containing a functionalized ester, such as the maleimide-4-PEG succinimide, gives the maleimide dimer 6. Deprotection of the Boc protecting group with TFA followed by coupling with a cell binding agent (CBA) would give conjugate 8.

Example 3

Figure 3A:
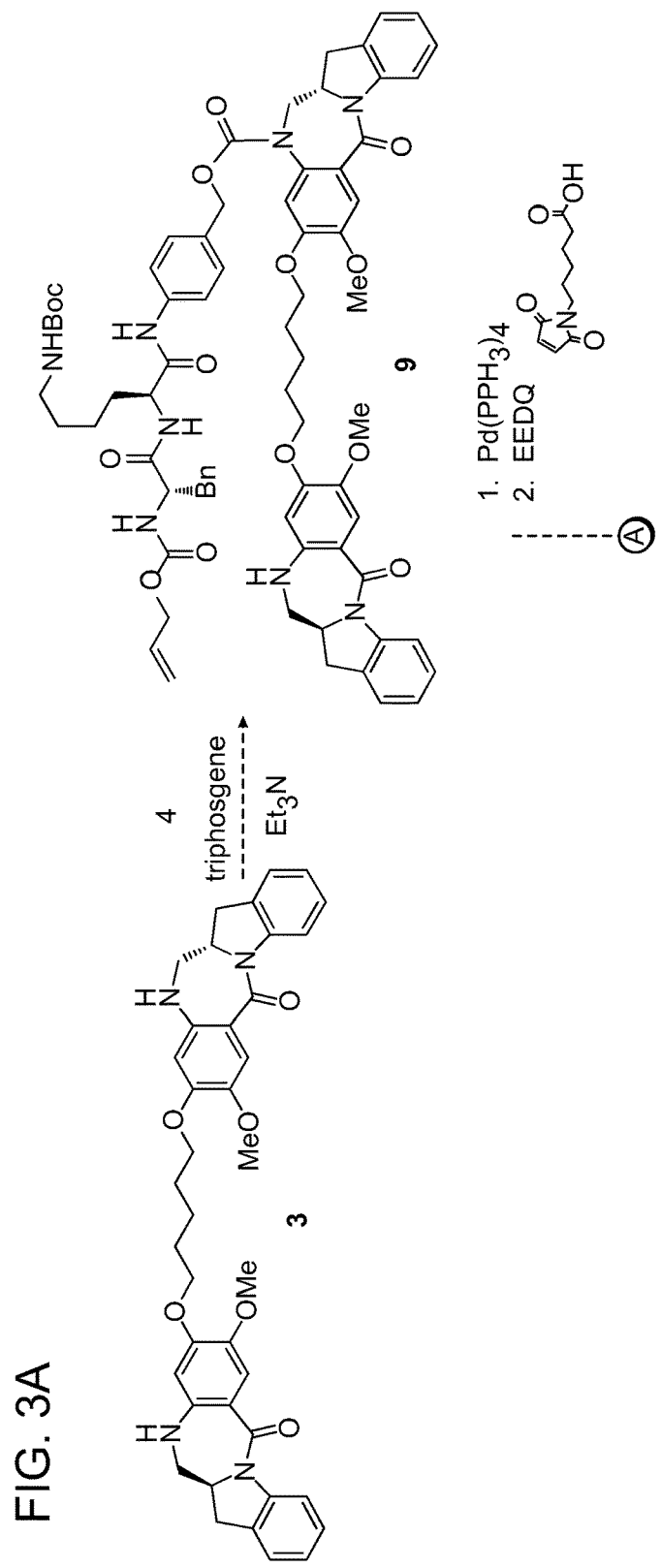
Figure 3B:
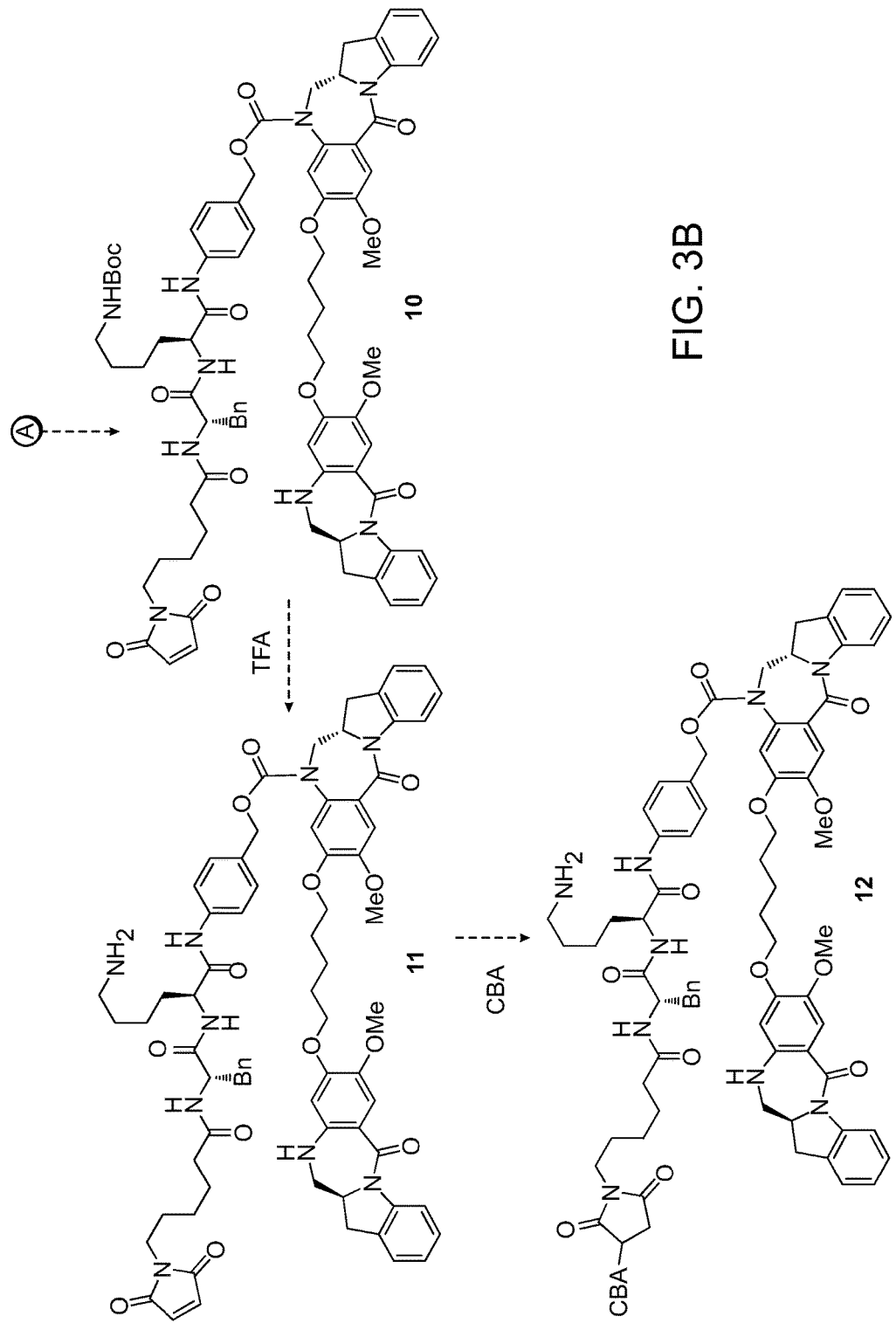

Cell binding agent conjugates of IBD di-amine dimers of the invention are prepared as shown in FIG. 3. In a similar fashion as that described in Example 2, the fully reduced dimer 3 could be treated analogously to provide the desired conjugate.

Example 4

Figure 4A:
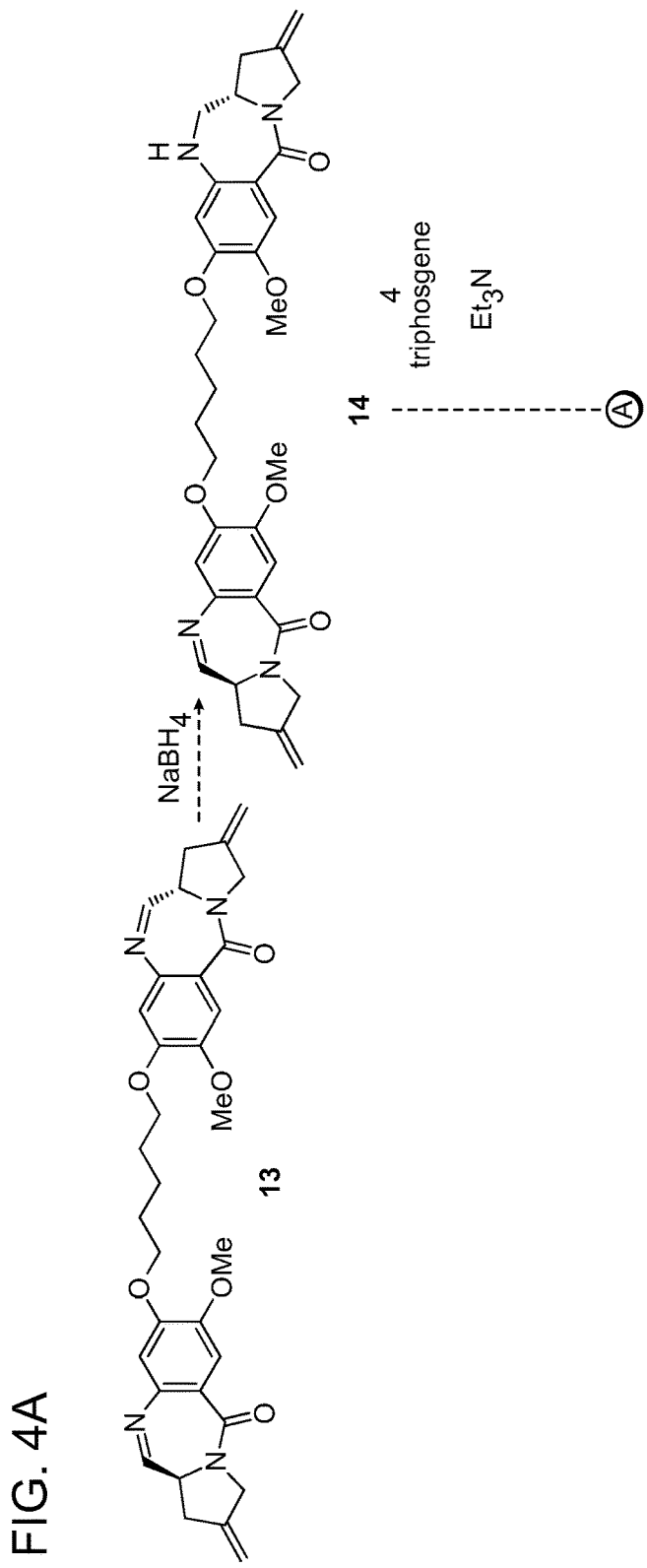
Figure 4B:
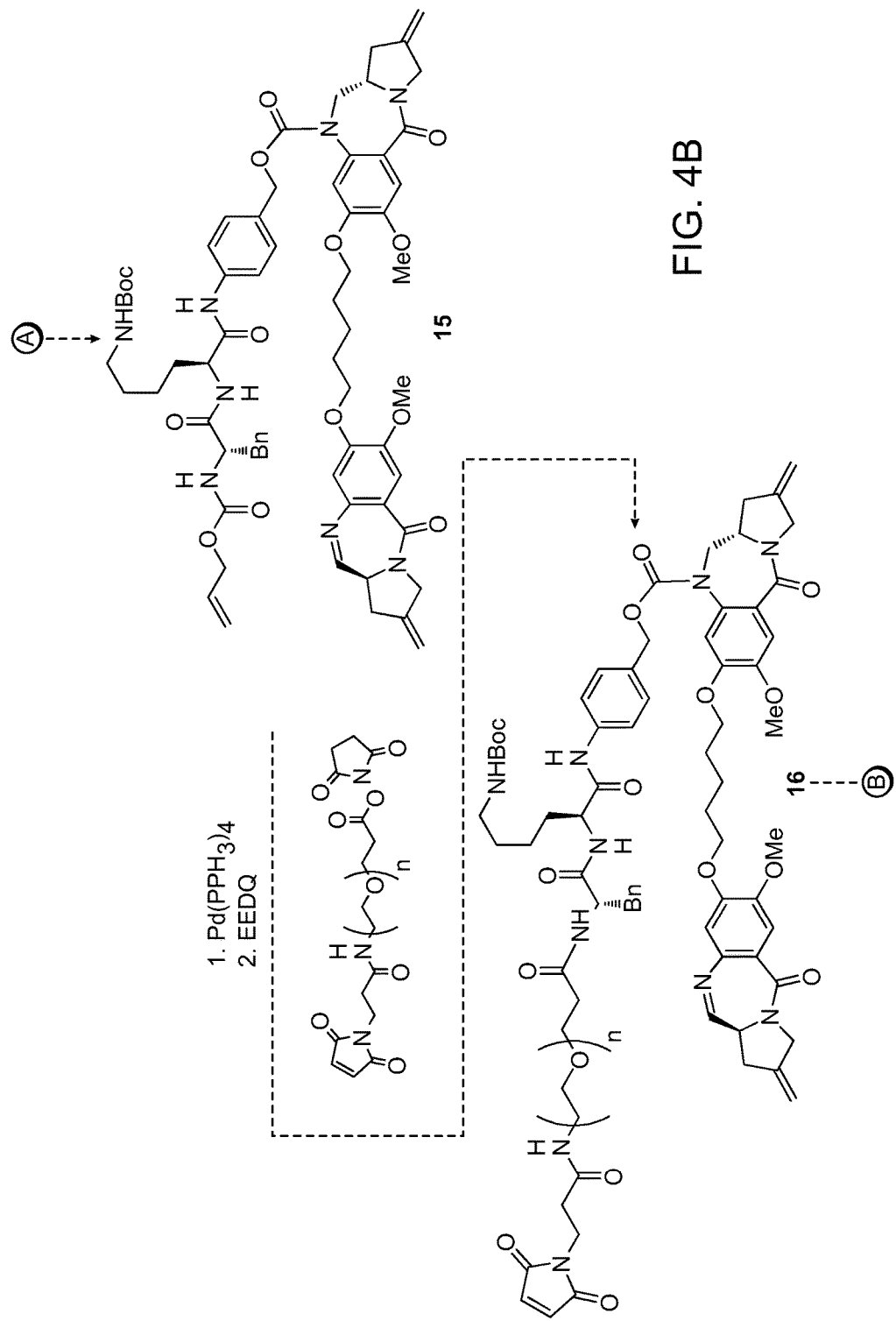
Figure 4C:
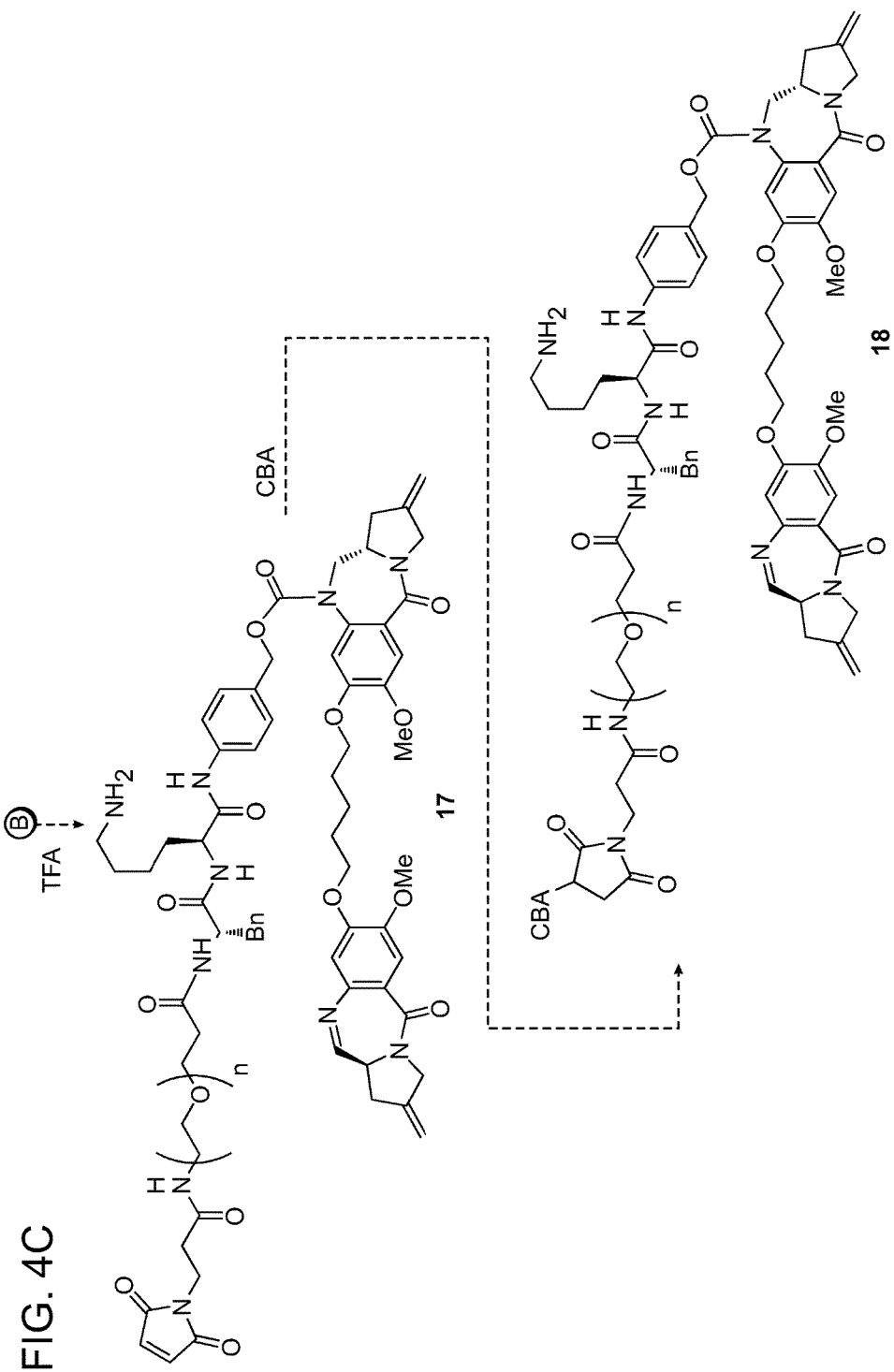
Figure 5A:
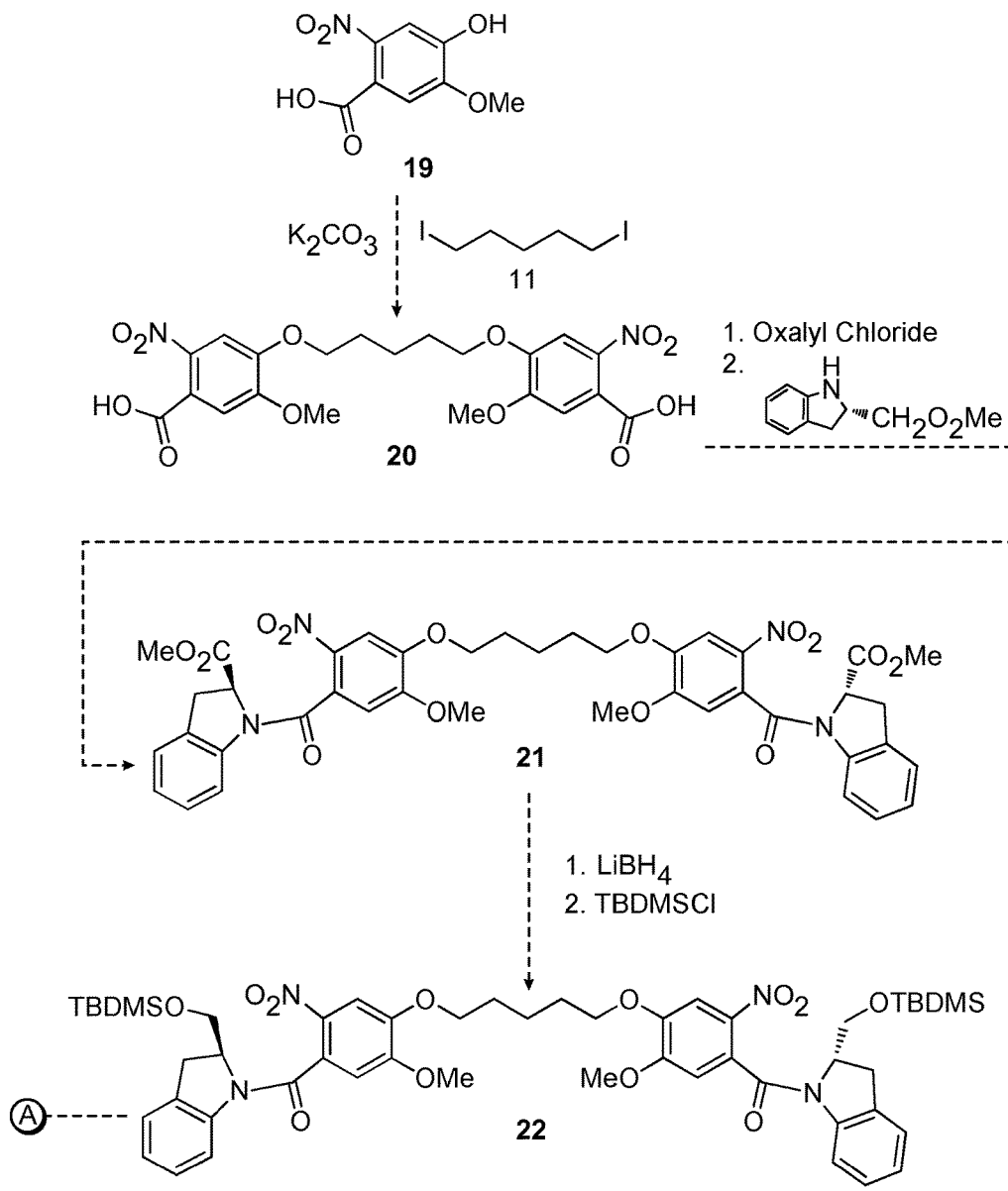
Figure 5B:
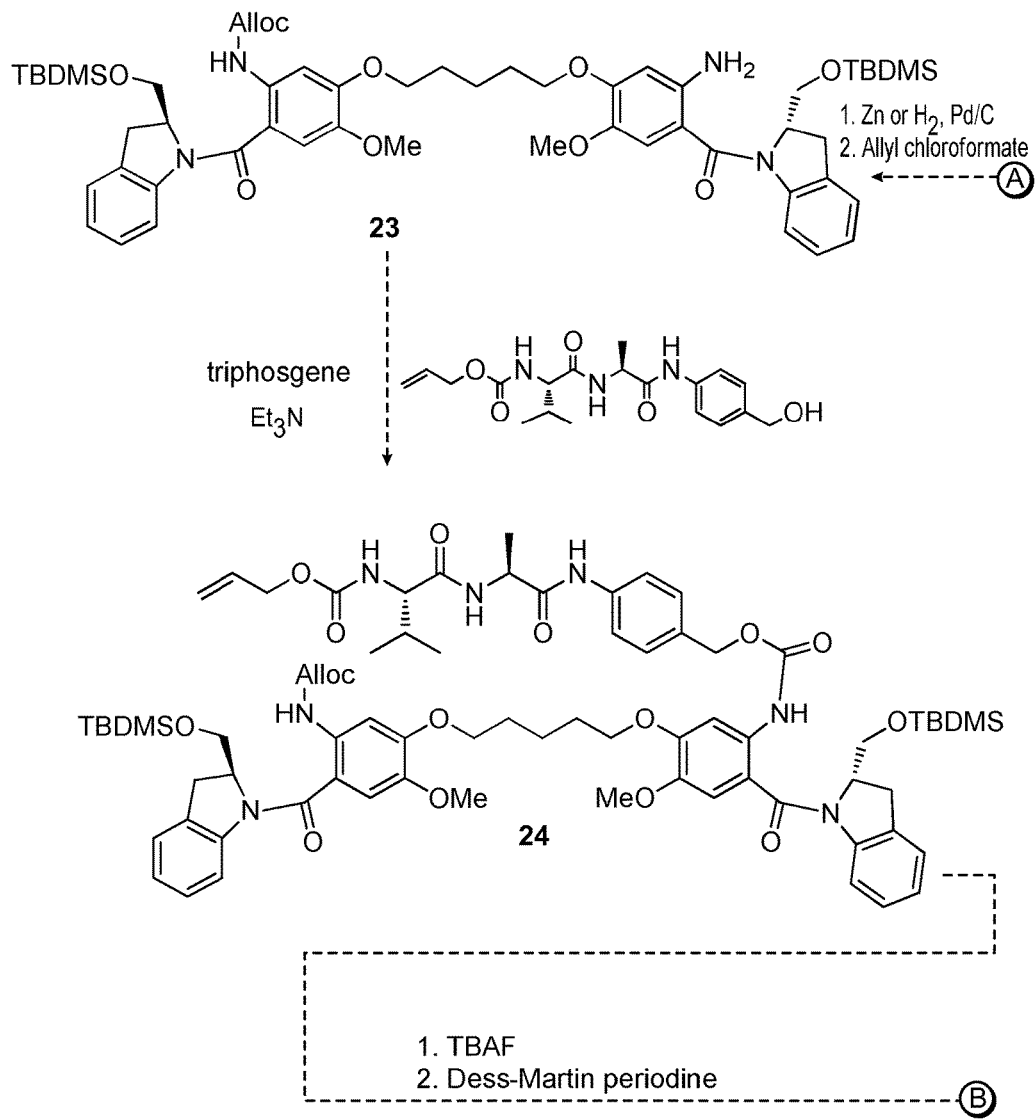
Figure 5C:
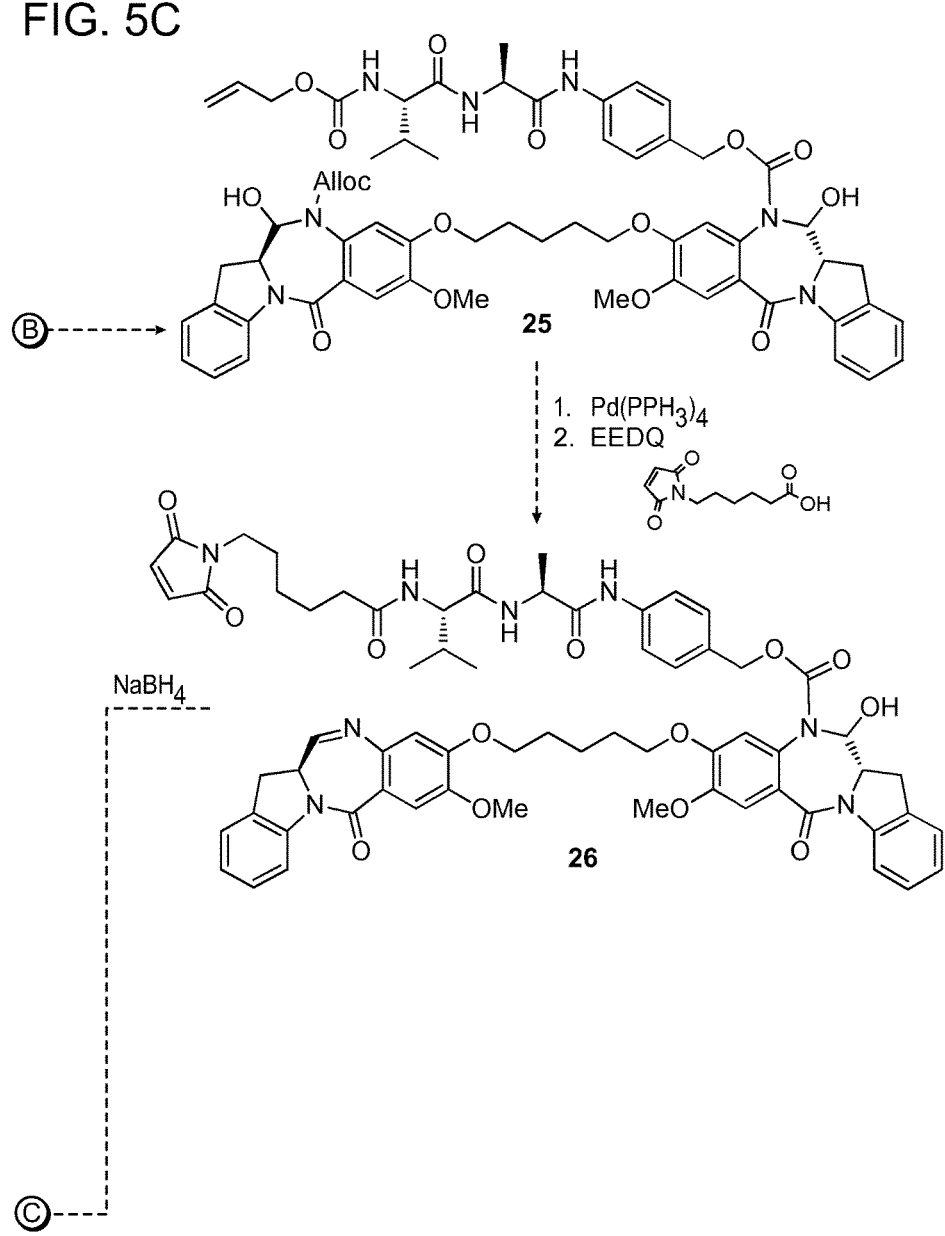
Figure 5D:
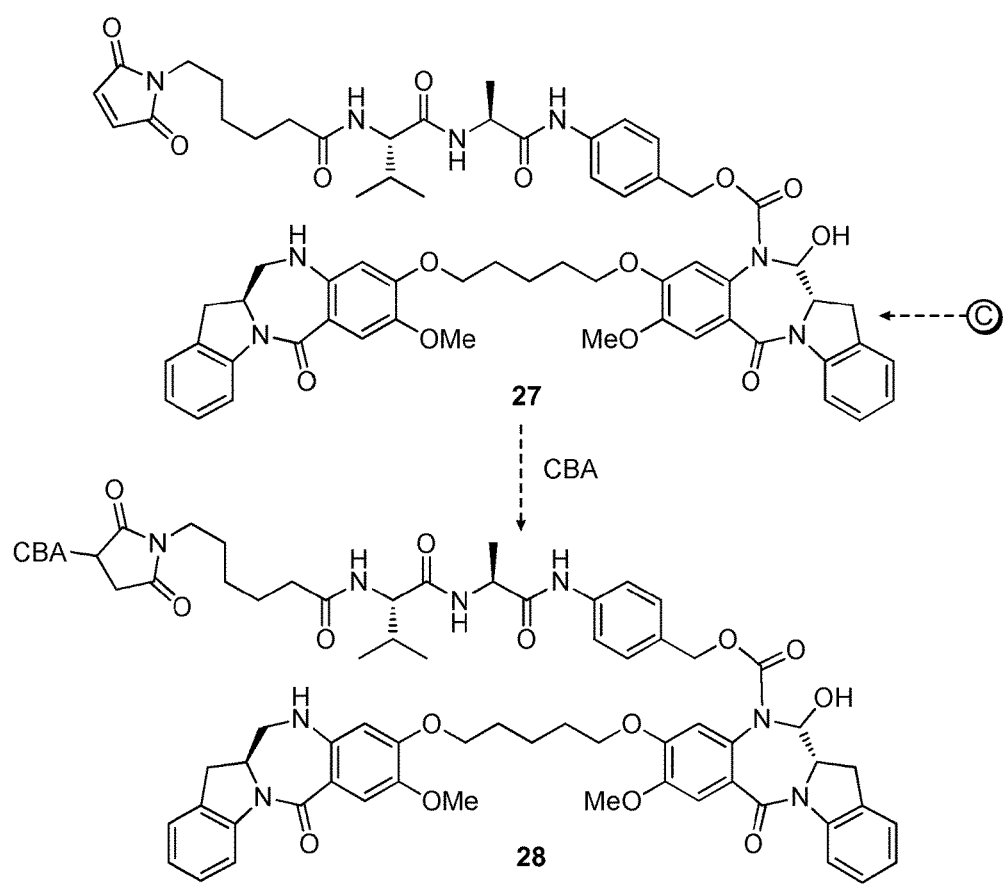

The corresponding fully reduced or partially reduced PBD dimer compounds are synthesized in an analogous manner. Thus, the dimine PBD dimer (such as 13) is reduced with an agent such as sodium borohydride (or any of the reducing agents listed in Example 1) to provide the mono-imine or diamine PBD dimer. Cell binding agent conjugates are then prepared as shown in FIG. 4 and performed in a manner similar to that described in Examples 2 and 3.

Example 5

An alternative synthetic method to provide the mono-imine containing dimers of the instant invention is shown in FIG. 5. The nitrobenzoic acid compound 19 is first coupled to diiodopentane using potassium carbonate. Activation of the acid with oxalyl chloride followed by the addition of the hydrochloride salt of (S)-methyl indoline-2-carboxylate gives the di-methyl ester 21. Reduction of the carboxylic acids with lithium borohydride and subsequent alcohol protection with TBDMSCl gives compound 22. Reduction of the nitro functional groups with either Zn or H$_2$ using Pd/C gives the free amine which can then be mono protected using a substochiometric amount of allyl chlorofomate to give 23. Treatment of the remaining amine in a fashion similar to that described in FIG. 2 gives the substituted amino benzyl compound 24. TBAF deprotection of the silyl protecting groups followed by oxidation with Dess-Martin periodinane brings about cyclization to give compound 25. Removal of the Alloc protecting group and coupling of the free amine generated with an activated ester as before gives the maleimide containing compound 26. Reduction of the imine thus generated with sodium borohydride gives compound 27 which may be coupled to a CBA through the incorporated maleimide.

Figure 6A:
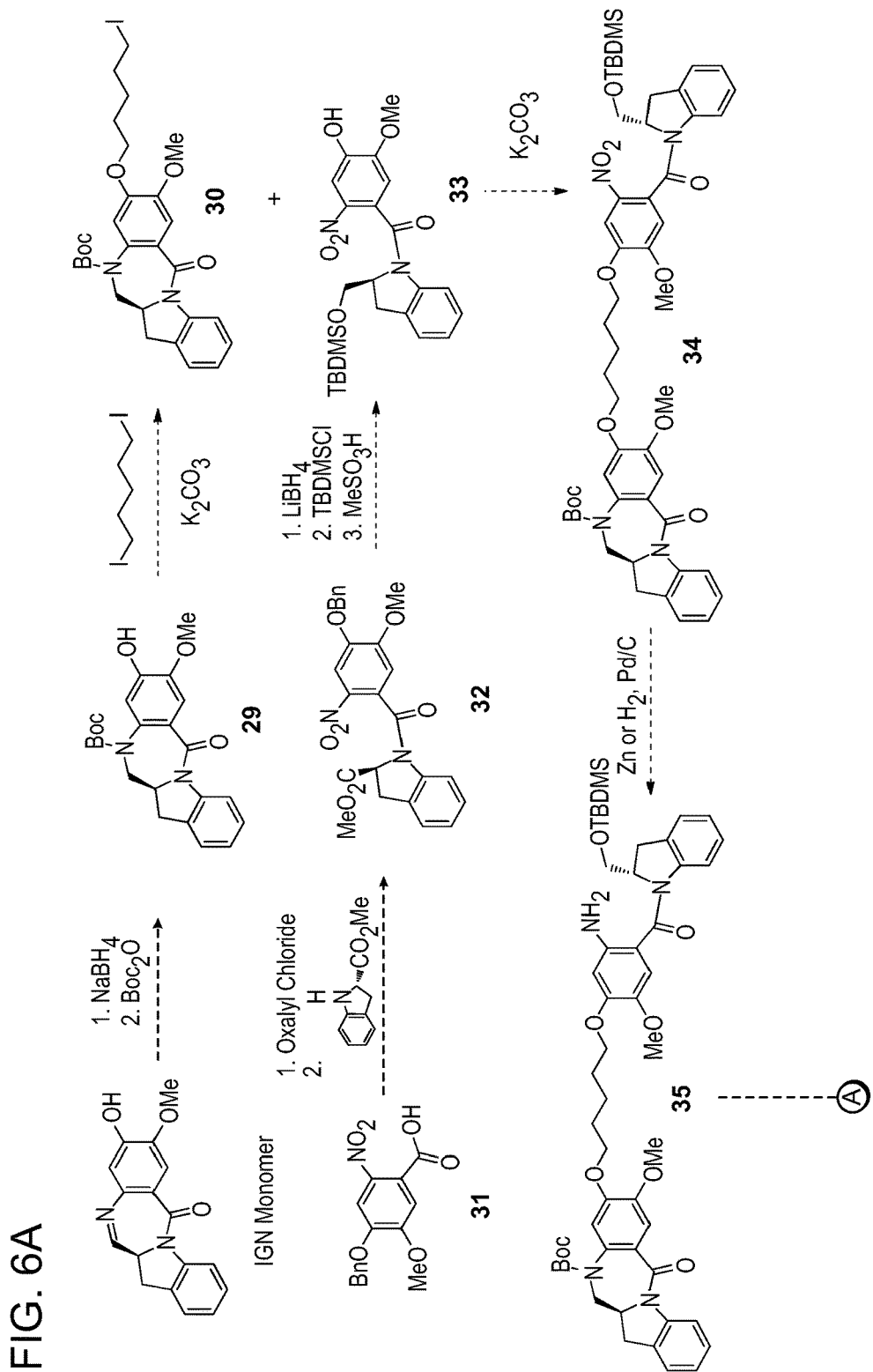
Figure 6B:
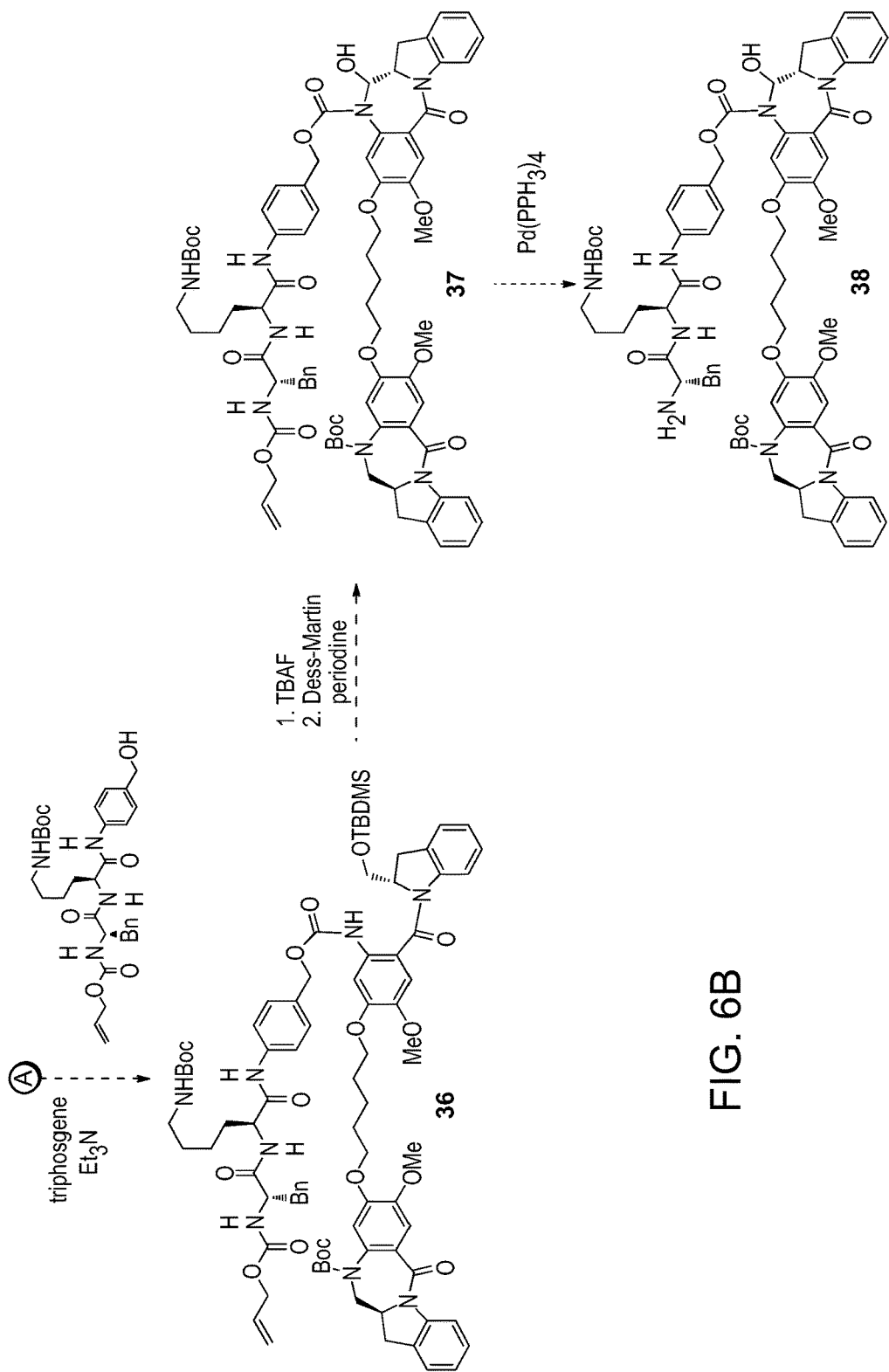
Figure 7A:
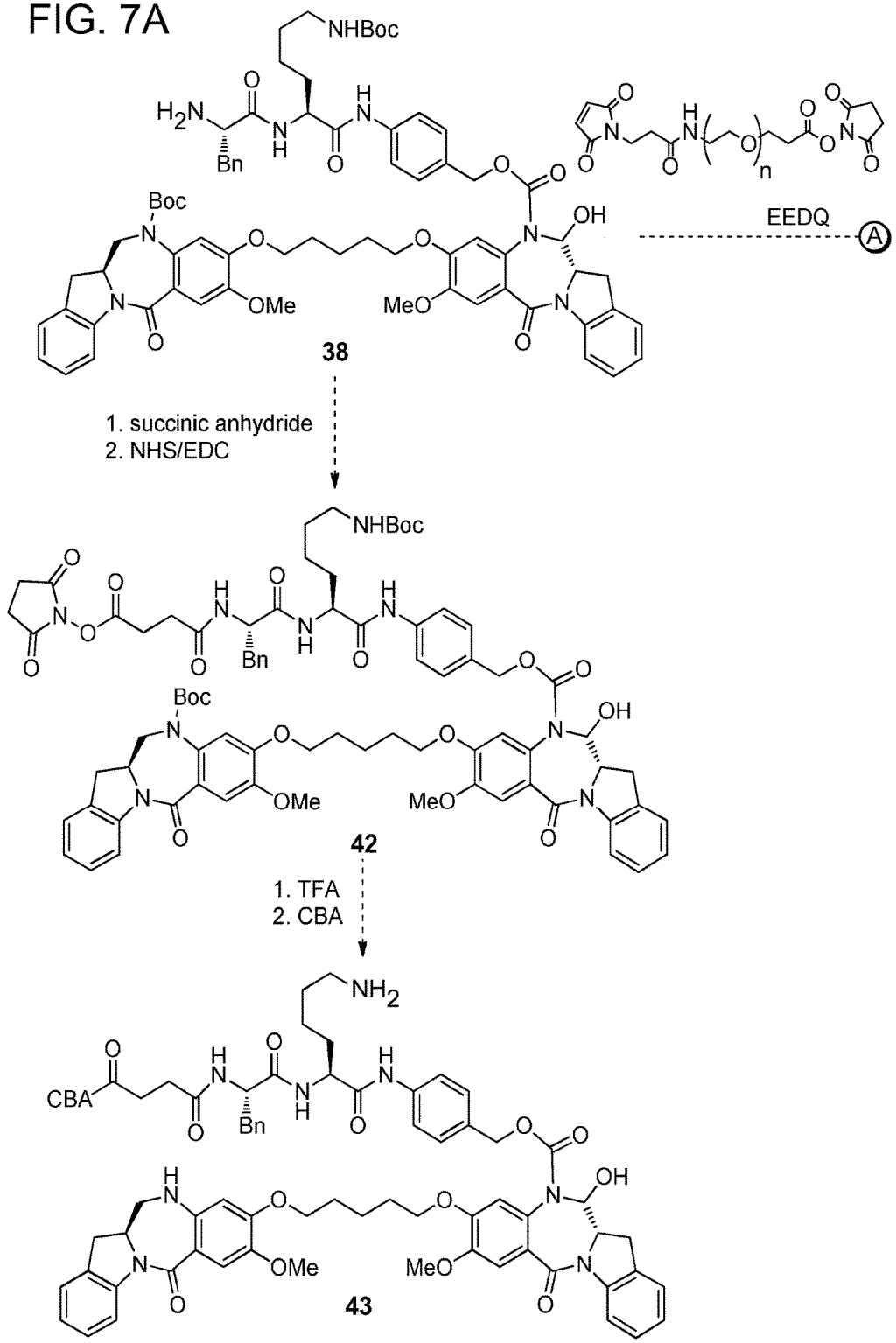
Figure 7B:
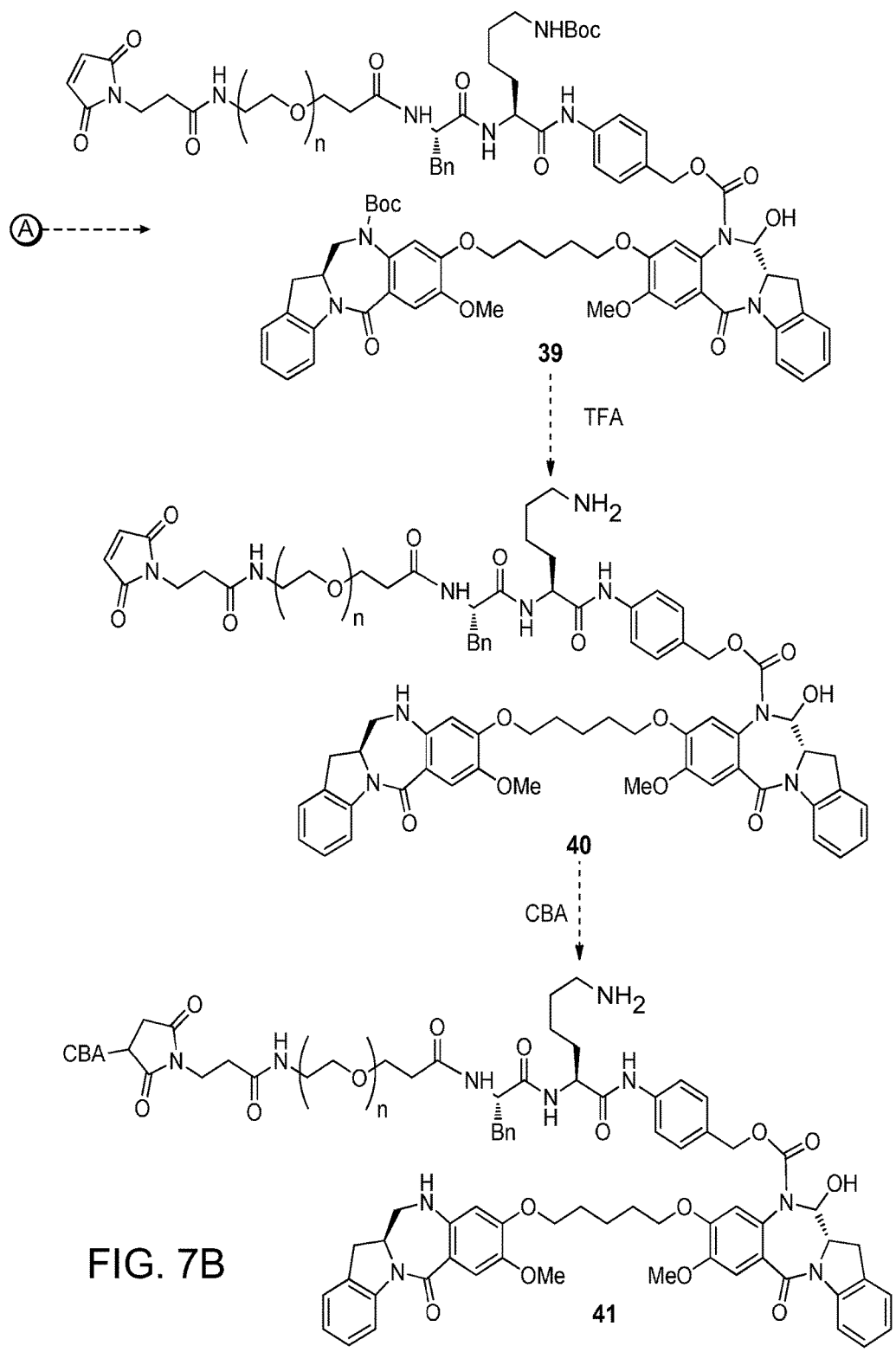

Additionally, FIG. 6 shows the synthesis of the described compounds using a monomer subunit with a modified precursor to that subunit. Thus, the IGN monomer can be reduced with sodium borohydride and the amine generated protected with a protecting group such as Boc. Treatment of 29 with an excess of diiodopentane would give the iodide 30. Separately, the benzyl protected nitro benzoic acid 31 can be converted to the acid chloride with oxalyl chloride and then coupled with the hydrochloride salt of (S)-methyl indoline-2-carboxylate to give the methyl ester 32. Treatment of the methyl ester under conditions similar to that described for 21 and benzyl deprotection with methanesulfonic acid gives the phenol 33. This phenol may be coupled with 30 using potassium carbonate to generate the mono Boc protected compound 34. Treatment of 34 under conditions previously described would give the free amine 38. As shown in FIG. 7, 38 could be treated as described before giving the maleimide containing compound 40, which can be coupled to a CBA. Alternatively, 38 could be treated with succinic acid and then activated with N-hydroxysuccinimide to give 42. Removal of the Boc protecting group with TFA and coupling to a CBA would give 43.

Experimental

All pertinent experimental details, including specific assay conditions, can be found in US 2011/0256157 A1 (incorporated herein by reference).

REFERENCES

All references cited in US 2011/0256157 A1 are incorporated by reference in their entirety.

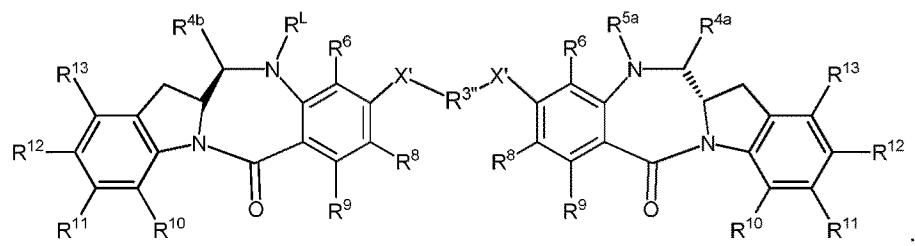

The invention claimed is:

1. A conjugate represented by the following structural formula:

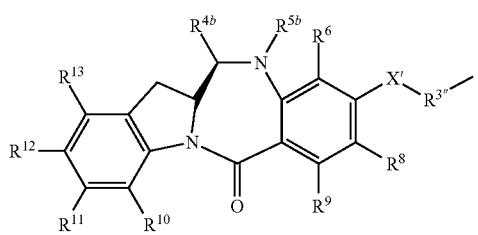

-continued

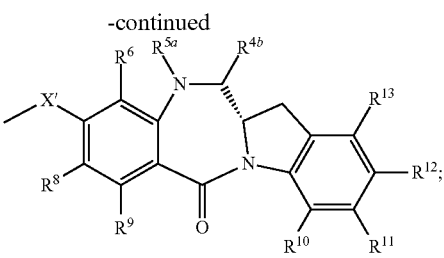

wherein:
- $R^{3''}$ is a $C_{3-12}$ alkylene group, which chain may be interrupted by one or more heteroatoms, and/or aromatic rings, which rings are optionally substituted by —NH₂;
- each X', for each occurrence, is independently —O—, —S— or —N(H)—;
- $R^{4a}$ is selected from —H, an oxo group, an optionally substituted linear, branched or cyclic alkyl, alkenyl or alkynyl having from 1 to 10 carbon atoms, an optionally substituted 6- to 18-membered aryl, an optionally substituted 5- to 18-membered heteroaryl ring containing one or more heteroatoms independently selected from nitrogen, oxygen, or sulfur, and an optionally substituted 3- to 18-membered heterocyclic ring having 1 to 6 heteroatoms;
- $R^{4b}$ is a leaving group selected from —OR⁶', —OCOR⁴', —OCOOR⁴', —OCONR⁴'R⁵', —NR⁴'R⁵', —NR⁴'COR⁵', —NR⁴'NR⁴'R⁵', an optionally substituted 5- or 6-membered nitrogen-containing heterocycle, a guanidinium represented by —NR⁴'(C=NH)NR⁴'R⁵', an amino acid, or a peptide represented by —NR⁶'COP', wherein P' is an amino acid or a polypeptide containing between 2 to 20 amino acid units, —SR⁶', —SOR⁴', —SO₂M, —SO₃M, —OSO₃M, halogen, cyano and an azido;
- $R^{5a}$ is —H, a protecting group, a peptide, an optionally substituted linear, branched or cyclic alkyl, alkenyl or alkynyl having from 1 to 10 carbon atoms, a polyethylene glycol unit —(CH₂CH₂O)ₙ—Rᶜ, an optionally substituted aryl having 6 to 18 carbon atoms, an optionally substituted 5- to 18-membered heteroaryl ring containing one or more heteroatoms independently selected from nitrogen, oxygen, and sulfur, and an optionally substituted 3- to 18-membered heterocyclic ring containing 1 to 6 heteroatoms independently selected from O, S, N and P;
- $R^{5b}$ is a group represented by the following formula:

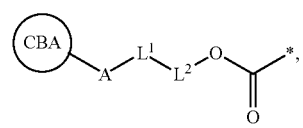

wherein CBA is a cell-binding agent, the asterisk indicates the point of attachment to the N10 position, $L^1$ comprises a dipeptide —X₁—X₂—, and wherein the dipeptide in $L^1$ as represented by —NH—X₁—X₂—CO— is selected from: -Phe-Lys-, -Val-Ala-, -Val-Lys-, -Ala-Lys-, -Val-Cit-, -Phe-Cit-, -Leu-Cit-, -Ile-Cit-, -Phe-Arg-, -Trp-Cit-, Lys-Lys, Phe-Ala, Phe-N⁹-tosyl-Arg, Phe-N⁹-nitro-Arg, Val-Arg, Arg-Val, Arg-Arg, Val-D-Cit, Val-D-Lys, Val-D-Arg, D-Val-Cit, D-Val-Lys, D-Val-Arg, D-Val-D-Cit, D-Val-D-Lys, D-Val-D-Arg, and D-Arg-D-Arg, where Cit is citrulline; or $L^1$ comprises a tripeptide —X₁—X₂—X₃— and wherein the tripeptide in $L^1$ as represented by —NH—X₁—X₂—X₃—CO— is selected from Gly-Gly-Gly, Phe-Phe-Lys, D-Phe-Phe-Lys, Gly-Phe-Lys, Leu-Ala-Leu, Ile-Ala-Leu and Val-Ala-Val; or $L^1$ comprises a tetrapeptide —X₁—X₂—X₃—X₄— and wherein the tetrapeptide in $L^1$ as represented by —NH—X₁—X₂—X₃—X₄—CO— is selected from Ala-Leu-Ala-Leu, β-Ala-Leu-Ala-Leu and Gly-Phe-Leu-Gly, A is:

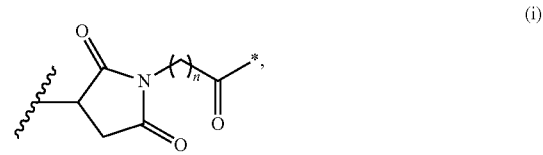

(i)

where the asterisk indicates the point of attachment to $L^1$, the wavy line indicates the point of attachment to the CBA and n is 0 to 6:

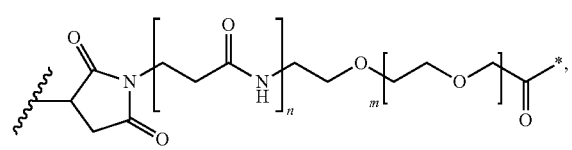

(ii)

where the asterisk indicates the point of attachment to $L^1$, the wavy line indicates the point of attachment to the CBA and the CBA, n is 0 or 1, and m is 0 to 30;

(iii)

where the asterisk indicates the point of attachment to $L^1$, the wavy line indicates the point of attachment to the CBA, and n is 1 to 6;

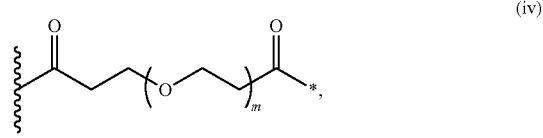

(iv)

where the asterisk indicates the point of attachment to $L^1$, the wavy line indicates the point of attachment to the CBA, and m is 1 to 30;

135

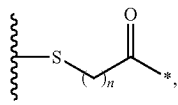

(v)

where the asterisk indicates the point of attachment to $L^1$, the wavy line indicates the point of attachment to the CBA, and n is 2 to 6; or

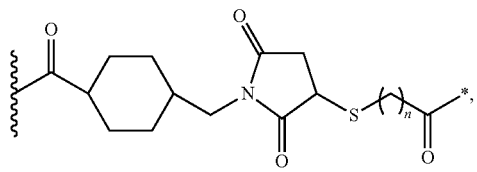

(vi)

where the asterisk indicates the point of attachment to $L^1$, the wavy line indicates the point of attachment to the CBA, and
n is 2 to 6;
$L^2$ together with —OC(=O)— form the group:

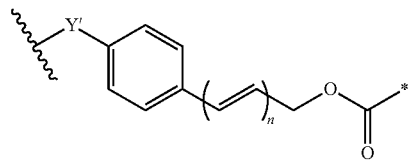

where the asterisk indicates the point of attachment to the N10 position, the wavy line indicates the point of attachment to the linker $L^1$, Y' is —NH—, —O—, —C(=O)NH— or —C(=O)O—, and n is 0 to 3;
$R^6$, $R^8$, and $R^9$ are independently selected from —H, —$R^{1'}$, —OH, —$OR^{1'}$, —SH, —$SR^{1'}$, —$NH_2$, —$NHR^{1'}$, —$NR^{1'}R^{3'}$, —$NO_2$, $Me_3Sn$ and halo;
$R^{10}$, $R^{11}$, $R^{12}$ and $R^{13}$ are each independently selected from the group consisting of —H, an optionally substituted linear, branched or cyclic alkyl, alkenyl or alkynyl having from 1 to 10 carbon atoms, a polyethylene glycol unit —$(OCH_2CH_2)_n$—$R^b$, halogen, guanidinium [—NH(C=NH)$NH_2$], —$OR^{6'}$, —$NR^{4'}R^{5'}$, —$NO_2$, —NCO, —$NR^{4'}COR^{5'}$, —$SR^{6'}$, a sulfoxide represented by —$SOR^{4'}$, a sulfone represented by —$SO_2R^{4'}$, a sulfonate —$SO_3^-M^+$, a sulfate —$OSO_3^-M^+$, a sulfonamide represented by —$SO_2NR^{4'}R^{5'}$, cyano, an azido, —$COR^{4'}$, —$OCOR^{4'}$, —$OCONR^{4'}R^{5'}$;
$R^{1'}$ and $R^{3'}$ are each independently selected from optionally substituted $C_{1-12}$ alkyl, $C_{3-20}$ heterocyclyl or $C_{5-20}$ aryl groups, and optionally in relation to the group —$NR^{1'}R^{3'}$, $R^{1'}$ and $R^{3'}$ together with the nitrogen atom to which they are attached form an optionally substituted 4-, 5-, 6- or 7-membered heterocyclic ring;
$R^{4'}$ and $R^{5'}$ are each independently selected from —H, —OH, —$OR^{6'}$, —$NHR^{6'}$, —$NR^{6'}_2$, —$COR^{6'}$, an optionally substituted linear, branched or cyclic alkyl, alkenyl or alkynyl having from 1 to 10 carbon atoms, a polyethylene glycol unit —$(CH_2CH_2O)_n$—$R^b$, or an optionally substituted 3-18-membered heterocyclic ring having 1 to 6 heteroatoms independently selected from O, S, N or P;

136

$R^{6'}$, for each occurrence, is independently selected from the group consisting of —H, an optionally substituted linear, branched or cyclic alkyl, alkenyl or alkynyl having from 1 to 10 carbon atoms, a polyethylene glycol unit —$(CH_2CH_2O)_n$—$R^b$, an optionally substituted aryl having 6 to 18 carbon atoms, an optionally substituted 5- to 18-membered heteroaryl ring containing one or more heteroatoms independently selected from nitrogen, oxygen, or sulfur, and an optionally substituted 3- to 18-membered heterocyclic ring containing 1 to 6 heteroatoms independently selected from O, S, N or P;
$R^b$ is —H or an optionally substituted linear or branched alkyl having 1 to 4 carbon atoms;
M is H or a pharmaceutically acceptable cation; and
n is an integer from 1 to 24, wherein the optional substituent is selected from the group consisting of $R^{1'}$, $OR^{1'}$, $SR^{1'}$, $NR^{1'}R^{3'}$, $NO_2$, halo, $CO_2R^{1'}$, $CONH_2$, $CONHR^{1'}$ and $CONR^{1'}R^{3'}$.

2. The conjugate of claim 1, wherein X' is —O—.
3. The conjugate of claim 1, wherein $R^{3''}$ is a $C_3$ alkylene group, a $C_4$ alkylene group, or a $C_5$ alkylene group.
4. The conjugate of claim 1, wherein $L^1$ and $L^2$ together with —OC(=O)— comprise a group selected from:

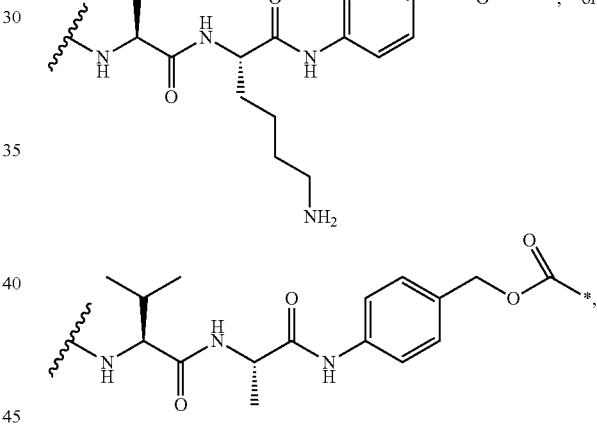

where the asterisk indicates the point of attachment to the N10 position, and the wavy line indicates the point of attachment to the remaining portion of the linker $L^1$ or the point of attachment to A.

5. The conjugate of claim 1, wherein the cell binding agent is connected to A through a thioether bond formed from a cysteine thiol residue of the cell binding agent and a malemide group of A; or the cell binding agent is connected to A through an amide bond formed from a lysine residue of the cell binding agent and a carboxyl group of A.

6. The conjugate of claim 1, wherein the cell binding agent is an antibody or an active fragment thereof.

7. The conjugate of claim 1, wherein $R^{5a}$ is H or an amine protecting group; $R^{4b}$ is selected from —$OR^{6'}$, —$OCOR^{4'}$, —$SR^6$, —$NR^{4'}R^{5'}$, an optionally substituted 5- or 6-membered nitrogen-containing heterocycle, —$SO_3M$, —$SO_2M$ and a sulfate —$OSO_3M$; $R^6$, $R^9$, $R^{10}$, $R^{11}$, $R^{12}$ and $R^{13}$ are all —H and $R^8$ is —OMe.

8. A pharmaceutical composition comprising the conjugate of claim 1, and a pharmaceutically acceptable diluent, carrier or excipient.

9. A compound represented by the following structural formula:

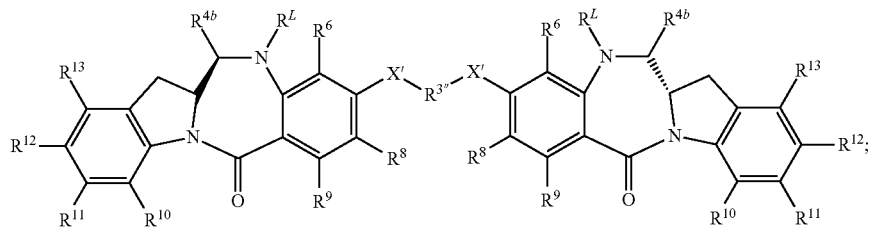

wherein:
- $R^{3''}$ is a $C_{3-12}$ alkylene group, which chain may be interrupted by one or more heteroatoms, and/or aromatic rings, which rings are optionally substituted by —$NH_2$;
- each X', for each occurrence, is independently —O—, —S— or —N(H)—;
- $R^{4a}$ is selected from —H, an oxo group, an optionally substituted linear, branched or cyclic alkyl, alkenyl or alkynyl having from 1 to 10 carbon atoms, an optionally substituted 6- to 18-membered aryl, an optionally substituted 5- to 18-membered heteroaryl ring containing one or more heteroatoms independently selected from nitrogen, oxygen, or sulfur, and an optionally substituted 3- to 18-membered heterocyclic ring having 1 to 6 heteroatoms;
- $R^{4b}$ is a leaving group selected from —$OR^{6'}$, —$OCOR^{4'}$, —$OCOOR^{4'}$, —$OCONR^{4'}R^{5'}$, —$NR^{4'}R^{5'}$, —$NR^{4'}COR^{5'}$, —$NR^{4'}NR^{4'}R^{5'}$, an optionally substituted 5- or 6-membered nitrogen-containing heterocycle, a guanidinium represented by —$NR^{4'}(C=NH)NR^{4'}R^{5'}$, an amino acid, or a peptide represented by —$NR^{6'}COP'$, wherein P' is an amino acid or a polypeptide containing between 2 to 20 amino acid units, —$SR^6$, —$SOR^{4'}$, —$SO_2M$, —$SO_3M$, —$OSO_3M$, halogen, cyano and an azido;
- $R^{5a}$ is —H, a protecting group, a peptide, an optionally substituted linear, branched or cyclic alkyl, alkenyl or alkynyl having from 1 to 10 carbon atoms, a polyethylene glycol unit —$(CH_2CH_2O)_n$—$R^c$, an optionally substituted aryl having 6 to 18 carbon atoms, an optionally substituted 5- to 18-membered heteroaryl ring containing one or more heteroatoms independently selected from nitrogen, oxygen, and sulfur, and an optionally substituted 3- to 18-membered heterocyclic ring containing 1 to 6 heteroatoms independently selected from O, S, N and P;
- $R^L$ is a group represented by the following formula:

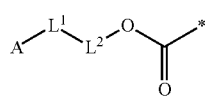

where the asterisk indicates the point of attachment to the N10 position, $L^1$ is a dipeptide —$X_1$—$X_2$—, and wherein the dipeptide in $L^1$ as represented by —NH—$X_1$—$X_2$—CO— is selected from: -Phe-Lys-, -Val-Ala-, -Val-Lys-, -Ala-Lys-, -Val-Cit-, -Phe-Cit-, -Leu-Cit-, -Ile-Cit-, -Phe-Arg-, -Trp-Cit-, -Lys-Lys, Phe-Ala, Phe-N9-tosyl-Arg, Phe-N9-nitro-Arg, Val-Arg, Arg-Val, Arg-Arg, Val-D-Cit, Val-D-Lys, Val-D-Arg, D-Val-Cit, D-Val-Lys, D-Val-Arg, D-Val-D-Cit, D-Val-D-Lys, D-Val-D-Arg, and D-Arg-D-Arg, where Cit is citrulline; or $L^1$ comprises a tripeptide —$X_1$—$X_2$—$X_3$— and wherein the tripeptide in $L^1$ as represented by —NH—$X_1$—$X_2$—$X_3$—CO— is selected from Gly-Gly-Gly, Phe-Phe-Lys, D-Phe-Phe-Lys, Gly-Phe-Lys, Leu-Ala-Leu, Ile-Ala-Leu and Val-Ala-Val; or $L^1$ comprises a tetrapeptide —$X_1$—$X_2$—$X_3$—$X_4$— and wherein the tetrapeptide in $L^1$ as represented by —NH—$X_1$—$X_2$—$X_3$—$X_4$—CO— is selected from Ala-Leu-Ala-Leu, β-Ala-Leu-Ala-Leu and Gly-Phe-Leu-Gly, A is:

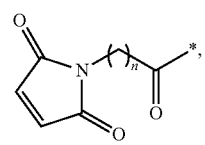

where the asterisk indicates the point of attachment to $L^1$, and n is 0 to 6;

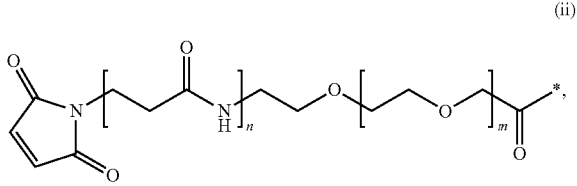

where the asterisk indicates the point of attachment to $L^1$, n is 0 or 1, and m is 0 to 30;

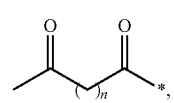

where the asterisk indicates the point of attachment to $L^1$, and n is 1 to 6;

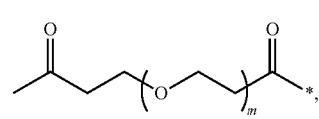

where the asterisk indicates the point of attachment to $L^1$, and m is 1 to 30;

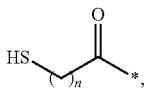

(v)

where the asterisk indicates the point of attachment to $L^1$, and n is 2 to 6; or

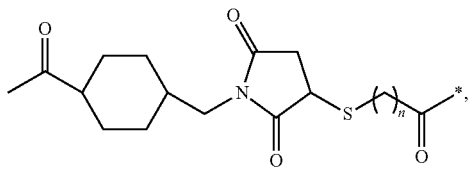

(vi)

where the asterisk indicates the point of attachment to $L^1$, and n is 2 to 6, $L^2$ together with —OC(=O)— form the group:

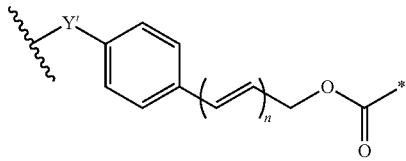

where the asterisk indicates the point of attachment to the N10 position, the wavy line indicates the point of attachment to the linker $L^1$, Y' is —NH—, —O—, —C(=O)NH— or —C(=O)O—, and n is 0 to 3;

$R^6$, $R^8$, and $R^9$ are independently selected from —H, —$R^{1'}$, —OH, —$OR^{1'}$, —SH, —$SR^{1'}$, —$NH_2$, —$NHR^{1'}$, —$NR^{1'}R^{3'}$, —$NO_2$, $Me_3Sn$ and halo;

$R^{10}$, $R^{11}$, $R^{12}$ and $R^{13}$ are each independently selected from the group consisting of —H, an optionally substituted linear, branched or cyclic alkyl, alkenyl or alkynyl having from 1 to 10 carbon atoms, a polyethylene glycol unit —$(OCH_2CH_2)_n$—$R^b$, halogen, guanidinium [—NH(C=NH)$NH_2$], —$OR^{6'}$, —$NR^{4'}R^{5'}$, —$NO_2$, —NCO, —$NR^{4'}COR^{5'}$, —$SR^{6'}$, a sulfoxide represented by —$SOR^{4'}$, a sulfone represented by —$SO_2R^{4'}$, a sulfonate —$SO_3^-M^+$, a sulfate —$OSO_3^-M^+$, a sulfonamide represented by —$SO_2NR^{4'}R^{5'}$, cyano, an azido, —$COR^{4'}$, —$OCOR^{4'}$, —$OCONR^{4'}R^{5'}$;

$R^{1'}$ and $R^{3'}$ are each independently selected from optionally substituted $C_{1-12}$ alkyl, $C_{3-20}$heterocyclyl or $C_{5-20}$ aryl groups, and optionally in relation to the group —$NR^{1'}R^{3'}$, $R^{1'}$ and $R^{3'}$ together with the nitrogen atom to which they are attached form an optionally substituted 4-, 5-, 6- or 7-membered heterocyclic ring;

$R^{4'}$ and $R^{5'}$ are each independently selected from —H, —OH, —$OR^{6'}$, —$NHR^{6'}$, —$NR^{6'}{}_2$, —$COR^{6'}$, an optionally substituted linear, branched or cyclic alkyl, alkenyl or alkynyl having from 1 to 10 carbon atoms, a polyethylene glycol unit —$(CH_2CH_2O)_n$—$R^b$, or an optionally substituted 3-18-membered heterocyclic ring having 1 to 6 heteroatoms independently selected from O, S, N or P;

$R^{6'}$, for each occurrence, is independently selected from the group consisting of —H, an optionally substituted linear, branched or cyclic alkyl, alkenyl or alkynyl having from 1 to 10 carbon atoms, a polyethylene glycol unit —$(CH_2CH_2O)_n$—$R^b$, an optionally substituted aryl having 6 to 18 carbon atoms, an optionally substituted 5- to 18-membered heteroaryl ring containing one or more heteroatoms independently selected from nitrogen, oxygen, or sulfur, and an optionally substituted 3- to 18-membered heterocyclic ring containing 1 to 6 heteroatoms independently selected from O, S, N or P;

$R^b$ is —H or an optionally substituted linear or branched alkyl having 1 to 4 carbon atoms;

M is H or a pharmaceutically acceptable cation; and n is an integer from 1 to 24, wherein the optional substituent is selected from the group consisting of $R^{1'}$, $OR^{1'}$, $SR^{1'}$, $NR^{1'}R^{3'}$, $NO_2$, halo, $CO_2R^{1'}$, $CONH_2$, $CONHR^{1'}$ and $CONR^{1'}R^{3'}$.

10. The compound of claim 9, wherein X' is —O—.

11. The compound of claim 9, wherein $R^{3''}$ is a C3 alkylene group, a C4 alkylene group, or a C5 alkylene group.

12. The compound of claim 9, wherein $L^1$ and $L^2$ together with —OC(=O)— comprise a group selected from:

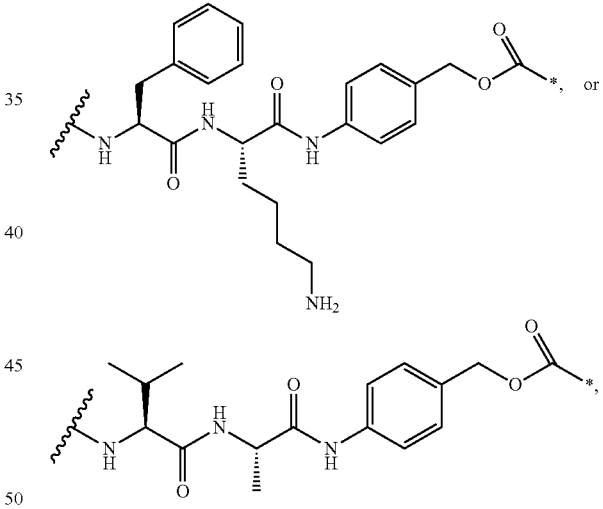

where the asterisk indicates the point of attachment to the N10 position, and the wavy line indicates the point of attachment to the remaining portion of the linker $L^1$ or the point of attachment to A.

13. The compound of claim 9, wherein $R^{5a}$ is H or an amine protecting group; $R^{4b}$ is selected from —$OR^{6'}$, —$OCOR^{4'}$, —$SR^{6'}$, —$NR^{4'}R^{5'}$, an optionally substituted 5- or 6-membered nitrogen-containing heterocycle, —$SO_3M$, —$SO_2M$ and a sulfate -$OSO_3M$; $R^6$, $R^9$, $R^{10}$, $R^{11}$, $R^{12}$ and $R^{13}$ are all —H and $R^8$ is —OMe.

14. A method of preparing a conjugate of claim 1, or a salt or solvate thereof, the method comprising reacting a cell binding agent with a dimer compound, or a salt or solvate of the dimer, wherein the dimer compound is represented by the following formula:

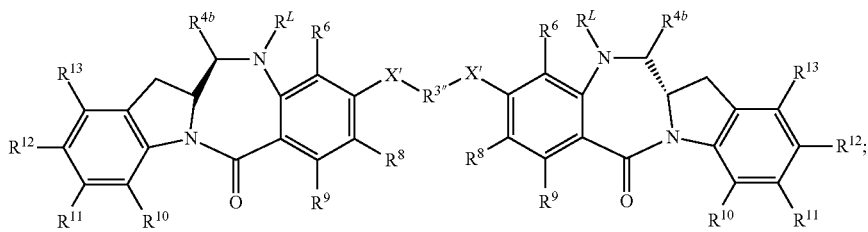

wherein:
- $R^{3''}$ is a $C_{3-12}$ alkylene group, which chain may be interrupted by one or more heteroatoms, and/or aromatic rings, which rings are optionally substituted by —$NH_2$;
- each X', for each occurrence, is independently —O—, —S— or —N(H)—;
- $R^{4a}$ is selected from —H, an oxo group, an optionally substituted linear, branched or cyclic alkyl, alkenyl or alkynyl having from 1 to 10 carbon atoms, an optionally substituted 6- to 18-membered aryl, an optionally substituted 5- to 18-membered heteroaryl ring containing one or more heteroatoms independently selected from nitrogen, oxygen, or sulfur, and an optionally substituted 3- to 18-membered heterocyclic ring having 1 to 6 heteroatoms;
- $R^{4b}$ is a leaving group selected from —$OR^{6'}$, —$OCOR^{4'}$, —$OCOOR^{4'}$, —$OCONR^{4'}R^{5'}$, —$NR^{4'}R^{5'}$, —$NR^{4'}COR^{5'}$, —$NR^{4'}NR^{4'}R^{5'}$, an optionally substituted 5- or 6-membered nitrogen-containing heterocycle, a guanidinium represented by —$NR^{4'}(C=NH)NR^{4'}R^{5'}$, an amino acid, or a peptide represented by —$NR^{6'}COP'$, wherein P' is an amino acid or a polypeptide containing between 2 to 20 amino acid units, —$SR^{6}$, —$SOR^{4'}$, —$SO_2M$, —$SO_3M$, —$OSO_3M$, halogen, cyano and an azido;
- $R^{5a}$ is —H, a protecting group, a peptide, an optionally substituted linear, branched or cyclic alkyl, alkenyl or alkynyl having from 1 to 10 carbon atoms, a polyethylene glycol unit —$(CH_2CH_2O)_n$—$R^c$, an optionally substituted aryl having 6 to 18 carbon atoms, an optionally substituted 5- to 18-membered heteroaryl ring containing one or more heteroatoms independently selected from nitrogen, oxygen, and sulfur, and an optionally substituted 3- to 18-membered heterocyclic ring containing 1 to 6 heteroatoms independently selected from O, S, N and P;
- $R^L$ is a group represented by the following formula:

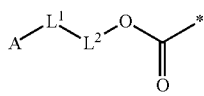

where the asterisk indicates the point of attachment to the N10 position, $L^1$ is a dipeptide —$X_1$—$X_2$—, and wherein the dipeptide in $L^1$ as represented by —NH—$X_1$—$X_2$—CO— is selected from: -Phe-Lys-, -Val-Ala-, -Val-Lys-, -Ala-Lys-, -Val-Cit-, -Phe-Cit-, -Leu-Cit-, -Ile-Cit-, -Phe-Arg-, -Trp-Cit-, Lys-Lys, Phe-Ala, Phe-N9-tosyl-Arg, Phe-N9-nitro-Arg, Val-Arg, Arg-Val, Arg-Arg, Val-D-Cit, Val-D-Lys, Val-D-Arg, D-Val-Cit, D-Val-Lys, D-Val-Arg, D-Val-D-Cit D-Val-D-Lys D-Val-D-Arg and D-Arg-D-Arg where Cit is citrulline; or $L^1$ comprises a tripeptide —$X_1$—$X_2$—$X_3$— and wherein the tripeptide in $L^1$ as represented by —NH—$X_1$—$X_2$—$X_3$—CO— is selected from Gly-Gly-Gly, Phe-Phe-Lys, D-Phe-Phe-Lys, Gly-Phe-Lys, Leu-Ala-Leu, Ile-Ala-Leu and Val-Ala-Val; or $L^1$ comprises a tetrapeptide —$X_1$—$X_2$—$X_3$—$X_4$— and wherein the tetrapeptide in $L^1$ as represented by —NH—$X_1$—$X_2$—$X_3$—$X_4$—CO— is selected from Ala-Leu-Ala-Leu, β-Ala-Leu-Ala-Leu and Gly-Phe-Leu-Gly, A is:

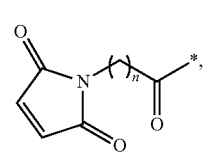

(i)

where the asterisk indicates the point of attachment to $L^1$, and n is 0 to 6;

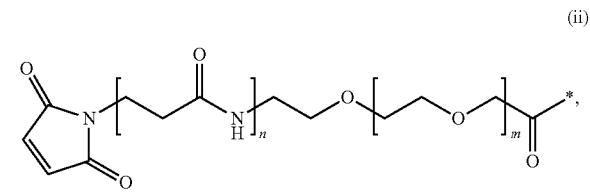

(ii)

where the asterisk indicates the point of attachment to $L^1$, n is 0 or 1, and m is 0 to 30;

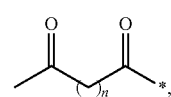

(iii)

where the asterisk indicates the point of attachment to $L^1$, and n is 1 to 6;

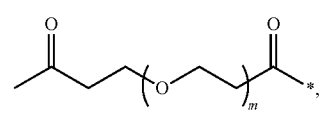

(iv)

where the asterisk indicates the point of attachment to $L^1$, and m is 1 to 30;

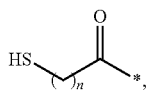

where the asterisk indicates the point of attachment to L¹, and n is 2 to 6; or

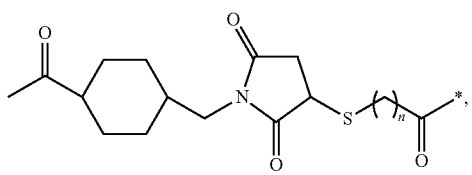

where the asterisk indicates the point of attachment to L¹, and n is 2 to 6,

L² together with —OC(=O)— form the group:

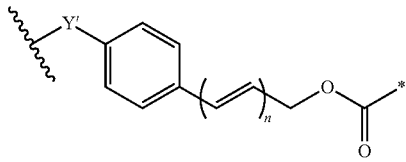

where the asterisk indicates the point of attachment to the N10 position, the wavy line indicates the point of attachment to the linker L¹, Y' is —NH—, —O—, —C(=O)NH— or —C(=O)O—, and n is 0 to 3;

$R^6$, $R^8$, and $R^9$ are independently selected from —H, —$R^{1'}$, —OH, —$OR^{1'}$, —SH, —$SR^{1'}$, —$NH_2$, —$NHR^{1'}$, —$NR^{1'}R^{3'}$, —$NO_2$, $Me_3Sn$ and halo;

$R^{10}$, $R^{11}$, $R^{12}$ and $R^{13}$ are each independently selected from the group consisting of —H, an optionally substituted linear, branched or cyclic alkyl, alkenyl or alkynyl having from 1 to 10 carbon atoms, a polyethylene glycol unit —$(OCH_2CH_2)_n$—$R^b$, halogen, guanidinium [—NH(C=NH)$NH_2$], —$OR^{6'}$, —$NR^{4'}R^{5'}$, —$NO_2$, —NCO, —$NR^{4'}COR^{5'}$, —$SR^{6'}$, a sulfoxide represented by —$SOR^{4'}$, a sulfone represented by —$SO_2R^{4'}$, a sulfonate —$SO_3^-M^+$, a sulfate —$OSO_3^-M^+$, a sulfonamide represented by —$SO_2NR^{4'}R^{5'}$, cyano, an azido, —$COR^{4'}$, —$OCOR^{4'}$, —$OCONR^{4'}R^{5'}$;

$R^{1'}$ and $R^{3'}$ are each independently selected from optionally substituted $C_{1-12}$ alkyl, $C_{3-20}$heterocyclyl or $C_{5-20}$ aryl groups, and optionally in relation to the group —$NR^{1'}R^{3'}$, $R^{1'}$ and $R^{3'}$ together with the nitrogen atom to which they are attached form an optionally substituted 4-, 5-, 6- or 7-membered heterocyclic ring;

$R^{4'}$ and $R^{5'}$ are each independently selected from —H, —OH, —$OR^{6'}$, —$NHR^{6'}$, —$NR^{6'}_2$, —$COR^{6'}$, an optionally substituted linear, branched or cyclic alkyl, alkenyl or alkynyl having from 1 to 10 carbon atoms, a polyethylene glycol unit —$(CH_2CH_2O)_n$—$R^b$, or an optionally substituted 3-18-membered heterocyclic ring having 1 to 6 heteroatoms independently selected from O, S, N or P;

$R^{6'}$, for each occurrence, is independently selected from the group consisting of —H, an optionally substituted linear, branched or cyclic alkyl, alkenyl or alkynyl having from 1 to 10 carbon atoms, a polyethylene glycol unit —$(CH_2CH_2O)_n$—$R^b$, an optionally substituted aryl having 6 to 18 carbon atoms, an optionally substituted 5- to 18-membered heteroaryl ring containing one or more heteroatoms independently selected from nitrogen, oxygen, or sulfur, and an optionally substituted 3- to 18-membered heterocyclic ring containing 1 to 6 heteroatoms independently selected from O, S, N or P;

$R^b$ is —H or an optionally substituted linear or branched alkyl having 1 to 4 carbon atoms;

M is H or a pharmaceutically acceptable cation; and n is an integer from 1 to 24, wherein the optional substituent is selected from the group consisting of $R^{1'}$, $OR^{1'}$, $SR^{1'}$, $NR^{1'}R^{3'}$, $NO_2$, halo, $CO_2R^{1'}$, $CONH_2$, $CONHR^{1'}$ and $CONR^{1'}R^{3'}$.

15. An article of manufacture comprising a pharmaceutical composition of claim 8; a container; and a package insert or label indicating that the pharmaceutical composition can be used to treat cancer.

16. The conjugate of claim 1, wherein the conjugate is represented by the following formula:

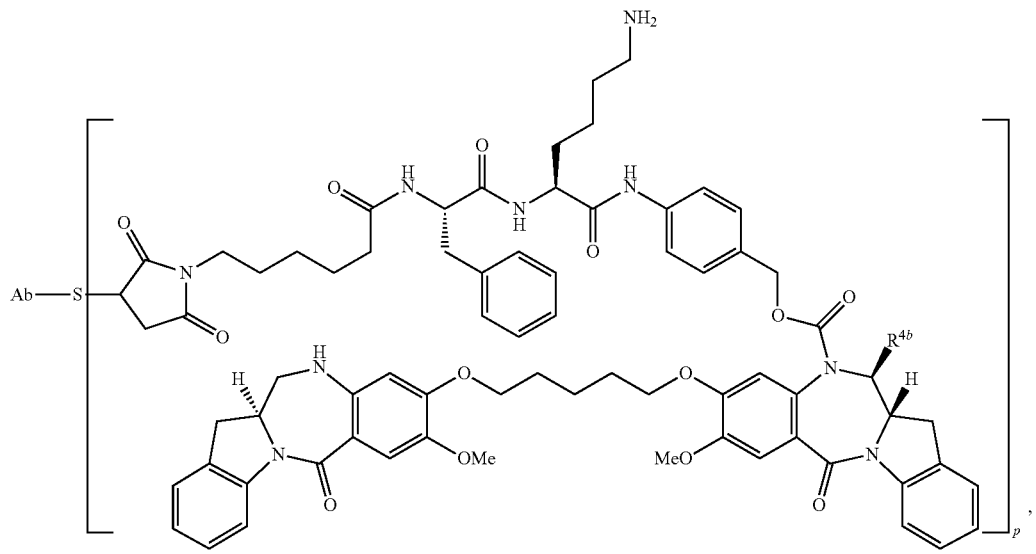

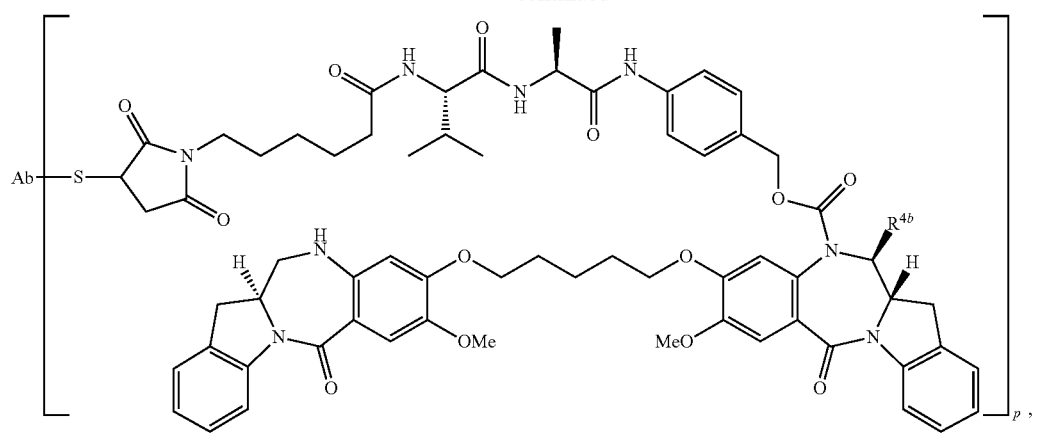
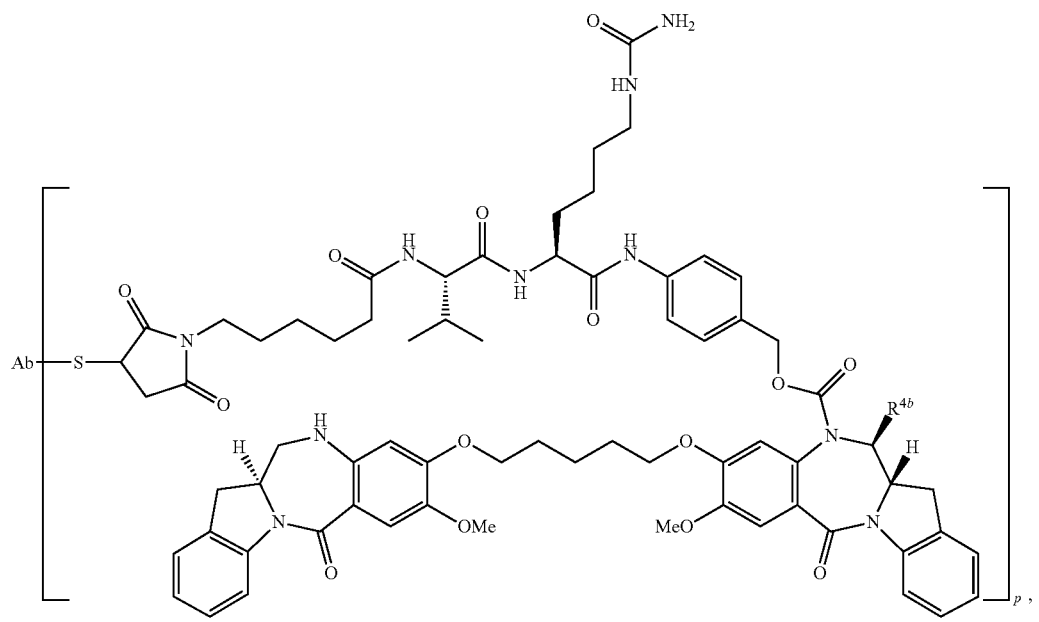
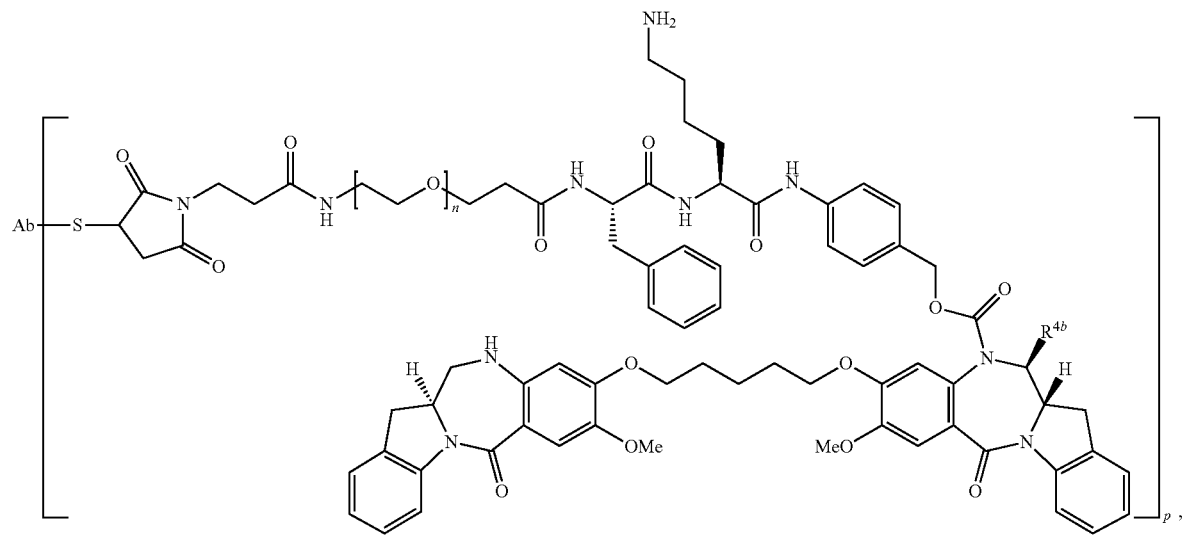

147
-continued
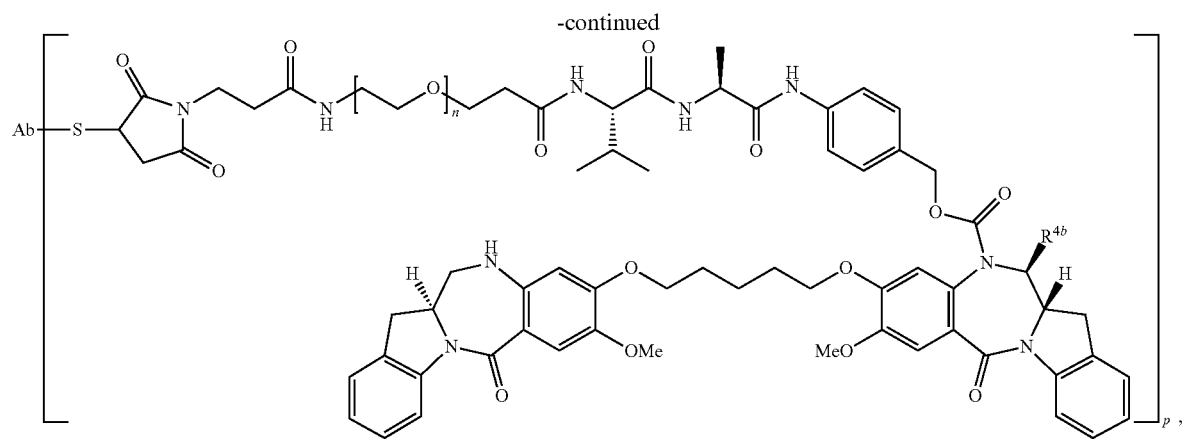
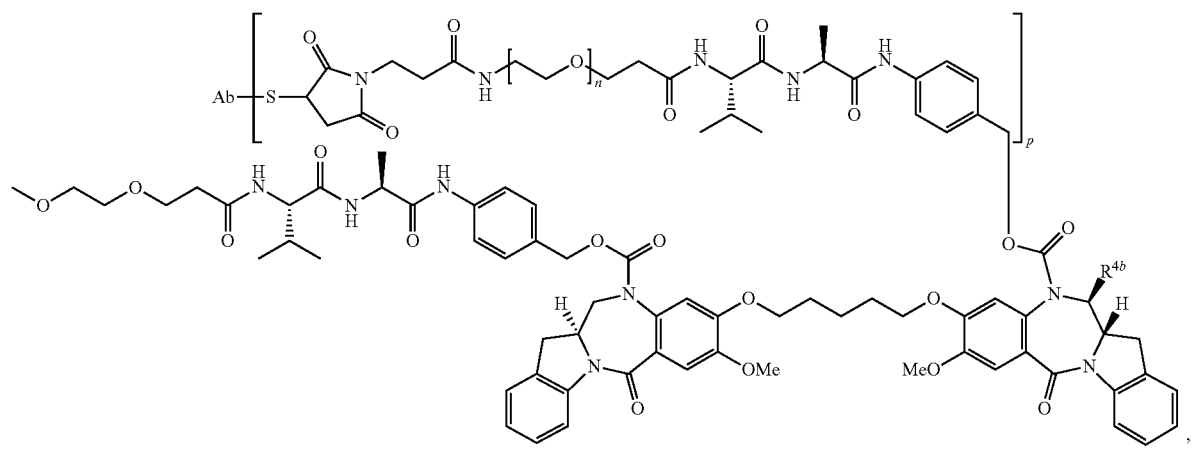
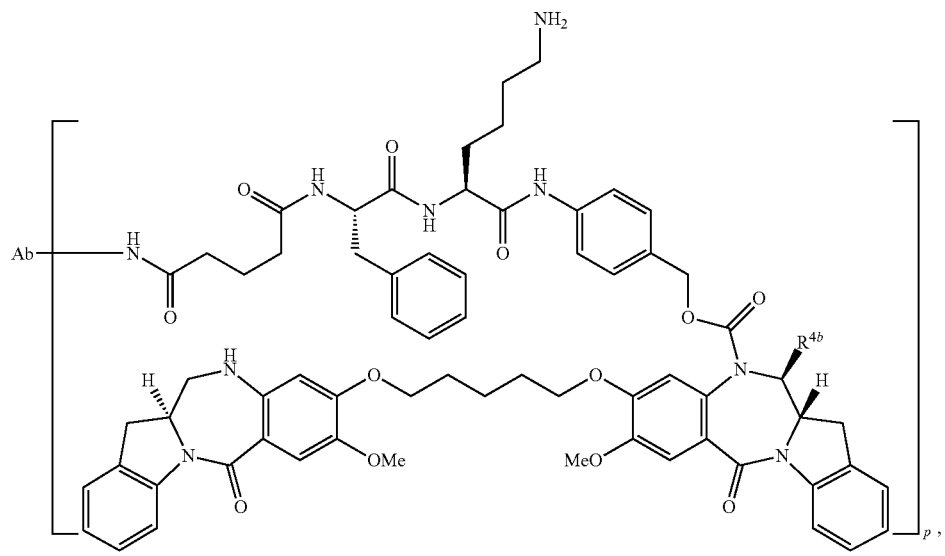
148

-continued
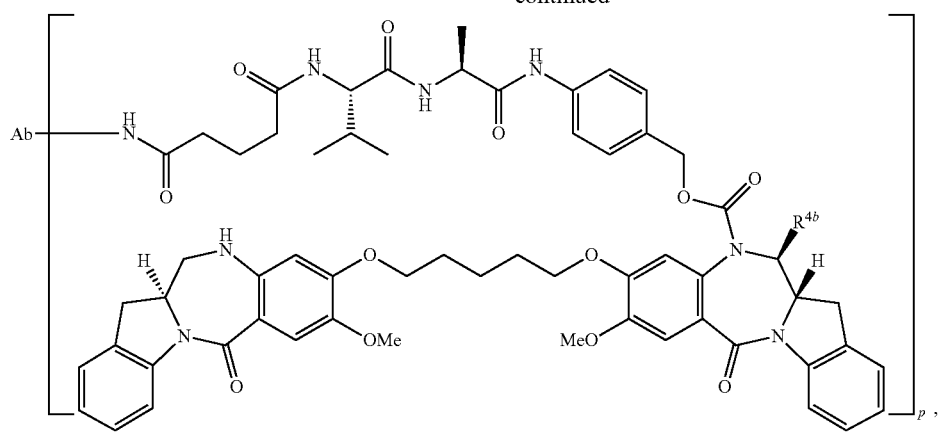
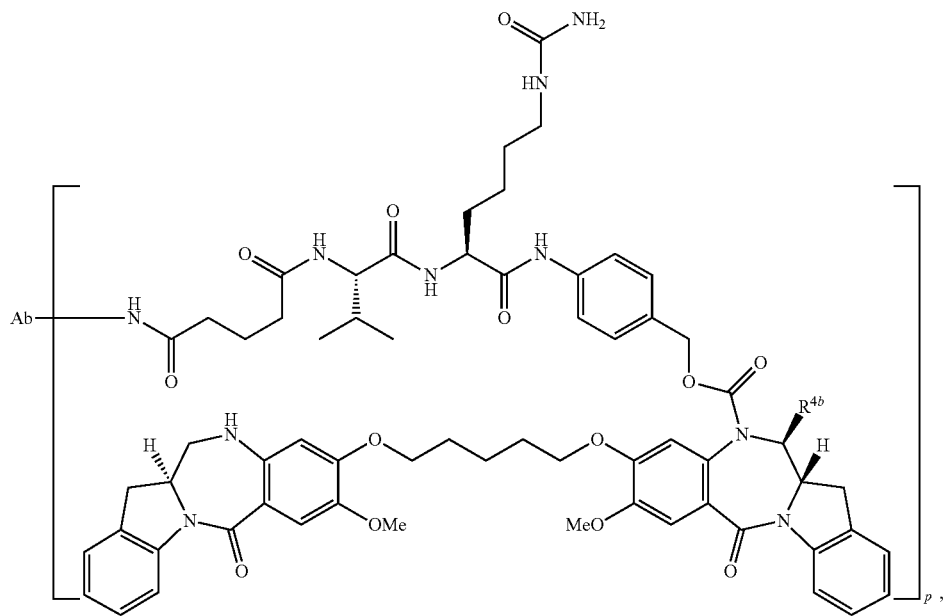
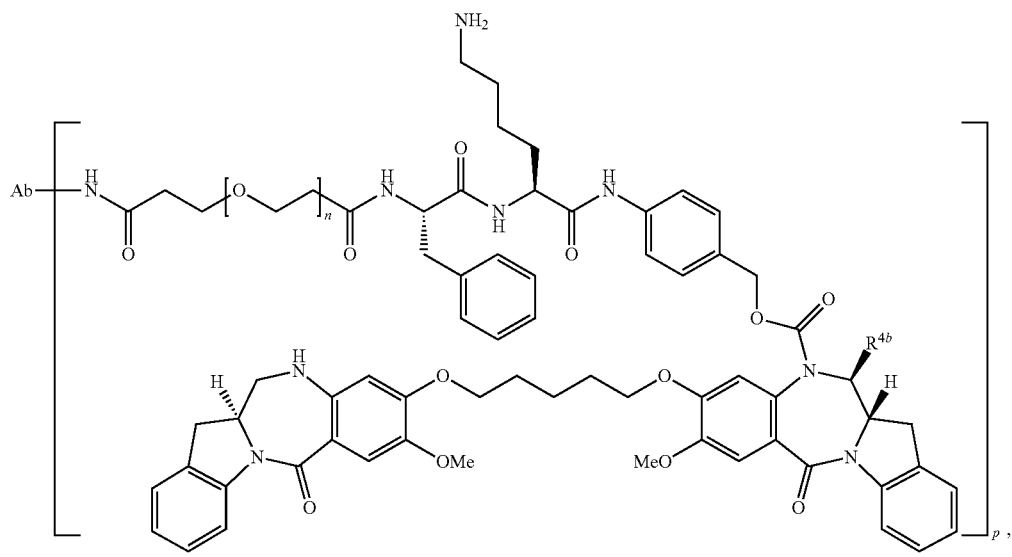

151
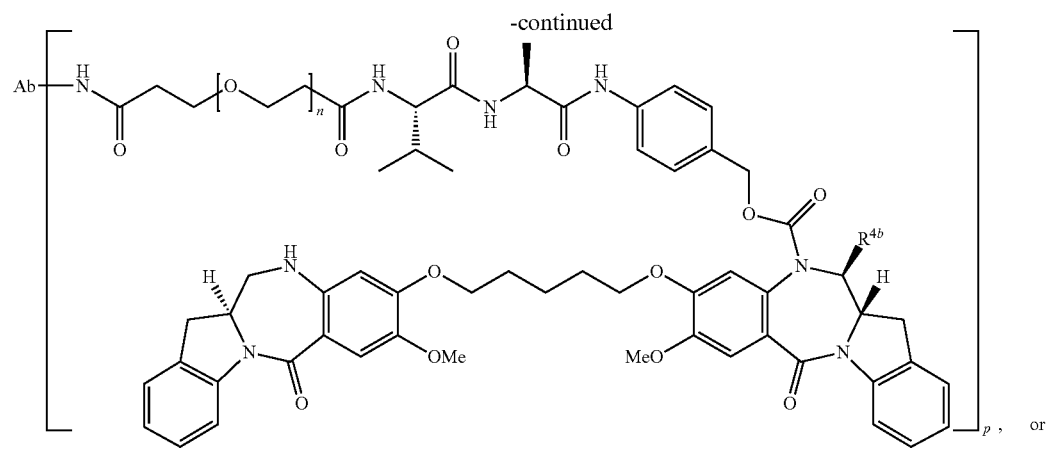
-continued
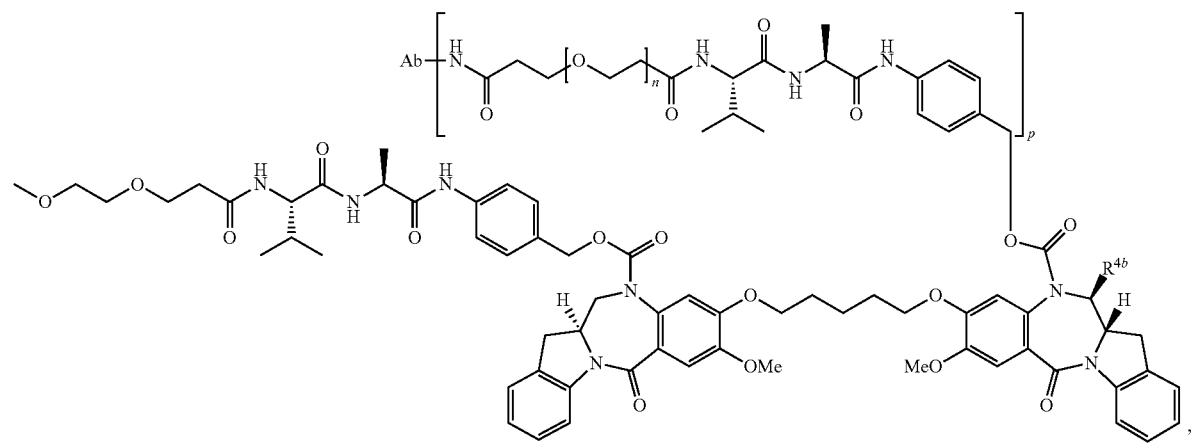
wherein:
p is an integer from 1 to 8;
n is an integer from 1 to 24, and
$R^{4b}$ is —OH or —SO$_3$M.
17. The compound of claim 9, wherein the compound is represented by the following formula:
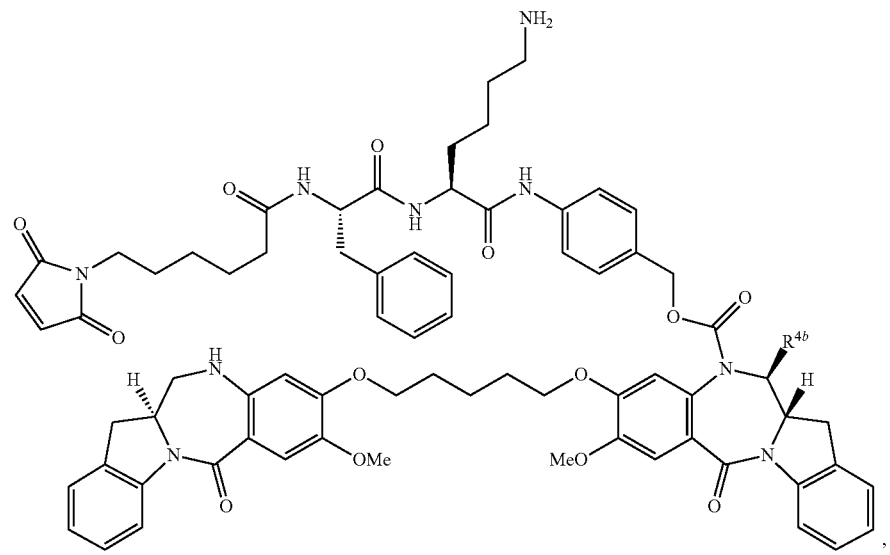

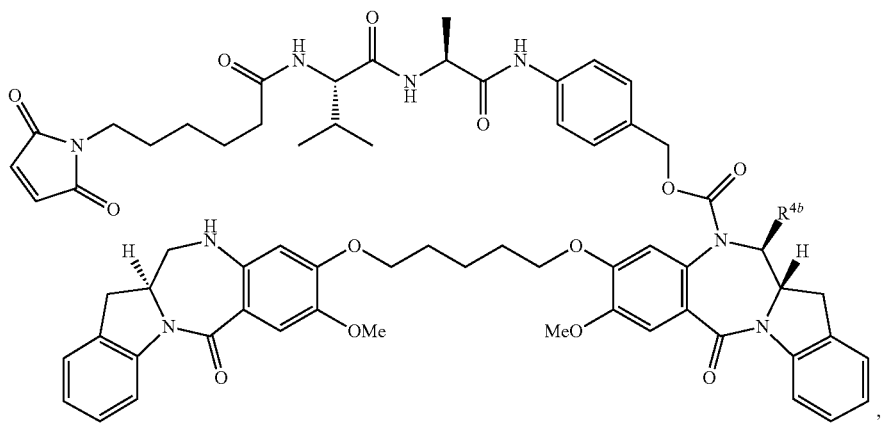
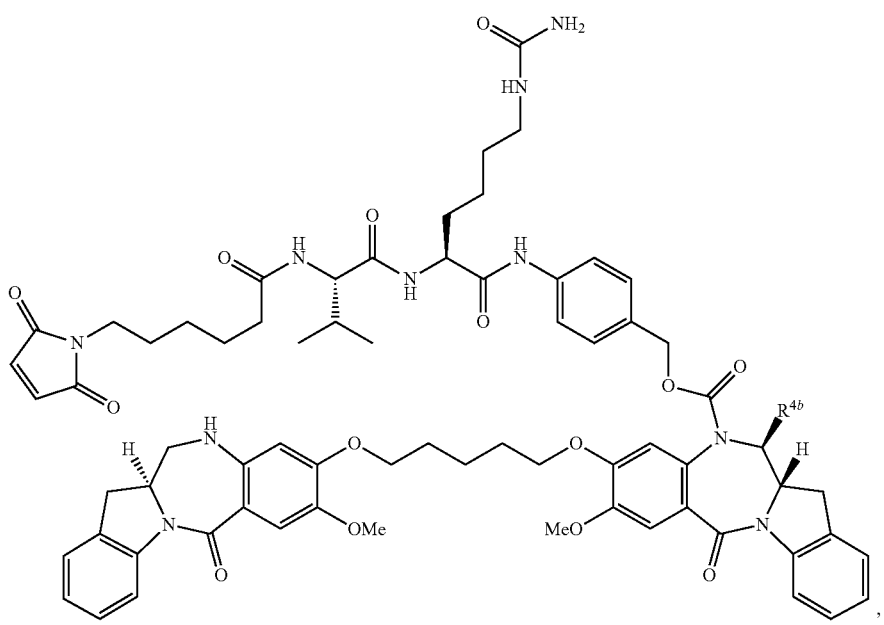
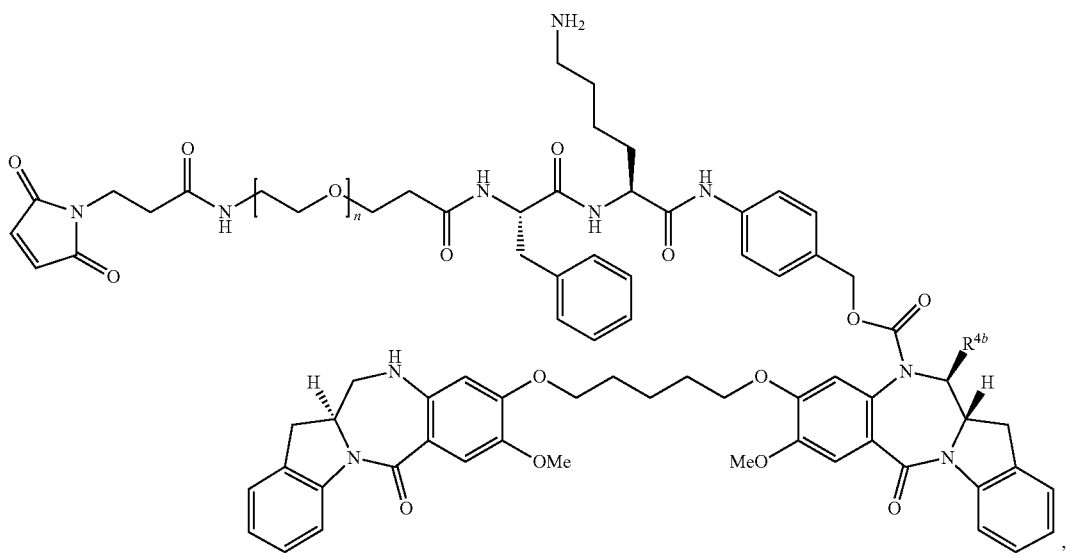

155
156
-continued
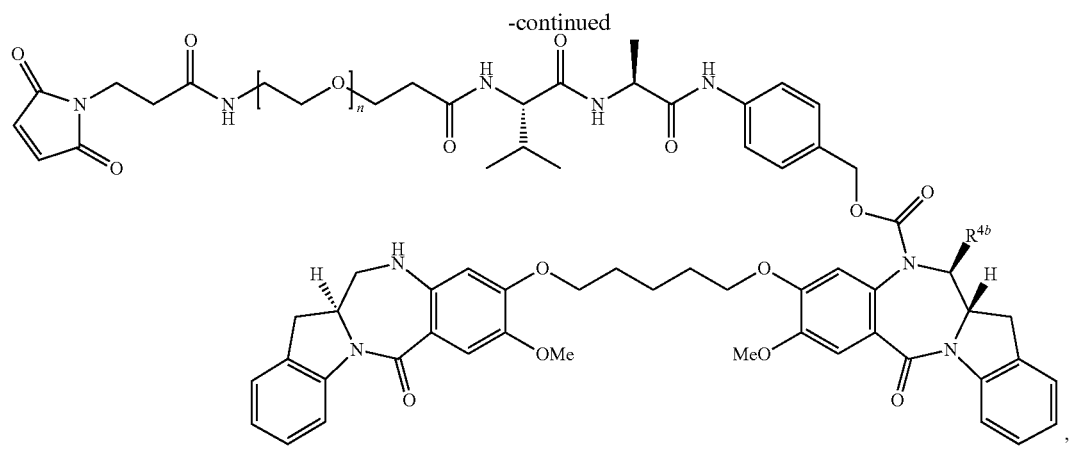
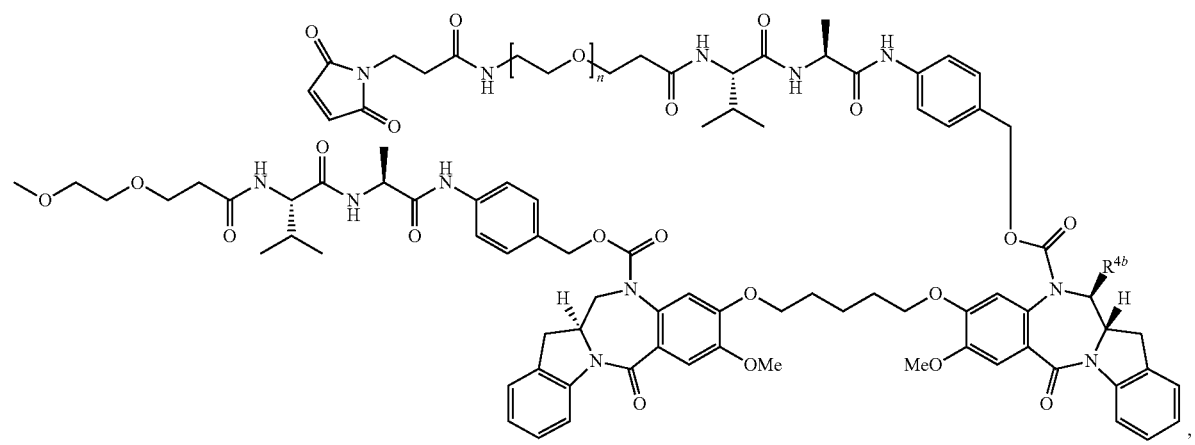
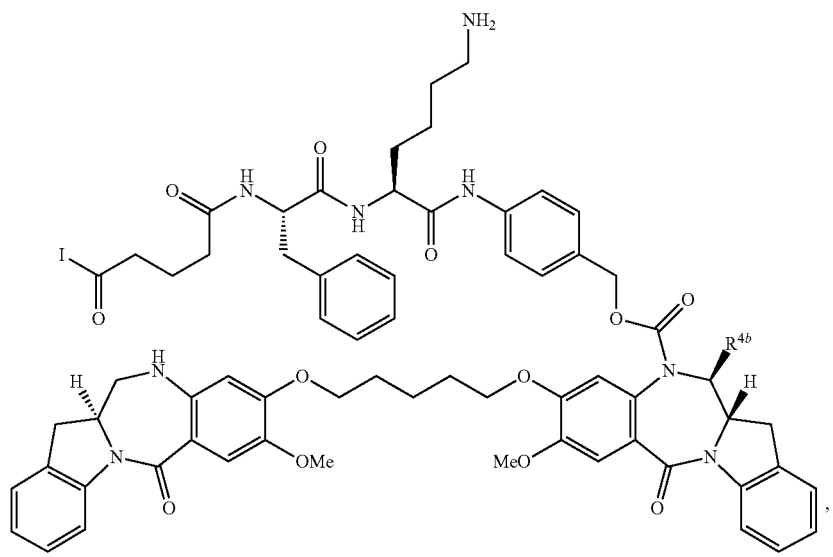

-continued
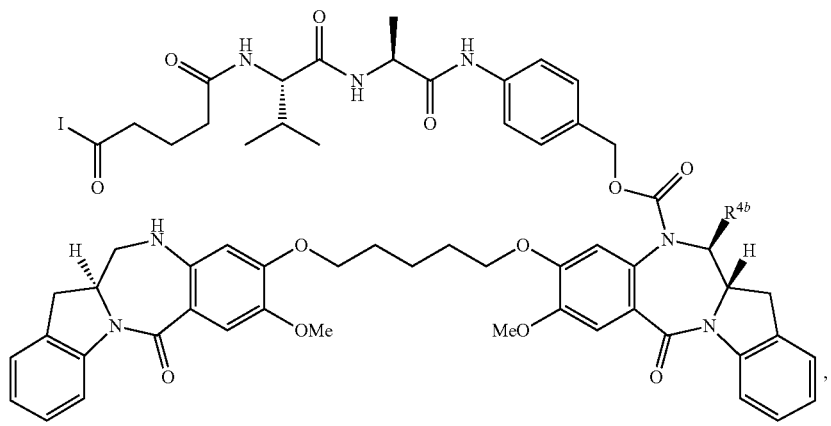
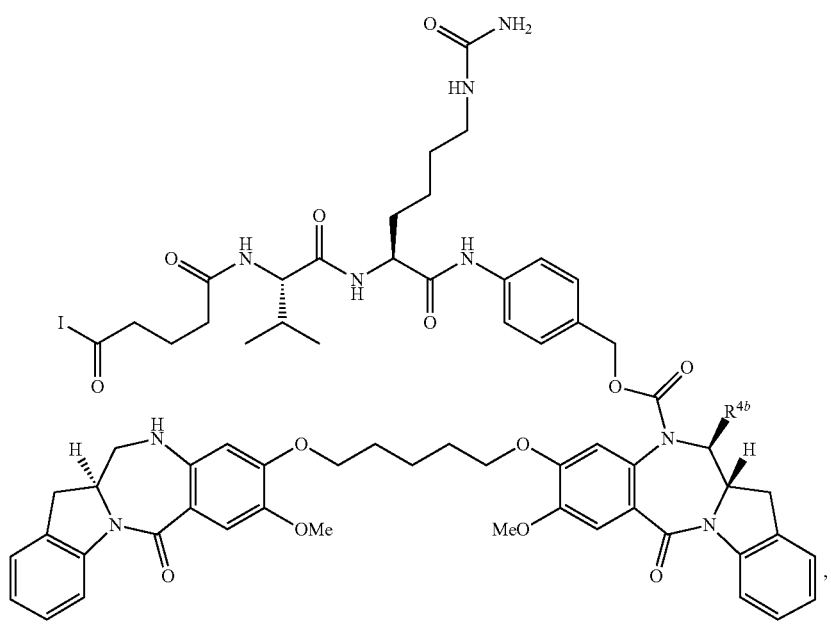
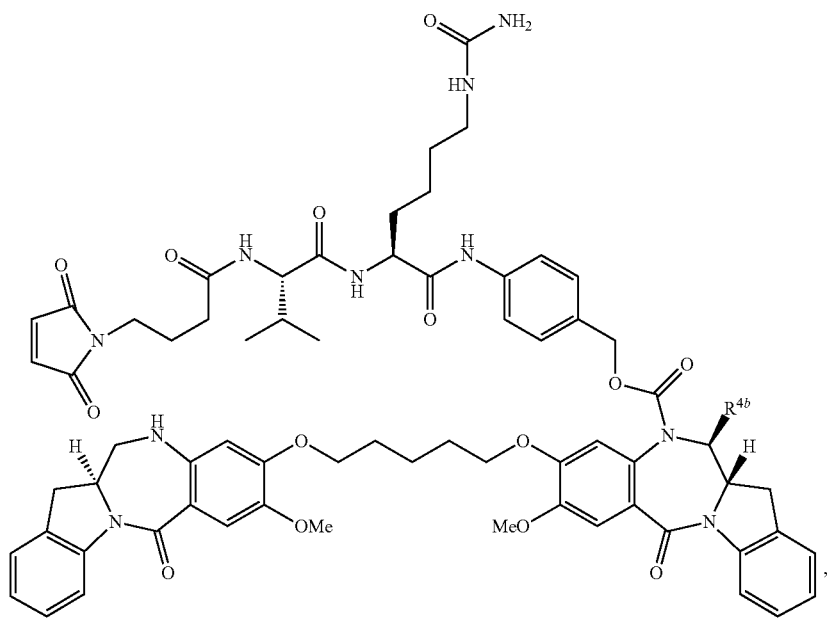

-continued
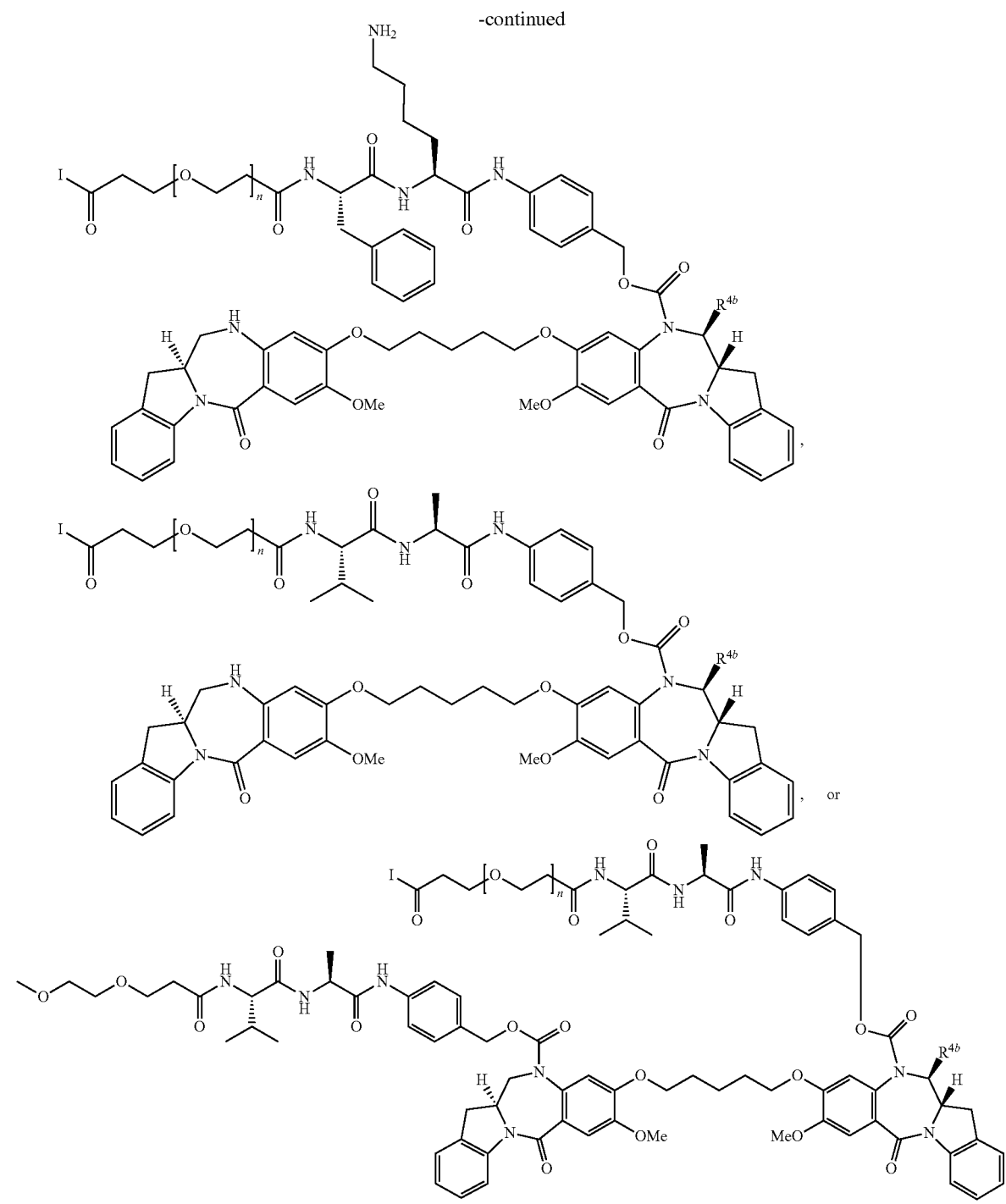
or a pharmaceutically acceptable salt thereof, wherein $R^{4b}$ is —OH or —SO$_3$M.
18. The conjugate of claim 7, wherein $R^{5a}$ is H.
19. The conjugate of claim 18, wherein $R^{4b}$ is —OH or —SO$_3$M.
20. The compound of claim 13, wherein $R^{5a}$ is H.
21. The compound of claim 20, wherein $R^{4b}$ is —OH or —SO$_3$M.
* * * * *

UNITED STATES PATENT AND TRADEMARK OFFICE
CERTIFICATE OF CORRECTION

PATENT NO. : 10,046,063 B2
APPLICATION NO. : 15/416797
DATED : August 14, 2018
INVENTOR(S) : Ravi V. J. Chari et al.

Page 1 of 2

It is certified that error appears in the above-identified patent and that said Letters Patent is hereby corrected as shown below:

In the Claims

In Claim 1, at Columns 132 and 133, please replace the formula below:

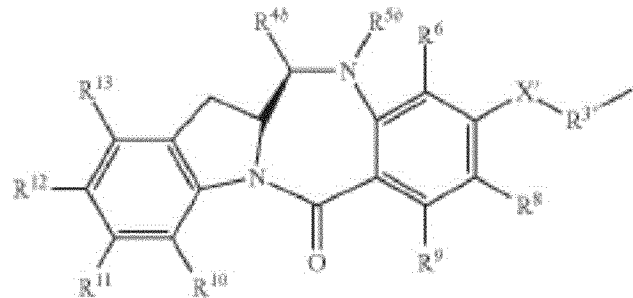

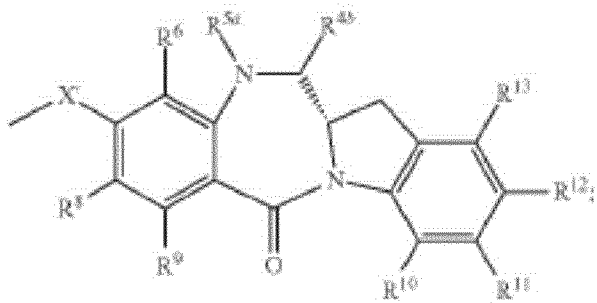

With the following formula:

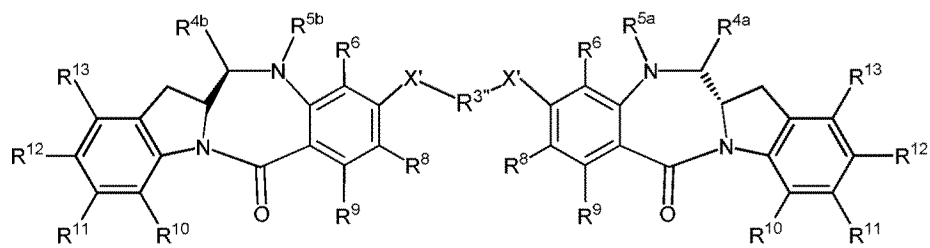

In Claim 9, at Columns 137 and 138, please replace the formula below:

Signed and Sealed this
Thirtieth Day of October, 2018

Andrei Iancu
*Director of the United States Patent and Trademark Office*

CERTIFICATE OF CORRECTION (continued)
U.S. Pat. No. 10,046,063 B2

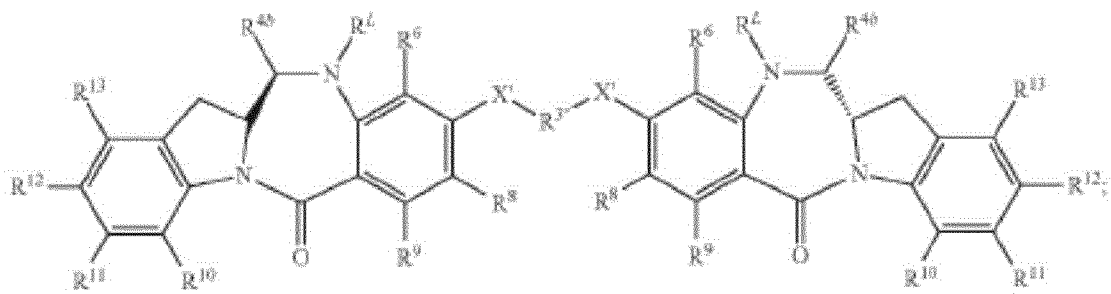

With the following formula:

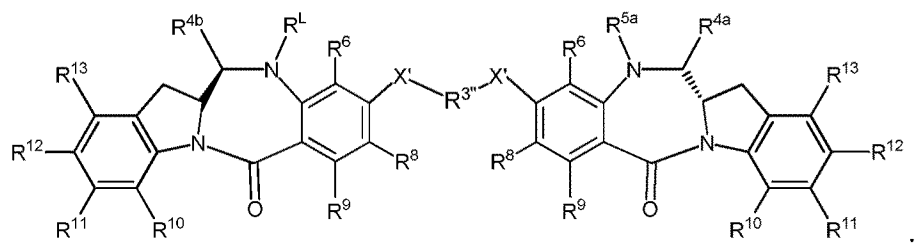

In Claim 13, at Columns 141 and 142, please replace the formula below:

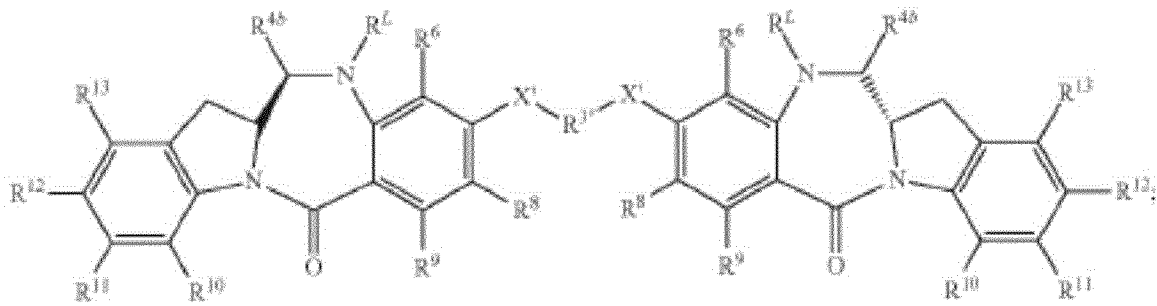

With the following formula: